(12) United States Patent
Burgess et al.

(10) Patent No.: US 8,637,509 B2
(45) Date of Patent: Jan. 28, 2014

(54) AZAINDAZOLES

(75) Inventors: Joelle Lorraine Burgess, Collegeville, PA (US); Neil Johnson, Collegeville, PA (US); Steven D. Knight, Collegeville, PA (US); Louis LaFrance, Collegeville, PA (US); William H. Miller, Collegeville, PA (US); Kenneth Newlander, Collegeville, PA (US); Stuart Romeril, Collegeville, PA (US); Meagan B. Rouse, Collegeville, PA (US); Xinrong Tian, Collegeville, PA (US); Sharad Kumar Verma, Collegeville, PA (US); Dominic Suarez, Collegeville, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 13/696,601

(22) PCT Filed: May 5, 2011

(86) PCT No.: PCT/US2011/035344
§ 371 (c)(1),
(2), (4) Date: Nov. 7, 2012

(87) PCT Pub. No.: WO2012/005805
PCT Pub. Date: Jan. 12, 2012

(65) Prior Publication Data
US 2013/0059849 A1 Mar. 7, 2013

Related U.S. Application Data

(60) Provisional application No. 61/332,314, filed on May 7, 2010.

(51) Int. Cl.
*A61K 31/444* (2006.01)
*A61P 35/00* (2006.01)
*A61K 31/506* (2006.01)
*A61K 31/5377* (2006.01)
*A61K 31/513* (2006.01)
*C07D 471/04* (2006.01)
*A61K 31/4545* (2006.01)

(52) U.S. Cl.
USPC ............... 514/234.2; 514/303; 514/253.04; 514/274; 514/272; 544/127; 544/362; 544/310; 544/331; 546/120

(58) Field of Classification Search
USPC .............. 514/234.2, 303, 253.04, 274, 272; 546/120; 544/127, 362, 310, 331
See application file for complete search history.

(56) References Cited

U.S. PATENT DOCUMENTS

2008/0182844 A1\* 7/2008 Bjergarde et al. .......... 514/234.2
2010/0113415 A1 5/2010 Rajapakse et al.

FOREIGN PATENT DOCUMENTS

WO  WO 2012/118812 A2  9/2012

\* cited by examiner

*Primary Examiner* — Niloofar Rahmani
(74) *Attorney, Agent, or Firm* — Duke M. Fitch; Kathryn A. Lutomski; John Lemanowicz

(57) ABSTRACT

Herein are disclosed azaindazoles of formula (I)

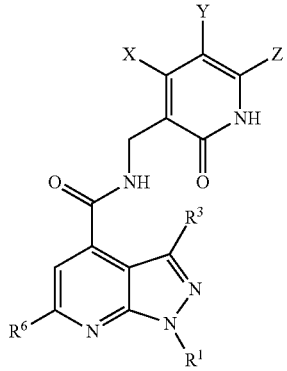

where the various groups are defined herein, and which are useful for treating cancer.

6 Claims, No Drawings

AZAINDAZOLES

This application is a 371 of International Application No. PCT/US2011/035344, filed 5 May 2011, which claims the benefit of U.S. Provisional Application No. 61/332,314, filed 7 May 2010, which are incorporated herein in their entireties.

FIELD OF THE INVENTION

This invention relates to substituted azaindazoles which inhibit EZH2 and thus are useful for inhibiting the proliferation of and/or inducing apoptosis in cancer cells.

BACKGROUND OF THE INVENTION

Epigenetic modifications play an important role in the regulation of many cellular processes including cell proliferation, differentiation, and cell survival. Global epigenetic modifications are common in cancer, and include global changes in DNA and/or histone methylation, dysregulation of non-coding RNAs and nucleosome remodeling leading to aberrant activation or inactivation of oncogenes, tumor suppressors and signaling pathways. However, unlike genetic mutations which arise in cancer, these epigenetic changes can be reversed through selective inhibition of the enzymes involved. Several methylases involved in histone or DNA methylation are known to be dysregulated in cancer. Thus, selective inhibitors of particular methylases will be useful in the treatment of proliferative diseases such as cancer.

EZH2 (enhancer of zeste homolog 2; human EZH2 gene: Cardoso, C, et al; *European J of Human Genetics*, Vol. 8, No. 3 Pages 174-180, 2000) is the catalytic subunit of the Polycomb Repressor Complex 2 (PRC2) which functions to silence target genes by tri-methylating lysine 27 of histone H3 (H3K27me3). Histone H3 is one of the five main histone proteins involved in the structure of chromatin in eukaryotic cells. Featuring a main globular domain and a long N-terminal tail, Histones are involved with the structure of the nucleosomes, a 'beads on a string' structure. Histone proteins are highly post-translationally modified however Histone H3 is the most extensively modified of the five histones. The term "Histone H3" alone is purposely ambiguous in that it does not distinguish between sequence variants or modification state. Histone H3 is an important protein in the emerging field of epigenetics, where its sequence variants and variable modification states are thought to play a role in the dynamic and long term regulation of genes.

Increased EZH2 expression has been observed in numerous solid tumors including those of the prostate, breast, skin, bladder, liver, pancreas, head and neck and correlates with cancer aggressiveness, metastasis and poor outcome (Varambally et al., 2002; Kleer et al., 2003; Breuer et al., 2004; Bachmann et al., 2005; Weikert et al., 2005; Sudo et al., 2005; Bachmann et al., 2006). For instance, there is a greater risk of recurrence after prostatectomy in tumors expressing high levels of EZH2, increased metastasis, shorter disease-free survival and increased death in breast cancer patients with high EZH2 levels (Varambally et al., 2002; Kleer et al., 2003). More recently, inactivating mutations in UTX (ubiquitously transcribed tetratricopeptixe repeats X), a H3K27 demethylase which functions in opposition to EZH2, have been identified in multiple solid and hematological tumor types (including renal, glioblastoma, esophageal, breast, colon, non-small cell lung, small cell lung, bladder, multiple myeloma, and chronic myeloid leukemia tumors), and low UTX levels correlate with poor survival in breast cancer suggesting that loss of UTX function leads to increased H3K27me3 and repression of target genes (Wang et al., 2010). Together, these data suggest that increased H3K27me3 levels contribute to cancer aggressiveness in many tumor types and that inhibition of EZH2 activity may provide therapeutic benefit.

Numerous studies have reported that direct knockdown of EZH2 via siRNA or shRNA or indirect loss of EZH2 via treatment with the SAH hydrolase inhibitor 3-deazaneplanocin A (DZNep) decreases cancer cell line proliferation and invasion in vitro and tumor growth in vivo (Gonzalez et al., 2008, GBM 2009). While the precise mechanism by which aberrant EZH2 activity leads to cancer progression is not known, many EZH2 target genes are tumor suppressors suggesting that loss of tumor suppressor function is a key mechanism (refs). In addition, EZH2 overexpression in immortalized or primary epithelial cells promotes anchorage independent growth and invasion and requires EZH2 catalytic activity. (Kleer et al., 2003; Cao et al., 2008).

Thus, there is strong evidence to suggest that inhibition of EZH2 activity decreases cellular proliferation and invasion. Accordingly, compounds that inhibit EZH2 activity would be useful for the treatment of cancer. The azaindazoles of this invention provide such treatment.

SUMMARY OF THE INVENTION

In a first instance, this invention relates to compounds of formula (I)

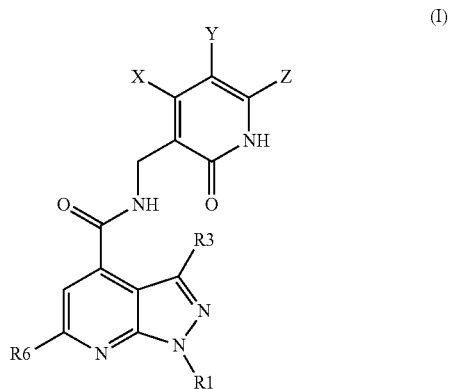

wherein

X and Z are selected independently from the group consisting of hydrogen, $(C_1-C_8)$alkyl, $(C_2-C_8)$alkenyl, $(C_2-C_8)$alkynyl, unsubstituted or substituted $(C_3-C_8)$cycloalkyl, unsubstituted or substituted $(C_3-C_8)$cycloalkyl-$(C_1-C_8)$alkyl or -$(C_2-C_8)$alkenyl, unsubstituted or substituted $(C_5-C_8)$cycloalkenyl, unsubstituted or substituted $(C_5-C_8)$cycloalkenyl-$(C_1-C_8)$alkyl or -$(C_2-C_8)$alkenyl, $(C_6-C_{10})$bicycloalkyl, unsubstituted or substituted heterocycloalkyl, unsubstituted or substituted heterocycloalkyl-$(C_1-C_8)$alkyl or -$(C_2-C_8)$alkenyl, unsubstituted or substituted aryl, unsubstituted or substituted aryl-$(C_1-C_8)$alkyl or -$(C_2-C_8)$alkenyl, unsubstituted or substituted heteroaryl, unsubstituted or substituted heteroaryl-$(C_1-C_8)$alkyl or -$(C_2-C_8)$alkenyl, halo, cyano, —$COR^a$, —$CO_2R^a$, —$CONR^aR^b$, —$CONR^aNR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$NR^aNR^aC(O)OR^a$, —$OR^a$, —$OC(O)R^a$, and —$OC(O)NR^aR^b$;

Y is H or halo;

$R^1$ is $(C_1-C_8)$alkyl, $(C_2-C_8)$alkenyl, $(C_2-C_8)$alkynyl, unsubstituted or substituted $(C_3-C_8)$cycloalkyl, unsubstituted or substituted $(C_3-C_8)$cycloalkyl-$(C_1-C_8)$alkyl or -$(C_2-C_8)$alkenyl, unsubstituted or substituted $(C_5-C_8)$cycloalkenyl, unsubstituted or substituted $(C_5-C_8)$cycloalkenyl-$(C_1-C_8)$alkyl or -$(C_2-C_8)$alkenyl, unsubstituted or substituted $(C_6-C_{10})$bicycloalkyl, unsubstituted or substituted heterocycloalkyl or -$(C_2-C_8)$alkenyl, unsubstituted or substituted heterocycloalkyl-$(C_1-C_8)$alkyl, unsubstituted or substituted aryl, unsubstituted or substituted aryl-$(C_1-C_8)$alkyl or -$(C_2-C_8)$alkenyl, unsubstituted or substituted heteroaryl, unsubstituted or substituted heteroaryl-$(C_1-C_8)$alkyl or -$(C_2-C_8)$alkenyl, $-COR^a$, $-CO_2R^a$, $-CONR^aR^b$, $-CONR^aNR^aR^b$;

$R^3$ is hydrogen, $(C_1-C_8)$alkyl, cyano, trifluoromethyl, $-NR^aR^b$, or halo;

$R^6$ is selected from the group consisting of hydrogen, halo, $(C_1-C_8)$alkyl, $(C_2-C_8)$alkenyl, $(C_2-C_8)$alkynyl, unsubstituted or substituted $(C_3-C_8)$cycloalkyl, unsubstituted or substituted $(C_3-C_8)$cycloalkyl-$(C_1-C_8)$alkyl, unsubstituted or substituted $(C_5-C_8)$cycloalkenyl, unsubstituted or substituted $(C_5-C_8)$cycloalkenyl-$(C_1-C_8)$alkyl, $(C_6-C_{10})$bicycloalkyl, unsubstituted or substituted heterocycloalkyl, unsubstituted or substituted heterocycloalkyl-$(C_1-C_8)$alkyl, unsubstituted or substituted aryl, unsubstituted or substituted aryl-$(C_1-C_8)$alkyl, unsubstituted or substituted heteroaryl, unsubstituted or substituted heteroaryl-$(C_1-C_8)$alkyl, cyano, $-COR^a$, $-CO_2R^a$, $-CONR^aR^b$, $-CONR^aNR^aR^b$, $-SR^a$, $-SOR^a$, $-SO_2R^a$, $-SO_2NR^aR^b$, nitro, $-NR^aR^b$, $-NR^aC(O)R^b$, $-NR^aC(O)NR^aR^b$, $-NR^aC(O)OR^a$, $-NR^aSO_2R^b$, $-NR^aSO_2NR^aR^b$, $-NR^aNR^aR^b$, $-NR^aNR^aC(O)R^b$, $-NR^aNR^aC(O)NR^aR^b$, $-NR^aNR^aC(O)OR^a$, $-OR^a$, $-OC(O)R^a$, $-OC(O)NR^aR^b$;

wherein any $(C_1-C_8)$alkyl, $(C_2-C_8)$alkenyl, $(C_2-C_8)$alkynyl, cycloalkyl, cycloalkenyl, bicycloalkyl, heterocycloalkyl, aryl, or heteroaryl group is optionally substituted by 1, 2 or 3 groups independently selected from the group consisting of halo, $(C_1-C_6)$alkyl, $(C_3-C_8)$cycloalkyl, $(C_5-C_8)$cycloalkenyl, $(C_1-C_6)$haloalkyl, cyano, $-COR^a$, $-CO_2R^a$, $-CONR^aR^b$, $-SR^a$, $-SOR^a$, $-SO_2R^a$, $-SO_2NR^aR^b$, nitro, $-NR^aR^b$, $-NR^aC(O)R^b$, $-NR^aC(O)NR^aR^b$, $-NR^aC(O)OR^a$, $-NR^aSO_2R^b$, $-NRaSO_2NR^aR^b$, $-OR^a$, $-OC(O)R^a$, $-OC(O)NR^aR^b$, heterocycloalkyl, aryl, heteroaryl, aryl$(C_1-C_4)$alkyl, and heteroaryl$(C_1-C_4)$alkyl;

wherein any aryl or heteroaryl moiety of said aryl, heteroaryl, aryl$(C_1-C_4)$alkyl, or heteroaryl$(C_1-C_4)$alkyl is optionally substituted by 1, 2 or 3 groups independently selected from the group consisting of halo, $(C_1-C_6)$alkyl, $(C_3-C_8)$cycloalkyl, $(C_5-C_8)$cycloalkenyl, $(C_1-C_6)$haloalkyl, cyano, $-COR^a$, $-CO_2R^a$, $-CONR^aR^b$, $-SR^a$, $-SOR^a$, $-SO_2R^a$, $-SO_2NR^aR^b$, nitro, $-NR^aR^b$, $-NR^aC(O)R^b$, $-NR^aC(O)NR^aR^b$, $-NR^aC(O)OR^a$, $-NR^aSO_2R^b$, $-NR^aSO_2NR^aR^b$, $-OR^a$, $-OC(O)R^a$, and $-OC(O)NR^aR^b$;

$R^a$ and $R^b$ are each independently hydrogen, $(C_1-C_8)$alkyl, $(C_2-C_8)$alkenyl, $(C_2-C_8)$alkynyl, $(C_3-C_8)$cycloalkyl, $(C_5-C_8)$cycloalkenyl, $(C_6-C_{10})$bicycloalkyl, heterocycloalkyl, aryl, heteroaryl, wherein said $(C_1-C_8)$alkyl, $(C_2-C_8)$alkenyl, $(C_2-C_8)$alkynyl, cycloalkyl, cycloalkenyl, bicycloalkyl, heterocycloalkyl, aryl or heteroaryl group is optionally substituted by 1, 2 or 3 groups independently selected from halo, hydroxyl, $(C_1-C_4)$alkoxy, amino, $(C_1-C_4)$alkylamino, $((C_1-C_4)$alkyl)$((C_1-C_4)$alkyl)amino, $-CO_2H$, $-CO_2(C_1-C_4)$alkyl, $-CONH_2$, $-CONH(C_1-C_4)$alkyl, $-CON((C_1-C_4)$alkyl)$((C_1-C_4)$alkyl), $-SO_2(C_1-C_4)$alkyl, $-SO_2NH_2$, $-SO_2NH(C_1-C_4)$alkyl, or $-SO_2N((C_1-C_4)$alkyl)$((C_1-C_4)$alkyl);

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from $(C_1-C_4)$alkyl, $(C_1-C_4)$haloalkyl, amino, $(C_1-C_4)$alkylamino, $((C_1-C_4)$alkyl)$((C_1-C_4)$alkyl)amino, hydroxyl, oxo, $(C_1-C_4)$alkoxy, and $(C_1-C_4)$alkoxy$(C_1-C_4)$alkyl, wherein said ring is optionally fused to a $(C_3-C_8)$cycloalkyl, heterocycloalkyl, aryl, or heteroaryl ring;

or $R^a$ and $R^b$ taken together with the nitrogen to which they are attached represent a 6- to 10-membered bridged bicyclic ring system optionally fused to a $(C_3-C_8)$cycloalkyl, heterocycloalkyl, aryl, or heteroaryl ring;

or a salt thereof.

In a further iteration of this invention it relates to a method of treating cancer.

Another aspect of the invention are pharmaceutical preparations comprising compounds of formula (I) and pharmaceutically acceptable excipients.

In a fourth aspect, there is provided the use of a compound of formula (I) or a pharmaceutically acceptable salt or solvate thereof, in the preparation of a medicament for use in the treatment of a disorder mediated by inhibiting EZH2, such as inducing apoptosis in cancer cells.

In a fifth aspect there is provided methods of co-administering the presently invented compounds of formula (I) with another active ingredients.

DETAILED DESCRIPTION OF THE INVENTION

For the avoidance of doubt, unless otherwise indicated, the term "substituted" means substituted by one or more defined groups. In the case where groups may be selected from a number of alternative groups the selected groups may be the same or different.

The term "independently" means that where more than one substituent is selected from a number of possible substituents, those substituents may be the same or different.

An "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein the term "alkyl" refers to a straight- or branched-chain hydrocarbon radical having the specified number of carbon atoms, so for example, as used herein, the terms "$C_1-C_8$alkyl" refers to an alkyl group having at least 1 and up to 8 carbon atoms respectively. Examples of such branched or straight-chained alkyl groups useful in the present invention include, but are not limited to, methyl, ethyl, n-propyl, isopropyl, isobutyl, n-butyl, t-butyl, n-pentyl, isopentyl, n-hexyl, n-heptyl, and n-octyl and branched analogs of the latter 5 normal alkanes.

The term "alkoxy" as used herein means $-O(C_1-C_8\text{alkyl})$ including $-OCH_3$, $-OCH_2CH_3$ and $-OC(CH_3)_3$ and the like per the definition of alkyl above.

The term "alkylthio" as used herein is meant $-S(C_1-C_8\text{alkyl})$ including $-SCH_3$, $-SCH_2CH_3$ and the like per the definition of alkyl above.

The term "acyloxy" means —OC(O)C$_1$-C$_8$alkyl and the like per the definition of alkyl above.

"Acylamino" means -N(H)C(O)C$_1$-C$_8$alkyl and the like per the definition of alkyl above.

"Aryloxy" means —O(aryl), —O(substituted aryl), —O(heteroaryl) or —O(substituted heteroaryl).

"Arylamino" means —NH(aryl), —NH(substituted aryl), —NH(heteroaryl) or —NH(substituted heteroaryl), and the like.

When the term "alkenyl" (or "alkenylene") is used it refers to straight or branched hydrocarbon chains containing the specified number of carbon atoms and at least 1 and up to 5 carbon-carbon double bonds. Examples include ethenyl (or ethenylene) and propenyl (or propenylene).

When the term "alkynyl" (or "alkynylene") is used it refers to straight or branched hydrocarbon chains containing the specified number of carbon atoms and at least 1 and up to 5 carbon-carbon triple bonds. Examples include ethynyl (or ethynylene) and propynyl (or propynylene).

"Haloalkyl" refers to an alkyl group group that is substituted with one or more halo substituents, suitably from 1 to 6 substituents. Haloalkyl includes trifluoromethyl.

When "cycloalkyl" is used it refers to a non-aromatic, saturated, cyclic hydrocarbon ring containing the specified number of carbon atoms. So, for example, the term "C$_3$-C$_8$cycloalkyl" refers to a non-aromatic cyclic hydrocarbon ring having from three to eight carbon atoms. Exemplary "C$_3$-C$_8$cycloalkyl" groups useful in the present invention include, but are not limited to, cyclopropyl, cyclobutyl, cyclopentyl, cyclohexyl, cycloheptyl and cyclooctyl.

The term "C$_5$-C$_8$cycloalkenyl" refers to a non-aromatic monocyclic carboxycyclic ring having the specified number of carbon atoms and up to 3 carbon-carbon double bonds. "Cycloalkenyl" includes by way of example cyclopentenyl and cyclohexenyl.

Where "C$_3$-C$_8$heterocycloalkyl" is used, it means a non-aromatic heterocyclic ring containing the specified number of ring atoms being, saturated or having one or more degrees of unsaturation and containing one or more heteroatom substitutions independently selected from O, S and N. Such a ring may be optionally fused to one or more other "heterocyclic" ring(s) or cycloalkyl ring(s). Examples are given herein below.

"Aryl" refers to optionally substituted monocyclic or polycarbocyclic unfused or fused groups having 6 to 14 carbon atoms and having at least one aromatic ring that complies with Hückel's Rule. Examples of aryl groups are phenyl, biphenyl, naphthyl, anthracenyl, phenanthrenyl, and the like, as further illustrated below.

"Heteroaryl" means an optionally substituted aromatic monocyclic ring or polycarbocyclic fused ring system wherein at least one ring complies with Hückel's Rule, has the specified number of ring atoms, and that ring contains at least one heteratom independently selected from N, O and S. Examples of "heteroaryl" groups are given herein below.

The term "optionally" means that the subsequently described event(s) may or may not occur, and includes both event(s), which occur, and events that do not occur.

Herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

While the compounds encompassed by the general structure of formula (I) as defined herein are believed to be useful for inducing apoptosis in cancer cells, some of these compounds are more active that others. In that vein, the following subgroups delineate certain compounds believed to have greater potency or other properties which suggest they may be a better choice for use in therapy, versus other. Those subgroups are represented as follows:

Subgroup A

X and Z are selected from the group consisting of (C$_1$-C$_8$)alkyl, (C$_3$-C$_8$)cycloalkyl, heterocycloalkyl, aryl, heteroaryl, —NR$^a$R$^b$, and —OR$^a$;

Y is H or F;

R$^1$ is selected from the group consisting of (C$_1$-C$_8$)alkyl, (C$_3$-C$_8$)cycloalkyl, heterocycloalkyl, aryl, and heteroaryl;

R$^3$ is selected from the group consisting of hydrogen, (C$_1$-C$_8$)alkyl, cyano, trifluoromethyl, —NR$^a$R$^b$, and halo;

R$^6$ is selected from the group consisting of hydrogen, halo, cyano, trifluoromethyl, amino, (C$_1$-C$_8$)alkyl, (C$_3$-C$_8$)cycloalkyl, aryl, heteroaryl, acylamino; (C$_2$-C$_8$)alkynyl, arylalkynyl, heteroarylalkynyl; —SO$_2$R$^a$; —SO$_2$NR$^a$R$^b$ and —NR$^a$SO$_2$R$^b$;

wherein any (C$_1$-C$_8$)alkyl, (C$_3$-C$_8$)cycloalkyl, (C$_2$-C$_8$)alkynyl, arylalkynyl, heteroarylalkynyl group is optionally substituted by 1, 2 or 3 groups independently selected from halo, (C$_1$-C$_6$)alkyl, (C$_3$-C$_8$)cycloalkyl, (C$_5$-C$_8$)cycloalkenyl, (C$_1$-C$_6$)haloalkyl, cyano, —COR$^a$, —CO$_2$R$^a$, —CONR$^a$R$^b$, —SR$^a$, —SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, —OC(O)NR$^a$R$^b$, heterocycloalkyl, aryl, heteroaryl, aryl(C$_1$-C$_4$)alkyl, and heteroaryl(C$_1$-C$_4$)alkyl;

R$^a$ and R$^b$ are each independently hydrogen, (C$_1$-C$_8$)alkyl, (C$_2$-C$_8$)alkenyl, (C$_2$-C$_8$)alkynyl, (C$_3$-C$_8$)cycloalkyl, (C$_5$-C$_8$)cycloalkenyl, (C$_6$-C$_{10}$)bicycloalkyl, heterocycloalkyl, aryl, heteroaryl, wherein said (C$_1$-C$_8$)alkyl, (C$_2$-C$_8$)alkenyl, (C$_2$-C$_8$)alkynyl, cycloalkyl, cycloalkenyl, bicycloalkyl, heterocycloalkyl, aryl or heteroaryl group is optionally substituted by 1, 2 or 3 groups independently selected from halo, hydroxyl, (C$_1$-C$_4$)alkoxy, amino, (C$_1$-C$_4$)alkylamino, ((C$_1$-C$_4$)alkyl)((C$_1$-C$_4$)alkyl)amino, —CO$_2$H, —CO$_2$(C$_1$-C$_4$)alkyl, —CONH$_2$, —CONH(C$_1$-C$_4$)alkyl, —CON((C$_1$-C$_4$)alkyl)((C$_1$-C$_4$)alkyl), —SO$_2$(C$_1$-C$_4$)alkyl, —SO$_2$NH$_2$, —SO$_2$NH(C$_1$-C$_4$)alkyl, and —SO$_2$N((C$_1$-C$_4$)alkyl)((C$_1$-C$_4$)alkyl);

or R$^a$ and R$^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from (C$_1$-C$_4$)alkyl, (C$_1$-C$_4$)haloalkyl, amino, (C$_1$-C$_4$)alkylamino, ((C$_1$-C$_4$)alkyl)((C$_1$-C$_4$)alkyl)amino, hydroxyl, oxo, (C$_1$-C$_4$)alkoxy, and (C$_1$-C$_4$)alkoxy(C$_1$-C$_4$)alkyl, wherein said ring is optionally fused to a (C$_3$-C$_8$)cycloalkyl, heterocycloalkyl, aryl, or heteroaryl ring;

or R$^a$ and R$^b$ taken together with the nitrogen to which they are attached represent a 6- to 10-membered bridged bicyclic ring system optionally fused to a (C$_3$-C$_8$)cycloalkyl, heterocycloalkyl, aryl, or heteroaryl ring. An aryl or heteroaryl group in this particular subgroup A is selected independently from the group consisting of furan, thiophene, pyrrole, oxazole, thiazole, imidazole, pyrazole, oxadiazole, thiadiazole, triazole, tetrazole, benzofuran, benzothiophene, benzoxazole, benzothiazole, phenyl, pyridine, pyridazine, pyrimidine, pyrazine, triazine, tetrazine, quinoline, cinnoline, quinazoline, quinoxaline, and naphthyridine or another aryl or heteroaryl group as follows:

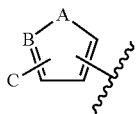

(1)

wherein in (1),
 A is O, NH, or S; B is CH or N, and C is hydrogen or $C_1$-$C_8$ alkyl; or

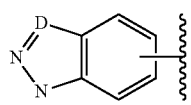

(2)

wherein in (2),
 D is N or C optionally substituted by hydrogen or $C_1$-$C_8$ alkyl; or

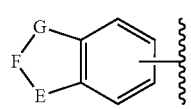

(3)

wherein in (3),
 E is NH or $CH_2$; F is O or CO; and G is NH or $CH_2$; or

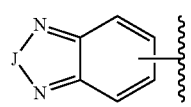

(4)

wherein in (4),
 J is O, S or CO; or

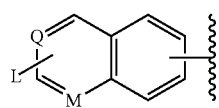

(5)

wherein in (5),
 Q is CH or N;
 M is CH or N; and
 L/(5) is hydrogen, halo, amino, cyano, ($C_1$-$C_8$)alkyl, ($C_3$-$C_8$)cycloalkyl, —$COR^a$, —$CO_2R^a$, —$CONR^aR^b$, —$CONR^aNR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$OR^a$,
  wherein any ($C_1$-$C_8$)alkyl, ($C_3$-$C_8$)cycloalkyl, group is optionally substituted by 1, 2 or 3 groups independently selected from ($C_1$-$C_6$)alkyl, ($C_3$-$C_8$)cycloalkyl, ($C_5$-$C_8$)cycloalkenyl, ($C_1$-$C_6$)haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$; wherein $R^a$ and $R^b$ are defined as above; or

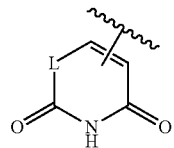

(6)

wherein in 6,
 L/(6) is NH or $CH_2$; or

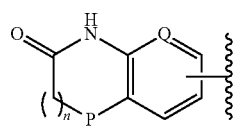

(7)

wherein in 7,
 M/(7) is hydrogen, halo, amino, cyano, ($C_1$-$C_8$)alkyl, ($C_3$-$C_8$)cycloalkyl, heterocycloalkyl, —$COR^a$, —$CO_2R^a$, —$CONR^aR^b$, —$CONR^aNR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$OR^a$,
  wherein any ($C_1$-$C_8$)alkyl, ($C_3$-$C_8$)cycloalkyl, heterocycloalkyl group is optionally substituted by 1, 2 or 3 groups independently selected from ($C_1$-$C_6$)alkyl, ($C_3$-$C_8$)cycloalkyl, ($C_5$-$C_8$)cycloalkenyl, ($C_1$-$C_6$)haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NRaSO_2R^b$, —$NR^aSO_2NR^aR^b$, —$OR^a$, —$OC(O)R^a$, —$OC(O)NR^aR^b$; wherein $R^a$ and $R^b$ are defined as above; or

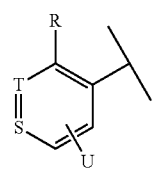

(8)

wherein in (8),
 P is $CH_2$, NH, O, or S; Q/(8) is CH or N; and n is 0-2; or (9)

wherein in (9),
 S/(9) and T(9) is C, or S/(9) is C and T(9) is N, or S/(9) is N and T/(9) is C;
 R is hydrogen, amino, methyl, trifluoromethyl, halo;
 U is hydrogen, halo, amino, cyano, nitro, trifluoromethyl, ($C_1$-$C_8$)alkyl, ($C_3$-$C_8$)cycloalkyl, —$COR^a$, —$CO_2R^a$, —$CONR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, 4-(1H-pyrazol-4-yl), wherein any (C₁-C₈)alkyl, (C₃-C₈)cycloalkyl, group is optionally substituted by 1, 2 or 3 groups independently selected from (C₁-C₆)alkyl, (C₃-C₈)cycloalkyl, (C₅-C₈)cycloalkenyl, (C₁-C₆)haloalkyl, cyano, —COR$^a$, —CO₂R$^a$, —CONR$^a$R$^b$, —SOr$^a$, —SO₂R$^a$, —SO₂NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO₂R$^b$, —NR$^a$SO₂NR$^a$R$^b$, —OC(O)R$^a$, —OC(O)NR$^a$R$^b$; wherein R$^a$ and R$^b$ are defined as above.

Subgroup B

X and Z are selected independently from the group consisting of (C₁-C₈)alkyl, (C₃-C₈)cycloalkyl, heterocycloalkyl, aryl, heteroaryl, —NR$^a$R$^b$, and —OR$^a$;

Y is H;

R¹ is (C₁-C₈)alkyl, (C₃-C₈)cycloalkyl, or heterocycloalkyl;

R³ is hydrogen, (C₁-C₈)alkyl or halo;

R⁶ is hydrogen, halo, cyano, trifluoromethyl, amino, (C₁-C₈)alkyl, (C₃-C₈)cycloalkyl, aryl, heteroaryl, acylamino; (C₂-C₈)alkynyl, arylalkynyl, heteroarylalkynyl; —SO₂R$^a$; —SO₂NR$^a$R$^b$, or —NR$^a$SO₂R$^b$;

wherein any (C₁-C₈)alkyl, (C₃-C₈)cycloalkyl, (C₂-C₈)alkynyl, arylalkynyl, heteroarylalkynyl group is optionally substituted by 1, 2 or 3 groups independently selected from halo, (C₁-C₆)alkyl, (C₃-C₈)cycloalkyl, (C₅-C₈)cycloalkenyl, (C₁-C₆)haloalkyl, cyano, —COR$^a$, —CO₂R$^a$, —CONR$^a$R$^b$, —SR$^a$, —SOR$^a$, —SO₂R$^a$, —SO₂NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO₂R$^b$, —NR$^a$SO₂NR$^a$R$^b$, —OR$^a$, —OC(O)R$^a$, —OC(O)NR$^a$R$^b$, heterocycloalkyl, aryl, heteroaryl, aryl(C₁-C₄)alkyl, and heteroaryl(C₁-C₄)alkyl;

R$^a$ and R$^b$ are each independently hydrogen, (C₁-C₈)alkyl, (C₂-C₈)alkenyl, (C₂-C₈)alkynyl, (C₃-C₈)cycloalkyl, (C₅-C₈)cycloalkenyl, (C₆-C₁₀)bicycloalkyl, heterocycloalkyl, aryl, heteroaryl, wherein said (C₁-C₈)alkyl, (C₂-C₈)alkenyl, (C₂-C₈)alkynyl, cycloalkyl, cycloalkenyl, bicycloalkyl, heterocycloalkyl, aryl or heteroaryl group is optionally substituted by 1, 2 or 3 groups independently selected from halo, hydroxyl, (C₁-C₄)alkoxy, amino, (C₁-C₄)alkylamino, ((C₁-C₄)alkyl)((C₁-C₄)alkyl)amino, —CO₂H, —CO₂(C₁-C₄)alkyl, —CONH₂, —CONH(C₁-C₄)alkyl, —CON((C₁-C₄)alkyl)((C₁-C₄)alkyl), —SO₂(C₁-C₄)alkyl, —SO₂NH₂, —SO₂NH(C₁-C₄)alkyl, and —SO₂N((C₁-C₄)alkyl)((C₁-C₄)alkyl);

or R$^a$ and R$^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from (C₁-C₄)alkyl, (C₁-C₄)haloalkyl, amino, (C₁-C₄)alkylamino, ((C₁-C₄)alkyl)((C₁-C₄)alkyl)amino, hydroxyl, oxo, (C₁-C₄)alkoxy, and (C₁-C₄)alkoxy(C₁-C₄)alkyl, wherein said ring is optionally fused to a (C₃-C₈)cycloalkyl, heterocycloalkyl, aryl, or heteroaryl ring;

or R$^a$ and R$^b$ taken together with the nitrogen to which they are attached represent a 6- to 10-membered bridged bicyclic ring system optionally fused to a (C₃-C₈)cycloalkyl, heterocycloalkyl, aryl, or heteroaryl ring. Aryl and heteroaryl in this definition are selected from the group consisting of furan, thiophene, pyrrole, oxazole, thiazole, imidazole, pyrazole, oxadiazole, thiadiazole, triazole, tetrazole, benzofuran, benzothiophene, benzoxazole, benzothiazole, phenyl, pyridine, pyridazine, pyrimidine, pyrazine, triazine, tetrazine, quinoline, cinnoline, quinazoline, quinoxaline, and naphthyridine as or a compound of or another aryl or heteroaryl group as follows:

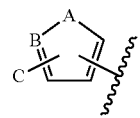
(1)

wherein in (1),
A is O, NH, or S; B is CH or N, and C is hydrogen or C₁-C₈ alkyl; or

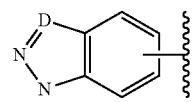
(2)

wherein in (2),
D is N or C optionally substituted by hydrogen or C₁-C₈ alkyl; or

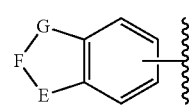
(3)

wherein in (3),
E is NH or CH₂; F is O or CO; and G is NH or CH₂; or

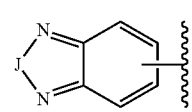
(4)

wherein in (4),
J is O, S or CO; or

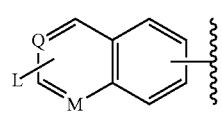
(5)

wherein in (5),
Q is CH or N;
M is CH or N; and
L/(5) is hydrogen, halo, amino, cyano, (C₁-C₈)alkyl, (C₃-C₈)cycloalkyl, —COR$^a$, —CO₂R$^a$, —CONR$^a$R$^b$, —CONR$^a$NR$^a$R$^b$, —SO₂NR$^a$, —SO₂NR$^a$R$^b$, —NR$^a$R$^b$, —NR$^a$C(O)R$^b$, —NR$^a$SO₂R$^b$, —NR$^a$SO₂NR$^a$R$^b$, —NR$^a$NR$^a$R$^b$, —NR$^a$NR$^a$C(O)R$^b$, —NR$^a$NR$^a$C(O)NR$^a$R$^b$, —OR$^a$, wherein any (C₁-C₈)alkyl, (C₃-C₈)cycloalkyl, group is optionally substituted by 1, 2 or 3 groups independently selected from (C₁-C₆)alkyl, (C₃-C₈)cycloalkyl, (C₅-C₈)cycloalkenyl, (C₁-C₆)haloalkyl, cyano, —COR$^a$, —CO₂R$^a$, —CONR$^a$R$^b$, —SR$^a$, —SOR$^a$, —SO₂R$^a$, —SO₂NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO₂R$^b$, —NR$^a$SO₂NR$^a$R$^b$, —OR$^a$, —OC(O)R$^a$, —OC(O)NR$^a$R$^b$, wherein R$^a$ and R$^b$ are defined as above; or

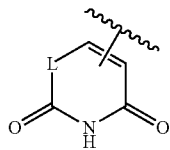
(6)

wherein in 6,
  L/(6) is NH or CH$_2$; or

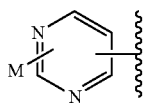
(7)

wherein in 7,
  M/(7) is hydrogen, halo, amino, cyano, (C$_1$-C$_8$)alkyl, (C$_3$-C$_8$)cycloalkyl, heterocycloalkyl, —COR$^a$, —CO$_2$R$^a$, —CONR$^a$R$^b$, —CONR$^a$NR$^a$R$^b$, —SO$_2$R$^a$, —SO$_2$NR$^a$R$^b$, —NR$^a$R$^b$, —NR$^a$C(O)R$^b$, —NR$^a$SO$_2$R$^b$, —NR$^a$SO$_2$NR$^a$R$^b$, —NR$^a$NR$^a$R$^b$, —NR$^a$NR$^a$C(O)R$^b$, —NR$^a$NR$^a$C(O)NR$^a$R$^b$, —OR$^a$,
  wherein any (C$_1$-C$_8$)alkyl, (C$_3$-C$_8$)cycloalkyl, heterocycloalkyl group is optionally substituted by 1, 2 or 3 groups independently selected from (C$_1$-C$_6$)alkyl, (C$_3$-C$_8$)cycloalkyl, (C$_5$-C$_8$)cycloalkenyl, (C$_1$-C$_6$)haloalkyl, cyano, —COR$^a$, —CO$_2$R$^a$, —CONR$^a$R$^b$, —SR$^a$, —SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, —OC(O)NR$^a$R$^b$; wherein R$^a$ and R$^b$ are defined as above; or

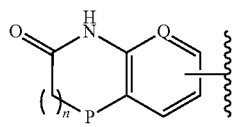
(8)

wherein in (8),
  P is CH$_2$, NH, O, or S; Q/(8) is CH or N; and n is 0-2; or

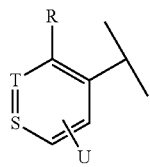
(9)

wherein in (9),
  S/(9) and T(9) is C, or S/(9) is C and T(9) is N, or S/(9) is N and T/(9) is C;
  R is hydrogen, amino, methyl, trifluoromethyl, halo;
  U is hydrogen, halo, amino, cyano, nitro, trifluoromethyl, (C$_1$-C$_8$)alkyl, (C$_3$-C$_8$)cycloalkyl, —COR$^a$, —CO$_2$R$^a$, —CONR$^a$R$^b$, —SO$_2$R$^a$, —SO$_2$NR$^a$R$^b$, —NR$^a$R$^b$, —NR$^a$C(O)R$^b$, —NR$^a$SO$_2$R$^b$, —NR$^a$SO$_2$NR$^a$R$^b$, —NR$^a$NR$^a$R$^b$, —NR$^a$NR$^a$C(O)R$^b$, —OR$^a$, 4-(1H-pyrazol-4-yl),
  wherein any (C$_1$-C$_8$)alkyl, (C$_3$-C$_8$)cycloalkyl, group is optionally substituted by 1, 2 or 3 groups independently selected from (C$_1$-C$_6$)alkyl, (C$_3$-C$_8$)cycloalkyl, (C$_5$-C$_8$)cycloalkenyl, (C$_1$-C$_6$)haloalkyl, cyano, —COR$^a$, —CO$_2$R$^a$, —CONR$^a$R$^b$, —SR$^a$, —SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)Ra, —OC(O)NR$^a$R$^b$, wherein R$^a$ and R$^b$ are defined as above.

Subgroup C

X is methyl, ethyl, n-propyl, isopropyl, cyclopropyl, cyclobutyl, cyclopentyl, cyclohexyl, phenyl, trifluoromethyl, tetrahydropyran, hydroxymethyl, methoxymethyl, or benzyl;
Y is H;
Z is methyl, ethyl, n-propyl, isopropyl, trifluoromethyl, or benzyl;
R$^1$ is isopropyl, tert-butyl, cyclobutyl, cyclopentyl, cyclohexyl, (1-methylethyl)cyclopropyl, 1,1-dioxo-tetrahydrothiophene-3-yl, 1-Me-piperidin-4-yl, tetrahydrofuran-3-yl, tetrahydropyran-4-yl, N,N-dimethyl-1-propanaminyl, benzyl, or 4-pyridyl;
R$^3$ is H, methyl, or Br; and
R$^6$ is methyl, bis(1,1-dimethylethyl), bis(1-methylethyl), cyclopropyl, propyl, dimethylamino, ethylamino, (2-hydroxyethyl)amino, 2-propen-1-ylamino, 1-piperazinyl, 1-piperidinyl, 4-morpholinyl, 4-piperidinylamino, tetrahydro-2H-pyran-4-ylamino, phenylamino, (phenylmethyl)amino, (4-pyridinylmethyl)amino, [2-(2-pyridinylamino)ethyl]amino, 2-(dimethylamino)ethyl]amino, 4-pyridinylamino, 4-(aminocarbonyl)phenyl]amino, 3-hydroxy-3-methyl-1-butyn-1-yl, 4-pyridinylethynyl, phenylethynyl, 2-furanyl, 3-thienyl; 1H-pyrazol-4-yl, 1H-indazol-5-yl, 1H-indazol-6-yl, 3-methyl-1H-indazol-5-yl, 1H-1,2,3-benzotriazol-5-yl, 2-oxo-2,3-dihydro-1H-benzimidazol-5-yl, 2-oxo-2,3-dihydro-1H-indol-5-yl, 2-oxo-2,3-dihydro-1H-indol-6-yl, 2,1,3-benzoxadiazol-5-yl, 2-amino-6-quinazolinyl, 2,4-dioxo-1,2,3,4-tetrahydro-5-pyrimidinyl, 2-amino-5-pyrimidinyl, 7-oxo-1,5,6,7-tetrahydro-1,8-naphthyridin-3-yl, phenyl, 2-methylphenyl, 2-nitrophenyl, 2-phenylethyl, 3-aminophenyl, 4-aminophenyl, 4-chlorophenyl, 4-fluorophenyl, 4-(methyloxy)phenyl, 3-(acetylamino)phenyl, 4-(acetylamino)phenyl, 4-(aminocarbonyl)phenyl, 4-(1H-pyrazol-4-yl)phenyl, 4-(aminosulfonyl)phenyl, 4-(methylsulfonyl)phenyl, 4-[(dimethylamino)sulfonyl]phenyl, 4-[(methylamino)carbonyl]phenyl, 4-[(methylamino)sulfonyl]phenyl, 4-[(methylsulfonyl)amino]phenyl, 3-pyridinyl, 4-pyridinyl, 2-(4-morpholinyl)-4-pyridinyl, 2-amino-4-pyridinyl, 5-(methyloxy)-3-pyridinyl, 5-(methylsulfonyl)-3-pyridinyl, 5-[(cyclopropylsulfonyl)amino]-6-(methyloxy)-3-pyridinyl, 5-[(phenylsulfonyl)amino]-3-pyridinyl, 6-(4-methyl-1-piperazinyl)-3-pyridinyl, 6-(4-morpholinyl)-3-pyridinyl, 6-(acetylamino)-3-pyridinyl, 6-(dimethylamino)-3-pyridinyl, 6-(methyloxy)-3-pyridinyl, 6-[(methylamino)carbonyl]-3-pyridinyl, 6-[(methylamino)sulfonyl]-3-pyridinyl, 6-methyl-3-pyridinyl, 4-pyridinyloxy.

Individual compounds can be found in the Examples set out below.

By the term "co-administering" and derivatives thereof as used herein is meant either simultaneous administration or any manner of separate sequential administration of one or more additional pharmaceutically active compounds, whether for treating cancer, the side effects of cancer or cancer therapy, or some other disease. Preferably, if the administration is not simultaneous, the compounds are administered in a close time proximity to each other. Furthermore, it does not matter if the compounds are administered in the same dosage form, e.g. one compound may be administered topically and another compound may be administered orally.

In certain embodiments, compounds according to Formula I may contain an acidic functional group, one acidic enough to form salts. Representative salts include pharmaceutically-acceptable metal salts such as sodium, potassium, lithium, calcium, magnesium, aluminum, and zinc salts; carbonates and bicarbonates of a pharmaceutically-acceptable metal cation such as sodium, potassium, lithium, calcium, magnesium, aluminum, and zinc; pharmaceutically-acceptable organic primary, secondary, and tertiary amines including aliphatic amines, aromatic amines, aliphatic diamines, and hydroxy alkylamines such as methylamine, ethylamine, 2-hydroxyethylamine, diethylamine, triethylamine, ethylenediamine, ethanolamine, diethanolamine, and cyclohexylamine.

In certain embodiments, compounds according to Formula (I) may contain a basic functional group and are therefore capable of forming pharmaceutically-acceptable acid addition salts by treatment with a suitable acid. Suitable acids include pharmaceutically-acceptable inorganic acids and pharmaceutically-acceptable organic acids. Representative pharmaceutically-acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate) and napthalene-2-sulfonate.

All tautomeric forms of the compounds described herein, including mixtures thereof, are intended to be encompassed within the scope of the invention. Generally, the compounds exemplified herein have been assigned names based on the structure of the tautomer of formula (IA). It should be understood that any reference to named compounds of this invention is intended to encompass all tautomers of the named compounds and any mixtures of tautomers of the named compounds.

The compounds of formula (I) may be prepared in crystalline or non-crystalline form, and, if crystalline, may optionally be solvated, e.g. as the hydrate. This invention includes within its scope stoichiometric solvates (e.g. hydrates) as well as compounds containing variable amounts of solvent (e.g. water).

Certain of the compounds described herein may contain one or more chiral atoms, or may otherwise be capable of existing as two enantiomers. The compounds claimed below include mixtures of enantiomers as well as purified enantiomers or enantiomerically enriched mixtures. Also included within the scope of the invention are the individual isomers of the compounds represented by formula (I), or claimed below, as well as any wholly or partially equilibrated mixtures thereof. The present invention also covers the individual isomers of the claimed compounds as mixtures with isomers thereof in which one or more chiral centers are inverted.

Where there are different isomeric forms they may be separated or resolved one from the other by conventional methods, or any given isomer may be obtained by conventional synthetic methods or by stereospecific or asymmetric syntheses.

While it is possible that, for use in therapy, a compound of formula (I), as well as salts, solvates and the like, may be administered as a neat preparation, i.e. no additional carrier, the more usual practice is to present the active ingredient confected with a carrier or diluent. Accordingly, the invention further provides pharmaceutical compositions, which includes a compound of formula (I) and salts, solvates and the like, and one or more pharmaceutically acceptable carriers, diluents, or excipients. The compounds of formula (I) and salts, solvates, etc, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I), or salts, solvates etc, with one or more pharmaceutically acceptable carriers, diluents or excipients.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of the invention may act as prodrugs of other compounds of the invention. All protected derivatives and prodrugs of compounds of the invention are included within the scope of the invention. It will further be appreciated by those skilled in the art, that certain moieties, known to those skilled in the art as "pro-moieties" may be placed on appropriate functionalities when such functionalities are present within compounds of the invention. Preferred prodrugs for compounds of the invention include: esters, carbonate esters, hemi-esters, phosphate esters, nitro esters, sulfate esters, sulfoxides, amides, carbamates, azo-compounds, phosphamides, glycosides, ethers, acetals and ketals.

Treatments

The compounds and compositions of the invention are used to treat cellular proliferation diseases. Disease states which can be treated by the methods and compositions provided herein include, but are not limited to, cancer (further discussed below), autoimmune disease, fungal disorders, arthritis, graft rejection, inflammatory bowel disease, proliferation induced after medical procedures, including, but not limited to, surgery, angioplasty, and the like. It is appreciated that in some cases the cells may not be in a hyper or hypo proliferation state (abnormal state) and still requires treatment. For example, during wound healing, the cells may be proliferating "normally", but proliferation enhancement may be desired. Thus, in one embodiment, the invention herein includes application to cells or individuals afflicted or impending affliction with any one of these disorders or states.

The compositions and methods provided herein are particularly deemed useful for the treatment of cancer including tumors such as prostate, breast, brain, skin, cervical carcinomas, testicular carcinomas, etc. They are particularly useful in treating metastatic or malignant tumors. More particularly, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one or related of the above identified conditions.

The instant compounds can be combined with or co-administered with other therapeutic agents, particularly agents that may enhance the activity or time of disposition of the compounds. Combination therapies according to the invention comprise the administration of at least one compound of the invention and the use of at least one other treatment method. In one embodiment, combination therapies according to the invention comprise the administration of at least one compound of the invention and surgical therapy. In one embodiment, combination therapies according to the invention comprise the administration of at least one compound of the invention and radiotherapy. In one embodiment, combination therapies according to the invention comprise the administration of at least one compound of the invention and at least one supportive care agent (e.g., at least one antiemetic agent). In one embodiment, combination therapies according to the present invention comprise the administration of at least one compound of the invention and at least one other chemotherapeutic agent. In one particular embodiment, the invention comprises the administration of at least one compound of the invention and at least one anti-neoplastic agent. In yet another embodiment, the invention comprises a therapeutic regimen where the EZH2 inhibitors of this disclosure are not in and of themselves active or significantly active, but when combined with another therapy, which may or may not be active as a standalone therapy, the combination provides a useful therapeutic outcome.

By the term "co-administering" and derivatives thereof as used herein is meant either simultaneous administration or any manner of separate sequential administration of an EZH2 inhibiting compound, as described herein, and a further active ingredient or ingredients, known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of specified cancers in the present invention. Examples of such agents can be found in Cancer Principles and Practice of Oncology by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; DNA methyltransferase inhibitors such as azacitidine and decitabine; signal transduction pathway inhibitors; non-receptor tyrosine kinase angiogenesis inhibitors; immunotherapeutic agents; proapoptotic agents; and cell cycle signaling inhibitors.

Typically, any chemotherapeutic agent that has activity against a susceptible neoplasm being treated may be utilized in combination with the compounds the invention, provided that the particular agent is clinically compatible with therapy employing a compound of the invention. Typical anti-neoplastic agents useful in the present invention include, but are not limited to: alkylating agents, anti-metabolites, antitumor antibiotics, antimitotic agents, nucleoside analogues, topoisomerase I and II inhibitors, hormones and hormonal analogues; retinoids, histone deacetylase inhibitors; signal transduction pathway inhibitors including inhibitors of cell growth or growth factor function, angiogenesis inhibitors, and serine/threonine or other kinase inhibitors; cyclin dependent kinase inhibitors; antisense therapies and immunotherapeutic agents, including monoclonals, vaccines or other biological agents.

Nucleoside analogues are those compounds which are converted to deoxynucleotide triphosphates and incorporated into replicating DNA in place of cytosine. DNA methyltransferases become covalently bound to the modified bases resulting in an inactive enzyme and reduced DNA methylation. Examples of nucleoside analogues include azacitidine and decitabine which are used for the treatment of myelodysplastic disorder. Histone deacetylase (HDAC) inhibitors include vorinostat, for the treatment of cutaneous T-cell lymphoma. HDACs modify chromatin through the deactylation of histones. In addition, they have a variety of substrates including numerous transcription factors and signaling molecules. Other HDAC inhibitors are in development.

Signal transduction pathway inhibitors are those inhibitors which block or inhibit a chemical process which evokes an intracellular change. As used herein this change is cell proliferation or differentiation or survival. Signal transduction pathway inhibitors useful in the present invention include, but are not limited to, inhibitors of receptor tyrosine kinases, non-receptor tyrosine kinases, SH2/SH3 domain blockers, serine/threonine kinases, phosphatidyl inositol-3-OH kinases, myoinositol signaling, and Ras oncogenes. Signal transduction pathway inhibitors may be employed in combination with the compounds of the invention in the compositions and methods described above.

Receptor kinase angiogenesis inhibitors may also find use in the present invention. Inhibitors of angiogenesis related to VEGFR and TIE-2 are discussed above in regard to signal transduction inhibitors (both are receptor tyrosine kinases). Other inhibitors may be used in combination with the compounds of the invention. For example, anti-VEGF antibodies, which do not recognize VEGFR (the receptor tyrosine kinase), but bind to the ligand; small molecule inhibitors of integrin (alpha$_v$ beta$_3$) that inhibit angiogenesis; endostatin and angiostatin (non-RTK) may also prove useful in combination with the compounds of the invention. One example of a VEGFR antibody is bevacizumab (AVASTIN®).

Several inhibitors of growth factor receptors are under development and include ligand antagonists, antibodies, tyrosine kinase inhibitors, anti-sense oligonucleotides and aptamers. Any of these growth factor receptor inhibitors may be employed in combination with the compounds of the invention in any of the compositions and methods/uses described herein. Trastuzumab (Herceptin®) is an example of an anti-erbB2 antibody inhibitor of growth factor function. One example of an anti-erbB1 antibody inhibitor of growth factor function is cetuximab (Erbitux™, C225). Bevacizumab (Avastin®) is an example of a monoclonal antibody directed against VEGFR. Examples of small molecule inhibitors of epidermal growth factor receptors include but are not limited to lapatinib (Tykerb™) and erlotinib (TARCEVA®). Imatinib mesylate (GLEEVEC®) is one example of a PDGFR inhibitor. Examples of VEGFR inhibitors include pazopanib, ZD6474, AZD2171, PTK787, sunitinib and sorafenib.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2$/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem, Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. intern, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine, N-tert-butyl ester, 13-ester with 5β-20-epoxy-1,2α,4,7β,10β, 13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine[R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine[1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2(1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl)methyl]methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino)carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I: DNA: irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Pharmaceutical compositions may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula (I), depending on the condition being treated, the route of administration and the age, weight and condition of the patient, or pharmaceutical compositions may be presented in unit dose forms containing a predetermined amount of active ingredient per unit dose. Preferred unit dosage compositions are those containing a daily dose or sub-dose, as herein above recited, or an appropriate fraction thereof, of an active ingredient. Furthermore, such pharmaceutical compositions may be prepared by any of the methods well known in the pharmacy art.

Pharmaceutical compositions may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by bringing into association a compound of formal (I) with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of a compound of formula (I). Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit pharmaceutical compositions for oral administration can be microencapsulated. The formulation can also be prepared to prolong or sustain the release as for example by coating or embedding particulate material in polymers, wax or the like.

Pharmaceutical compositions adapted for rectal administration may be presented as suppositories or as enemas.

Pharmaceutical compositions adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The pharmaceutical compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the pharmaceutical compositions may include other agents conventional in the art having regard to the type of formulation in question, for example those suitable for oral administration may include flavouring agents.

A therapeutically effective amount of a compound of the present invention will depend upon a number of factors including, for example, the age and weight of the intended recipient, the precise condition requiring treatment and its severity, the nature of the formulation, and the route of administration, and will ultimately be at the discretion of the attendant prescribing the medication. However, an effective amount of a compound of formula (I) for the treatment of anemia will generally be in the range of 0.001 to 100 mg/kg body weight of recipient per day, suitably in the range of 0.01 to 10 mg/kg body weight per day. For a 70 kg adult mammal, the actual amount per day would suitably be from 7 to 700 mg and this amount may be given in a single dose per day or in a number (such as two, three, four, five or six) of sub-doses per day such that the total daily dose is the same. An effective amount of a salt or solvate, etc., may be determined as a proportion of the effective amount of the compound of formula (I) per se. It is envisaged that similar dosages would be appropriate for treatment of the other conditions referred to above.

Chemical Background

The compounds of this invention may be made by a variety of methods, including standard chemistry. Any previously defined variable will continue to have the previously defined meaning unless otherwise indicated. Illustrative general synthetic methods are set out below and then specific compounds of the invention as prepared are given in the examples.

Compounds of general formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of formula (I). Those skilled in the art will recognize if a stereocenter exists in compounds of formula (I). Accordingly, the present invention includes both possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994).

EXAMPLES

General Experimental Methods

The following abbreviations are used throughout the experimental and have the following meaning:
aq aqueous
BINAP 2,2'-bis(diphenylphosphino)-1,1'-binapthyl
ca. circa
$CDCl_3$-d chloroform-d
$CD_3OD$-$d_4$ methanol-$d_4$
$Cs_2CO_3$ cesium carbonate
$CHCl_3$ chloroform
ACN acetonitrile
$CH_3CN$ acetonitrile
Celite® registered trademark of Celite Corp. brand of diatomaceous earth
DBU 1,8-diazabicyclo[5.4.0]undeca-7-ene
DCE dichloroethane
DCM methylene chloride
DME 1,2 dimethoxyethane
DMF N,N-dimethyl formamide
DIEA diisopropyl ethylamine
DMSO-$d_6$ dimethylsulfoxide-$d_6$
EtOAc ethyl acetate
EDC 1-(3-dimethylaminopropyl)-3-ethylcarbodimmide hydrochloride
h hour(s)
$^1$H NMR proton nuclear magnetic resonance
HCl hydrochloric acid
HOAT 1-hydroxy-7-azabenzotriazole
HPLC high performance liquid chromatography
IPA 2-propanol
$K_2CO_3$ potassium carbonate
KOH potassium hydroxide
LC/MS liquid chromatography/mass spectroscopy
$MgSO_4$ magnesium sulfate
MeOH methanol
min minute(s)
MTBE methyl tert-butyl ether
MS mass spectrometry
NaOH sodium hydroxide
$Na_2SO_4$ sodium sulfate
$NH_4OH$ ammonium hydroxide
NMM 4-methylmorpholine
NMP N-methyl-2-pyrrolidone
Pd/C palladium (10% by wt) on carbon
$PdCl_2(dppf)$-$CH_2Cl_2$ 1,1'-bis(diphenylphosphino)ferrocene-palladium(II)dichloride dichloromethane complex
$Pd(Ph_3P)_4$ tetrakis(triphenylphosphine)palladium(0)
$SOCl_2$ thionyl chloride
SPhos 2-dicyclohexylphosphino-2',6'-dimethoxybiphenyl
TFA trifluoroacetic acd
THF tetrahydrofuran
TLC thin layer chromatography The following guidelines apply to all experimental procedures described herein. All reactions were conducted under a positive pressure of nitrogen using oven-dried glassware, unless otherwise indicated. Temperatures designated are external (i.e. bath temperatures), and are approximate. Air and moisture-sensitive liquids were transferred via syringe. Reagents were used as received. Solvents utilized were those listed as "anhydrous" by vendors. Molarities listed for reagents in solutions are approximate, and were used without prior titration against a corresponding standard. All reactions were agitated by stir bar, unless otherwise indicated. Heating was conducted using heating baths containing silicon oil, unless otherwise indicated. Reactions conducted by microwave irradiation (0-400 W at 2.45 GHz) were done so using a Biotage Initiator™ 2.0 instrument with Biotage microwave EXP vials (0.2-20 mL) and septa and caps. Irradiation levels utilized (i.e. high, normal, low) based on solvent and ionic charge were based on vendor specifications. Cooling to temperatures below −70° C. was conducted using dry ice/acetone or dry ice/2-propanol. Magnesium sulfate and sodium sulfate used as drying agents were of anhydrous grade, and were used interchangeably. Solvents described as being removed "in vacuo" or "under reduced pressure" were done so by rotary evaporation.

Preparative normal phase silica gel chromatography was carried out using either a Teledyne ISCO CombiFlash Companion instrument with RediSep or ISCO Gold silica gel cartridges (4 g-330 g), or an Analogix IF280 instrument with SF25 silica gel cartridges (4 g-3-00 g), or a Biotage SP1 instrument with HP silica gel cartridges (10 g-100 g). Purification by reverse phase HPLC was conducted using a YMC-pack column (ODS-A 75×30 mm) as solid phase, unless otherwise noted. A mobile phase of 25 mL/min A (acetonitrile-0.1% TFA): B (water-0.1% TFA), 10-80% gradient A (10 min) was utilized, with UV detection at 214 nM, unless otherwise noted.

A PE Sciex API 150 single quadrupole mass spectrometer (PE Sciex, Thornhill, Ontario, Canada) was operated using electrospray ionization in the positive ion detection mode. The nebulizing gas was generated from a zero air generator (Balston Inc., Haverhill, Mass., USA) and delivered at 65 psi and the curtain gas was high purity nitrogen delivered from a Dewar liquid nitrogen vessel at 50 psi. The voltage applied to the electrospray needle was 4.8 kV. The orifice was set at 25 V and mass spectrometer was scanned at a rate of 0.5 scan/sec using a step mass of 0.2 amu and collecting profile data.

Method A LCMS. Samples were introduced into the mass spectrometer using a CTC PAL autosampler (LEAP Technologies, Carrboro, N.C.) equipped with a hamilton 10 uL syringe which performed the injection into a Valco 10-port injection valve. The HPLC pump was a Shimadzu LC-10ADvp (Shimadzu Scientific Instruments, Columbia, Md.) operated at 0.3 mL/min and a linear gradient 4.5% A to 90% B in 3.2 min. with a 0.4 min. hold. The mobile phase was composed of 100% ($H_2O$ 0.02% TFA) in vessel A and 100% ($CH_3CN$ 0.018% TFA) in vessel B. The stationary phase is Aquasil (C18) and the column dimensions were 1 mm×40 mm. Detection was by UV at 214 nm, evaporative light-scattering (ELSD) and MS.

Method B, LCMS. Alternatively, an Agilent 1100 analytical HPLC system with an LC/MS was used and operated at 1 mL/min and a linear gradient 5% A to 100% B in 2.2 min with a 0.4 min hold. The mobile phase was composed of 100% ($H_2O$ 0.02% TFA) in vessel A and 100% ($CH_3CN$ 0.018% TFA) in vessel B. The stationary phase was Zobax (C8) with a 3.5 um partical size and the column dimensions were 2.1 mm×50 mm. Detection was by UV at 214 nm, evaporative light-scattering (ELSD) and MS.

Method C, LCMS. Alternatively, an MDSSCIEX API 2000 equipped with a capillary column of (50×4.6 mm, 5 μm) was used. HPLC was done on Agilent-1200 series UPLC system equipped with column Zorbax SB-C18 (50×4.6 mm, 1.8 μm) eluting with $CH_3CN$: ammonium acetate buffer. The reactions were performed in the microwave (CEM, Discover).

$^1$H-NMR spectra were recorded at 400 MHz using a Bruker AVANCE 400 MHz instrument, with ACD Spect manager v. 10 used for reprocessing. Multiplicities indicated are: s=singlet, d=doublet, t=triplet, q=quartet, quint=quintet, sxt=sextet, m=multiplet, dd=doublet of doublets, dt=doublet of triplets etc. and br indicates a broad signal.

Analytical HPLC: Products were analyzed by Agilent 1100 Analytical Chromatography system, with 4.5×75 mm Zorbax XDB-C18 column (3.5 um) at 2 mL/min with a 4 min gradient from 5% $CH_3CN$ (0.1% formic acid) to 95% $CH_3CN$ (0.1% formic acid) in $H_2O$ (0.1% formic acid) and a 1 min hold.

The compounds of the present invention were prepared according to the following schemes 1-4 described in detail below. The groups and substituents shown in the schemes 1-4, such as X, Y, Z and the various R groups have the same definition in what follows as they have herein above. The solvents and conditions referred to are illustrative and are not intended to be limiting.

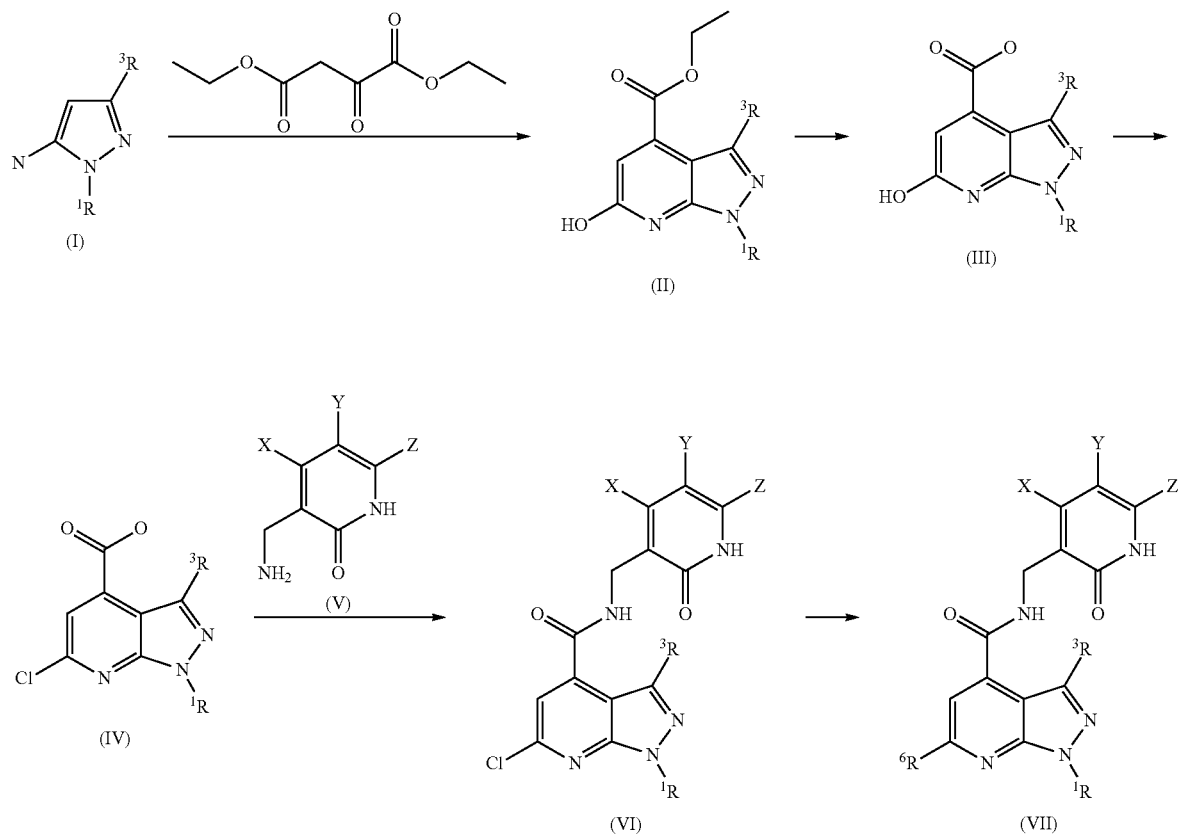

Scheme 1

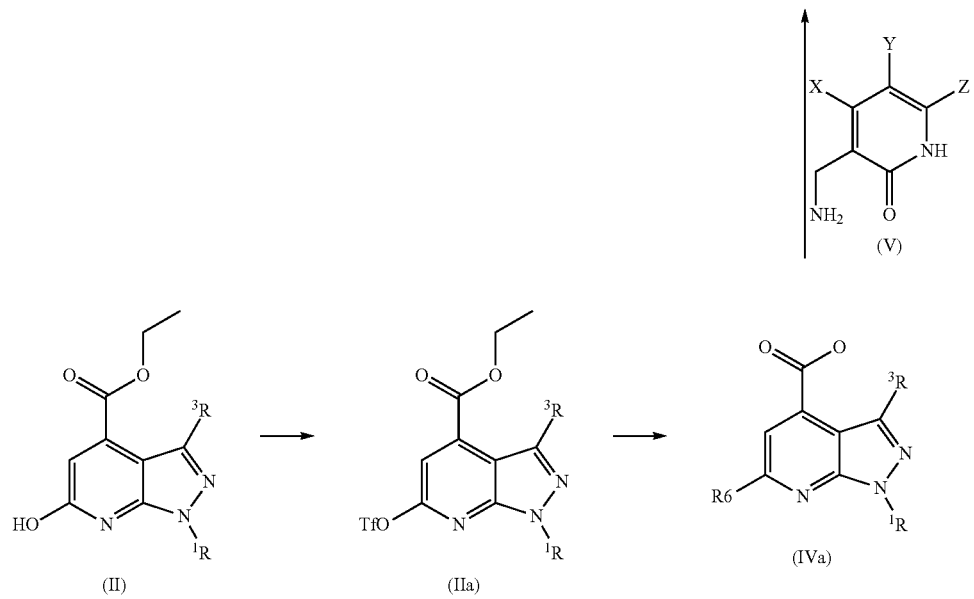

(V)

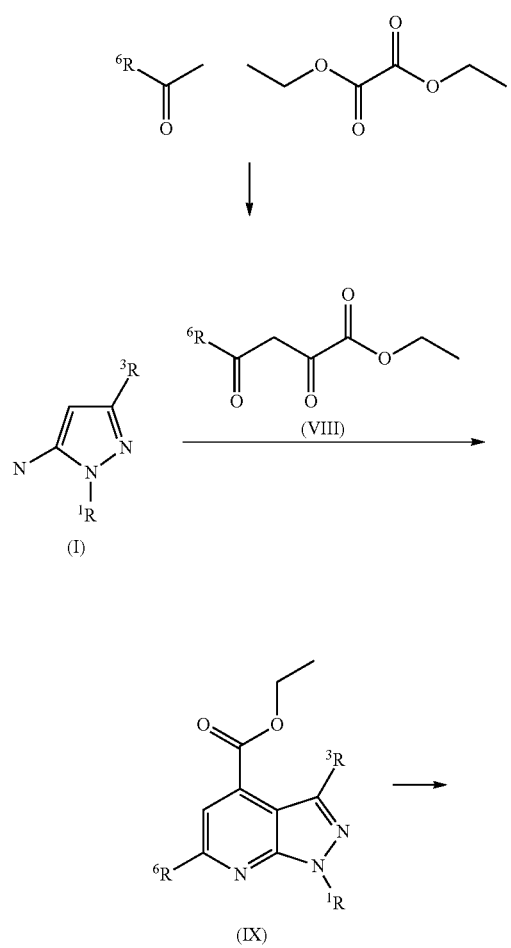

Scheme 1 illustrates two methods to synthesize a compound of formula (VII). Substituted aminopyrazoles of formula (I) are heated with diethyl oxobutanedione in benzene or toluene at 62° C. overnight. Treatment of the putative intermediate with acetic acid and typically heating at reflux furnishes azaindazole compounds of formula (II). Compounds of formula (II) are converted to compounds of formula (III) by base-catalyzed hydrolysis of the ethyl ester and then chlorination of the putative carboxylic acid intermediate with $POCl_3$ under standard conditions to afford compounds of formula (IV). Treatment of compounds of formula (IV) with substituted aminomethylpyridones of formula (V) using EDC, HOAT, N-methylmorpholine, and DMSO for a period of no less than 12 h stirring typically at room temperature (in some instances, heating at 40° C. may be required), affords compounds of formula (VI). Compounds of formula (VI) are substituted at the 6-position using standard methods known to those skilled in the art (i.e. nucleophillic substitution, palladium mediated cross couplings), to afford compounds of formula (VII). Alternatively, compounds of formula (VII) can be obtained from a compound of formula (II) via compounds (IIa) and (IVa). In this route, compounds of formula (II) are converted to the corresponding triflate (IIa) using standard methods. Compounds of formula (IIa) are then substituted at the 6-pos. using standard palladium mediated cross-coupling conditions, followed by base-catalyzed hydrolysis of the ethyl ester group to afford compounds of formula (IVa). Treatment of compounds of formula (IVa) with substituted aminomethylpyridones of formula (V) using EDC, HOAT, N-methylmorpholine, and DMSO at room temperature for a period of no less than 12 h stirring at room temperature affords compounds of formula (VII).

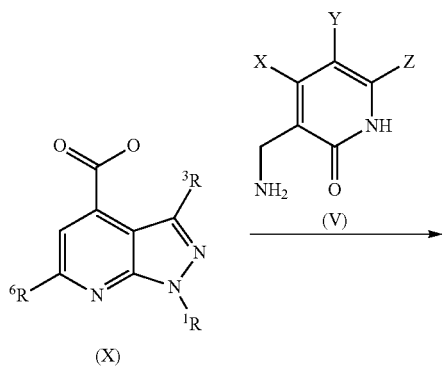

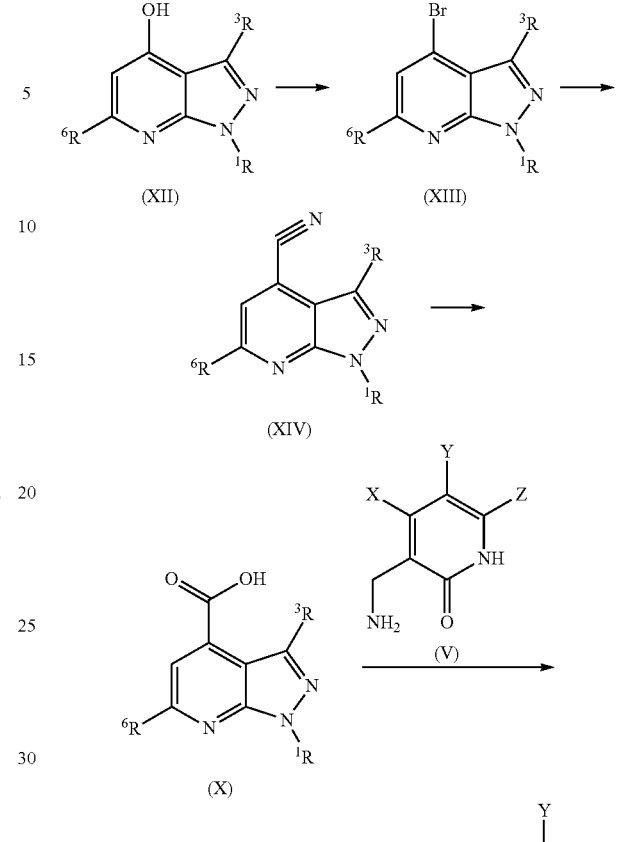

Compounds of formula (VII) are also prepared as depicted in scheme 2. In this embodiment, substituted oxobutanediones of formula (VIII) (prepared by Claisen condensation between an appropriately substitutued ketone and diethyloxalate) are heated with substituted aminopyrazoles of formula (I) (as described for scheme 1), to afford compounds of formula (IX). Compounds of formula (IX) are converted to compounds of formula (X) by base-catalyzed hydrolysis. Substitutions respectively at either the R3-position, or on the R6 substituted group of compounds of formulas (IX) and (X) are done so using methods known to those skilled in the art (e.g. bromination, nitration). Treatment of compounds of formula (X) with substituted aminomethylpyridones of formula (V) using EDC, HOAT, N-methylmorpholine, and DMSO at room temperature for a period no less than 12 h stirring at room temperature, affords compounds of formula (VII).

Scheme 3

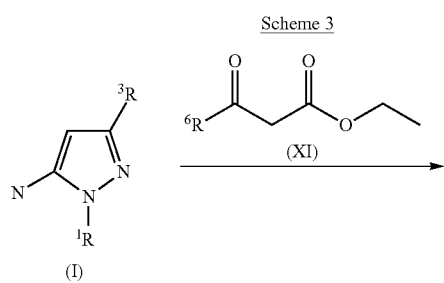

Compounds of formula (VII) are also prepared as depicted in scheme 3. In this embodiment, substituted aminopyrazoles of formula (I) are heated with a keto-ester of formula (XI) in benzene containing catalytic acetic acid at 62° C. overnight. Exposure of the putative intermediate to refluxing Dowtherm A overnight affords a compound of formula (XII). Compounds of formula (XI) that are not commercially available are prepared using standard methods known to those skilled in the art, and are described herein. Compounds of formula (XII) are converted to compounds of formula (XIII) by bromination with refluxing $POBr_3$ in toluene/DMF for 1 h. Heating of compounds of formula (XIII) with dicyano zinc, tris (dibenzylideneacetone)dipalladium(0), and SPhos in DMF and water at 120° C. for 2 hours furnishes compounds of formula (XIV). The compounds of formula (XIV) are hydrolyzed to the compounds of formula (X) using standard base-catalyzed hydrolysis conditions.

Compounds of formula (X) are treated with substituted aminomethylpyridones of formula (V) using EDC, HOAT, N-methylmorpholine, and DMSO at room temperature for a period no less than 12 h stirring at room temperature, to afford compounds of formula (VII).

Scheme 4

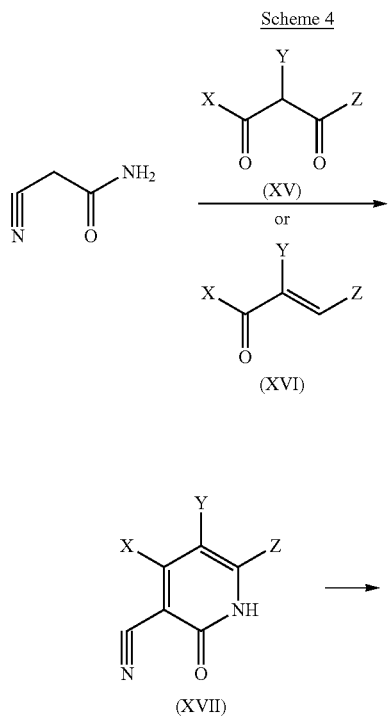

Scheme 4 illustrates the method to synthesize a compound of formula (V). Heating of compounds of formula (XV) with cyanoacetamide in ethanol at reflux containing catalytic piperidine for typically 30 min, affords compounds of formula (XVII). Alternatively, treatment of compounds of formula (XVI) with cyanoacetamide in DMSO at room temperature with an excess of potassium tert-butoxide under an atmosphere of oxygen for ca. 90 min. also affords compounds of formula (XVII). Regioisomeric mixtures, are separable and the individual compounds regiochemical assignments can be confirmed by 2D HNMR techniques. Compounds of formula (XV) and (XVI) which are not commercially available are prepared using standard methods known to those skilled in the art, and are described herein. Compounds of formula (XVII) can be converted to compounds of formula (V) either by hydrogenation using sodium acetate, palladium on carbon, and platinum oxide, or reduction conditions using NaBH$_4$ with either iodine or NiCl$_2$·6H$_2$O.

Examples

Intermediate 1

6-Hydroxy-1-(1-methylethyl)-1H-pyrazolo[3,4-b]pyridine-4-carboxylic acid

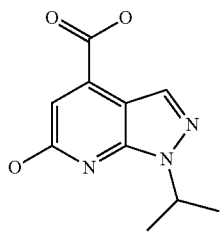 [SMILES: CC(C)n1ncc2c(C(=O)O)cc(O)nc21]

Step 1

1-(1-methylethyl)-1H-pyrazol-5-amine

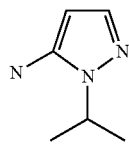

To a solution of ethyl (2Z)-2-cyano-3-(ethyloxy)-2-propenoate (114.2 g, 0.67 mol) in ethanol (250 mL) was slowly added isopropylhydrazine (55 g, 0.74 mol) in a dropwise manner. The mixture was heated at reflux for 4 h, and then cooled to room temperature. The mixture was concentrated in vacuo. Approximately half of the crude 5-amino-1-isopropyl-1H-pyrazole-4-carboxylic acid ethyl ester (50 g) was suspended in an aqueous solution of sodium hydroxide (4M, 130 mL), and stirred with heating at reflux for 2 h. The reaction mixture was then cooled to room temperature and adjusted to pH=3.5 with concentrated HCl, wherein precipitate formation ensued. The solid was collected by filtration and dried in vacuum oven overnight to afford crude 5-amino-1-isopropyl-1H-pyrazole-4-carboxylic acid (30 g). The solid was suspended in diphenyl ether (120 mL) and stirred with heating at 160-165° C. for 2 h. The solution was then cooled to room temperature and the solvent removed in vacuo. The crude product was purified by silica gel chromatography (eluent: petroleum ether/EtOAc=1:1) to afford the product as 12 g. $^1$H NMR (400 MHz, DMSO-d$_6$) δ ppm 1.24 (d, 6H, J=6.4 Hz), 4.32 (m, 1H), 5.06 (s, 2H), 5.21 (s, 1H), 7.00 (s, 1H).

Step 2

To a solution of diethyl 2-oxobutanedione (96 g) in toluene (500 mL) was added 1-(1-methylethyl)-1H-pyrazol-5-amine (30 g, 0.24 mol) and the mixture was stirred at 60° C. overnight. The mixture was concentrated in vacuo, the crude residue dissolved into acetic acid (500 mL), and then heated at reflux for 2 h. The mixture was then cooled to room temperature and concentrated in vacuo to give a residue, which was recrystallized from DCM to afford the product as a yellow colored solid, collected as 40 g. This solid was suspended in in ethanol (700 mL) and THF (100 mL), followed by addition of 3 M NaOH (150 mL). The reaction mixture was stirred at 40° C. for 40 min. The mixture was concentrated in vacuo to remove the volatiles, and the aqueous layer then acidified using 1M HCl. The resulting precipitate was collected by filtration and dried under high vacuum to give the title compound, 6-hydroxy-1-(1-methylethyl)-1H-pyrazolo[3,4-b]pyridine-4-carboxylic acid, as 27 g. LCMS E-S (M+H)=222.0. $^1$H NMR (400 MHz, DMSO-d$_6$) δ ppm 1.48 (d, J=6.82 Hz, 6H), 4.89-4.96 (m, 1H), 6.81 (s, 1H), 8.13 (s, 1H).

Intermediate 2

3-Methyl-1-(1-methylethyl)-6-oxo-6,7-dihydro-1H-pyrazolo[3,4-b]pyridine-4-carboxylic acid

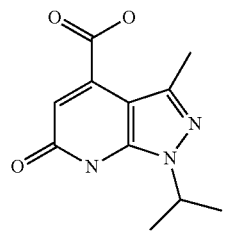 [SMILES: Cc1nn(C(C)C)c2[nH]c(=O)cc(C(=O)O)c12]

Step 1

3-Methyl-1-(1-methylethyl)-1H-pyrazol-5-amine

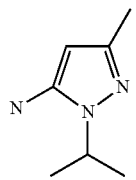

3-Amino-2-butenenitrile (33.3 g, 0.41 mol) and ethanol (170 mL) were combined and stirred at room temperature for 30 min., after which time isopropylhydrazine (50 g, 0.67 mol) was added at once. After stirring at room temperature for 5 min., the contents were then heated at reflux for 10 h. After cooling to room temperature, the mixture was concentrated in vacuo to give the desired product (85 g) which was used in the next step directly. $^1$H NMR (400 MHz, DMSO-d$_6$) δ ppm 1.21 (d, 6H, J=6.4 Hz), 1.94 (s, 3H), 4.21 (m, 1H), 4.93 (s, 2H), 5.02 (s, 1H).

Step 2

To a solution of diethyl 2-oxobutanedione (176 g, 0.94 mol) in toluene (2 L) was added 3-methyl-1-(1-methylethyl)-1H-pyrazol-5-amine (82.5 g, 0.59 mol), and the mixture stirred at 62° C., overnight. After cooling to room temperature, the mixture was concentrated in vacuo and the crude residue dissolved into acetic acid (1.5 L). The mixture was heated at reflux for 2 h. After cooling to room temperature, the mixture was concentrated in vacuo to afford a solid residue, which was recrystallized from DCM to afford the desired product as a yellow colored solid. The collected solid was suspended in ethanol (1510 mL) and THF (216 mL) followed by addition of 3N NaOH (334 mL) and the reaction mixture was stirred at 40° C. for 40 min. The mixture was concentrated in vacuo to remove the volatiles and the aqueous phase acidified using 1N HCl. The resulting precipitate was collected by filtration and dried under high vacuum to give the title compound, 3-methyl-1-(1-methylethyl)-6-oxo-6,7-dihydro-1H-pyrazolo[3,4-b]pyridine-4-carboxylic acid, as 51.38 g. LCMS E-S (M+H)=236.1. $^1$H NMR (400 MHz, DMSO-d$_6$) δ ppm 1.35 (d, J=6.8 Hz, 6H), 2.41 (s, 3H), 4.84-4.91 (m, 1H), 6.64 (s, 1H). Carboxylic acid proton not observed.

Intermediate 3

Ethyl 1-(1,1-dimethylethyl)-6-hydroxy-3-methyl-1H-pyrazolo[3,4-b]pyridine-4-carboxylate

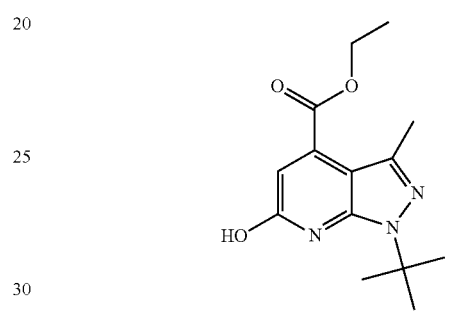

1-(1,1-Dimethylethyl)-3-methyl-1H-pyrazol-5-amine (5 g, 32.6 mmol), diethyl 2-oxobutanedione (6.14 g, 32.6 mmol) and toluene (100 mL) were heated at 70° C. for 16 hours. The solvent was removed in vacuo, the crude residue dissolved in acetic acid (100 mL), and heated at reflux for 4 hours. The solvent was removed in vacuo, and the crude product purified via silica gel chromatography (eluent: gradient of 0 to 10% EtOAc/Hexanes). The product was collected as a solid, 6.32 g (70%). LCMS E-S (M+H)=278.4. $^1$H NMR (400 MHz, DMSO-d$_6$) δ ppm 11.39 (s, 1H), 6.82 (s, 1H), 4.36 (q, 2H, J=7.2 Hz), 2.45 (s, 3H), 1.69 (s, 9H), 1.32 (t, 3H, J=7.2 Hz).

Intermediate 4

1-(1,1-Dimethylethyl)-6-hydroxy-3-methyl-1H-pyrazolo[3,4-b]pyridine-4-carboxylic acid

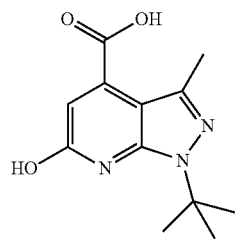 [SMILES: Cc1nn(C(C)(C)C)c2nc(O)cc(C(=O)O)c12]

Sodium hydroxide (52.6 mL, 52.6 mmol) was added to an EtOH solution (100 mL) of ethyl 1-(1,1-dimethylethyl)-3-methyl-6-oxo-6,7-dihydro-1H-pyrazolo[3,4-b]pyridine-4-carboxylate (7.3 g, 26.3 mmol) and stirred at room temperature for 16 h. The solvent was removed in vacuo. The crude residue was suspended in water, and extracted with EtOAc.

The combined organic layers were washed with water, dried over MgSO$_4$, filtered, and concentrated in vacuo. The solid product obtained was set aside. The aqueous phase was concentrated in vacuo and the crude product purified by reverse phase HPLC (mobile phase: 20-50% ACN/H$_2$O, 0.1% TFA) to afford additional product. The combined products were collected as a solid, 5.76 g (88%). LCMS E-S (M+H)=250.3. $^1$H NMR (400 MHz, DMSO-d$_6$) δ ppm 13.5-13.9 (br s, 1H), 11.2-11.5 (br s, 1H), 6.78 (s, 1H), 2.46 (s, 3H), 1.70 (s, 9H).

Intermediate 5

6-Chloro-1-(1-methylethyl)-1H-pyrazolo[3,4-b]pyridine-4-carboxylic acid

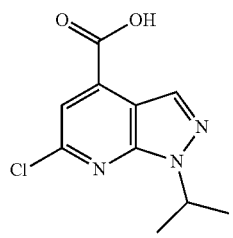 [SMILES: CC(C)n1ncc2c(C(=O)O)cc(Cl)nc21]

To a 75 mL pressure vessel was added 1-(1-methylethyl)-6-oxo-6,7-dihydro-1H-pyrazolo[3,4-b]pyridine-4-carboxylic acid (4.12 g, 18.62 mmol), followed by phosphorous oxychloride (26.0 ml, 279 mmol). The flask was sealed and the stirring mixture heated at ca. 105° C. for ca. 18 h. After cooling to room temperature, the contents were concentrated in vacuo to remove most of volatiles. The residual contents were poured into a mixture of ice and 3M NaOH (60 mL), followed by additional 3M NaOH to ensure the pH stayed basic. The mixture was stirred for 30 min., and then cooled in an ice bath. The heterogenous mixture was slowly acidified to pH=3-4 with 6M HCl. The resulting suspension was extracted with EtOAc (3×). The combined organic layers were dried over MgSO$_4$, filtered, and concentrated in vacuo to afford a yellow solid which was dried in a hi-vac oven overnight. The title compound was collected as 4.11 g (90%), and used without further purification. LCMS E-S (M+H)=240.2/242.2. $^1$H NMR (400 MHz, DMSO-d$_6$) δ ppm 1.51 (d, J=6.57 Hz, 6H) 5.17 (quin, J=6.63 Hz, 1H) 7.65 (s, 1H) 8.41 (s, 1H) 14.25 (br. s., 1H).

Intermediate 6

6-Chloro-3-methyl-1-(1-methylethyl)-1H-pyrazolo[3,4-b]pyridine-4-carboxylic acid

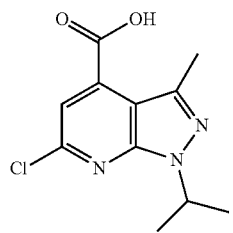 [SMILES: Cc1nn(C(C)C)c2nc(Cl)cc(C(=O)O)c12]

3-Methyl-1-(1-methylethyl)-6-oxo-6,7-dihydro-1H-pyrazolo[3,4-b]pyridine-4-carboxylic acid (1.5 g, 6.38 mmol) was added to a solution of THF (15 mL) followed by addition of phosphorous oxychloride (8.9 mL, 96 mmol), and the contents heated at 105° C. overnight. After cooling to room temperature, the contents were concentrated in vacuo to remove most of the volatiles. The residual contents were slowly poured into a solution of iced water and 1N NaOH (10 mL), and the contents were stirred at room temperature for 24 h, during which time solid precipitation ensued. Additional 1N NaOH was added, upon which the solids went into solution. After stirring at room temperature for an additional 30 min., the contents were cooled in an ice bath and the mixture slowly acidified to pH=3-4 by slow addition of 6N HCl, to afford a heterogenous mixture. The mixture was filtered and a white solid set aside. The aq. layer was further extracted with EtOAc and DCM. The combined organic layers dried were dried over MgSO$_4$, filtered and concentrated in vacuo. The resultant light brown solid was triturated in EtOAc/EtOH (1:1) and filtered to afford a first crop of white solid product, which was set aside. The filtrate was again concentrated in vacuo. The residue was diluted with EtOAc, sonicated, treated with hexanes, and filtered. The process was repeated. The isolated solid product crops were dried under vacuum (3 h) and collected as 1.33 g (80%). LCMS E-S (M+H): 254.3 $^1$H NMR (400 MHz, DMSO-d$_6$) δ ppm 1.46 (d, 6H), 2.60 (s, 3H), 5.10 (quin, J=6.63 Hz, 1H), 7.50 (s, 1H), 14.17 (br. s., 1H).

Intermediate 7

6-Chloro-1-(1,1-dimethylethyl)-3-methyl-1H-pyrazolo[3,4-b]pyridine-4-carboxylic acid

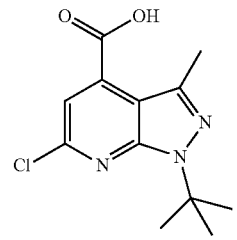 [SMILES: Cc1nn(C(C)(C)C)c2nc(Cl)cc(C(=O)O)c12]

1-(1,1-Dimethylethyl)-3-methyl-6-oxo-6,7-dihydro-1H-pyrazolo[3,4-b]pyridine-4-carboxylic acid (5.07 g, 20.34 mmol) and phosphorus oxychloride (28.4 ml, 305 mmol) were heated at 100° C. for 16 hours. The contents were concentrated in vacuo. The residue was added to ice water followed by 1N NaOH until basic (pH>10). After stirring for 15 minutes, the mixture was adjusted to pH 3-4 by addition of 1N HCl. The contents were extracted with EtOAc, then washed with water, brine and concentrated in vacuo. The crude product was purified by reverse phase HPLC (40-70% ACN/H$_2$O, 0.1% TFA). The product was collected as a solid, 0.50 g (9%). LCMS E-S (M+H)=268.3 $^1$H NMR (400 MHz, DMSO-d$_6$) δ ppm 1.73 (s, 9H), 2.56 (s, 3H), 7.48 (s, 1H), 14.17 (br. s., 1H).

Intermediate 8

3-(Aminomethyl)-4,6-dimethyl-2(1H)-pyridinone hydrochloride

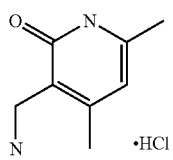

Sodium acetate (10.24 g, 124.8 mmol), 10% palladium on carbon (1.08 g) and platinum oxide (76 mg) were placed in a dried Parr bottle under nitrogen, and a small amount of acetic acid was added to wet the catalysts. A solution of 4,6-dimethyl-2-oxo-1,2-dihydro-pyridine-3-carbonitrile (10 g, 67.6 mmol) in acetic acid was added to the Parr bottle followed by additional acetic acid. The bottle was capped, placed on Parr apparatus, and shaken under an atmosphere of hydrogen (45 psi) for 12 h. The reaction mixture was filtered. The solvent was removed to give a residue, which was dried. After addition of 50 mL of conc. HCl, the formed solids were filtered. The yellow filtrate was concentrated and dried, followed by addition of 10 mL conc. HCl, and 50 mL of EtOH. The mixture was stored at ca. 0° C. (i.e. freezer) for 2 h. The formed solids were filtered and washed with cold EtOH, and dried to give the product as an HCl salt (39 g, 76%). $^1$H NMR (400 MHz, DMSO-$d_6$) δ ppm 11.85 (br. s., 1H) 8.13 (br. s., 3H) 5.93-6.01 (m, 1H) 3.72-3.80 (m, 2H) 2.22 (s, 3H) 2.16 (s, 3H).

Intermediate 9

3-(Aminomethyl)-6-methyl-4-(trifluoromethyl)-2(1H)-pyridinone

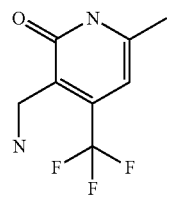

To a dried 500 mL Parr bottle equipped with nitrogen inlet were placed sodium acetate (1.502 g, 18.30 mmol), 10% palladium on carbon (1.579 g, 0.742 mmol), platinum(IV) oxide (0.011 g, 0.049 mmol) and a small amount of acetic acid to wet the catalysts under nitrogen stream. Next added 2-hydroxy-6-methyl-4-(trifluoromethyl)-3-pyridinecarbonitrile (2.0 g, 9.89 mmol) followed by acetic acid (175 mL) while under nitrogen atmosphere. The contents were sealed, placed on a Parr shaker, and reacted at 40 psi of $H_2$ for ca. 6 hr., keeping the $H_2$ psi between 20 and 40 psi (vessel was refilled twice). The vessel was purged with nitrogen and the reaction mixture filtered through Celite, and the filter pad was further washed with a small amount of acetic acid. The volatiles were removed in vacuo to afford a residue, which was dried under hi-vacuum for 45 min. The solid was suspended in conc. HCl (12 mL), stirred, and filtered (removed NaCl). The clear filtrate was concentrated in vacuo and the residue dried under hi-vacuum. The collected solid was suspended in conc. HCl (2 mL) and diluted with EtOH (13 mL). The contents were agitated (i.e. spatula) and stored at ca. 0° C. (i.e. freezer) for 30 min to give a white solid. The solid was filtered and washed with cold ethanol (5 mL). The solid was filtered and dried in vacuum oven for 1 h. The final product was collected as 0.95 g (40%). LCMS E-S (M+H)=206.9. $^1$H NMR (400 MHz, DMSO-$d_6$) δ ppm 2.31 (s, 3H), 3.87 (d, J=5.05 Hz, 2H), 6.41 (s, 1H), 8.12-8.37 (m, 3H).

Intermediate 10

3-(Aminomethyl)-4-cyclohexyl-6-methyl-2(1H)-pyridinone

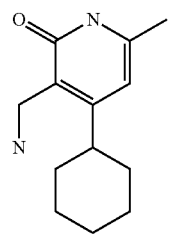 [SMILES: Cc1cc(C2CCCCC2)c(CN)c(=O)[nH]1]

Step 1

To a stirred suspension of $CrCl_2$ (58 g, 472.8 mmol in THF (1500 mL) was added a THF solution (500 mL) of 1,1-dichloro-2-propanone (10 g, 78.8 mmol) and cyclohexanecarbaldehyde (8.84 g, 78.8 mmol). The reaction mixture was heated at reflux for 2 h, and then quenched by the addition of 1.0 M HCl. The reaction mixture was filtered through a pad of Celite and concentrated in vacuo. The crude residue (10 g) was added to a solution of DMSO (150 mL) containing t-BuOK (7.5 g, 65.7 mmol), and cyanoacetamide (6.1 g, 72.3 mmol) and stirred at room temperature for 30 min. Additional t-BuOK (22.5 g, 197.1 mmol) was added and the reaction mixture was stirred under an atmosphere of oxygen for an additional 1 h. The contents were purged with argon, diluted with 4 volumes of $H_2O$, and then 5 volumes of 4 N HCl, which were added slowly. The reaction mixture was filtered, washed with water and dried to give 4-cyclohexyl-6-methyl-2-oxo-1, 2-dihydro-3-pyridinecarbonitrile as 4.5 g (32%). $^1$H NMR (400 MHz, DMSO-$d_6$) δ ppm 6.25 (s, 1H), 2.61-2.65 (m, 1H), 2.22 (s, 3H), 1.66-1.79 (m, 4H), 1.24-1.46 (m, 6H).

Step 2

To an ice-bath cooled THF (100 mL) solution of the product from step 1 (2 g, 9.26 mmol) were added $NaBH_4$ (0.81 g, 21.3 mmol), and $I_2$ (2.3 g, 9.26 mmol), and the mixture stirred for 30 min. The reaction mixture was then heated at reflux for 3 h, and then allowed to cool to room temperature. After cooling to 0° C., the reaction mixture was acidified by slow addition of 3N HCl (1 mL). The reaction mixture was concentrated in vacuo and the crude product purified by reverse phase HPLC to give the title compound as a solid (TFA salt), 0.5 g (25%). LCMS E-S (M+H)=221.1. $^1$H NMR (400 MHz, DMSO-$d_6$) δ ppm 11.8-11.9 (br s, 1H), 7.80-7.93 (br s, 3H), 6.07 (s, 1H), 3.69 (s, 2H), 2.67-2.75 (m, 1H), 2.17 (s, 3H), 1.58-1.72 (m, 5H), 1.19-1.41 (m, 5H).

Intermediate 11

3-(Aminomethyl)-4-cyclopropyl-6-methyl-2(1H)-pyridinone hydrochloride

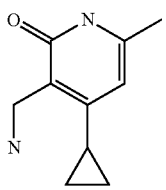

The title compound was prepared in the same manner as described for intermediate 10 (step 2) from 4-cyclopropyl-6-methyl-2-oxo-1,2-dihydro-3-pyridinecarbonitrile (5 g, 28.7 mmol). The product was collected as a TFA salt, 0.50 g. LCMS E-S (M+H)=179.1. $^1$H NMR (400 MHz, DMSO-d$_6$) δ ppm 11.76-11.78 (br s, 1H), 7.82-7.92 (br s, 3H), 5.61 (s, 1H), 3.94-3.99 (m, 2H), 2.11 (s, 3H), 1.98-2.05 (m, 1H), 0.95-1.01 (m, 2H), 0.74-0.79 (m, 2H).

Intermediate 12

3-(Aminomethyl)-6-methyl-4-propyl-2(1H)-pyridinone

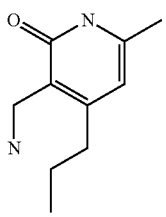

Step 1

To a solution of DMSO (300 mL) containing t-BuOK (20 g, 178 mmol) and cyanoacetamide (16.5 g, 196 mmol) was added (3E)-3-hepten-2-one (20 g, 178 mmol), and contents stirred at room temperature for 30 min. Additional t-BuOK (60 g, 534 mmol) was added and the reaction mixture was under an atmosphere of oxygen for an additional 1 h. The reaction mixture was purged with argon, diluted with 4 volumes of H$_2$O, and then 5 volumes of 4 N HCl, which were added slowly. The reaction mixture was filtered, washed with water, and dried to give the product as 10 g (32%). $^1$H NMR (400 MHz, DMSO-d$_6$) δ ppm 12.25-12.40 (br s, 1H), 6.18 (s, 1H), 2.53 (t, 2H), 2.22 (s, 3H), 1.57-1.64 (m, 2H), 0.84 (t, 3H).

Step 2

The title compound was prepared in the same manner as described for intermediate 10 (step 2) from the product of step 1 (2 g, 11.2 mmol). The product was collected as 1.2 g (60%). LCMS E-S (M+H)=181.1. $^1$H NMR (400 MHz, DMSO-d$_6$) δ ppm 7.85-7.95 (br s, 3H), 5.99 (s, 1H), 3.80-3.85 (m, 2H), 2.42 (t, 2H), 2.14 (s, 3H), 1.43-1.49 (m, 2H), 0.86 (t, 3H).

Intermediate 13

3-(Aminomethyl)-6-methyl-4-phenyl-2(1H)-pyridinone

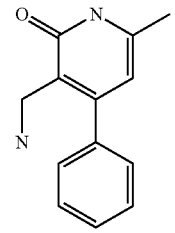 [SMILES: Cc1cc(-c2ccccc2)c(CN)c(=O)[nH]1]

The title compound was prepared in the same manner as described for intermediate 12 (steps 1 and 2) from (3E)-4-phenyl-3-buten-2-one (20 g, 137 mmol). The crude nitrile intermediate was obtained as 10 g (35%), of which 4 g of this putative intermediate was converted to the title compound 1.2 g as a TFA salt. LCMS E-S (M+H)=215.0. $^1$H NMR (400 MHz, DMSO-d$_6$) δ ppm 12.2-12.3 (br s, 1H), 7.88-8.00 (br s, 3H), 7.43-7.51 (m, 3H), 7.29-7.38 (m, 2H), 6.08 (s, 1H), 3.67-3.70 (m, 2H), 2.23 (s, 3H).

Intermediate 14

3-(Aminomethyl)-6-methyl-4-(1-methylethyl)-2(1H)-pyridinone

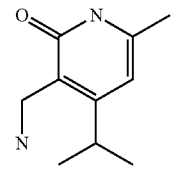

The title compound was prepared in the same manner as described for intermediate 12 (steps 1 and 2) from (3E)-5-methyl-3-hexen-2-one (20 g, 137 mmol). The crude nitrile intermediate was obtained as 7 g (22%), of which 3 g of this putative intermediate was converted to the title compound 1.3 g as a TFA salt. LCMS E-S (M+H)=181.1. $^1$H NMR (400 MHz, DMSO-d$_6$) δ ppm 11.8-11.9 (br s, 1H), 7.86-7.96 (br s, 3H), 6.10 (s, 1H), 3.82-3.86 (m, 2H), 3.02-3.09 (m, 1H), 2.17 (s, 3H), 1.08 (d, 6H).

Intermediate 15

3-(Aminomethyl)-4-methyl-6-propyl-2(1H)-pyridinone

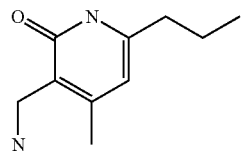

Step 1

To a solution of NaNH$_2$ (32.5 g, 862 mmol) in anhydrous ether (500 mL) at 30° C. was added dropwise a mixture of butyric acid ethyl ester (50 g, 431 mmol) and acetone (37.5 g 646.5 mol). After addition, the reaction mixture was stirred for 4 h. The reaction mixture was poured onto ice water with stirring. Additional ether was added, and the layers were separated. The aqueous layer was acidified to pH 5.0 with 2 N HCl and then to pH 7.5 with Na$_2$CO$_3$. The aq. layer was then extracted with ether. The combined organic layers were dried over Na$_2$SO$_4$, filtered, and concentrated in vacuo. The crude product (20 g, 156 mmol) and 2-cyanoacetamide (13.12 g, 156 mmol) were suspended in EtOH (160 mL) at 75° C., followed by addition of piperidine (13.2 g, 156 mmol). The contents were stirred and heated at reflux for 1 h. The mixture was cooled to room temperature, and filtered. The collected solid was suspended in water and stirred for 1 h. The mixture was filtered and dried to give 4-methyl-2-oxo-6-propyl-1,2-dihydro-3-pyridinecarbonitrile (11 g, 40%). LCMS E-S (M+H)=181.1. $^1$H NMR (400 MHz, DMSO-d$_6$) δ ppm 12.3-12.4 (br s, 1H), 6.25 (s, 1H), 3.64 (s, 3H), 2.50 (t, 2H), 1.63 (m, 2H), 0.94 (t, 3H).

Step 2

Sodium acetate (3.5 g, 42.6 mmol), palladium on carbon (0.81 g) and platinum oxide (0.1 g) were placed in a dried Parr bottle flushed with nitrogen, followed by addition of a small amount of acetic acid (to wet the catalysts). A solution of 4-methyl-2-oxo-6-propyl-1,2-dihydro-pyridine-3-carbonitrile (5 g, 28 mmol) in acetic acid was added to the Parr bottle followed by additional acetic acid (200 mL). The vessel was capped, placed on Parr apparatus and hydrogenated at 45 psi for 12 h. The reaction mixture was filtered and the filtrate concentrated in vacuo. The crude product was purified by preparative HPLC to afford the title compound (TFA salt) as 4.1 g. LCMS E-S (M+H)=181.1. $^1$H NMR (400 MHz, DMSO-d$_6$) δ ppm 11.8-11.9 (br s, 1H), 7.83-7.88 (br s, 3H), 5.99 (s, 1H), 3.77-3.81 (m, 2H), 2.37 (t, 2H), 1.53 (m, 2H), 0.83 (t, 3H).

Intermediate 16

3-(Aminomethyl)-6-cyclopropyl-4-methyl-2(1H)-pyridinone

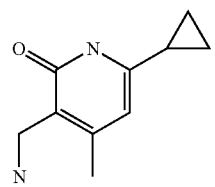

Step 1

1-Cyclopropyl-1,3-butanedione

To a a stirring solution of THF (100 mL) was suspended potassium tert-butoxide (5.60 g, 49.5 mmol), followed by a mixture of cyclopropyl methyl ketone (3.27 mL, 33 mmol) and ethyl acetate (9.69 mL, 99 mmol) in 30 mL THF at 35° C., via addition funnel over a 25 min period. The contents were heated and stirred at 60° C. After 3 h, the contents were removed from heating, and allowed to stir with cooling to room temperature. The reaction mixture was carefully diluted with 30 mL 2N HCl and stirred for 10 min. The mixture was extracted with diethyl ether (3×50 mL), and the combined organic layers washed with brine (1×50 mL). The organic layer was dried over MgSO$_4$, filtered, and concentrated in vacuo. The crude oil was chromatographed on silica gel (eluent: 0 to 15% EtOAc in hexanes) with good separation to afford the desired product as a light yellow colored oil, 3.9 g in ~75% purity (residual solvent), for an overall yield of 70%. $^1$H NMR (400 MHz, CHLOROFORM-d) δ ppm 0.89-0.96 (m, 2H), 1.09-1.15 (m, 2H), 1.59-1.69 (m, 1H), 2.04 (s, 3H), 5.63 (s, 1H), 15.5-16.0 (br s, 1H).

Step 2

6-Cyclopropyl-4-methyl-2-oxo-1,2-dihydro-3-pyridinecarbonitrile

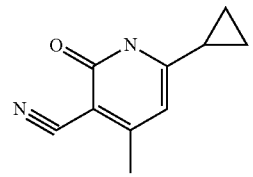

To a stirring solution of ethanol (5 mL) were suspended 1-cyclopropyl-1,3-butanedione (505 mg, 3.00 mmol) and cyanoacetamide (252 mg, 3.00 mmol), and the heterogenous contents heated until homogenous (ca. 75° C.). Next added piperidine (0.395 mL, 4.00 mmol), and the mixture was stirred with warming at reflux for 30 min. The reaction mixture was allowed to cool to room temperature, wherein precipitation ensued. The solid precipitate was filtered and set aside. The filtrate was concentrated in vacuo, and the oily residue treated with minimal EtOAc and then 10 mL hexanes to afford a 2nd crop of solid. The solid product crops were combined, suspended in water (7 mL), vigorously stirred, and vacuum filtered to afford a nearly white solid as 380 mg (73%). LCMS E-S (M+H)=175.1. $^1$H NMR (400 MHz, CHLOROFORM-d) δ ppm 1.01-1.09 (m, 2H), 1.28 (dd, J=8.59, 2.27 Hz, 2H), 1.95-2.01 (m, 1H), 2.43 (s, 3H), 5.82 (s, 1H).

Step 3

1,1-Dimethylethyl[(6-cyclopropyl-4-methyl-2-oxo-1,2-dihydro-3-pyridinyl)methyl]carbamate

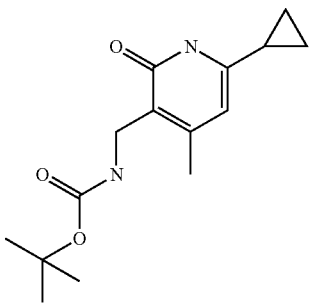 [SMILES: Cc1cc(C2CC2)[nH]c(=O)c1CNC(=O)OC(C)(C)C]

6-Cyclopropyl-4-methyl-2-oxo-1,2-dihydro-3-pyridinecarbonitrile (0.35 g, 2.01 mmol) was added to methanol (20 mL) and the stirring contents cooled to −10° C. Next added di-tert-butyloxycarbonyl (0.933 mL, 4.02 mmol) and the suspension was stirred for 15 min. Next added in NiCl$_2$·6H$_2$O (0.055 g, 0.201 mmol) as a solid and stirred for 5 min. Next added NaBH$_4$ (0.532 g, 14.06 mmol) in 6 portions with 5 min. increments between each portion. After completed addition (ca. 30 min), the ice bath was removed and the contents were stirred with warming to room temperature overnight. The reaction mixture was returned to −10° C., followed by addition of 3 more portions of NaBH$_4$ (0.532 g, 14.06 mmol). The ice bath was removed and the mixture stirred at room temperature for 1 h. The contents were quenched by addition of diethylethylene amine (0.218 mL, 2.01 mmol) and stirred for 45 min. at room temperature. The volatiles were removed in vacuo and the residue suspended in EtOAc and sat. NaHCO$_3$. The organic layer was washed with additional NaHCO$_3$. The layers were separated, and the organic layer dried over MgSO$_4$, filtered, and concentrated in vacuo. The crude product was purified by silica gel chromatography (eluent: 10% Methanol in Dichloromethane). The collected product was dried under hi-vacuum for 1 h, and then treated with ether and filtered. After drying in vacuum oven at 45° C. for 2 h, the product was collected as 0.28 g (50%). $^1$H NMR (400 MHz, DMSO-d$_6$) δ ppm 0.73-0.80 (m, 2H), 0.88-0.96 (m, 2H), 1.36 (s, 9H), 1.70-1.82 (m, 1H), 2.11 (s, 3H), 3.95 (d, J=5.31 Hz, 2H), 5.66 (s, 1H), 6.51 (t, J=4.80 Hz, 1H), 11.50 (br. s., 1H).

Step 4

3-(Aminomethyl)-6-cyclopropyl-4-methyl-2(1H)-pyridinone hydrochloride 1,1-Dimethylethyl[(6-cyclopropyl-4-methyl-2-oxo-1,2-dihydro-3-pyridinyl)methyl]carbamate (0.28 g, 1.006 mmol) was added to EtOAc (9 mL) and methanol (1.0 mL). The suspension was stirred at room temperature for 5 min., followed by addition of 4M HCl in dioxane (5.03 mL, 20.12 mmol), and the contents were stirred at room temperature overnight. The volatiles were then removed in vacuo to afford a solid. The solid was triturated with ether, filtered, and dried in a vacuum oven at 45° C. for 4 h. The title compound was collected as 0.22 g (100% yield). $^1$H NMR (400 MHz, DMSO-d$_6$) δ ppm 0.78-0.86 (m, 2H), 0.95-1.03 (m, 2H), 1.83 (tt, J=8.46, 5.05 Hz, 1H), 2.16-2.22 (m, 3H), 3.75 (q, J=5.47 Hz, 2H), 5.79 (s, 1H), 8.02 (br. s., 3H), 11.92 (br. s., 1H).

Example 1

6-Chloro-N-[(4,6-dimethyl-2-oxo-1,2-dihydro-3-pyridinyl)methyl]-1-(1-methylethyl)-1H-pyrazolo[3,4-b]pyridine-4-carboxamide

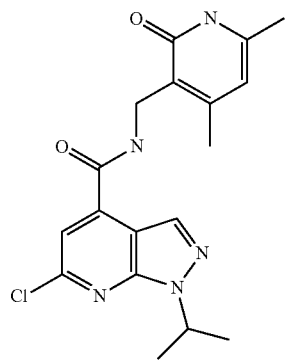 [SMILES: Cc1cc(C)c(CNC(=O)c2cc(Cl)nc3c2cnn3C(C)C)c(=O)[nH]1]

6-Chloro-1-(1-methylethyl)-1H-pyrazolo[3,4-b]pyridine-4-carboxylic acid (0.12 g, 0.501 mmol), 1-hydroxy-7-azabenzotriazole (0.102 g, 0.751 mmol), EDC (0.144 g, 0.751 mmol), and 3-(aminomethyl)-4,6-dimethyl-2(1H)-pyridinone (0.123 g, 0.651 mmol) were dissolved in dimethyl sulfoxide (3.0 mL) and stirred at room temperature. Added next to the stirring contents was N-methylmorpholine (0.220 mL, 2.003 mmol) via syringe at once. After stirring at room temperature overnight, the reaction mixture was slowly added to water (75 mL) and stirred for 10 min. After sitting for 10 min. at room temperature, the contents were filtered to afford a tan solid which was washed with water and then cold 50% aq EtOH. The contents were filtered, air-dried for 10 min., and then dried under vacuum for 1 hr. The collected solid was then further dried in a vacuum oven at 45° C. for 4 hr. The title compound was collected as 0.105 g (55%). LCMS E-S (M+H)=373.9. $^1$H NMR (400 MHz, DMSO-d$_6$) δ ppm 1.49 (d, J=6.82 Hz, 6H), 2.13 (s, 3H), 2.20 (s, 3H), 4.35 (d, J=4.80 Hz, 2H), 5.07-5.20 (m, 1H), 5.89 (s, 1H), 7.66 (s, 1H), 8.39 (s, 1H), 8.91 (t, J=4.80 Hz, 1H), 11.55 (s, 1H).

Example 2

6-Chloro-N-[(4,6-dimethyl-2-oxo-1,2-dihydro-3-pyridinyl)methyl]-3-methyl-1-(1-methylethyl)-1H-pyrazolo[3,4-b]pyridine-4-carboxamide

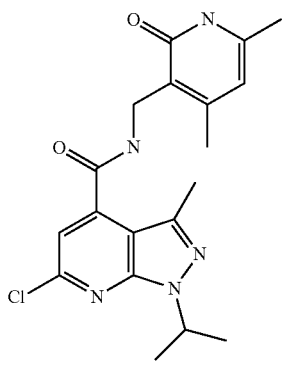 [SMILES: Cc1cc(C)c(CNC(=O)c2cc(Cl)nc3c2c(C)nn3C(C)C)c(=O)[nH]1]

The title compound was prepared in the same manner as described in example 17 using 6-chloro-3-methyl-1-(1-methylethyl)-1H-pyrazolo[3,4-b]pyridine-4-carboxylic acid (486.6 mg, 1.92 mmol), 3-(aminomethyl)-4,6-dimethyl-2 (1H)-pyridinone HCl (489 mg, 2.59 mmol), 1-hydroxy-7-azabenzotriazole (392 mg, 2.88 mmol), N-methylmorpholine (0.84 ml, 7.67 mmol) and EDC (552 mg, 2.88 mmol). An additional 10 mL DMSO was added to the reaction mixture to facilitate stirring, and 10% K$_2$CO$_3$ was used instead of 50% aq. NaOH during the work up. LCMS E-S (M+H)=388.1. $^1$H NMR (400 MHz, DMSO-d$_6$) δ ppm 1.44 (d, 6H), 2.12 (s, 3H), 2.22 (s, 3H), 2.40 (s, 3H), 4.34 (d, J=5.05 Hz, 2H), 5.05 (quin, J=6.63 Hz, 1H), 5.88 (s, 1H), 7.16 (s, 1H), 8.78 (t, J=4.93 Hz, 1H), 11.53 (br. s., 1H).

Example 3

6-Chloro-1-(1,1-dimethylethyl)-N-[(4,6-dimethyl-2-oxo-1,2-dihydro-3-pyridinyl)methyl]-3-methyl-1H-pyrazolo[3,4-b]pyridine-4-carboxamide

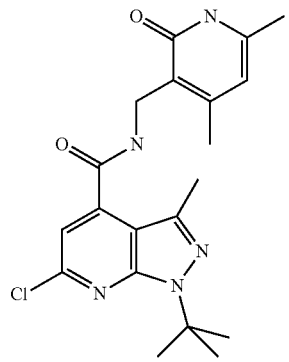 [SMILES: Cc1cc(C)c(CNC(=O)c2cc(Cl)nc3c2c(C)nn3C(C)(C)C)c(=O)[nH]1]

To a solution of 6-chloro-1-(1,1-dimethylethyl)-3-methyl-1H-pyrazolo[3,4-b]pyridine-4-carboxylic acid (320 mg, 1.195 mmol) in DMSO (7 mL) were added 3-(aminomethyl)-4,6-dimethyl-2(1H)-pyridinone (338 mg, 1.793 mmol), N-methylmorpholine (0.526 mL, 4.78 mmol), 1-hydroxy-7-azabenzotriazole (325 mg, 2.391 mmol) and EDC (458 mg, 2.391 mmol), and the reaction mixture was stirred overnight. The reaction mixture was quenched with water (20 mL) and stirred for 10 min. The precipitate was collected by filtration and further dried under high vacuum to give the product as a solid, 450 mg (94%). LCMS E-S (M+H)=402.1. $^1$H NMR (400 MHz, DMSO-$d_6$) δ ppm 1.71 (s, 9H), 2.12 (s, 3H), 2.22 (s, 3H), 2.37 (s, 3H), 4.33 (d, J=4.80 Hz, 2H), 5.88 (s, 1H), 7.09-7.21 (m, 1H), 8.77 (t, J=4.93 Hz, 1H), 11.53 (s, 1H).

Example 4

N-[(4,6-Dimethyl-2-oxo-1,2-dihydro-3-pyridinyl)methyl]-1-(1-methylethyl)-6-(4-pyridinyloxy)-1H-pyrazolo[3,4-b]pyridine-4-carboxamide

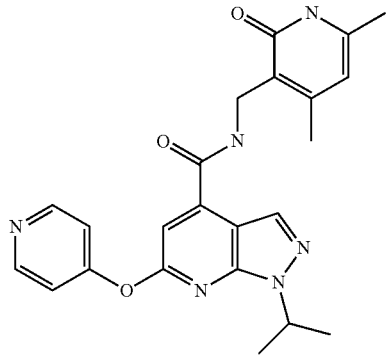 [SMILES: Cc1cc(C)c(CNC(=O)c2cc(Oc3ccncc3)nc3c2cnn3C(C)C)c(=O)[nH]1]

6-Chloro-N-[(4,6-dimethyl-2-oxo-1,2-dihydro-3-pyridinyl)methyl]-1-(1-methylethyl)-1H-pyrazolo[3,4-b]pyridine-4-carboxamide (0.15 g, 0.401 mmol), 4-pyridinol (0.057 g, 0.602 mmol), cesium carbonate (0.261 g, 0.802 mmol), and 1-(2-pyridinyl)-2-propanone (10.85 mg, 0.080 mmol) were sequentially dissolved in DMSO (4.0 mL). Next added copper(I) bromide (5.76 mg, 0.040 mmol) and the suspension was stirred under nitrogen (degassed) for 1 min. The sealed reaction mixture was stirred with heating at 110° C. (heating block) for 20 h, and then allowed to cool to room temperature overnight. The reaction mixture was diluted with EtOAc (25 mL) and water. The contents were vigorously stirred and then filtered through Celite, washing the filter pad with 20% THF/EtOAc. The layers were separated and the aq. layer extracted with EtOAc. The combined organic layers were dried over MgSO$_4$, filtered, and concentrated in vacuo to a dark residue that was dried under hi-vacuum overnight. The crude product was purified by silica gel chromatography (eluent: gradient of 5-95% Dichloromethane/Chloroform containing 2M Ammonia (in methanol). The collected product was washed with MTBE, filtered, and dried in a vacuum oven at 45° C. for 5 hr. The final product was collected as 0.075 g (42%). LCMS E-S (M+H)=433.2. $^1$H NMR (400 MHz, DMSO-$d_6$) δ ppm $^1$H NMR (400 MHz, DMSO-$d_6$) δ ppm 1.52 (d, J=6.57 Hz, 6H), 2.13 (s, 3H), 2.22 (s, 3H), 4.41 (d, J=5.05 Hz, 2H), 5.18-5.30 (m, 1H), 5.91 (s, 1H), 6.30-6.40 (m, 2H), 7.91 (s, 1H), 8.41 (s, 1H), 8.57-8.65 (m, 2H), 8.92 (t, J=4.93 Hz, 1H), 11.58 (s, 1H).

Example 5

N-[(4,6-Dimethyl-2-oxo-1,2-dihydro-3-pyridinyl)methyl]-1-(1-methylethyl)-6-(2-propen-1-ylamino)-1H-pyrazolo[3,4-b]pyridine-4-carboxamide

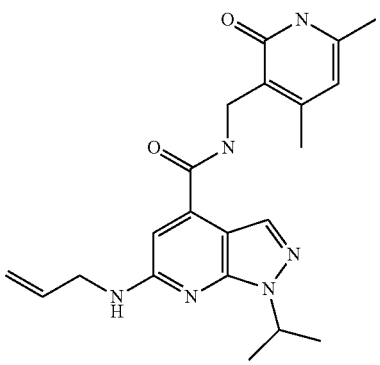 [SMILES: C=CCNc1cc(C(=O)NCc2c(C)cc(C)[nH]c2=O)c2cnn(C(C)C)c2n1]

6-Chloro-N-[(4,6-dimethyl-2-oxo-1,2-dihydro-3-pyridinyl)methyl]-1-(1-methylethyl)-1H-pyrazolo[3,4-b]pyridine-4-carboxamide (0.25 g, 0.669 mmol) was suspended in ethanol (4 mL) followed by addition of allylamine (0.753 mL, 10.03 mmol). The sealed contents were heated (heat block) at 140° C. for ca. 60 h, and then allowed to cool to room temperature. The reaction mixture was diluted with water (100 mL) and then filtered. The collected solid was washed with additional water and then dried in vacuum oven at 45° C. for 18 h. The final product was isolated as an off-white solid, 0.225 g (83%). LCMS E-S (M+H)=394.2. $^1$H NMR (400 MHz, DMSO-$d_6$) δ ppm 1.42 (d, J=6.82 Hz, 6H), 2.12 (s, 3H), 2.21 (s, 3H), 4.00 (t, J=5.43 Hz, 2H), 4.32 (d, J=5.05 Hz, 2H), 4.94 (quin, J=6.69 Hz, 1H), 5.09 (dd, J=10.36, 1.77 Hz, 1H), 5.18-5.29 (m, 1H), 5.85-6.01 (m, 2H), 6.68 (s, 1H), 7.37 (t, J=5.56 Hz, 1H), 7.84 (s, 1H), 8.45 (t, J=5.05 Hz, 1H), 11.55 (br. s., 1H).

Example 6

6-Amino-N-[(4,6-dimethyl-2-oxo-1,2-dihydro-3-pyridinyl)methyl]-1-(1-methylethyl)-1H-pyrazolo[3,4-b]pyridine-4-carboxamide

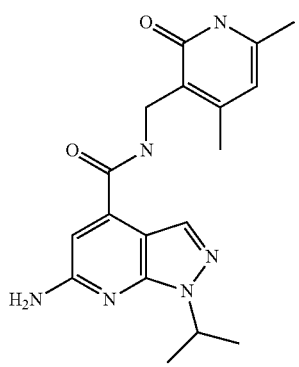 [SMILES: Cc1cc(C)c(CNC(=O)c2cc(N)nc3c2cnn3C(C)C)c(=O)[nH]1]

A mixture of 10% Pd/C (0.200 g, 0.188 mmol) and N-[(4,6-dimethyl-2-oxo-1,2-dihydro-3-pyridinyl)methyl]-1-(1-methylethyl)-6-(2-propen-1-ylamino)-1H-pyrazolo[3,4-b]pyridine-4-carboxamide (0.200 g, 0.507 mmol) was suspended in ethanol (10 mL) and stirred. Added next was methanesulfonic acid (0.033 mL, 0.507 mmol), and the stirring contents were heated at reflux for 2 h. After cooling to room temperature, the reaction mixture was diluted with DCM and filtered through Celite. The filter pad was washed with 10% MeOH/DCM. The filtrate was pre-adsorped onto silica gel, and the crude product purified by silica gel chromatography (dry loaded, eluent: gradient of 5-80% Dichloromethane/Chloroform containing 10% 2M Ammonia (in methanol)). The collected product was dried in vacuum oven at 45° C. overnight. The final product was collected as 0.065 g (36%). LCMS E-S (M+H)=355.3. $^1$H NMR (400 MHz, DMSO-$d_6$) δ ppm 1.40 (d, J=6.82 Hz, 6H), 2.12 (s, 3H), 2.21 (s, 3H), 4.31 (d, J=5.05 Hz, 2H), 4.85-5.00 (m, 1H), 5.89 (s, 1H), 6.49-6.68 (m, 3H), 7.85 (s, 1H), 8.46 (t, J=5.05 Hz, 1H), 11.54 (br. s., 1H).

Example 7

6-Cyclopropyl-1-(1-methylethyl)-N-[(4-methyl-2-oxo-6-propyl-1,2-dihydro-3-pyridinyl)methyl]-1H-pyrazolo[3,4-b]pyridine-4-carboxamide

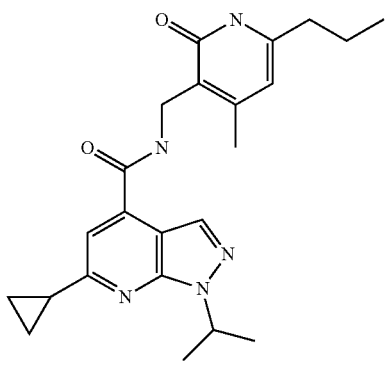 [SMILES: CCCc1cc(C)c(CNC(=O)c2cc(C3CC3)nc3c2cnn3C(C)C)c(=O)[nH]1]

6-Cyclopropyl-1-(1-methylethyl)-1H-pyrazolo[3,4-b]pyridine-4-carboxylic acid (167 mg, 0.680 mmol), 3-(aminomethyl)-4-methyl-6-propyl-2(1H)-pyridinone trifluoroacetate (200 mg, 0.680 mmol), HOAT (139 mg, 1.019 mmol), EDC (195 mg, 1.019 mmol), and N-methylmorpholine (0.299 mL, 2.72 mmol) were dissolved in DMF (6 mL) and stirred at 40° C. for 24 h. The reaction mixture was poured into water (20 mL) and extracted with ethyl acetate (3×50 mL). The combined organic layers were dried over sodium sulfate and concentrated to an orange oil. The residue was dissolved in DMSO, and purified by reverse phase HPLC (mobile phase: 40-60% ACN in H$_2$O, 0.1% TFA). The isolated product was dried in a vacuum oven overnight and furnished the TFA salt of the title compound as a white solid, 0.113 g (32%). LCMS E-S (M+H)=408.1. $^1$H NMR (400 MHz, DMSO-$d_6$) δ ppm 0.80-0.98 (m, 3H), 1.06 (d, J=7.07 Hz, 4H), 1.46 (d, J=6.82 Hz, 6H), 1.52-1.67 (m, 2H), 2.17-2.31 (m, 4H), 2.37 (t, J=7.58 Hz, 2H), 4.36 (d, J=4.80 Hz, 2H), 5.02-5.27 (m, 1H), 5.91 (s, 1H), 7.43 (s, 1H), 8.21 (s, 1H), 8.62-8.87 (m, 1H), 11.54 (br. s., 1H).

Example 8

6-Cyclopropyl-1-(1-methylethyl)-N-{[6-methyl-4-(1-methylethyl)-2-oxo-1,2-dihydro-3-pyridinyl]methyl}-1H-pyrazolo[3,4-b]pyridine-4-carboxamide

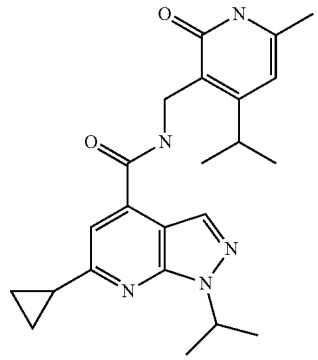 [SMILES: Cc1cc(C(C)C)c(CNC(=O)c2cc(C3CC3)nc3c2cnn3C(C)C)c(=O)[nH]1]

The title compound was prepared in the same manner as described in example 7 from 6-cyclopropyl-1-(1-methylethyl)-1H-pyrazolo[3,4-b]pyridine-4-carboxylic acid (250 mg, 1.019 mmol), 3-(aminomethyl)-6-methyl-4-(1-methylethyl)-2(1H)-pyridinone.TFA (300 mg, 1.019 mmol), HOAT (208 mg, 1.529 mmol), EDC (293 mg, 1.529 mmol), N-methylmorpholine (0.448 mL, 4.08 mmol), and DMF (6 mL), wherein the reaction time was 48 h. The final product was collected following a basic extraction (to remove residual starting material) as a white solid, 30 mg (7%). LCMS E-S (M+H)=408.3. $^1$H NMR (400 MHz, DMSO-$d_6$) δ ppm 0.95-1.16 (m, 10H), 1.38-1.54 (m, 6H), 2.16 (s 3H), 2.19-2.30 (m, 1H), 3.12-3.29 (m, 1H), 4.29-4.48 (m, 2H), 5.03-5.21 (m, 1H), 6.03 (s, 1H), 7.39 (s, 1H), 8.21 (s, 1H), 8.63-8.81 (m, 1H), 11.56 (s, 1H).

Example 9

1-(1-Methylethyl)-N-[(4-methyl-2-oxo-6-propyl-1,2-dihydro-3-pyridinyl)methyl]-6-(4-pyridinyl)-1H-pyrazolo[3,4-b]pyridine-4-carboxamide

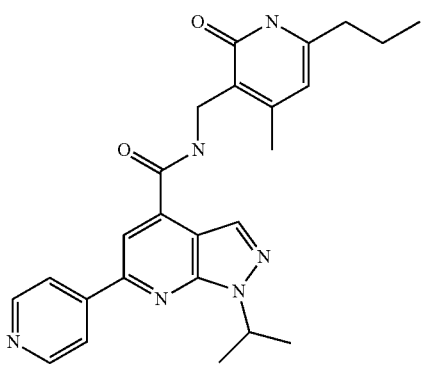 [SMILES: CCCc1cc(C)c(CNC(=O)c2cc(-c3ccncc3)nc3c2cnn3C(C)C)c(=O)[nH]1]

1-(1-Methylethyl)-6-(4-pyridinyl)-1H-pyrazolo[3,4-b]pyridine-4-carboxylic acid (192 mg, 0.680 mmol), 3-(aminomethyl)-4-methyl-6-propyl-2(1H)-pyridinone.TFA (200 mg, 0.680 mmol), HOAT (139 mg, 1.019 mmol), EDC (195 mg, 1.019 mmol), and N-methylmorpholine (0.299 mL, 2.72 mmol) were sequentially added to DMF (6 mL), and the mixture stirred at 40° C. overnight. The reaction mixture was then filtered. The collected solid was washed with ethanol, and dried, affording the final product as a white solid, 0.160 g (53%). LCMS E-S (M+H)=445.3. $^1$H NMR (400 MHz, DMSO-$d_6$) δ ppm 0.88 (t, 3H), 1.46-1.65 (m, 8H), 2.24 (s, 3H), 2.38 (t, J=7.58 Hz, 2H), 4.43 (d, J=4.80 Hz, 2H), 5.37 (s, 1H), 5.93 (s, 1H), 8.23 (d, J=5.81 Hz, 2H), 8.30 (s, 1H), 8.45 (s, 1H), 8.78 (d, J=5.31 Hz, 2H), 9.00 (br. s., 1H), 11.56 (s, 1H).

Example 10

N-[(6-Ethyl-4-methyl-2-oxo-1,2-dihydro-3-pyridinyl)methyl]-1-(1-methylethyl)-6-(4-pyridinyl)-1H-pyrazolo[3,4-b]pyridine-4-carboxamide

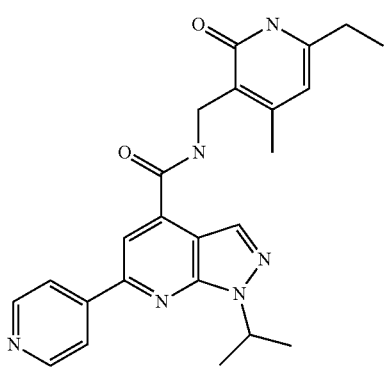 [SMILES: CCc1cc(C)c(CNC(=O)c2cc(-c3ccncc3)nc3c2cnn3C(C)C)c(=O)[nH]1]

The title compound was prepared in the same manner as described in example 9 from 1-(1-methylethyl)-6-(4-pyridinyl)-1H-pyrazolo[3,4-b]pyridine-4-carboxylic acid (403 mg, 1.427 mmol), 3-(aminomethyl)-6-ethyl-4-methyl-2(1H)-pyridinone.TFA (400 mg, 1.427 mmol), HOAT (291 mg, 2.141 mmol), EDC (1094 mg, 5.71 mmol), N-methylmorpholine (0.628 mL, 5.71 mmol), and DMF (6 mL). The final product was collected as a white solid, 232 mg (38%). LCMS E-S (M+H)=432.4. $^1$H NMR (400 MHz, DMSO-$d_6$) δ ppm 1.14 (t, 3H), 1.56 (d, J=6.57 Hz, 6H), 2.25 (s, 3H), 2.42 (q, J=7.41 Hz, 2H), 4.43 (d, J=4.55 Hz, 2H), 5.29-5.45 (m, 1H), 5.93 (s, 1H), 8.22 (d, J=6.06 Hz, 2H), 8.30 (s, 1H), 8.45 (s, 1H), 8.78 (d, J=5.81 Hz, 2H), 9.01 (t, J=4.55 Hz, 1H), 11.58 (s, 1H).

Example 11

1-(1-Methylethyl)-N-[(6-methyl-2-oxo-4-propyl-1,2-dihydro-3-pyridinyl)methyl]-6-(4-pyridinyl)-1H-pyrazolo[3,4-b]pyridine-4-carboxamide

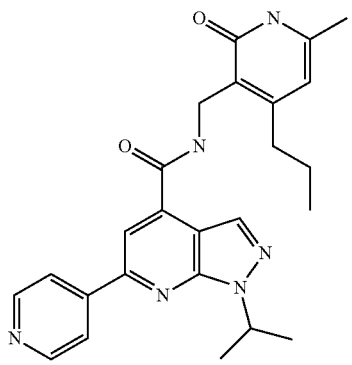 [SMILES: CCCc1cc(C)[nH]c(=O)c1CNC(=O)c1cc(-c2ccncc2)nc2c1cnn2C(C)C]

1-(1-Methylethyl)-6-(4-pyridinyl)-1H-pyrazolo[3,4-b]pyridine-4-carboxylic acid (150 mg, 0.531 mmol), 3-(aminomethyl)-6-methyl-4-propyl-2(1H)-pyridinone (115 mg, 0.531 mmol), EDC (122 mg, 0.638 mmol), HOAt (72.3 mg, 0.531 mmol), and N-methylmorpholine (0.233 mL, 2.12 mmol) were suspended in DMF (5 mL) and stirred at room temperature overnight. water was added to the reaction mixture, and the contents were filtered. The filter cake was washed with additional water (2×). The crude solid was purified by reverse phase HPLC (mobile phase: 10-30% ACN in $H_2O$, 0.1% TFA). The isolated solid was then neutralized with saturated $NaHCO_3$, and washed with EtOAc (5×15 mL). The combined organic layers were dried over $Na_2SO_4$, filtered, and concentrated in vacuo to afford the title compound as an off-white solid, 0.060 g (24%). LCMS E-S (M+H)=445.3. $^1$H NMR (400 MHz, DMSO-$d_6$) δ ppm 0.84-0.92 (m, 3H), 1.47-1.54 (m, 2H), 1.57 (d, J=6.82 Hz, 6H), 2.14 (s, 3H), 2.48-2.52 (m, 2H), 4.42-4.49 (m, 2H), 5.33-5.43 (m, 1H), 5.90-5.96 (m, 1H), 8.28-8.37 (m, 3H), 8.44-8.48 (m, 1H), 8.82-8.87 (m, 2H), 8.99-9.04 (m, 1H), 11.58 (s, 1H).

Example 12

1-(1-Methylethyl)-N-{[6-methyl-4-(1-methylethyl)-2-oxo-1,2-dihydro-3-pyridinyl]methyl}-6-(4-pyridinyl)-1H-pyrazolo[3,4-b]pyridine-4-carboxamide

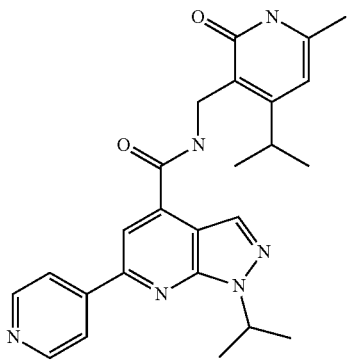 [SMILES: Cc1cc(C(C)C)c(CNC(=O)c2cc(-c3ccncc3)nc3c2cnn3C(C)C)c(=O)[nH]1]

A DMF solution (6 mL) of 1-(1-methylethyl)-6-(4-pyridinyl)-1H-pyrazolo[3,4-b]pyridine-4-carboxylic acid (288 mg, 1.019 mmol), 3-(aminomethyl)-6-methyl-4-(1-methylethyl)-2(1H)-pyridinone.TFA (300 mg, 1.019 mmol), HOAT (208 mg, 1.529 mmol), EDC (782 mg, 4.08 mmol), and N-methylmorpholine (0.448 mL, 4.08 mmol) was stirred overnight at 40° C. After cooling to room temperature, the reaction mixture was poured into H$_2$O (50 mL) and EtOAc (50 mL). The aqueous layer was extracted with EtOAC (2×50 mL). The organic layers were dried over sodium sulfate, filtered, and concentrated in vacuo. The residue was dissolved in DMSO and purified by reverse phase (15-40% ACN in H$_2$O, 0.1% TFA). The product fractions were poured into sodium bicarbonate and extracted with ethyl acetate. The organic layer was dried over sodium sulfate, filtered, and concentrated in vacuo to afford the title compound as a white solid (123 mg, 27% yield). LCMS E-S (M+H)=445.4. $^1$H NMR (400 MHz, DMSO-d$_6$) δ ppm 1.10 (m, 6H), 1.56 (m, 6H), 2.17 (s, 3H), 3.17-3.28 (m, 1H), 4.45-4.56 (m, 2H), 5.29-5.43 (m, 1H), 5.99-6.12 (m, 1H), 8.16-8.23 (m, 2H), 8.24-8.29 (m, 1H), 8.40-8.46 (m, 1H), 8.71-8.82 (m, 2H), 8.96-9.04 (m, 1H), 11.53-11.63 (m, 1H).

Example 13

6-Cyclopropyl-1-(1-methylethyl)-N-[(6-methyl-2-oxo-4-propyl-1,2-dihydro-3-pyridinyl)methyl]-1H-pyrazolo[3,4-b]pyridine-4-carboxamide

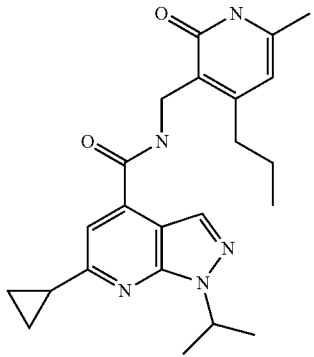 [SMILES: CCCc1cc(C)[nH]c(=O)c1CNC(=O)c1cc(C2CC2)nc2c1cnn2C(C)C]

The title compound was prepared in the same manner as described in example 11 from 1-(1-methylethyl)-6-(cyclopropyl)-1H-pyrazolo[3,4-b]pyridine-4-carboxylic acid (150 mg, 0.612 mmol). The product was collected as a white solid, 0.043 g (16%). LCMS E-S (M+H)=408.3. $^1$H NMR (400 MHz, DMSO-d$_6$) δ ppm 0.89 (t, J=7.20 Hz, 3H), 1.06 (d, J=2.78 Hz, 3H), 1.08 (br. s., 1H), 1.47 (d, J=6.57 Hz, 8H), 1.49-1.57 (m, 2H), 2.14 (s, 3H), 2.19-2.30 (m, 1H), 4.38 (d, J=4.80 Hz, 2H), 5.03-5.18 (m, 1H), 5.92 (s, 1H), 7.40 (s, 1H), 8.21 (s, 1H), 8.69-8.76 (m, 1H), 11.55 (s, 1H).

Example 14

1-(1-Methylethyl)-N-[(6-methyl-2-oxo-4-phenyl-1,2-dihydro-3-pyridinyl)methyl]-6-(4-pyridinyl)-1H-pyrazolo[3,4-b]pyridine-4-carboxamide

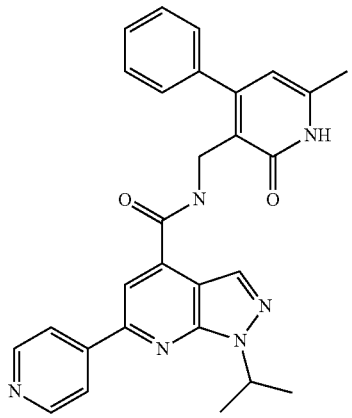 [SMILES: Cc1cc(-c2ccccc2)c(CNC(=O)c2cc(-c3ccncc3)nc3c2cnn3C(C)C)c(=O)[nH]1]

The title compound was prepared in the same manner as described in example 11 from 1-(1-methylethyl)-6-(4-pyridinyl)-1H-pyrazolo[3,4-b]pyridine-4-carboxylic acid (150 mg, 0.531 mmol) and 3-(aminomethyl)-6-methyl-4-phenyl-2(1H)-pyridinone (133 mg, 0.531 mmol). The product was collected as a white solid, 0.041 g (15%). LCMS E-S (M+H)=479.3. $^1$H NMR (400 MHz, DMSO-d$_6$) δ ppm 1.57 (d, J=6.82 Hz, 6H) 2.23 (s, 3H) 4.23-4.27 (m, 2H) 5.33-5.42 (m, 1H) 6.02-6.04 (m, 1H) 7.35-7.42 (m, 1H) 7.43 (s, 4H) 8.23-8.26 (m, 1H) 8.34-8.39 (m, 2H) 8.41-8.42 (m, 1H) 8.84-8.88 (m, 2H) 8.91-8.96 (m, 1H) 11.91 (s, 1H).

Example 15

N-[(4-Cyclohexyl-6-methyl-2-oxo-1,2-dihydro-3-pyridinyl)methyl]-1-(1-methylethyl)-6-(4-pyridinyl)-1H-pyrazolo[3,4-b]pyridine-4-carboxamide

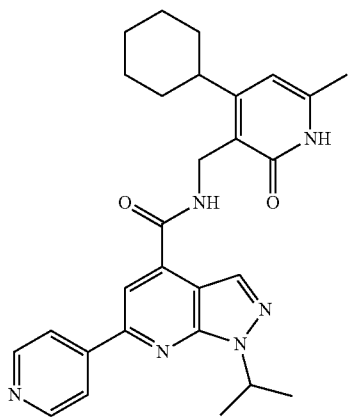 [SMILES: Cc1cc(C2CCCCC2)c(CNC(=O)c2cc(-c3ccncc3)nc3c2cnn3C(C)C)c(=O)[nH]1]

A mixture of 1-(1-methylethyl)-6-(4-pyridinyl)-1H-pyrazolo[3,4-b]pyridine-4-carboxylic acid (169 mg, 0.6 mmol), 3-(aminomethyl)-4-cyclohexyl-6-methyl-2(1H)-pyridinone trifluoroacetate (221 mg, 0.660 mmol), EDC (150 mg, 0.780 mmol), HOAT (106 mg, 0.780 mmol), and N-methylmorpholine (0.264 mL, 2.400 mmol) in DMF (3 mL) were stirred at room temperature for 6 days. water (15 mL) was added to the slurry, and it was stirred for an hour. The precipitate was then collected by vacuum filtration and rinsed with EtOH (4 mL), and the solid was dried in the vacuum oven overnight to give the title compounds as an off-white solid (137 mg, 45%). LCMS E-S (M+H)=485.2. $^1$H NMR (400 MHz, DMSO-$d_6$) δ ppm 1.09-1.44 (m, 5H), 1.56 (d, J=6.57 Hz, 6H), 1.55-1.72 (m, 5H), 2.15 (s, 3H), 2.80-2.92 (m, 1H), 4.53 (d, J=4.55 Hz, 2H), 5.36 (spt, J=6.53 Hz, 1H), 6.03 (s, 1H), 8.18-8.23 (m, 2H), 8.26 (s, 1H), 8.45 (s, 1H), 8.75-8.82 (m, 2H), 9.01 (t, J=4.55 Hz, 1H), 11.59 (s, 1H).

Example 16

N-[(4-Cyclohexyl-6-methyl-2-oxo-1,2-dihydro-3-pyridinyl)methyl]-6-cyclopropyl-1-(1-methylethyl)-1H-pyrazolo[3,4-b]pyridine-4-carboxamide

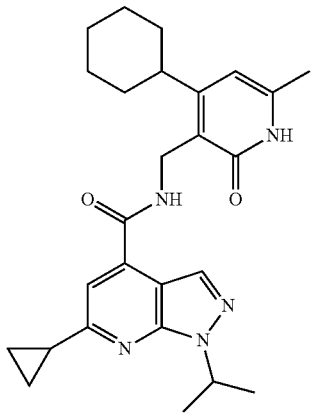 [SMILES: Cc1cc(C2CCCCC2)c(CNC(=O)c2cc(C3CC3)nc3c2cnn3C(C)C)c(=O)[nH]1]

The title compound was prepared in the same manner as described in example 15 from 6-cyclopropyl-1-(1-methylethyl)-1H-pyrazolo[3,4-b]pyridine-4-carboxylic acid (147 mg, 0.60 mmol), 3-(aminomethyl)-4-cyclohexyl-6-methyl-2(1H)-pyridinone trifluoroacetate (221 mg, 0.660 mmol), EDC (150 mg, 0.780 mmol), HOAT (106 mg, 0.780 mmol), N-methylmorpholine (0.264 mL, 2.400 mmol) and DMF (3 mL), wherein the stir time was 3 d and the final product was not treated with EtOH. The final product was collected as 193 mg (68%). LCMS E-S (M+H)=448.4. $^1$H NMR (400 MHz, DMSO-$d_6$) δ ppm 1.01-1.11 (m, 4H), 1.15-1.43 (m, 5H), 1.47 (d, J=6.57 Hz, 6H), 1.55-1.76 (m, 5H), 2.15 (s, 3H), 2.19-2.28 (m, 1H), 2.83 (t, J=11.12 Hz, 1H), 4.45 (d, J=5.05 Hz, 2H), 5.12 (spt, J=6.69 Hz, 1H), 6.02 (s, 1H), 7.37 (s, 1H), 8.21 (s, 1H), 8.74 (t, J=4.80 Hz, 1H), 11.56 (s, 1H).

Example 17

6-Cyclopropyl-1-(1-methylethyl)-N-[(6-methyl-2-oxo-4-phenyl-1,2-dihydro-3-pyridinyl)methyl]-1H-pyrazolo[3,4-b]pyridine-4-carboxamide

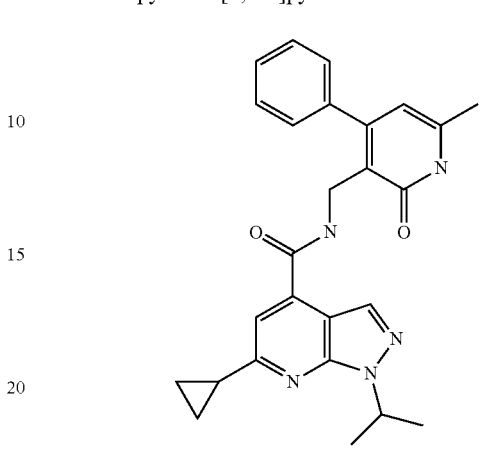

The title compound was prepared in the same manner as described in example 11 from 1-(1-methylethyl)-6-(cyclopropyl)-1H-pyrazolo[3,4-b]pyridine-4-carboxylic acid (150 mg, 0.612 mmol) and 3-(aminomethyl)-6-methyl-4-phenyl-2(1H)-pyridinone (153 mg, 0.612 mmol). The product was collected as a white solid, 0.067 g (24%). LCMS E-S (M+H)=442.3. $^1$H NMR (400 MHz, DMSO-$d_6$) δ ppm 1.04-1.11 (m, 3H), 1.47 (d, J=6.57 Hz, 5H), 2.22 (s, 3H), 2.24-2.29 (m, 1H), 3.17 (d, J=5.31 Hz, 2H), 4.07-4.15 (m, 1H), 4.19 (d, J=4.29 Hz, 2H), 5.06-5.18 (m, 1H), 6.01 (s, 1H), 7.36 (s, 1H), 7.38-7.49 (m, 5H), 8.18 (s, 1H), 8.70 (s, 1H), 11.88 (s, 1H).

Example 18

N-[(4-Cyclopropyl-6-methyl-2-oxo-1,2-dihydro-3-pyridinyl)methyl]-1-(1-methylethyl)-6-(4-pyridinyl)-1H-pyrazolo[3,4-b]pyridine-4-carboxamide

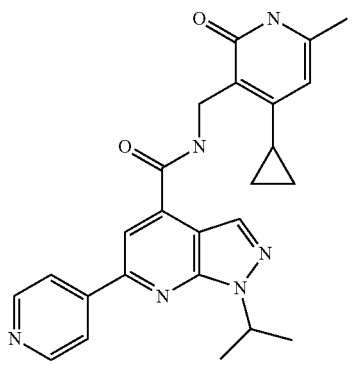 [SMILES: Cc1cc(C2CC2)c(CNC(=O)c2cc(-c3ccncc3)nc3c2cnn3C(C)C)c(=O)[nH]1]

1-(1-Methylethyl)-6-(4-pyridinyl)-1H-pyrazolo[3,4-b]pyridine-4-carboxylic acid (100 mg, 0.354 mmol), 3-(aminomethyl)-4-cyclopropyl-6-methyl-2(1H)-pyridinone (104 mg, 0.354 mmol), EDC (81 mg, 0.425 mmol), HOAt (48 mg, 0.354 mmol), and N-methylmorpholine (0.156 mL, 1.42 mmol) were suspended in DMF (5 mL) and stirred at room temperature overnight. The contents were filtered, washed with ethanol, and then concentrated in vacuo. The crude solid was purified by reverse phase HPLC (mobile phase: 20-40%, ACN in $H_2O$, 0.1% TFA). The isolated solid was then neutralized with saturated $NaHCO_3$, and washed with EtOAc (3×). The combined organic layers were dried over $Na_2SO_4$, filtered, and concentrated in vacuo to afford the title compound as an off-white solid, 0.042 g (26%). LCMS E-S (M+H)=443.3. $^1$H NMR (400 MHz, DMSO-$d_6$) δ ppm 0.71-0.78 (m, 2H), 0.94 (dd, J=8.34, 2.27 Hz, 2H), 1.57 (d, J=6.57 Hz, 6H), 2.12 (s, 3H), 2.13-2.18 (m, 1H), 4.62 (d, J=4.80 Hz, 2H), 5.38 (s, 1H), 5.54 (s, 1H), 8.37 (s, 1H), 8.44-8.54 (m, 3H), 8.91 (d, J=6.06 Hz, 2H), 9.04 (s, 1H), 11.51 (br. s., 1H).

Example 19

6-Cyclopropyl-N-[(6-cyclopropyl-4-methyl-2-oxo-1,2-dihydro-3-pyridinyl)methyl]-1-(1-methylethyl)-1H-pyrazolo[3,4-b]pyridine-4-carboxamide

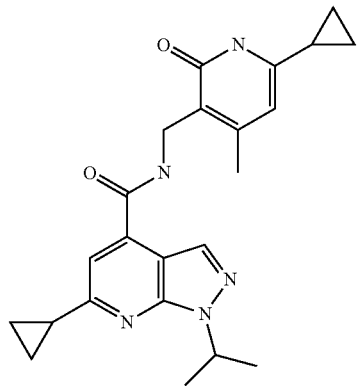 [SMILES: Cc1cc(C2CC2)[nH]c(=O)c1CNC(=O)c1cc(C2CC2)nc2c1cnn2C(C)C]

To a 4 mL solution of DMSO were sequentially added 6-cyclopropyl-1-(1-methylethyl)-1H-pyrazolo[3,4-b]pyridine-4-carboxylic acid (0.11 g, 0.448 mmol), 3-(aminomethyl)-6-cyclopropyl-4-methyl-2(1H)-pyridinone hydrochloride (0.106 g, 0.493 mmol), 1-hydroxy-7-azabenzotriazole (0.073 g, 0.538 mmol), EDC (0.103 g, 0.538 mmol), and then N-methylmorpholine (0.197 mL, 1.79 mmol) via syringe. After stirring overnight at room temperature, the suspension was diluted with 50 mL of water and stirred for 15 min. After standing at room temperature for 15 min., the reaction mixture was filtered and the collected solid washed with additional water. The solid was then dried in a vacuum oven at 45° C. for 4 h. The product was obtained as 0.165 g (89%). LCMS E-S (M+H)=406.5. $^1$H NMR (400 MHz, DMSO-$d_6$) δ ppm 0.76-0.82 (m, 2H), 0.91-0.98 (m, 2H), 1.03-1.12 (m, 4H), 1.46 (d, J=6.82 Hz, 6H), 1.74-1.84 (m, 1H), 2.19 (s, 3H), 2.21-2.31 (m, 1H), 4.34 (d, J=5.05 Hz, 2H), 5.05-5.18 (m, 1H), 5.73 (s, 1H), 7.42 (s, 1H), 8.21 (s, 1H), 8.72 (t, J=4.93 Hz, 1H), 11.61 (br. s., 1H).

Example 20

N-[(5-Fluoro-4,6-dimethyl-2-oxo-1,2-dihydro-3-pyridinyl)methyl]-1-(1-methylethyl)-6-(4-pyridinyl)-1H-pyrazolo[3,4-b]pyridine-4-carboxamide

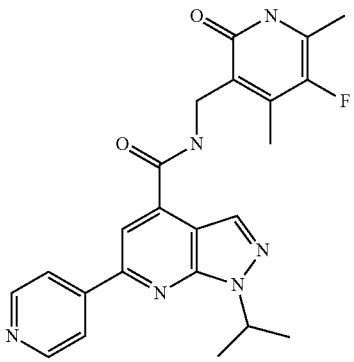 [SMILES: Cc1[nH]c(=O)c(CNC(=O)c2cc(-c3ccncc3)nc3c2cnn3C(C)C)c(C)c1F]

A mixture of 1-(1-methylethyl)-6-(4-pyridinyl)-1H-pyrazolo[3,4-b]pyridine-4-carboxylic acid (169 mg, 0.60 mmol), 3-(aminomethyl)-5-fluoro-4,6-dimethyl-2(1H)-pyridinone hydrochloride (136 mg, 0.660 mmol), EDC (150 mg, 0.780 mmol), HOAT (106 mg, 0.780 mmol), and N-methylmorpholine (0.264 mL, 2.400 mmol) in DMF (3 mL) was stirred at room temperature for 3 days. water (15 mL) was added to the slurry, and it was stirred for an hour. The precipitate was then collected by vacuum filtration and rinsed with EtOH (4 mL), and the solid was dried in the vacuum oven overnight to give the title compound as 220 mg (76%). LCMS E-S (M+H)=435.0. $^1$H NMR (400 MHz, DMSO-$d_6$) δ ppm 1.56 (d, 7H), 2.18 (d, J=2.78 Hz, 3H), 2.25 (d, J=2.02 Hz, 3H), 4.45 (d, J=4.80 Hz, 2H), 5.37 (spt, J=6.65 Hz, 1H), 8.19-8.25 (m, 2H), 8.29 (s, 1H), 8.44 (s, 1H), 8.74-8.81 (m, 2H), 9.07 (t, J=4.80 Hz, 1H), 11.66 (br. s., 1H).

Example 21

N-[(4,6-Dimethyl-2-oxo-1,2-dihydro-3-pyridinyl)methyl]-6-(ethylamino)-1-(1-methylethyl)-1H-pyrazolo[3,4-b]pyridine-4-carboxamide

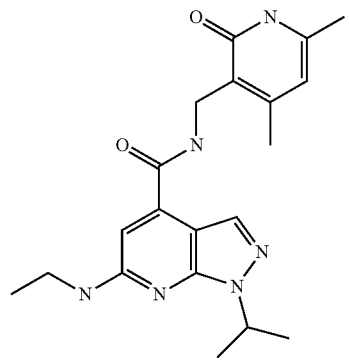 [SMILES: CCNc1cc(C(=O)NCc2c(C)cc(C)[nH]c2=O)c2cnn(C(C)C)c2n1]

To a 10 mL microwave vial equipped with stir bar, septum cap and nitrogen inlet were added 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (23 mg, 0.062 mmol) and ethanol (1 mL). Added next to the stirring suspension was ethylamine (0.100 mL, 1.230 mmol) via syringe at once. The sealed reaction mixture was irradiated (microwave) at 110° C. for 40 min, followed by addition of 0.1 mL ethylamine and further irradiation for 7 hr at 130° C. After cooling to room temperature, about 50% of the volatiles were removed by a stream of nitrogen. The reaction mixture was diluted with water (20 mL) and stirred for 10 min. The mixture was then filtered and the collected solid washed with water. The solid was dried in vacuum oven at 50° C. for 18 h, to afford the title compound as 0.17 g (71%). LCMS E-S (M+H)=383.3. $^1$H NMR (400 MHz, DMSO-$d_6$) δ ppm 1.17 (t, J=7.07 Hz, 3H), 1.43 (d, J=6.57 Hz, 6H), 2.12 (s, 3H), 2.21 (s, 3H), 3.35-3.39 (m, 2H), 4.31 (d, J=5.05 Hz, 2H), 4.89-5.01 (m, 1H), 5.89 (s, 1H), 6.61 (s, 1H), 7.18 (t, J=5.31 Hz, 1H), 7.83 (s, 1H), 8.44 (t, J=5.05 Hz, 1H), 11.55 (br. s., 1H).

Example 22

N-[(4,6-Dimethyl-2-oxo-1,2-dihydro-3-pyridinyl)methyl]-1-(1-methylethyl)-1H-pyrazolo[3,4-b]pyridine-4-carboxamide

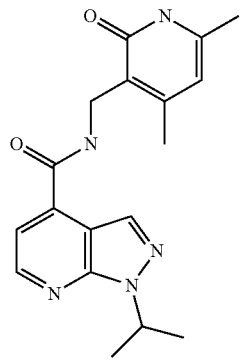 [SMILES: Cc1cc(C)c(CNC(=O)c2ccnc3c2cnn3C(C)C)c(=O)[nH]1]

To a 50 mL round bottom flask fitted with a 3-way inlet was placed 10% Pd/C (0.071 g, 0.033 mmol) followed by degassing with $N_2$, and then addition of 2 mL ethanol. Added next to the stirring slurry was 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (0.25 g, 0.669 mmol). Additional ethanol (8 mL) and THF (10 mL) were added with slight warming to facilitate dissolution. The stirring contents were allowed to cool (15 min.) then fitted with a balloon of $H_2$ and allowed to stir at room temperature overnight. The contents were then purged with $N_2$. The mixture was then diluted with 10% MeOH/DCM (20 mL), stirred for 10 min., and filtered through Celite. The filtrate was concentrated in vacuo and the crude solid was triturated with ethanol. After filtration and washing the collected solid with additional ethanol (cold), the solid was air-dried for 15 min, then in vacuum oven at 40° C. overnight. The final product was collected as 185 mg (80%). LCMS E-S (M+H)=340.2. $^1$H NMR (400 MHz, DMSO-$d_6$) δ ppm 1.50 (d, J=6.82 Hz, 6H), 2.13 (s, 3H), 2.22 (s, 3H), 4.37 (d, J=4.80 Hz, 2H), 5.18-5.31 (m, 1H), 5.89 (s, 1H), 7.54 (d, J=4.80 Hz, 1H), 8.36 (s, 1H), 8.63 (d, J=4.55 Hz, 1H), 8.82 (t, J=4.93 Hz, 1H), 11.56 (s, 1H).

Example 23

6-Cyclopropyl-1-(1-methylethyl)-N-{[6-methyl-2-oxo-4-(trifluoromethyl)-1,2-dihydro-3-pyridinyl]methyl}-1H-pyrazolo[3,4-b]pyridine-4-carboxamide

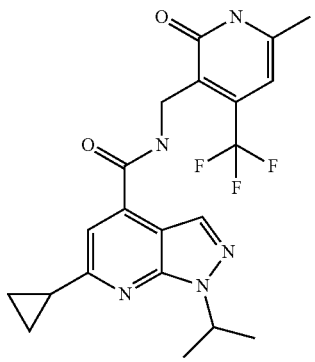 [SMILES: Cc1cc(C(F)(F)F)c(CNC(=O)c2cc(C3CC3)nc3c2cnn3C(C)C)c(=O)[nH]1]

The title compound was prepared in the same manner as described in example 19 from 6-cyclopropyl-1-(1-methylethyl)-1H-pyrazolo[3,4-b]pyridine-4-carboxylic acid (0.12 g, 0.489 mmol), 1-hydroxy-7-azabenzotriazole (0.100 g, 0.734 mmol), 3-(aminomethyl)-6-methyl-4-(trifluoromethyl)-2(1H)-pyridinone (0.154 g, 0.636 mmol, DMSO (3.0 mL), N-methylmorpholine (0.215 mL, 1.957 mmol), and EDC (0.141 g, 0.734 mmol) The crude solid was purified by silica gel chromatography (eluent: gradient 5-100% of 10% 2M $NH_3$ (in MeOH/DCM) and DCM) and the collected product dried in vacuum oven for 5 h. The final product was collected as 0.112 g (50%). LCMS E-S (M+H)=434.3. $^1$H NMR (400 MHz, DMSO-$d_6$) δ ppm 1.03-1.12 (m, 4H), 1.47 (d, J=6.82 Hz, 6H), 2.20-2.33 (m, 4H), 4.34-4.54 (m, 2H), 5.12 (quin, J=6.63 Hz, 1H), 6.33 (s, 1H), 7.39 (s, 1H), 8.18 (s, 1H), 8.70 (t, J=4.04 Hz, 1H), 12.43 (s, 1H).

Example 24

6-(Dimethylamino)-N-[(4,6-dimethyl-2-oxo-1,2-dihydro-3-pyridinyl)methyl]-1-(1-methylethyl)-1H-pyrazolo[3,4-b]pyridine-4-carboxamide

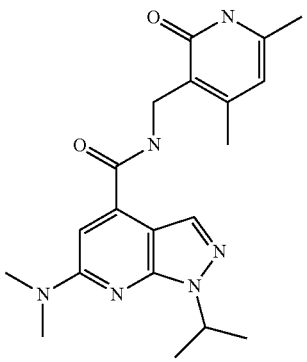

The title compound was prepared in the same manner as described in example 21 from 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (23 mg, 0.062 mmol), ethanol (0.7 mL), and dimethylamine (0.461 mL, 0.923 mmol). The product was dried in vacuum oven at 50° C. for 5 hr and collected as 0.016 g (67%). LCMS E-S (M+H)=383.3. $^1$H NMR (400 MHz, DMSO-$d_6$) δ ppm 1.44

(d, J=6.57 Hz, 6H), 2.05-2.25 (m, 6H), 3.14 (s, 6H), 4.34 (d, J=4.80 Hz, 2H), 4.99 (dt, J=13.39, 6.69 Hz, 1H), 5.89 (s, 1H), 6.94 (s, 1H), 7.96 (s, 1H), 8.64 (t, J=4.93 Hz, 1H), 11.56 (br. s., 1H).

Example 25

N-[(4,6-Dimethyl-2-oxo-1,2-dihydro-3-pyridinyl)methyl]-1-(1-methylethyl)-6-(1-piperidinyl)-1H-pyrazolo[3,4-b]pyridine-4-carboxamide

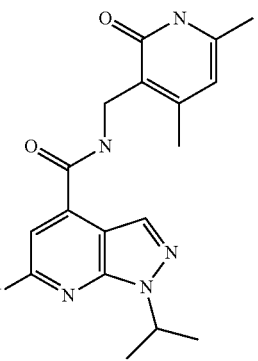

To a 10 mL reaction vial containing stir bar were added 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (0.060 g, 0.160 mmol), ethanol (1.5 mL), and then piperidine (0.318 mL, 3.21 mmol) via syringe at once. The contents were capped, placed into a heat block, and heated at 120° C. for 18 h. After cooling to room temperature, the reaction mixture was diluted with water (40 mL), adjusted to pH 6-7, and stirred for 15 min. The contents were filtered and washed with water. The product was dried in vacuum oven at 50° C. for 5 hr. The product was obtained as 57 mg (82%). LCMS E-S (M+H)=422.8. $^1$H NMR (400 MHz, DMSO-$d_6$) δ ppm 1.43 (d, J=6.82 Hz, 6H), 1.53-1.67 (m, 6H), 2.12 (s, 3H), 2.20 (s, 3H), 3.61-3.73 (m, 4H), 4.34 (d, J=5.05 Hz, 2H), 4.91-5.04 (m, 1H), 5.89 (s, 1H), 7.10 (s, 1H), 7.97 (s, 1H), 8.65 (t, J=4.93 Hz, 1H), 11.51 (br. s., 1H).

Example 26

N-[(4,6-Dimethyl-2-oxo-1,2-dihydro-3-pyridinyl)methyl]-1-(1-methylethyl)-6-(4-morpholinyl)-1H-pyrazolo[3,4-b]pyridine-4-carboxamide

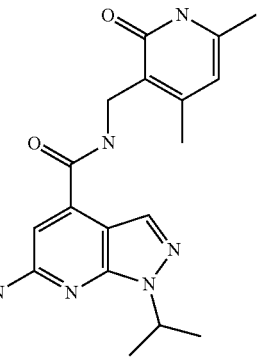

To a 10 mL reaction vial containing stir bar were added 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (0.060 g, 0.160 mmol), ethanol (1.5 mL), and then morpholine (0.280 mL, 3.21 mmol) via syringe at once. The contents were capped, placed into a heat block, and heated at 120° C. for 18 h and then at 135° C. for 2 hr. After cooling to room temperature, the reaction mixture was diluted with water (40 mL), adjusted to pH 6-7, and stirred for 15 min. The contents were filtered and washed with water. The product was dried in vacuum oven at 50° C. for 5 hr. The product was obtained as 57 mg (79%). LCMS E-S (M+H)=425.0. $^1$H NMR (400 MHz, DMSO-$d_6$) δ ppm 1.44 (d, J=6.57 Hz, 6H), 2.12 (s, 3H), 2.19 (s, 3H), 3.56-3.66 (m, 4H), 3.69-3.78 (m, 4H), 4.35 (d, J=4.80 Hz, 2H), 5.00 (quin, J=6.63 Hz, 1H), 5.89 (s, 1H), 7.13 (s, 1H), 8.03 (s, 1H), 8.65 (t, J=4.93 Hz, 1H), 11.56 (br. s., 1H).

Example 27

N-[(4,6-Dimethyl-2-oxo-1,2-dihydro-3-pyridinyl)methyl]-3-methyl-1-(1-methylethyl)-6-[6-(4-methyl-1-piperazinyl)-3-pyridinyl]-1H-pyrazolo[3,4-b]pyridine-4-carboxamide

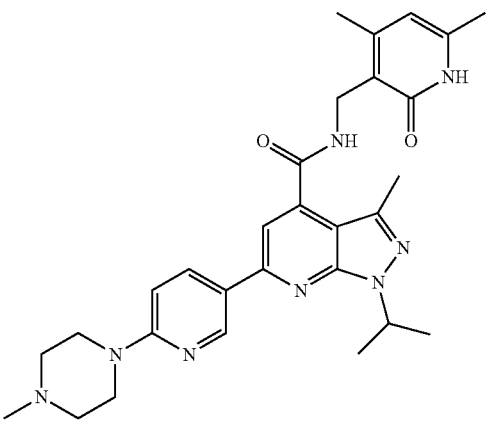

To a 10-mL microwave vial were added 6-chloro-N-[(4,6-dimethyl-2-oxo-1,2-dihydro-3-pyridinyl)methyl]-3-methyl-1-(1-methylethyl)-1H-pyrazolo[3,4-b]pyridine-4-carboxamide (70 mg, 0.180 mmol),1-methyl-4-[5-(4,4,5,5-tetramethyl-1,3,2-dioxaborolan-2-yl)-2-pyridinyl]piperazine (71.1 mg, 0.235 mmol), DMSO (2.0 mL) and sodium carbonate (0.271 mL, 0.541 mmol) and the mixture was degassed for 10 min under nitrogen. Bis(triphenylphosphine)palladium(II) chloride (10.13 mg, 0.014 mmol) was added and the contents were sealed. The mixture was irradiated (microwave) at 140° C. for 8 h. The reaction mixture was then quenched with water (5 mL) and filtered. The crude product was washed with water, dried, and then purified via silica gel chromatography (eluent: gradient of 0 to 15% (9:1 MeOH/NH$_4$OH)/DCM). The resulting product was treated with MeOH and 1N HCl. The mixture was concentrated in vacuo, dried under high vacuum and collected as the HCl salt, 42 mg (36%). LCMS E-S (M+H)=529.0 $^1$H NMR (400 MHz, DMSO-$d_6$) δ ppm 1.50 (d, 6H), 2.13 (s, 3H), 2.25 (s, 3H), 2.42 (s, 3H), 2.81 (d, J=4.55 Hz, 3H), 3.03-3.21 (m, 2H), 3.41 (br. s., 2H), 3.52 (d, J=11.37 Hz, 2H), 4.39 (d, J=5.05 Hz, 2H), 4.56 (d, J=14.40 Hz, 2H), 5.23 (quin, J=6.63 Hz, 1H), 5.91 (s, 1H), 7.19 (d, J=9.09 Hz, 1H), 7.68 (s, 1H), 8.50 (dd, J=9.09, 2.27 Hz, 1H), 8.73 (t, J=4.93 Hz, 3H), 8.98 (d, J=2.02 Hz, 3H), 10.97-11.21 (m, 2H)

Example 28

N-[(4,6-Dimethyl-2-oxo-1,2-dihydro-3-pyridinyl)methyl]-1-(1-methylethyl)-6-(1-piperazinyl)-1H-pyrazolo[3,4-b]pyridine-4-carboxamide

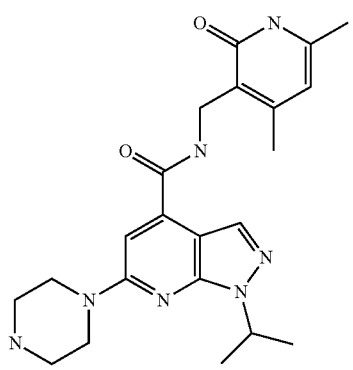 [SMILES: Cc1cc(C)c(CNC(=O)c2cc(N3CCOCC3)nc3c2cnn3C(C)C)c(=O)[nH]1]

To a 10 mL microwave vial equipped with stir bar were added 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (0.060 g, 0.160 mmol), ethanol (1.5 mL), and 1,1-dimethylethyl 1-piperazinecarboxylate (0.299 g, 1.605 mmol). The stirring suspension was placed onto heat block and heated at 120° C. for 18 h, and then irradiated (microwave) at 160° C. for 2 hr. The contents were cooled to room temperature, diluted into water (40 mL), and then adjusted to pH 6-7 and stirred for 15 min. The contents were filtered, washed with water, and then dried in hi-vac oven at 50° C. for 5 hr. The collected solid (52 mg) was dissolved in CH$_2$Cl$_2$/TFA (3 mL, 2:1) and stirred at room temperature for 2 hr. The volatiles were removed in vacuo to afford a residue which was then dissolved in CH$_2$Cl$_2$ and 10% 2M Ammonia (in methanol) in Chloroform. The crude product was purified by silica gel chromatography (eluent: gradient of 10% 2M Ammonia (in Methanol/Chloroform) and Dichloromethane). The isolated solid was dried in vacuum oven at 45° C. for 18 hr. to afford the final product as 38 mg (55% yield). LCMS E-S (M+H)=423.9. $^1$H NMR (400 MHz, DMSO-d$_6$) δ ppm 1.43 (d, J=6.82 Hz, 6H), 2.08-2.24 (m, 6H), 2.75-2.89 (m, 4H), 3.53-3.64 (m, 4H), 4.34 (d, J=4.80 Hz, 2H), 4.98 (quin, J=6.69 Hz, 1H), 5.89 (s, 1H), 7.10 (s, 1H), 8.00 (s, 1H), 8.65 (t, J=4.93 Hz, 1H), 11.55 (br. s., 1H).

Example 29

N-[(4,6-Dimethyl-2-oxo-1,2-dihydro-3-pyridinyl)methyl]-6-(3-hydroxy-3-methyl-1-butyn-1-yl)-1-(1-methylethyl)-1H-pyrazolo[3,4-b]pyridine-4-carboxamide

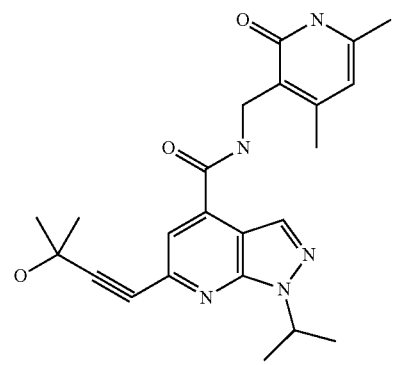 [SMILES: Cc1cc(C)c(CNC(=O)c2cc(C#CC(C)(C)O)nc3c2cnn3C(C)C)c(=O)[nH]1]

To a 10 mL microwave vial were sequentially added 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (0.15 g, 0.401 mmol), sodium iodide (0.012 g, 0.080 mmol), zinc (5.25 mg, 0.080 mmol), DMSO (2.5 mL), triethylamine (0.112 mL, 0.802 mmol), and DBU (0.121 mL, 0.802 mmol). The suspension was stirred and degassed with nitrogen for 5 min, forming an emulsion. Next added 2-methyl-3-butyn-2-ol (0.194 mL, 2.006 mmol) and Pd(Ph$_3$P)$_4$ (0.046 g, 0.040 mmol). The stirring contents were heated at 90° C. for 3 hr, and then allowed to cool to room temperature. The reaction mixture was poured into a solution of water and 20% THF/EtOAc, and stirred. The layers were separated, and the organic layer washed with brine. The organic layer was dried over MgSO$_4$, and then filtered through Celite, washing the filter pad with additional EtOAc. The filtrate was concentrated in vacuo and the crude residue dried overnight on a hi-vac pump. The crude product was purified by silica gel chromatography (eluent: gradient: 5-80% of DCM and Chloroform containing 10% 2M Ammonia (in methanol)). The collected product was dried in vacuum oven at 45° C. overnight, to afford the final product as 0.116 g (67% yield). LCMS E-S (M+H)=421.9. $^1$H NMR (400 MHz, DMSO-d$_6$) δ ppm 1.44-1.55 (m, 12H), 2.13 (s, 3H), 2.20 (s, 3H), 4.35 (d, J=4.80 Hz, 2H), 5.15-5.26 (m, 1H), 5.70 (s, 1H), 5.89 (s, 1H), 7.65 (s, 1H), 8.38 (s, 1H), 8.93 (t, J=4.80 Hz, 1H), 11.55 (s, 1H).

Example 30

N-[(4,6-Dimethyl-2-oxo-1,2-dihydro-3-pyridinyl)methyl]-1-(1-methylethyl)-6-(3-methyl-1H-indazol-5-yl)-1H-pyrazolo[3,4-b]pyridine-4-carboxamide

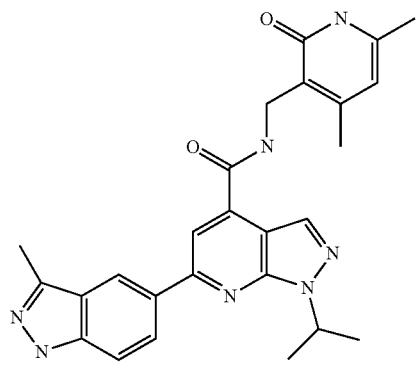 [SMILES: Cc1cc(C)c(CNC(=O)c2cc(-c3ccc4[nH]nc(C)c4c3)nc3c2cnn3C(C)C)c(=O)[nH]1]

To a 10 mL microwave vial were sequentially added 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (0.12 g, 0.321 mmol), 1,1-dimethylethyl 3-methyl-5-(4,4,5,5-tetramethyl-1,3,2-dioxaborolan-2-yl)-1H-indazole-1-carboxylate (0.138 g, 0.385 mmol), potassium phosphate (tribasic) (0.204 g, 0.963 mmol), 1,4-dioxane (3 mL), and water (0.75 mL). The stirring suspension was degassed with nitrogen for 10 min., wherein an emulsion had formed. Next added $PdCl_2(dppf)\text{-}CH_2Cl_2$ adduct (0.039 g, 0.048 mmol) and the contents were placed onto a heat block and stirred at 105° C. overnight. After cooling to room temperature, the reaction mixture was diluted with EtOAc and filtered through Celite. The filter pad was washed with 50% THF/EtOAc. Silica gel was added to the combined filtrates and the mixture concentrated in vacuo to a solid. The contents were purified by silica gel chromatography (dry loaded, eluent: 5-80% gradient of DCM and chloroform containing 10% 2M Ammonia (in methanol)). The isolated solid was dried in vacuum oven at 45° C. overnight to afford the final product as 0.126 g (81%). LCMS E-S (M+H)=470.3. $^1$H NMR (400 MHz, DMSO-$d_6$) δ ppm 1.56 (d, J=6.57 Hz, 6H), 2.13 (s, 3H), 2.25 (s, 3H), 2.60 (s, 3H), 4.43 (d, J=5.05 Hz, 2H), 5.31-5.43 (m, 1H), 5.91 (s, 1H), 7.60 (d, J=8.84 Hz, 1H), 8.22 (s, 1H), 8.29-8.37 (m, 2H), 8.60 (s, 1H), 8.97 (t, J=5.05 Hz, 1H), 11.58 (br. s., 1H), 12.84 (s, 1H).

Example 31

N-[(4,6-Dimethyl-2-oxo-1,2-dihydro-3-pyridinyl)methyl]-1-(1-methylethyl)-6-(phenylethynyl)-1H-pyrazolo[3,4-b]pyridine-4-carboxamide

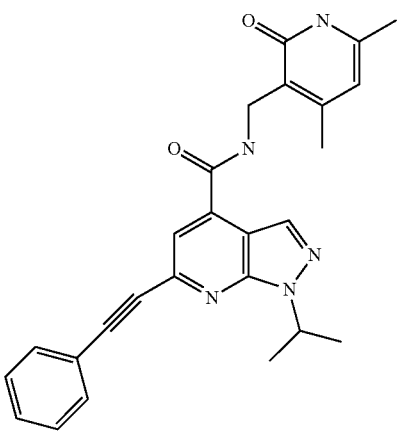 [SMILES: Cc1cc(C)c(CNC(=O)c2cc(C#Cc3ccccc3)nc3c2cnn3C(C)C)c(=O)[nH]1]

To a 10 mL microwave vial were sequentially added 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (0.125 g, 0.334 mmol), sodium iodide (10.02 mg, 0.067 mmol) and zinc (4.37 mg, 0.067 mmol), DMSO (2.5 mL), triethylamine (0.093 mL, 0.669 mmol) and DBU (0.101 mL, 0.669 mmol). The stirring suspension was degassed with nitrogen for 5 min., wherein an emulsion had formed. Added next were phenylacetylene (0.110 mL, 1.003 mmol) and Pd(Ph$_3$P)$_4$ (0.039 g, 0.033 mmol). The sealed reaction mixture was placed onto a heat block, stirred at 90° C. for 3 hr, and then allowed to cool to room temperature overnight. The contents were poured onto water and 20% THF/EtOAc, stirred, and the layers separted. The organic layer was washed with brine, dried over MgSO$_4$, filtered, and concentrated in vacuo. The filter pad was washed with additional EtOAc. The combined filtrates were concentrated in vacuo to a yellow/orange residue that was dried on hi-vac pump. The crude solid was then pre-adsorbed onto silica gel and purified by silica gel chromatography (dry loaded, eluent: 5-80% gradient of DCM and chloroform containing 10% 2M Ammonia (in methanol)). The isolated product was obtained as a yellow solid which was then further purified by reverse phase HPLC (mobile phase: 20-90% ACN in H$_2$O, 0.1% TFA, Gradient time: 8 min). The isolated solid was dissolved in 10% MeOH/CH$_2$Cl$_2$ and treated with 0.6 g of Silicycle carbonate resin for 30 min. The contents were filtered through Celite and the filter pad washed with additional 10% MeOH/CH$_2$Cl$_2$. The combined filtrates were concentrated in vacuo to afford a solid which was dried in vacuum oven for 18 hr. The final product was collected as 0.045 g (30%). LCMS E-S (M+H)=440.2. $^1$H NMR (400 MHz, DMSO-$d_6$) δ ppm 1.51 (d, J=6.82 Hz, 6H), 2.13 (s, 3H), 2.21 (s, 3H), 4.37 (d, J=4.80 Hz, 2H), 5.18-5.33 (m, 1H), 5.90 (s, 1H), 7.45-7.56 (m, 3H), 7.64-7.73 (m, 2H), 7.86 (s, 1H), 8.42 (s, 1H), 8.92 (t, J=4.80 Hz, 1H), 11.55 (br. s., 1H).

Example 32

N-[(4,6-Dimethyl-2-oxo-1,2-dihydro-3-pyridinyl)methyl]-1-(1-methylethyl)-6-(2-phenylethyl)-1H-pyrazolo[3,4-b]pyridine-4-carboxamide

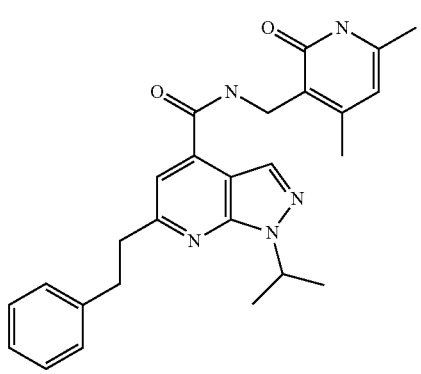 [SMILES: Cc1cc(C)c(CNC(=O)c2cc(CCc3ccccc3)nc3c2cnn3C(C)C)c(=O)[nH]1]

To a suspension of palladium on carbon (0.063 g, 0.059 mmol) in ethanol (1 mL) under nitrogen was added N-[(4,6-dimethyl-2-oxo-1,2-dihydro-3-pyridinyl)methyl]-1-(1-methylethyl)-6-(4-pyridinylethynyl)-1H-pyrazolo[3,4-b]pyridine-4-carboxamide (0.13 g, 0.295 mmol) and then ethanol (5 mL) and tetrahydrofuran (THF) (1.5 mL). The suspension was stirred under an atmosphere of hydrogen (ca. 1 atm, balloon) overnight. The reaction mixture was then evacuated with nitrogen, and diluted with 10% MeOH/DCM. Celite was added and the contents stirred for 15 min., and then filtered through Celite (analytical grade) and washed with 10% MeOH/DCM. The filtrate was concentrated in vacuo and purified by silica gel chromatography (eluent: gradient of 5-95%. Dichloromethane/Chloroform containing 10% 2M ammonia (in methanol). The collected solid was dried in vacuum oven at 45° C. for 18 h. The final product was collected as 0.112 g (84%). LCMS E-S (M+H)=445.3. $^1$H NMR (400 MHz, DMSO-$d_6$) δ ppm 1.46 (d, J=6.57 Hz, 6H), 2.13 (s, 3H), 2.21 (s, 3H), 3.08-3.18 (m, 2H), 3.22-3.29 (m, 2H), 4.36 (d, J=5.05 Hz, 2H), 5.18 (quin, J=6.69 Hz, 1H), 5.90 (s, 1H), 7.28 (d, J=6.06 Hz, 2H), 7.53 (s, 1H), 8.26 (s, 1H), 8.38-8.47 (m, 2H), 8.72 (t, J=5.05 Hz, 1H), 11.56 (s, 1H).

Example 33

N-[(4,6-Dimethyl-2-oxo-1,2-dihydro-3-pyridinyl)methyl]-1-(1-methylethyl)-6-(4-pyridinylethynyl)-1H-pyrazolo[3,4-b]pyridine-4-carboxamide

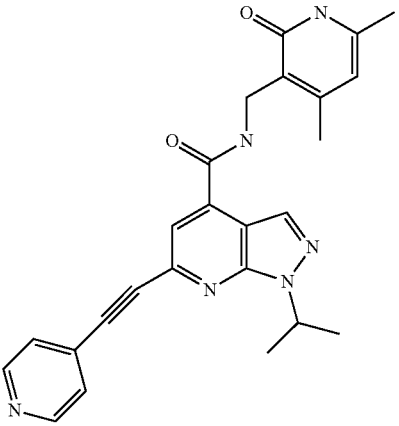 [SMILES: Cc1cc(C)c(CNC(=O)c2cc(C#Cc3ccncc3)nc3c2cnn3C(C)C)c(=O)[nH]1]

The title compound was prepared in the same manner as described in example 31 from 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (0.15 g, 0.401 mmol), sodium iodide (0.012 g, 0.080 mmol), zinc (5.25 mg, 0.080 mmol), DMSO (4.0 mL), triethylamine (0.168 mL, 1.204 mmol), DBU (0.121 mL, 0.802), 4-ethynylpyridine (0.112 g, 0.802 mmol), and Pd(Ph$_3$P)$_4$ (0.046 g, 0.040 mmol). The crude product was purified by silica gel chromatography (eluent: Gradient of 5-100% of DCM and chloroform containing 10% 2M Ammonia (in methanol)). The isolated product was dried in vacuum oven for 18 hr. to afford the final product as 0.032 g (18%). LCMS E-S (M+H)=441.1. $^1$H NMR (400 MHz, DMSO-$d_6$) δ ppm 1.51 (d, J=6.57 Hz, 6H), 2.13 (s, 3H), 2.21 (s, 3H), 4.37 (d, J=4.80 Hz, 2H), 5.20-5.32 (m, 1H), 5.90 (s, 1H), 7.62-7.69 (m, 2H), 7.93 (s, 1H), 8.45 (s, 1H), 8.67-8.75 (m, 2H), 8.93 (t, J=4.80 Hz, 1H), 11.55 (s, 1H).

Example 34

N-[(4,6-Dimethyl-2-oxo-1,2-dihydro-3-pyridinyl)methyl]-1-(1-methylethyl)-6-(phenylamino)-1H-pyrazolo[3,4-b]pyridine-4-carboxamide

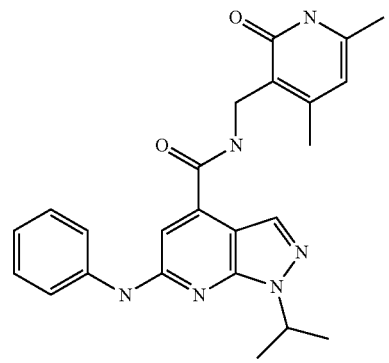 [SMILES: Cc1cc(C)c(CNC(=O)c2cc(Nc3ccccc3)nc3c2cnn3C(C)C)c(=O)[nH]1]

To a 10 mL microwave vial were sequentially added 6-chloro-N-[(4,6-dimethyl-2-oxo-1,2-dihydro-3-pyridinyl)methyl]-1-(1-methylethyl)-1H-pyrazolo[3,4-b]pyridine-4- carboxamide (0.100 g, 0.267 mmol), cesium carbonate (0.305 g, 0.936 mmol), 1,4-Dioxane (2.5 mL) and aniline (0.049 mL, 0.535 mmol). The stirring suspension was degassed with nitrogen for 10 min. Added next were BINAP (0.033 g, 0.053 mmol) and palladium(II) acetate (6.01 mg, 0.027 mmol). The sealed mixture was stirred at 105° C. overnight. After cooling to room temperature, the contents were poured onto EtOAc and filtered through Celite. The filter pad was washed with additional 50% THF/EtOAc. The combined filtrates were treated with silica gel and concentrated in vacuo. The crude product was purified by silica gel chromatography (dry loaded, eluent: Gradient 5-80% of DCM and chloroform containing 10% 2M Ammonia (in methanol))). The isolated solid was dried in a vacuum oven overnight and the final product collected as 0.061 g (52%). LCMS E-S (M+H)=431.3. $^1$H NMR (400 MHz, DMSO-$d_6$) δ ppm 1.50 (d, J=6.57 Hz, 6H), 2.13 (s, 3H), 2.23 (s, 3H), 4.35 (d, J=5.05 Hz, 2H), 4.98-5.11 (m, 1H), 5.90 (s, 1H), 6.93-7.00 (m, 2H), 7.34 (t, J=7.96 Hz, 2H), 7.86 (d, J=7.58 Hz, 2H), 7.97 (s, 1H), 8.59 (t, J=5.05 Hz, 1H), 9.62 (s, 1H), 11.58 (br. s., 1H).

Example 35

N-[(4,6-Dimethyl-2-oxo-1,2-dihydro-3-pyridinyl)methyl]-1-(1-methylethyl)-6-[(phenylmethyl)amino]-1H-pyrazolo[3,4-b]pyridine-4-carboxamide

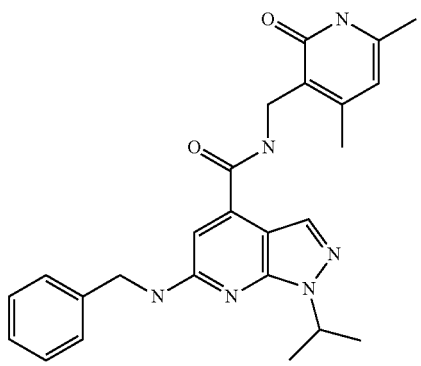 [SMILES: Cc1cc(C)c(CNC(=O)c2cc(NCc3ccccc3)nc3c2cnn3C(C)C)c(=O)[nH]1]

To a 10 mL microwave vial were sequentially added 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (0.100 g, 0.267 mmol), ethanol (2.0 mL) and then benzylamine (0.350 mL, 3.21 mmol) via syringe at once. The sealed contents were irradiated at 140° C. for 3 hr. The contents were transferred to a heat block and heated at 135° C. for 16 hr., and then at 145° C. for an additional 12 h. After cooling to room temperature, the contents were diluted with $CH_2Cl_2$ and pre-absorbed onto silica gel. The crude product was purified by silica gel chromatography (dry loaded, eluent; gradient of 5-80% DCM and chloroform containing 10% 2M Ammonia (in methanol)). The isolated solid was triturated with MTBE, filtered, and washed with additional MTBE. The collected solid was dried in vacuum oven at 45° C. overnight to afford the final product as 0.067 g (55%). LCMS E-S (M+H)=445.3. $^1$H NMR (400 MHz, DMSO-$d_6$) δ ppm 1.38 (d, J=6.57 Hz, 6H), 2.12 (s, 3H), 2.20 (s, 3H), 4.31 (d, J=5.05 Hz, 2H), 4.56 (d, J=6.06 Hz, 2H), 4.92 (quin, J=6.69 Hz, 1H), 5.88 (s, 1H), 6.69 (s, 1H), 7.18-7.25 (m, 1H), 7.26-7.35 (m, 2H), 7.35-7.43 (m, 2H), 7.77 (t, J=5.94 Hz, 1H), 7.83 (s, 1H), 8.47 (t, J=5.05 Hz, 1H), 11.55 (br. s., 1H).

Example 36

N-[(4,6-Dimethyl-2-oxo-1,2-dihydro-3-pyridinyl)methyl]-6-methyl-1-(1-methylethyl)-1H-pyrazolo[3,4-b]pyridine-4-carboxamide

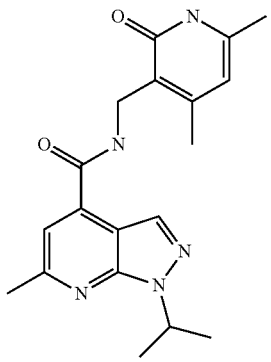

In a 25 mL sealable tube under nitrogen were combined 6-methyl-1-(1-methylethyl)-1H-pyrazolo[3,4-b]pyridine-4-carboxylic acid (60 mg, 0.27 mmol) and 3-(aminomethyl)-4,6-dimethyl-2(1H)-pyridinone.HCl (62 mg, 0.33 mmol) in DMSO (3 mL). 1-hydroxy-7-azabenzotriazole (56 mg, 0.41 mmol) was added and the resulting mixture was degassed with nitrogen for 10 minutes. N-methylmorpholine (0.11 ml, 0.96 mmol) and EDC (79 mg, 0.41 mmol) were added, the vessel was sealed, and the light brown mixture was stirred at room temperature for 2 days. Next added 2 mL of water and the mixture was stirred for 10 min. Solids that precipitated were sonicated, and allowed to stand at room temperature for 10 min. The contents were filtered, washed with water, and dried to afford the title compound (68 mg, 68%) as a light pink solid. LCMS E-S (M+H)=354.3. $^1$H NMR (400 MHz, DMSO-$d_6$) δ ppm 11.54 (s, 1H), 8.69 (t, J=4.80 Hz, 1H), 8.26 (s, 1H), 7.46 (s, 1H), 5.89 (s, 1H), 5.20 (quin, J=6.69 Hz, 1H), 4.36 (d, J=5.05 Hz, 2H), 2.63 (s, 3H), 2.21 (s, 3H), 2.13 (s, 3H), 1.48 (d, J=6.57 Hz, 6H).

Example 37

N-[(4,6-Dimethyl-2-oxo-1,2-dihydro-3-pyridinyl)methyl]-1,6-bis(1-methylethyl)-1H-pyrazolo[3,4-b]pyridine-4-carboxamide

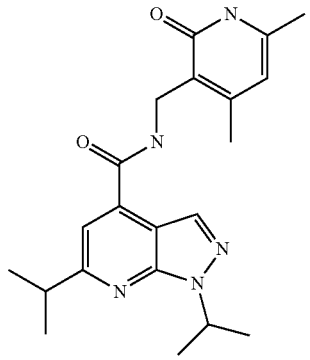 [SMILES: Cc1cc(C)c(CNC(=O)c2cc(C(C)C)nc3c2cnn3C(C)C)c(=O)[nH]1]

The title compound was prepared in the same manner as described in example 52 using 1,6-bis(1-methylethyl)-1H-pyrazolo[3,4-b]pyridine-4-carboxylic acid (70 mg, 0.28 mmol) to afford an off-white solid (95 mg, 86%). LCMS E-S (M+H)=382.3. $^1$H NMR (400 MHz, DMSO-$d_6$) δ ppm 11.56 (br. s., 1H, 8.76 (t, J=4.93 Hz, 1H), 8.26 (s, 1H), 7.50 (s, 1H), 5.90 (s, 1H), 5.15-5.25 (m, 1H), 4.37 (d, J=5.05 Hz, 2H), 3.13-3.23 (m, 1H), 2.22 (s, 3H), 2.13 (s, 3H), 1.50 (d, J=6.57 Hz, 6H), 1.32 (d, J=6.82 Hz, 6H).

Example 38

N-[(4,6-Dimethyl-2-oxo-1,2-dihydro-3-pyridinyl)methyl]-1-(1-methylethyl)-6-phenyl-1H-pyrazolo[3,4-b]pyridine-4-carboxamide

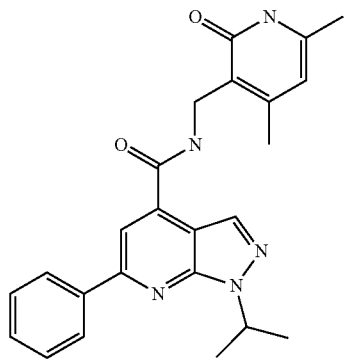 [SMILES: Cc1cc(C)c(CNC(=O)c2cc(-c3ccccc3)nc3c2cnn3C(C)C)c(=O)[nH]1]

In a 25 mL sealable tube under nitrogen were combined 1-(1-methylethyl)-6-phenyl-1H-pyrazolo[3,4-b]pyridine-4-carboxylic acid (70 mg, 0.25 mmol) and 3-(aminomethyl)-4,6-dimethyl-2(1H)-pyridinone.HCl (56.3 mg, 0.3 mmol) in DMSO (3 mL). 1-hydroxy-7-azabenzotriazole (51 mg, 0.37 mmol) was added and the resulting mixture was degassed with nitrogen for 10 min. N-methylmorpholine (0.1 ml, 0.87 mmol) and EDC (72 mg, 0.37 mmol) were added, the vessel was sealed, and the bright yellow mixture was stirred at room temperature for 2 days. Next added 2 mL of water, and the contents were stirred for 10 min. Solids that precipitated were sonicated, and allowed to stand at room temperature for 10 min. The reaction contents were filtered and washed with water. The solid was treated with 2 mL of EtOH, sonicated and heated, and then allowed to cool to room temperature. The contents were filtered, washed with water and dried to afford the title compound (74 mg, 70%) as a white solid. LCMS E-S (M+H)=416.3. $^1$H NMR (400 MHz, DMSO-d$_6$) δ ppm 11.58 (s, 1H), 8.98 (t, J=4.80 Hz, 1H), 8.38 (s, 1H), 8.25-8.30 (m, 2H), 8.17 (s, 1H), 7.49-7.59 (m, 3H), 5.91 (s, 1H), 5.30-5.38 (m, 1H), 4.42 (d, J=4.80 Hz, 2H), 2.23 (s, 3H), 2.13 (s, 3H), 1.55 (d, J=6.57 Hz, 6H).

Example 39

N-[(4,6-Dimethyl-2-oxo-1,2-dihydro-3-pyridinyl)methyl]-6-(4-fluorophenyl)-1-(1-methylethyl)-1H-pyrazolo[3,4-b]pyridine-4-carboxamide

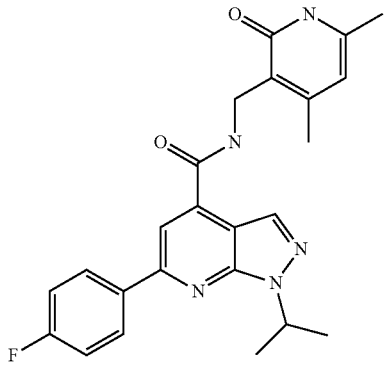 [SMILES: Cc1cc(C)c(CNC(=O)c2cc(-c3ccc(F)cc3)nc3c2cnn3C(C)C)c(=O)[nH]1]

In a 25 mL sealable tube under nitrogen were combined 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (90 mg, 0.24 mmol), (4-fluorophenyl)boronic acid (33.7 mg, 0.24 mmol) in 1,4-dioxane (3 mL). PdCl$_2$(dppf)-CH$_2$Cl$_2$ adduct (19.7 mg, 0.024 mmol) was added and the resulting mixture was degassed with nitrogen for 10 min. Sodium carbonate (77 mg, 0.72 mmol) was added, the vessel was sealed, and the mixture was heated at 85° C. for 2 hrs and then at 100° C. overnight. Added an additional 2 eq of boronic acid and 0.2 eq of PdCl$_2$(dppf)-CH$_2$Cl$_2$ adduct. The contents were heated at 120° C. for 4 hr. and then irradiated (microwave) first at 160° C. for 90 min, and then at 190° C. for 2 hrs. After cooling to room temperature, the solids were filtered, washed with DMSO and the filtrate was evaporated. The crude product was purified first by reverse-phase HPLC (C18, 5% to 80% CH$_3$CN in water with 0.1% TFA, 18 minute gradient) and then silica gel chromatography (eluent: gradient 0 to 90:10:1 DCM/MeOH/NH$_4$OH). The collected solid was dried to afford the title compound (13 mg, 12%) as a white solid. LCMS E-S (M+H)=434.2. $^1$H NMR (400 MHz, DMSO-d$_6$) δ ppm 11.58 (br. s., 1H), 8.96 (t, J=4.67 Hz, 1H), 8.38 (s, 1H), 8.33 (dd, J=8.84, 5.56 Hz, 2H), 8.16 (s, 1H), 7.40 (t, J=8.84 Hz, 2H), 5.91 (s, 1H), 5.33 (dt, J=13.26, 6.76 Hz, 1H), 4.41 (d, J=4.55 Hz, 2H), 2.23 (s, 3H), 2.13 (s, 3H), 1.55 (d, J=6.57 Hz, 6H).

Example 40

6-{4-[(Dimethylamino)sulfonyl]phenyl}-N-[(4,6-dimethyl-2-oxo-1,2-dihydro-3-pyridinyl)methyl]-1-(1-methylethyl)-1H-pyrazolo[3,4-b]pyridine-4-carboxamide

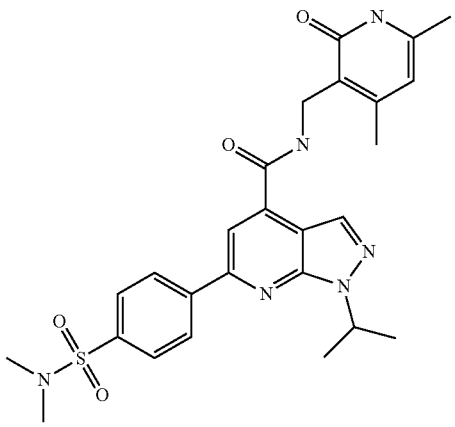

In a 25 mL sealable tube under nitrogen were combined 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (85 mg, 0.23 mmol) and {4-[(dimethylamino)sulfonyl]phenyl}boronic acid (104 mg, 0.46 mmol) in DME/water (3 ml:1 ml). PdCl$_2$(dppf)-CH$_2$Cl$_2$ adduct (9.3 mg, 0.011 mmol) was added and the resulting mixture was degassed with nitrogen for 10 min. Sodium bicarbonate (57.3 mg, 0.68 mmol) was added and the insoluble light brown mixture was heated in an oil bath at 110° C. for 3 hrs. After cooling, 2 mL of water was added to the black mixture and solids that precipitated were filtered. DMF was added along with a few drops of water and solids were filtered. DCM/MeOH (1:1) was added to the grey solids and they were filtered and dried to afford the title compound (69 mg, 57%)

as a grayish solid. LCMS E-S (M+H)=523.2. $^1$H NMR (400 MHz, DMSO-d$_6$) δ ppm 11.59 (br. s., 1H), 9.01 (br. s., 1H), 8.51 (m, J=8.34 Hz, 2H), 8.44 (s, 1H), 8.27 (s, 1H), 7.93 (m, J=8.34 Hz, 2H), 5.91 (s, 1H), 5.36 (dt, J=13.14, 6.57 Hz, 1H), 4.43 (d, J=4.55 Hz, 2H), 2.66 (s, 6H), 2.23 (s, 3H), 2.13 (s, 3H), 1.56 (d, J=6.57 Hz, 6H).

Example 41

6-[6-(Dimethylamino)-3-pyridinyl]-N-[(4,6-dimethyl-2-oxo-1,2-dihydro-3-pyridinyl)methyl]-1-(1-methylethyl)-1H-pyrazolo[3,4-b]pyridine-4-carboxamide

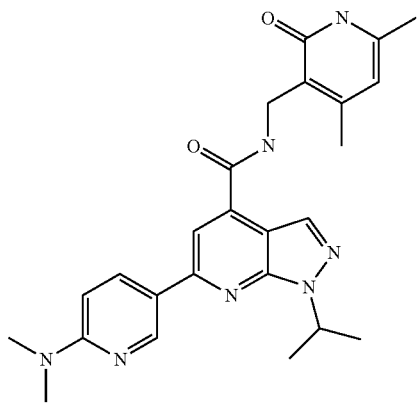

In a 25 mL sealable tube under nitrogen were combined 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (80 mg, 0.21 mmol) and [6-(dimethylamino)-3-pyridinyl]boronic acid (53.3 mg, 0.32 mmol) in DME/water (3 mL:1 mL). PdCl$_2$ (dppf)-CH$_2$Cl$_2$ adduct (8.7 mg, 0.011 mmol) was added and the resulting mixture was degassed with nitrogen for 10 min. Sodium bicarbonate (53.9 mg, 0.64 mmol) was added, the vessel was sealed, and the insoluble green mixture was irradiated (microwave) at 150° C. for 20 min. After cooling, 2 mL of water was added to the dark green mixture and solids that precipitated were filtered. EtOAc was added, the mixture was heated and some hexanes were added. Solids were filtered, dissolved in DCM/MeOH (1:1), and filtered through a pad of silica gel and the filtrate was evaporated. The residue was dissolved in DCM and purified by SiO$_2$ chromatography (eluent: gradient of 0 to 90:10 DCM/MeOH) to afford a residual oil that was triturated with EtOH/EtOAc (1:1). The resultant solid was filtered and dried to afford the title compound (46 mg, 45%) as a yellow solid. LCMS E-S (M+H)=460.2. $^1$H NMR (400 MHz, DMSO-d$_6$) δ ppm 11.58 (s, 1H), 9.02 (d, J=2.27 Hz, 1H), 8.87 (t, J=4.67 Hz, 1H), 8.36 (dd, J=8.84, 2.53 Hz, 1H), 8.31 (s, 1H), 8.08 (s, 1H), 6.79 (d, J=8.84 Hz, 1H), 5.91 (s, 1H), 5.25-5.34 (m, 1H), 4.40 (d, J=4.80 Hz, 2H), 3.12 (s, 6H), 2.23 (s, 3H), 2.13 (s, 3H), 1.53 (d, J=6.57 Hz, 6H).

Example 42

N-[(4,6-Dimethyl-2-oxo-1,2-dihydro-3-pyridinyl)methyl]-6-{4-[(methylamino)sulfonyl]phenyl}-1-(1-methylethyl)-1H-pyrazolo[3,4-b]pyridine-4-carboxamide

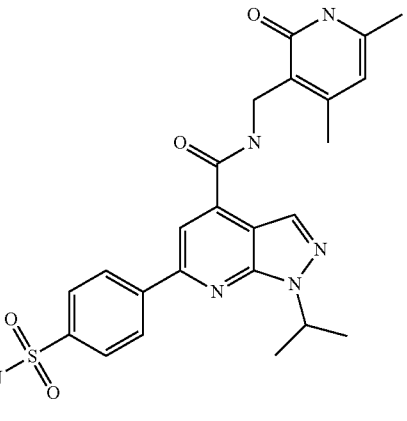

In a 25 mL sealable tube under nitrogen were combined 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (75 mg, 0.2 mmol), {4-[(methylamino)sulfonyl]phenyl}boronic acid (69 mg, 0.32 mmol) in DME/water (3 ml:1 ml). PdCl$_2$(dppf)-CH$_2$Cl$_2$ adduct (8.2 mg, 0.01 mmol) was added and the resulting mixture was degassed with nitrogen for 10 min. Sodium bicarbonate (50.6 mg, 0.6 mmol) was added, the vessel was sealed, and the insoluble mixture was heated in a microwave at 150° C. for 30 min. After cooling, 2 mL of water was added to the mixture and solids that precipitated were filtered. DCM/MeOH (1:1) was added and the solution was filtered through a pad of silica gel and the filtrate was evaporated. The residue was purified by silica gel chromatography (eluent: gradient of 0 to 90:10 DCM/MeOH) and the isolated solid triturated in EtOAc. The solids were filtered and dried to afford the title compound (29 mg, 28%) as an off-white solid. LCMS E-S (M+H)=509.0. $^1$H NMR (400 MHz, DMSO-d$_6$) δ ppm 11.58 (br. s., 1H), 8.99 (t, J=4.93 Hz, 1H), 8.47 (m, J=8.59 Hz, 2H), 8.43 (s, 1H), 8.25 (s, 1H), 7.95 (m, J=8.59 Hz, 2H), 7.60 (br. s., 1H), 5.91 (s, 1H), 5.36 (quin, J=6.69 Hz, 1H), 4.42 (d, J=4.80 Hz, 2H), 2.46 (s, 3H), 2.23 (s, 3H), 2.13 (s, 3H), 1.56 (d, J=6.82 Hz, 6H).

Example 43

6-(4-Aminophenyl)-N-[(4,6-dimethyl-2-oxo-1,2-dihydro-3-pyridinyl)methyl]-1-(1-methylethyl)-1H-pyrazolo[3,4-b]pyridine-4-carboxamide

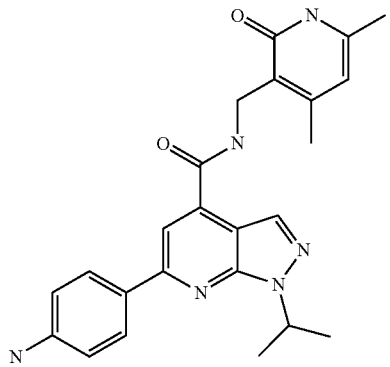

In a 25 mL sealable tube under nitrogen were combined 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (80 mg, 0.21 mmol) and (4-aminophenyl)boronic acid (44 mg, 0.32 mmol) in DME/water (3 ml:1 ml). PdCl$_2$(dppf)-CH$_2$Cl$_2$ adduct (8.74 mg, 0.011 mmol) was added and the resulting mixture was degassed with nitrogen for 10 min. Sodium bicarbonate (53.9 mg, 0.64 mmol) was added, the vessel was sealed, and the insoluble light pink mixture was irradiated (microwave) at 150° C. for 30 min. After cooling, DCM/MeOH (1:1) was added, it was pre-absorbed on silica gel and purified by silica gel chromatography (eluent: gradient 0 to 90:10:1 DCM/MeOH/NH$_4$OH). The isolated solid was treated with MeOH. The solids that precipitated were filtered and dried to afford the title compound (63 mg, 66%) as a yellow solid. LCMS E-S (M+H)=431.3. $^1$H NMR (400 MHz, DMSO-d$_6$) δ ppm 11.56 (s, 1H), 8.88 (t, J=4.93 Hz, 1H), 8.27 (s, 1H), 8.01 (s, 1H), 7.99 (d, J=2.02 Hz, 2H), 6.69 (s, 1H), 6.67 (s, 1H), 5.90 (s, 1H), 5.61 (s, 2H), 5.24-5.32 (m, 1H), 4.40 (d, J=4.80 Hz, 2H), 2.22 (s, 3H), 2.13 (s, 3H), 1.53 (s, 3H), 1.51 (s, 3H).

Example 44

6-[4-(acetylamino)phenyl]-N-[(4,6-dimethyl-2-oxo-1,2-dihydro-3-pyridinyl)methyl]-1-(1-methylethyl)-1H-pyrazolo[3,4-b]pyridine-4-carboxamide

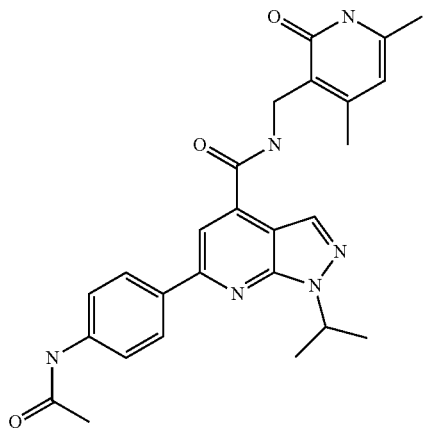 [SMILES: CC(=O)Nc1ccc(-c2cc(C(=O)NCc3c(C)cc(C)[nH]c3=O)c3cnn(C(C)C)c3n2)cc1]

In a 25 mL sealable tube under nitrogen were combined 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (80 mg, 0.21 mmol) and [4-(acetylamino)phenyl]boronic acid (57.5 mg, 0.32 mmol) in DME/water (3 ml:1 ml). PdCl$_2$(dppf)-CH$_2$Cl$_2$ adduct (8.7 mg, 0.010 mmol) was added and the resulting mixture was degassed with nitrogen for 10 min. Sodium bicarbonate (53.9 mg, 0.64 mmol) was added, the vessel was sealed, and the insoluble light brown mixture was heated at 110° C. for 2.5 h. After cooling, 2 mL of water was added to the dark grey mixture and solids that precipitated were filtered. EtOAc was added, the mixture was heated and some hexanes were added. The solids were filtered, dissolved in DCM/MeOH (1:1) and 1 mL of DMF. The contents were pre-absorbed onto silica gel and purified by silica gel chromatography (eluent: gradient 0 to 90:10:1 DCM/MeOH/NH$_4$OH). The isolated product was treated with MeOH, and the solids that precipitated were filtered, washed with hexanes and dried to afford the title compound (55 mg, 52%) as a white solid. LCMS E-S (M+H)=473.1. $^1$H NMR (400 MHz, DMSO-d$_6$) δ ppm 11.57 (s, 1H), 10.18 (s, 1H), 8.93 (t, J=4.93 Hz, 1H), 8.35 (s, 1H), 8.22 (m, J=8.84 Hz, 2H), 8.13 (s, 1H), 7.76 (m, J=8.84 Hz, 2H), 5.91 (s, 1H), 5.28-5.37 (m, 1H), 4.41 (d, J=4.80 Hz, 2H), 2.23 (s, 3H), 2.13 (s, 3H), 2.09 (s, 3H), 1.54 (d, J=6.82 Hz, 6H).

Example 45

6-(3-aminophenyl)-N-[(4,6-dimethyl-2-oxo-1,2-dihydro-3-pyridinyl)methyl]-1-(1-methylethyl)-1H-pyrazolo[3,4-b]pyridine-4-carboxamide

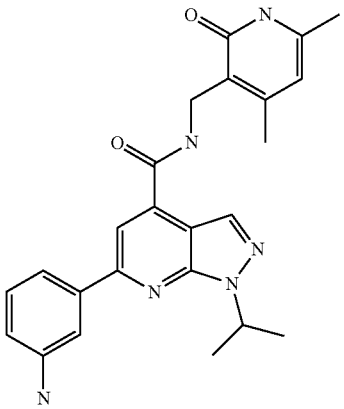 [SMILES: Cc1cc(C)c(CNC(=O)c2cc(-c3cccc(N)c3)nc3c2cnn3C(C)C)c(=O)[nH]1]

In a 25 mL sealable tube under nitrogen were combined 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (80 mg, 0.21 mmol) and (3-aminophenyl)boronic acid (46.9 mg, 0.34 mmol) in DME/water (3 ml:1 ml). PdCl$_2$(dppf)-CH$_2$Cl$_2$ adduct (8.74 mg, 0.01 mmol) was added and the resulting mixture was degassed with nitrogen for 10 min. Sodium bicarbonate (53.9 mg, 0.64 mmol) was added, the vessel was sealed, and the reaction mixture was irradiated (microwave) at 150° C. for 25 min. After cooling, 2 mL of water was added to the black mixture and solids that precipitated were filtered. DCM/MeOH (1:1) was added, the mixture was pre-absorbed on silica gel and purified by silica gel chromatography (eluent: gradient 0 to 90:10:1 DCM/MeOH/NH$_4$OH). The isolated product was treated with EtOH/EtOAc/hexanes (1:1:1). The solids that precipitated were filtered and dried to afford the title compound (40 mg, 42%) as a light grey solid. LCMS E-S (M+H)=431.3. $^1$H NMR (400

MHz, DMSO-d$_6$) δ ppm 11.56 (br. s., 1H), 8.96 (t, J=4.93 Hz, 1H), 8.34 (s, 1H), 8.02 (s, 1H), 7.46 (t, J=1.89 Hz, 1H), 7.36 (d, J=7.58 Hz, 1H), 7.18 (t, J=7.71 Hz, 1H), 6.69 (dd, J=7.83, 1.52 Hz, 1H), 5.90 (s, 1H), 5.25-5.37 (m, 3H), 4.40 (d, J=4.80 Hz, 2H), 2.22 (s, 3H), 2.13 (s, 3H), 1.55 (s, 3H), 1.54 (s, 3H).

Example 46

N-[(4,6-Dimethyl-2-oxo-1,2-dihydro-3-pyridinyl)methyl]-6-{4-[(methylamino)carbonyl]phenyl}-1-(1-methylethyl)-1H-pyrazolo[3,4-b]pyridine-4-carboxamide

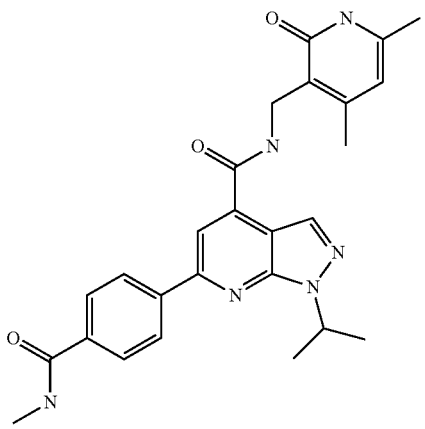 [SMILES: CNC(=O)c1ccc(-c2cc(C(=O)NCc3c(C)cc(C)[nH]c3=O)c3cnn(C(C)C)c3n2)cc1]

The title compound was prepared in the same manner as described in example 61 using {4-[(methylamino)carbonyl]phenyl}boronic acid (57.5 mg, 0.32 mmol) to afford a light grey solid (70 mg, 68%). LCMS E-S (M+H)=473.1. $^1$H NMR (400 MHz, DMSO-d$_6$) δ ppm 11.58 (s, 1H), 9.00 (t, J=4.80 Hz, 1H), 8.59 (q, J=4.38 Hz, 1H), 8.41 (s, 1H), 8.35 (m, J=8.59 Hz, 2H), 8.24 (s, 1H) 8.01 (m, J=8.59 Hz, 2H), 5.91 (s, 1H), 5.33-5.41 (m, 1H), 4.42 (d, J=4.80 Hz, 2H), 2.83 (d, J=4.55 Hz, 3H), 2.23 (s, 3H), 2.13 (s, 3H), 1.56 (s, 3H), 1.55 (s, 3H).

Example 47

6-[3-(Acetylamino)phenyl]-N-[(4,6-dimethyl-2-oxo-1,2-dihydro-3-pyridinyl)methyl]-1-(1-methylethyl)-1H-pyrazolo[3,4-b]pyridine-4-carboxamide

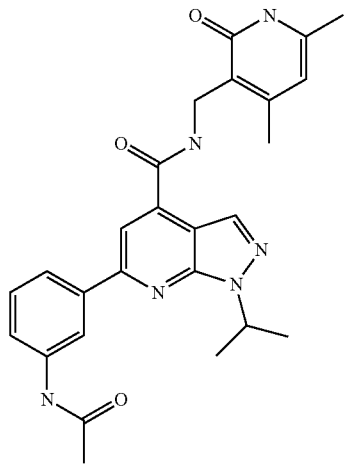 [SMILES: CC(=O)Nc1cccc(-c2cc(C(=O)NCc3c(C)cc(C)[nH]c3=O)c3cnn(C(C)C)c3n2)c1]

In a 25 mL sealable tube under nitrogen were combined 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (80 mg, 0.21 mmol) and [3-(acetylamino)phenyl]boronic acid (57.5 mg, 0.32 mmol) in DME/water (3 ml:1 ml). PdCl$_2$(dppf)-CH$_2$Cl$_2$ adduct (8.7 mg, 0.010 mmol) was added and the resulting mixture was degassed with nitrogen for 10 min. Sodium bicarbonate (53.9 mg, 0.64 mmol) was added, the vessel was sealed and the reaction mixture was irradiated (microwave) at 150° C. for 30 min. After cooling, 2 mL of water was added and solids that precipitated were filtered. DCM/MeOH (1:1) was added, the mixture was pre-absorbed on silica gel and purified by silica gel chromatography (eluent: gradient 0 to 90:10:1 DCM/MeOH/NH$_4$OH). The isolated product was treated with EtOH and DCM, filtered, and dried to afford the title compound (65 mg, 63%) as a white solid. LCMS E-S (M+H)=473.1. $^1$H NMR (400 MHz, DMSO-d$_6$) δ ppm 11.58 (s, 1H), 9.02 (t, J=4.80 Hz, 1H), 8.61-8.68 (m, 2H), 8.37-8.43 (m, 2H), 8.21 (s, 1H), 7.94 (d, J=7.83 Hz, 1H), 7.65 (t, J=7.83 Hz, 1H), 5.91 (s, 1H), 5.37 (quin, J=6.63 Hz, 1H), 4.42 (d, J=4.80 Hz, 2H), 2.84 (d, J=4.29 Hz, 3H), 2.24 (s, 3H), 2.13 (s, 3H), 1.57 (s, 3H), 1.55 (s, 3H).

Example 48

N-[(4,6-Dimethyl-2-oxo-1,2-dihydro-3-pyridinyl)methyl]-6-(2,4-dioxo-1,2,3,4-tetrahydro-5-pyrimidinyl)-1-(1-methylethyl)-1H-pyrazolo[3,4-b]pyridine-4-carboxamide In a 25 mL sealable tube under nitrogen were combined 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (80 mg, 0.21 mmol) and (2,4-dioxo-1,2,3,4-tetrahydro-5-pyrimidinyl)boronic acid (50 mg, 0.32 mmol) in DME/water (3 ml:1 ml). PdCl$_2$(dppf)-CH$_2$Cl$_2$ adduct (8.74 mg, 0.011 mmol) was added and the resulting mixture was degassed with nitrogen for 10 min. Sodium bicarbonate (53.9 mg, 0.64 mmol) was added, the vessel was sealed, and reaction mixture was heated in a microwave at 150° C. for 30 min. After cooling, 2 mL of water was added to the black mixture and solids that precipitated were filtered. DCM/MeOH (1:1) was added, the mixture was pre-absorbed on silica gel and purified by silica gel chromatography (eluent: gradient 0 to 90:10:1 DCM/MeOH/NH$_4$OH). The isolated product was treated with EtOH/EtOAc (1:1) and sonicated. The solids that precipitated were filtered, washed with EtOH and DCM, and dried to afford the title compound (41 mg, 42%) as a light grey solid. LCMS E-S (M+H)=449.9. $^1$H NMR (400 MHz, DMSO-d$_6$) δ ppm 11.58 (s, 1H), 11.52 (br. s., 1H), 11.47 (s, 1H), 8.75 (t, J=5.05 Hz, 1H), 8.36 (s, 1H), 8.31 (s, 1H), 8.23

(s, 1H), 5.90 (s, 1H), 5.27 (quin, J=6.69 Hz, 1H), 4.37 (d, J=5.05 Hz, 2H), 2.23 (s, 3H), 2.13 (s, 3H), 1.52 (s, 3H), 1.50 (s, 3H).

Example 49

6-(2-Amino-4-pyridinyl)-N-[(4,6-dimethyl-2-oxo-1,2-dihydro-3-pyridinyl)methyl]-1-(1-methylethyl)-1H-pyrazolo[3,4-b]pyridine-4-carboxamide

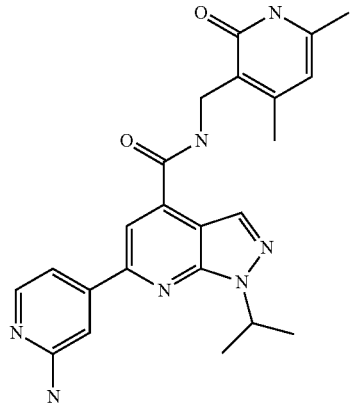 [SMILES: Cc1cc(C)c(CNC(=O)c2cc(-c3ccnc(N)c3)nc3c2cnn3C(C)C)c(=O)[nH]1]

The title compound was prepared in the same manner as example 48 using 4-(4,4,5,5-tetramethyl-1,3,2-dioxaborolan-2-yl)-2-pyridinamine (65.9 mg, 0.3 mmol) to afford an off-white solid (60 mg, 73%). LCMS E-S (M+H)=432.3. $^1$H NMR (400 MHz, DMSO-d$_6$) δ ppm 11.57 (s, 1H), 8.99 (t, J=4.80 Hz, 1H), 8.41 (s, 1H), 8.05-8.13 (m, 2H), 7.24-7.32 (m, 2H), 6.14 (s, 2H), 5.91 (s, 1H), 5.33 (quin, J=6.69 Hz, 1H), 4.41 (d, J=4.80 Hz, 2H), 2.22 (s, 3H), 2.13 (s, 3H), 1.55 (d, J=6.57 Hz, 6H).

Example 50

6-[4-(Aminosulfonyl)phenyl]-N-[(4,6-dimethyl-2-oxo-1,2-dihydro-3-pyridinyl)methyl]-1-(1-methylethyl)-1H-pyrazolo[3,4-b]pyridine-4-carboxamide

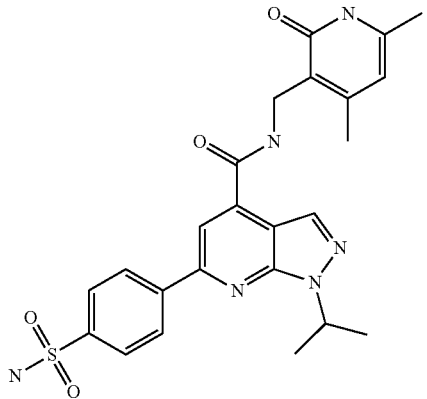 [SMILES: Cc1cc(C)c(CNC(=O)c2cc(-c3ccc(S(N)(=O)=O)cc3)nc3c2cnn3C(C)C)c(=O)[nH]1]

The title compound was prepared in the same manner as example 48 using [4-(aminosulfonyl)phenyl]boronic acid (64.5 mg, 0.32 mmol) to afford a light grey solid (76 mg, 74%). LCMS E-S (M+H)=495.0. $^1$H NMR (400 MHz, DMSO-d$_6$) δ ppm 11.58 (br. s., 1H), 8.99 (t, J=4.80 Hz, 1H), 8.41-8.48 (m, 3H), 8.25 (s, 1H), 8.00 (d, J=8.59 Hz, 2H), 7.50 (s, 2H), 5.91 (s, 1H), 5.37 (quin, J=6.69 Hz, 1H), 4.43 (d, J=4.80 Hz, 2H), 2.23 (s, 3H), 2.14 (s, 3H), 1.56 (d, J=6.57 Hz, 6H).

Example 51

N-[(4,6-Dimethyl-2-oxo-1,2-dihydro-3-pyridinyl)methyl]-1-(1-methylethyl)-6-{4-[(methylsulfonyl)amino]phenyl}-1H-pyrazolo[3,4-b]pyridine-4-carboxamide

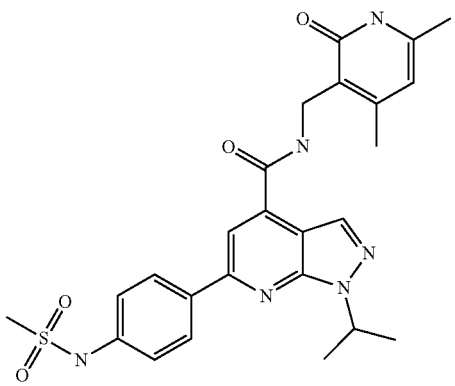

In a 25 mL sealable tube under nitrogen were combined 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (75 mg, 0.2 mmol) and {4-[(methylsulfonyl)amino]phenyl}boronic acid (43.1 mg, 0.2 mmol) in DME/water (3 ml:1 ml). PdCl$_2$(dppf)-CH$_2$Cl$_2$ adduct (8.2 mg, 0.01 mmol) was added and the resulting mixture was degassed with nitrogen for 10 min. Sodium bicarbonate (50.6 mg, 0.6 mmol) was added, the vessel was sealed, and the reaction mixture was irradiated (microwave) at 150° C. for 25 min. After cooling, 2 mL of water was added to the black mixture and solids that precipitated were filtered. DCM/MeOH (1:1) was added, the mixture was pre-absorbed on silica gel and purified by silica gel chromatography (eluent: gradient 0 to 90:10:1 DCM/MeOH/NH$_4$OH). The isolated product was suspended in EtOAc heated, and sonicated. Some hexanes was added and the contents allowed to cool to room temperature. Solids that precipitated were filtered. The solid was then suspended in EtOH, heated, and sonicated. After cooling to room temperature, the solids were filtered and dried to afford the title compound (38 mg, 36%) as a beige solid. LCMS E-S (M+H)=509.0. $^1$H NMR (400 MHz, DMSO-d$_6$) δ ppm 11.57 (s, 1H), 10.05 (br. s., 1H), 8.93 (t, J=4.93 Hz, 1H), 8.35 (s, 1H), 8.24 (m, J=8.59 Hz, 2H), 8.11 (s, 1H), 7.37 (m, J=8.84 Hz, 2H), 5.91 (s, 1H), 5.32 (quin, J=6.69 Hz, 1H), 4.41 (d, J=4.80 Hz, 2H), 3.08 (s, 3H), 2.23 (s, 3H), 2.13 (s, 3H), 1.55 (s, 3H), 1.54 (s, 3H).

Example 52

6-{4-[(Dimethylamino)sulfonyl]phenyl}-N-[(4,6-dimethyl-2-oxo-1,2-dihydro-3-pyridinyl)methyl]-3-methyl-1-(1-methylethyl)-1H-pyrazolo[3,4-b]pyridine-4-carboxamide

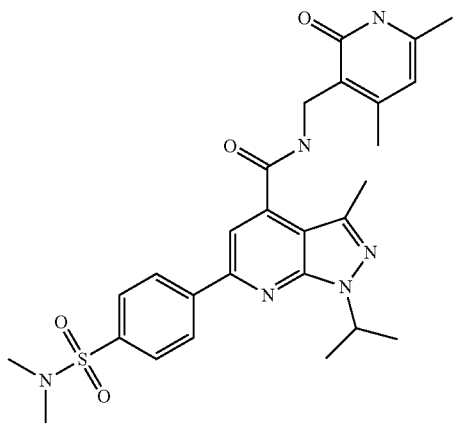

In a 25 mL sealable tube under nitrogen were combined 6-chloro-N-[(4,6-dimethyl-2-oxo-1,2-dihydro-3-pyridinyl)methyl]-3-methyl-1-(1-methylethyl)-1H-pyrazolo[3,4-b]pyridine-4-carboxamide (75 mg, 0.19 mmol) and N,N-dimethyl-4-(4,4,5,5-tetramethyl-1,3,2-dioxaborolan-2-yl)benzenesulfonamide (90 mg, 0.29 mmol) in DME/water (3 ml:1 ml). PdCl$_2$ (dppf)-CH$_2$Cl$_2$ adduct (7.9 mg, 0.009 mmol) was added and the resulting mixture was degassed with nitrogen for 10 min. Sodium bicarbonate (48.7 mg, 0.58 mmol) was added, the vessel was sealed, and the reaction mixture was irradiated (microwave) at 150° C. for 30 min. After cooling, 2 mL of water was added and solids that precipitated were filtered. DCM/MeOH (1:1) was added, the mixture was pre-absorbed on silica gel and purified by silica gel chromatography (eluent: gradient 0 to 90:10:1 DCM/MeOH/NH$_4$OH). The isolated product was treated with EtOH/EtOAc (1:1), the solids filtered and washed with EtOAc and DCM, and then dried to afford the title compound (83 mg, 78%) as a white solid. LCMS E-S (M+H)=537.1. $^1$H NMR (400 MHz, DMSO-d$_6$) δ ppm 11.54 (s, 1H) 8.79 (t, J=4.93 Hz, 1H) 8.47 (m, J=8.59 Hz, 2H) 7.90 (m, J=8.59 Hz, 2H) 7.80 (s, 1H) 5.89 (s, 1H) 5.28 (quin, J=6.69 Hz, 1H) 4.40 (d, J=5.05 Hz, 2H) 2.66 (s, 6H) 2.47 (s, 3H) 2.25 (s, 3H) 2.12 (s, 3H) 1.53 (s, 3H) 1.51 (s, 3H).

Example 53

N-[(4,6-Dimethyl-2-oxo-1,2-dihydro-3-pyridinyl)methyl]-1-(1-methylethyl)-6-(4-piperidinylamino)-1H-pyrazolo[3,4-b]pyridine-4-carboxamide

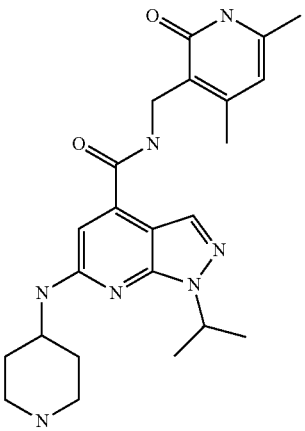 [SMILES: Cc1cc(C)c(CNC(=O)c2cc(NC3CCNCC3)nc3c2cnn3C(C)C)c(=O)[nH]1]

In a 25 mL sealable tube under nitrogen were combined 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (60 mg, 0.16 mmol) and 4-piperidinamine (2 mL) in EtOH (3 mL). The vessel was sealed and the reaction mixture was irradiated (microwave) at 125° C. for 5 hr and then at 160° C. for 90 min. The mixture was evaporated under vacuum and the resulting residue was partitioned between EtOAc and water. Organics were washed with water (2×) and brine, dried over MgSO$_4$, filtered and evaporated. The residue was purified by silica gel chromatography (eluent: gradient 0 to 90:10:1 DCM/MeOH/NH$_4$OH). The isolated product was treated with EtOAc/ether (1:1) and allowed to stand at room temperature overnight. The solids that had precipitated were triturated, filtered, and dried to afford the title compound as a pale yellow solid 25 mg (35%). LCMS E-S (M+H)=438.0. $^1$H NMR (400 MHz, DMSO-d$_6$) δ ppm 8.66 (t, J=4.67 Hz, 1H) 7.98 (s, 1H) 7.12 (s, 1H) 5.89 (s, 1H) 4.98 (dt, J=13.33, 6.60 Hz, 1H) 4.30-4.41 (m, 4H) 3.01 (t, J=11.62 Hz, 2H) 2.85 (br. s., 1H) 2.20 (s, 3H) 2.12 (s, 3H) 1.80 (d, J=10.36 Hz, 2H) 1.44 (s, 3H) 1.43 (s, 3H) 1.18-1.30 (m, 3H) 0.79-0.91 (m, 1H)

Example 54

N-[(4,6-Dimethyl-2-oxo-1,2-dihydro-3-pyridinyl)methyl]-1-(1-methylethyl)-6-(tetrahydro-2H-pyran-4-ylamino)-1H-pyrazolo[3,4-b]pyridine-4-carboxamide

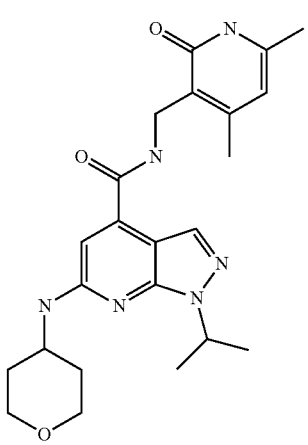 [SMILES: Cc1cc(C)c(CNC(=O)c2cc(NC3CCOCC3)nc3c2cnn3C(C)C)c(=O)[nH]1]

In a 25 mL sealable tube under nitrogen were combined 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (60 mg, 0.16 mmol) and tetrahydro-2H-pyran-4-amine (2 ml, 19 mmol) in EtOH (3 mL). The vessel was sealed and the reaction mixture was irradiated (microwave) at 125° C. for 2 hr. and then at 170° C. for 1 hr. The mixture was concentrated to ca. 20% volume and NMP (2 mL) added to the reaction mixture. The contents were again irradiated (microwave) first at 180° C. for 2.5 h and then at 190° C. for 75 min. The mixture was evaporated under vacuum, and the resulting residue was purified by silica gel chromatography (eluent: gradient 0 to 90:10:1 DCM/MeOH/NH$_4$OH). The isolated product was treated with EtOAc/hexanes (1:1), sonicated, and heated. After cooling, solids that precipitated were filtered and dried to afford the title compound (46 mg, 64%) as an off-white solid. LCMS E-S (M+H)=439.1. $^1$H NMR (400 MHz, DMSO-d$_6$) δ ppm 11.55 (s, 1H) 8.44 (t, J=5.05 Hz, 1H) 7.83 (s, 1H) 7.20 (d, J=7.33 Hz, 1H) 6.63 (s, 1H) 5.89 (s, 1H) 4.93 (quin, J=6.69 Hz, 1H) 4.32 (d, J=5.05 Hz, 2H) 3.99-4.06 (m, 1H) 3.88 (dt, J=11.49, 3.47 Hz, 2H) 3.45 (td, J=11.37, 2.02 Hz, 2H) 2.21 (s, 3H) 2.13 (s, 3H) 1.95 (d, J=10.61 Hz, 2H) 1.41-1.51 (m, 8H).

Example 55

N-[(4,6-Dimethyl-2-oxo-1,2-dihydro-3-pyridinyl)methyl]-1-(1-methylethyl)-6-[(4-pyridinylmethyl)amino]-1H-pyrazolo[3,4-b]pyridine-4-carboxamide

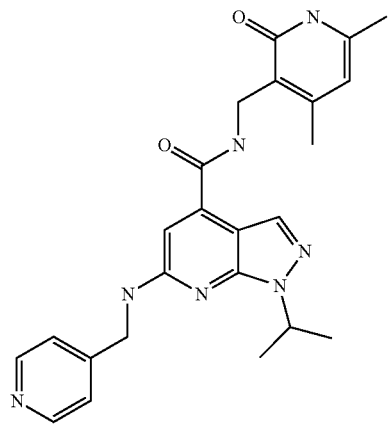 [SMILES: Cc1cc(C)c(CNC(=O)c2cc(NCc3ccncc3)nc3c2cnn3C(C)C)c(=O)[nH]1]

In a 25 mL sealable tube under nitrogen were combined 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (60 mg, 0.16 mmol) and (4-pyridinylmethyl)amine (0.065 ml, 0.64 mmol) in EtOH (2 mL). The vessel was sealed and the reaction mixture was heated at 90° C. overnight. An additional 1 mL of (4-pyridinylmethyl) amine was added and the mixture was heated in a microwave at 160° C. for 90 min. The EtOH solvent was removed under reduced pressure, 2 mL of NMP was added, and the mixture was then irradiated (microwave) at 180° C. for 90 min. The mixture was evaporated under vacuum, and the resulting residue was partitioned between EtOAc and water. The crude residue was extracted with EtOAc, DCM and DCM/isopropanol (70:30). The combined organics were washed with water (2×) and brine, dried over MgSO$_4$, filtered and evaporated. The residue was purified by silica gel chromatography (eluent: gradient 0 to 90:10:1 DCM/MeOH/NH$_4$OH). The isolated yellow oil was treated with EtOAc and sonicated. The filtered solid was washed with hexanes and dried to afford the title compound (26 mg, 36%) as a white solid. LCMS E-S (M+H)=446.1. $^1$H NMR (400 MHz, DMSO-d$_6$) δ ppm 11.56 (s, 1H) 8.50 (t, J=5.18 Hz, 1H) 8.43-8.48 (m, 2H) 7.89 (t, J=5.94 Hz, 1H) 7.84 (s, 1H) 7.34 (d, J=6.06 Hz, 2H) 6.73 (s, 1H) 5.89 (s, 1H) 4.83 (quin, J=6.69 Hz, 1H) 4.58 (d, J=5.81 Hz, 2H) 4.32 (d, J=5.05 Hz, 2H) 2.21 (s, 3H) 2.13 (s, 3H) 1.32 (d, J=6.82 Hz, 6H).

Example 56

6-{[2-(Dimethylamino)ethyl]amino}-N-[(4,6-dimethyl-2-oxo-1,2-dihydro-3-pyridinyl)methyl]-1-(1-methylethyl)-1H-pyrazolo[3,4-b]pyridine-4-carboxamide

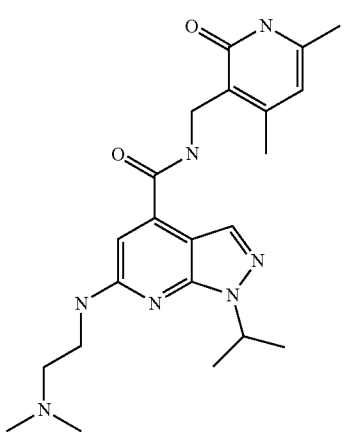

In a 25 mL sealable tube under nitrogen were combined 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (80 mg, 0.21 mmol) and (2-aminoethyl)dimethylamine (37.7 mg, 0.43 mmol) in NMP (2 mL). The vessel was sealed and the reaction mixture was irradiated (microwave) at 150° C. for 1 h. The mixture was evaporated under vacuum, and the resulting residue was partitioned between EtOAc and water. The contents were extracted with EtOAc, DCM and DCM/isopropanol (70:30). The combined organics were washed with water (2×) and brine, dried over MgSO$_4$, filtered and evaporated. The residue was purified by silica gel chromatography (eluent: gradient 0 to 90:10:1 DCM/MeOH/NH$_4$OH). The isolated yellow oil was treated with EtOAc and sonicated. Solids that precipitated were filtered, washed with hexanes, and dried to afford the title compound (60 mg, 65%) as a white solid. LCMS E-S (M+H)=425.9. $^1$H NMR (400 MHz, DMSO-d$_6$) δ ppm 11.55 (br. s., 1H) 8.43 (t, J=5.05 Hz, 1H) 7.84 (s, 1H) 7.08 (t, J=5.05 Hz, 1H) 6.67 (s, 1H) 5.89 (s, 1H) 4.94 (quin, J=6.63 Hz, 1H) 4.32 (d, J=5.05 Hz, 2H) 3.44 (q, J=6.48 Hz, 2H) 2.44 (t, J=6.69 Hz, 2H) 2.17-2.22 (m, 9H) 2.12 (s, 3H) 1.43 (d, J=6.57 Hz, 6H).

Example 57

N-[(4,6-Dimethyl-2-oxo-1,2-dihydro-3-pyridinyl)methyl]-6-[(2-hydroxyethyl)amino]-1-(1-methylethyl)-1H-pyrazolo[3,4-b]pyridine-4-carboxamide

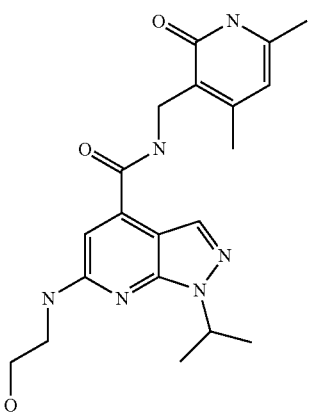 [SMILES: Cc1cc(C)c(CNC(=O)c2cc(NCCO)nc3c2cnn3C(C)C)c(=O)[nH]1]

In a 25 mL sealable tube under nitrogen were combined 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (80 mg, 0.21 mmol) and 2-aminoethanol (1 ml) in NMP (2 mL). The vessel was sealed and the reaction mixture was irradiated (microwave) at 130° C. for 1 h and then at 140° C. for 90 min. The mixture was evaporated under vacuum and the residue was purified by silica gel chromatography (eluent: gradient 0 to 90:10:1 DCM/MeOH/NH$_4$OH). The isolated yellow oil was treated with EtOAc, sonicated, and treated with hexanes. The solids were filtered, dissolved in DMF (1 mL), and a few drops of water were added. The solution was allowed to stand at room temperature overnight, and then sonicated. The filtered solid was washed with Hexanes/EtOAc (1:1), and then dried to afford the title compound (55 mg, 63%) as a light yellow solid. LCMS E-S (M+H)=399.0. $^1$H NMR (400 MHz, DMSO-d$_6$) δ ppm 11.56 (br. s., 1H) 8.44 (br. s., 1H) 7.84 (s, 1H) 7.20 (br. s., 1H) 6.68 (s, 1H) 5.89 (s, 1H) 4.95 (dt, J=13.01, 6.38 Hz, 1H) 4.72 (t, J=4.93 Hz, 1H) 4.32 (d, J=4.80 Hz, 2H) 3.58 (d, J=5.56 Hz, 2H) 3.38-3.46 (m, 2H) 2.21 (s, 3H) 2.12 (s, 3H) 1.43 (d, J=6.57 Hz, 6H)

Example 58

N-[(4,6-Dimethyl-2-oxo-1,2-dihydro-3-pyridinyl)methyl]-1-(1-methylethyl)-6-[5-(methyloxy)-3-pyridinyl]-1H-pyrazolo[3,4-b]pyridine-4-carboxamide

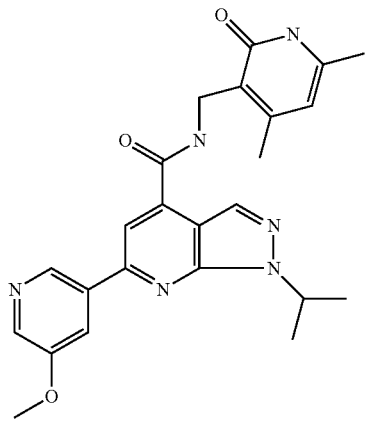 [SMILES: COc1cncc(-c2cc(C(=O)NCc3c(C)cc(C)[nH]c3=O)c3cnn(C(C)C)c3n2)c1]

To a 20 mL microwave vial were sequentially added 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (100 mg, 0.267 mmol, 3-(methyloxy)-5-(4,4,5,5-tetramethyl-1,3,2-dioxaborolan-2-yl)pyridine (69.2 mg, 0.294 mmol), PdCl$_2$(dppf)-CH$_2$Cl$_2$ adduct (21.84 mg, 0.027 mmol), (DME) (5 mL), and water (2 mL). The reaction mixture was degassed with nitrogen for 5 min. Sodium bicarbonate (67.4 mg, 0.802 mmol) was added and the contents sealed and irradiated (microwave) at 140° C. The reaction mixture was cooled to room temperature and poured on a silica column (through Na$_2$SO$_4$) and purified by silica gel chromatography (eluent: 5% MeOH/CH$_2$Cl$_2$) which provided the desired product as an off-white solid after precipitation from EtOAc/MeOH. The final product was collected as 0.090 g (76%). LCMS E-S (M+H) 447.2. $^1$H NMR (400 MHz, DMSO-d$_6$) δ ppm 11.57 (s., 1H), 9.06 (d, J=1.52 Hz, 1H), 8.92-9.00 (m, 1H), 8.39-8.48 (m, 2H), 8.24 (s, 1H), 8.14 (d, J=1.77 Hz, 1H), 5.91 (s, 1H), 5.30-5.45 (m, 1H), 4.42 (d, J=4.80 Hz, 2H), 3.97 (s, 3H), 2.24 (s, 3H), 2.13 (s, 3H), 1.55 (d, J=6.82 Hz, 6H).

Example 59

N-[(4,6-Dimethyl-2-oxo-1,2-dihydro-3-pyridinyl)methyl]-1-(1-methylethyl)-6-[2-(methyloxy)-4-pyridinyl]-1H-pyrazolo[3,4-b]pyridine-4-carboxamide

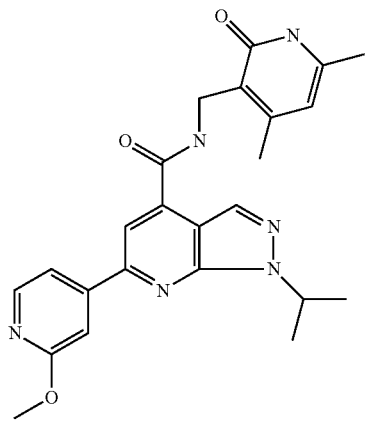 [SMILES: COc1cc(-c2cc(C(=O)NCc3c(C)cc(C)[nH]c3=O)c3cnn(C(C)C)c3n2)ccn1]

The title compound was prepared in the same manner as described in example 58 using 2-methoxypyridine-4-boronic acid pinacol ester (69.2 mg, 0.294 mmol) to give the desired product as a grey solid after evaporation and precipitation from EtOAc/MeOH. The final product was collected as 0.051 g (41%). LCMS E-S (M+H) 447.2. $^1$H NMR (400 MHz, DMSO-d$_6$) δ ppm 11.57 (br. s., 1H) 9.00 (t, J=4.80 Hz, 1H) 8.44 (s, 1H) 8.36 (s, 1H) 8.26 (s, 1H) 7.84 (dd, J=5.31, 1.52 Hz, 1H) 7.67 (s, 1H) 5.91 (s, 1H) 5.32-5.40 (m, 1H) 4.42 (d, J=4.80 Hz, 2H) 3.94 (s, 3H) 2.23 (s, 3H) 2.13 (s, 3H) 1.55 (d, 6H).

Example 60

6-(6-Amino-3-pyridinyl)-N-[(4,6-dimethyl-2-oxo-1,2-dihydro-3-pyridinyl)methyl]-1-(1-methylethyl)-1H-pyrazolo[3,4-b]pyridine-4-carboxamide

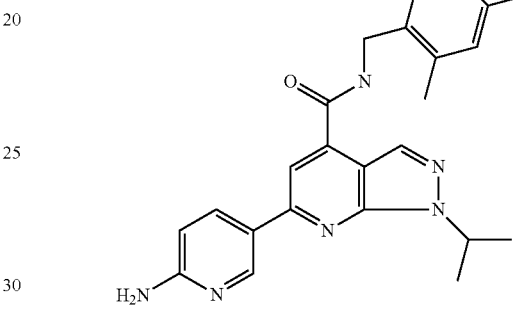

The title compound was prepared in the same manner as described in example 58 using 6-aminopyridine-3-boronic acid pinacol ester (64.8 mg, 0.294 mmol) to give the desired product as a grey solid after evaporation and preciptation from EtOAc/MeOH. The final product was collected as 0.060 g (49%). LCMS E-S (M+H)=432.2. $^1$H NMR (400 MHz, DMSO-d$_6$) δ ppm 11.57 (br. s., 1H) 8.85-8.92 (m, 2H) 8.31 (s, 1H) 8.26 (dd, J=8.59, 2.53 Hz, 1H) 8.04 (s, 1H) 6.57 (d, J=8.59 Hz, 1H) 6.46 (s, 2H) 5.90 (s, 1H) 5.25-5.33 (m, 1H) 4.40 (d, J=4.80 Hz, 2H) 2.22 (s, 3H) 2.13 (s, 3H) 1.53 (d, 6H).

Example 61

N-[(4,6-Dimethyl-2-oxo-1,2-dihydro-3-pyridinyl)methyl]-1-(1-methylethyl)-6-[5-(methylsulfonyl)-3-pyridinyl]-1H-pyrazolo[3,4-b]pyridine-4-carboxamide

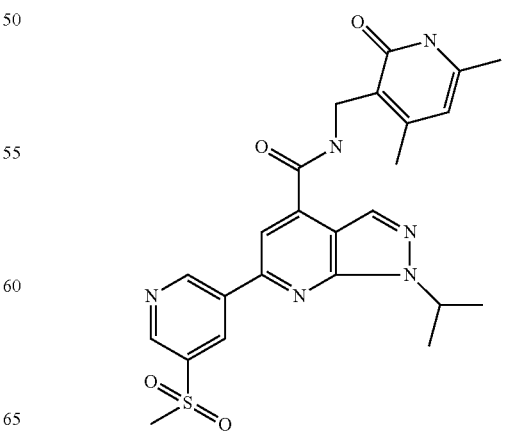

The title compound was prepared in the same manner as described in example 58 using [5-(methylsulfonyl)-3-pyridinyl]boronic acid (59.1 mg, 0.294 mmol) to give the desired product as an off-white solid after evaporation and preciptation from EtOAc/MeOH. The final product was collected as 0.079 g (59%). LCMS E-S (M+H)=495.0. ¹H NMR (400 MHz, DMSO-d₆) δ ppm 11.59 (br. s., 1H), 9.76 (d, J=2.27 Hz, 1H), 9.21 (d, J=2.02 Hz, 1H), 9.00-9.06 (m, 2H), 8.46 (s, 1H), 8.37 (s, 1H), 5.91 (s, 1H), 5.36-5.44 (m, 1H), 4.43 (d, J=4.80 Hz, 2H), 3.45 (s, 3H), 2.24 (s, 3H), 2.13 (s, 3H), 1.56 (d, 6H).

Example 62

N-[(4,6-Dimethyl-2-oxo-1,2-dihydro-3-pyridinyl)methyl]-6-(2-furanyl)-1-(1-methylethyl)-1H-pyrazolo[3,4-b]pyridine-4-carboxamide

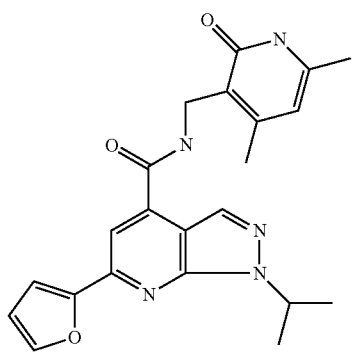 [SMILES: Cc1cc(C)c(CNC(=O)c2cc(-c3ccco3)nc3c2cnn3C(C)C)c(=O)[nH]1]

The title compound was prepared in the same manner as described in example 74 using 2-(2-furanyl)-4,4,5,5-tetramethyl-1,3,2-dioxaborolane (57.1 mg, 0.294 mmol) to give the desired product as an white solid after evaporation and preciptation from EtOAc/MeOH. The final product was collected as 0.049 g (44%). LCMS E-S (M+H) 406.2. ¹H NMR (400 MHz, DMSO-d₆) δ ppm 11.57 (s, 1H) 8.93 (t, J=4.93 Hz, 1H) 8.33 (s, 1H) 7.97 (s, 1H) 7.94 (d, J=1.01 Hz, 1H) 7.34 (d, J=2.78 Hz, 1H) 6.73 (dd, J=3.54, 1.77 Hz, 1H) 5.90 (s, 1H) 5.19-5.32 (m, 1H) 4.39 (d, J=4.80 Hz, 2H) 2.23 (s, 3H) 2.13 (s, 3H) 1.52 (d, 6H).

Example 63

N-[(4,6-Dimethyl-2-oxo-1,2-dihydro-3-pyridinyl)methyl]-6-[6-[(methylamino)carbonyl]-3-pyridinyl]-1-(1-methylethyl)-1H-pyrazolo[3,4-b]pyridine-4-carboxamide

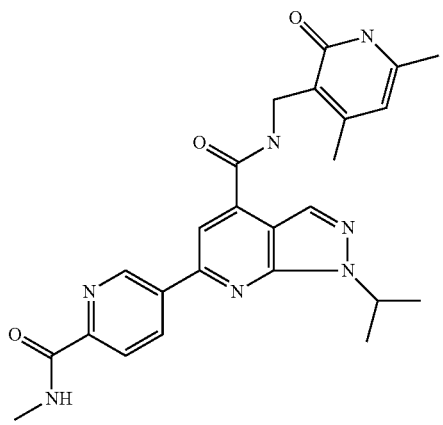 [SMILES: CNC(=O)c1ccc(-c2cc(C(=O)NCc3c(C)cc(C)[nH]c3=O)c3cnn(C(C)C)c3n2)cn1]

The title compound was prepared in the same manner as described in example 58 using 2-(N-methylamidocarboxy)-5-pyridineboronic acid pinacol ester (70.1 mg, 0.267 mmol) to give the desired product as an off-white solid after evaporation and preciptation from EtOAc/MeOH. The final product was collected as 0.080 g (60%). LCMS E-S (M+H)=474.1. ¹H NMR (400 MHz, DMSO-d₆) δ ppm 11.59 (br. s., 1H), 9.46 (d, J=1.52 Hz, 1H), 8.98 (t, J=4.55 Hz, 1H), 8.85 (d, J=5.05 Hz, 1H), 8.78 (dd, J=8.21, 2.15 Hz, 1H), 8.44 (s, 1H), 8.31 (s, 1H), 8.20 (d, J=8.08 Hz, 1H), 5.91 (s, 1H), 5.30-5.42 (m, 1H), 4.42 (d, J=4.55 Hz, 2H), 2.87 (d, J=4.80 Hz, 3H), 2.23 (s, 3H), 2.13 (s, 3H), 1.56 (d, 6H).

Example 64

6-[5-[(Cyclopropylsulfonyl)amino]-6-(methyloxy)-3-pyridinyl]-N-[(4,6-dimethyl-2-oxo-1,2-dihydro-3-pyridinyl)methyl]-1-(1-methylethyl)-1H-pyrazolo[3,4-b]pyridine-4-carboxamide

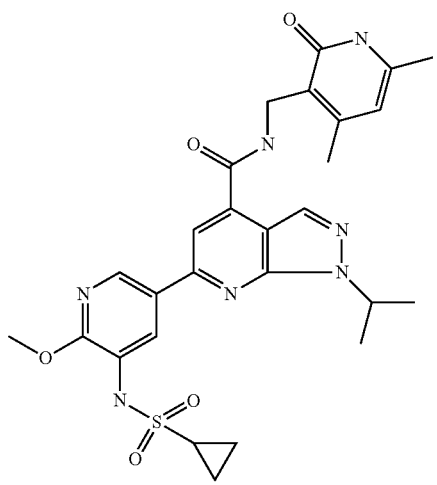

The title compound was prepared in the same manner as described in example 58 using N-[2-(methyloxy)-5-(4,4,5,5-tetramethyl-1,3,2-dioxaborolan-2-yl)-3-pyridinyl]cyclopropanesulfonamide (95 mg, 0.267 mmol) to give the desired product as an off-white solid after evaporation and preciptation from EtOAc/MeOH. The final product was collected as 0.100 g (66%). LCMS E-S (M+H) 566.4. ¹H NMR (400 MHz, DMSO-d₆) δ ppm 11.57 (s, 1H) 9.47 (s, 1H) 8.94 (t, J=4.93 Hz, 1H) 8.89 (d, J=2.27 Hz, 1H) 8.49 (d, J=2.27 Hz, 1H) 8.37 (s, 1H) 8.15 (s, 1H) 5.91 (s, 1H) 5.29 (m, 1H) 4.41 (d, J=4.80 Hz, 2H) 4.01 (s, 3H) 2.70-2.78 (m, 1H) 2.23 (s, 3H) 2.13 (s, 3H) 1.56 (d, J=6.57 Hz, 6H) 0.91-1.00 (m, 4H).

Example 65

N-[(4,6-Dimethyl-2-oxo-1,2-dihydro-3-pyridinyl)methyl]-1-(1-methylethyl)-6-{5-[(phenylsulfonyl)amino]-3-pyridinyl}-1H-pyrazolo[3,4-b]pyridine-4-carboxamide

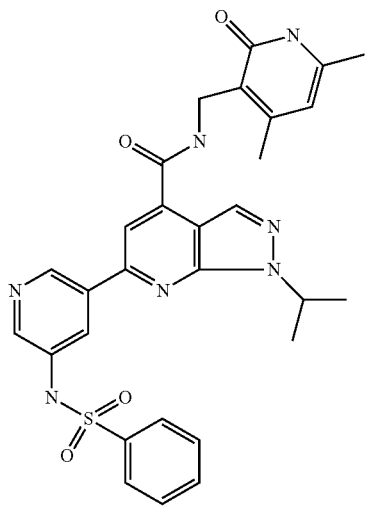 [SMILES: Cc1cc(C)c(CNC(=O)c2cc(-c3cncc(NS(=O)(=O)c4ccccc4)c3)nc3c2cnn3C(C)C)c(=O)[nH]1]

The title compound was prepared in the same manner as described in example 58 using N-[5-(4,4,5,5-tetramethyl-1,3,2-dioxaborolan-2-yl)-3-pyridinyl]benzenesulfonamide (96 mg, 0.267 mmol) to give the desired product as an off-white-solid after evaporation and preciptation from EtOAc/MeOH. The final product was collected as 0.050 g (33%). LCMS E-S (M+H)=572.2. $^1$H NMR (400 MHz, DMSO-$d_6$) δ ppm 11.57 (s, 1H), 10.83 (s, 1H), 9.10 (d, J=1.77 Hz, 1H), 8.95 (t, J=5.05 Hz, 1H), 8.37-8.45 (m, 2H), 8.32 (t, J=2.15 Hz, 1H), 8.17 (s, 1H), 7.82-7.91 (m, 2H), 7.55-7.69 (m, 3H), 5.90 (s, 1H), 5.18-5.30 (m, 1H), 4.41 (d, J=5.05 Hz, 2H), 2.22 (s, 3H), 2.13 (s, 3H), 1.58 (d, J=6.82 Hz, 6H).

Example 66

N-[(4,6-Dimethyl-2-oxo-1,2-dihydro-3-pyridinyl)methyl]-1-(1-methylethyl)-6-[2-(4-morpholinyl)-4-pyridinyl]-1H-pyrazolo[3,4-b]pyridine-4-carboxamide

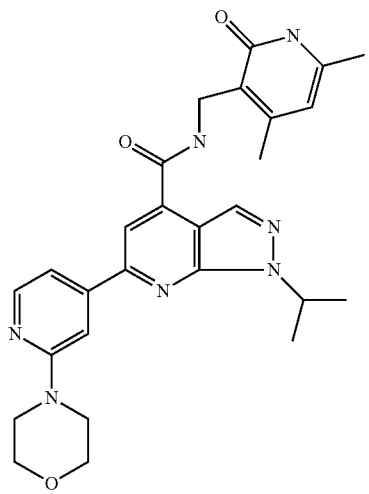 [SMILES: Cc1cc(C)c(CNC(=O)c2cc(-c3ccnc(N4CCOCC4)c3)nc3c2cnn3C(C)C)c(=O)[nH]1]

The title compound was prepared in the same manner as described in example 58 using 4-[4-(4,4,5,5-tetramethyl-1,3,2-dioxaborolan-2-yl)-2-pyridinyl]morpholine (78 mg, 0.267 mmol) to give the desired product as an off-white solid after evaporation and preciptation from EtOAc/MeOH. The final product was collected as 0.110 g (58%). LCMS E-S (M+H) 502.1. $^1$H NMR (400 MHz, DMSO-$d_6$) δ ppm 11.57 (s, 1H), 8.95 (t, J=5.05 Hz, 1H), 8.40 (s, 1H), 8.31 (d, J=5.30 Hz, 1H), 8.18 (s, 1H), 7.58 (s, 1H), 7.51 (dd, J=5.31, 1.26 Hz, 1H), 5.90 (s, 1H), 5.39-5.30 (m, 1H), 4.42 (d, J=4.80 Hz, 2H), 3.72-3.80 (m, 4H), 3.54-3.62 (m, 4H), 2.24 (s, 3H), 2.13 (s, 3H), 1.55 (d, J=6.57 Hz, 6H).

Example 67

N-[(4,6-Dimethyl-2-oxo-1,2-dihydro-3-pyridinyl)methyl]-1-(1-methylethyl)-6-[6-(4-morpholinyl)-3-pyridinyl]-1H-pyrazolo[3,4-b]pyridine-4-carboxamide

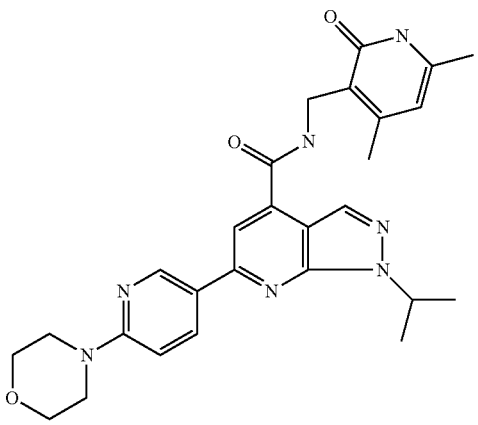 [SMILES: Cc1cc(C)c(CNC(=O)c2cc(-c3ccc(N4CCOCC4)nc3)nc3c2cnn3C(C)C)c(=O)[nH]1]

The title compound was prepared in the same manner as described in example 58 using 6-morpholinopyridine-3-boronic acid (55.6 mg 0.267 mmol) to give the desired product as an off-white solid after evaporation and preciptation from EtOAc/MeOH. The final product was collected as 0.110 g (82%). LCMS E-S (M+H) 502.1. $^1$H NMR (400 MHz, DMSO-$d_6$) δ ppm 11.57 (s, 1H), 9.06 (d, J=2.27 Hz, 1H), 8.88 (t, J=4.93 Hz, 1H), 8.41 (dd, J=8.97, 2.40 Hz, 1H), 8.33 (s, 1H), 8.11 (s, 1H), 7.00 (d, J=9.09 Hz, 1H), 5.91 (s, 1H), 5.34-5.28 (m, 1H), 4.40 (d, J=4.80 Hz, 2H), 3.71-3.78 (m, 4H), 3.55-3.62 (m, 4H), 2.23 (s, 3H), 2.13 (s, 3H), 1.54 (d, J=6.82 Hz, 6H).

Example 68

N-[(4,6-Dimethyl-2-oxo-1,2-dihydro-3-pyridinyl)methyl]-1-(1-methylethyl)-6-[6-(methyloxy)-3-pyridinyl]-1H-pyrazolo[3,4-b]pyridine-4-carboxamide

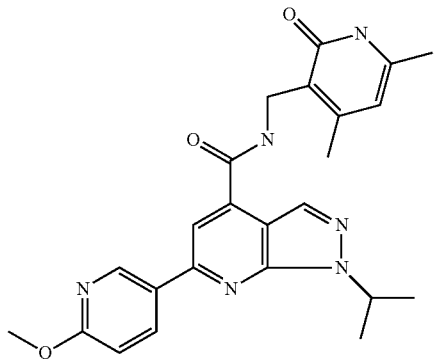

The title compound was prepared in the same manner as described in example 58 using [6-(methyloxy)-3-pyridinyl] boronic acid (40.9 mg 0.267 mmol) to give the desired product as an off-white solid after evaporation and preciptation from EtOAc/MeOH. The final product was collected as 0.060 g (50%). LCMS E-S (M+H) 447.2. $^1$H NMR (400 MHz, DMSO-$d_6$) δ ppm 11.58 (s, 1H), 9.07 (d, J=2.02 Hz, 1H), 8.90 (t, J=4.93 Hz, 1H), 8.55 (dd, J=8.59, 2.53 Hz, 1H), 8.37 (s, 1H), 8.17 (s, 1H), 7.01 (d, J=8.84 Hz, 1H), 5.91 (s, 1H), 5.36-5.28 (m, 1H), 4.41 (d, J=5.05 Hz, 2H), 3.95 (s, 3H), 2.23 (s, 3H), 2.13 (s, 3H), 1.55 (d, J=6.57 Hz, 6H).

Example 69

6-[6-(Acetylamino)-3-pyridinyl]-N-[(4,6-dimethyl-2-oxo-1,2-dihydro-3-pyridinyl)methyl]-1-(1-methylethyl)-1H-pyrazolo[3,4-b]pyridine-4-carboxamide

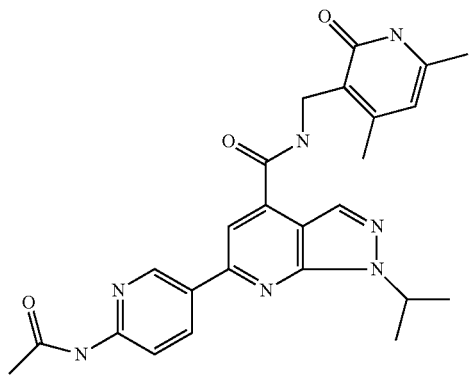 [SMILES: CC(=O)Nc1ccc(-c2cc(C(=O)NCc3c(C)cc(C)[nH]c3=O)c3cnn(C(C)C)c3n2)cn1]

The title compound was prepared in the same manner as described in example 58 using 2-acetamidopyridine-5-boronic acid pinacol ester (77 mg, 0.294 mmol) to give the desired product as an off-white solid after evaporation and preciptation from EtOAc/MeOH. The final product was collected as 0.065 g (51%). LCMS E-S (M+H)=474.0. $^1$H NMR (400 MHz, DMSO-$d_6$) δ ppm 11.57 (s, 1H), 10.76 (s, 1H), 9.19 (d, J=1.77 Hz, 1H), 8.93 (t, J=4.80 Hz, 1H), 8.61 (dd, J=8.84, 2.27 Hz, 1H), 8.38 (s, 1H), 8.25 (d, J=8.84 Hz, 1H), 8.20 (s, 1H), 5.91 (s, 1H), 5.30-5.40 (m, 1H), 4.42 (d, J=5.05 Hz, 2H), 2.23 (s, 3H), 2.14 (s, 3H), 2.13 (s, 3H), 1.54 (d, J=6.82 Hz, 6H).

Example 70

N-[(4,6-Dimethyl-2-oxo-1,2-dihydro-3-pyridinyl)methyl]-1-(1-methylethyl)-6-(2-methylphenyl)-1H-pyrazolo[3,4-b]pyridine-4-carboxamide

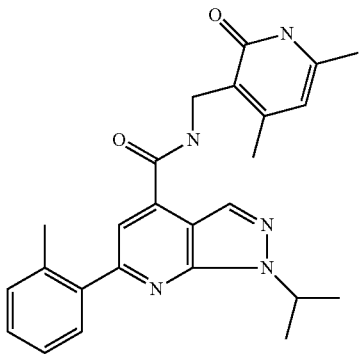 [SMILES: Cc1cc(C)c(CNC(=O)c2cc(-c3ccccc3C)nc3c2cnn3C(C)C)c(=O)[nH]1]

The title compound was prepared in the same manner as described in example 58 using 2-methylphenyl boronic acid (40.0 mg, 0.294 mmol) to give the desired product as an off-white solid after evaporation and preciptation from MeOH. The final product was collected as 0.065 g (51%). LCMS E-S (M+H)=430.2. $^1$H NMR (400 MHz, DMSO-$d_6$) δ ppm 11.54 (s, 1H) 8.89 (t, J=4.93 Hz, 1H) 8.39 (s, 1H) 7.74 (s, 1H) 7.56 (d, J=7.07 Hz, 1H) 7.31-7.41 (m, 3H) 5.89 (s, 1H) 5.20-5.27 (m, 1H) 4.38 (d, J=4.80 Hz, 2H) 2.40 (s, 3H) 2.21 (s, 3H) 2.12 (s, 3H) 1.53 (d, 6H).

Example 71

N-[(4,6-Dimethyl-2-oxo-1,2-dihydro-3-pyridinyl)methyl]-1-(1-methylethyl)-6-(1H-pyrazol-4-yl)-1H-pyrazolo[3,4-b]pyridine-4-carboxamide

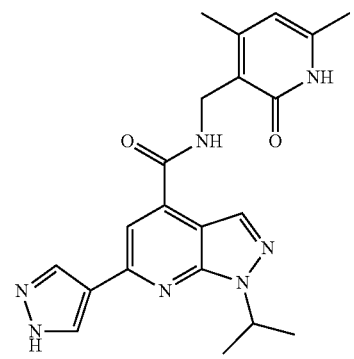 [SMILES: Cc1cc(C)c(CNC(=O)c2cc(-c3cn[nH]c3)nc3c2cnn3C(C)C)c(=O)[nH]1]

To a 5-mL microwave vial were added 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (70 mg, 0.187 mmol), 4-(4,4,5,5-tetramethyl-1,3,2-dioxaborolan-2-yl)-1H-pyrazole (47.2 mg, 0.243 mmol), DMSO (1.5 mL) and sodium carbonate (0.281 mL, 0.562 mmol), and the mixture was degassed with nitrogen for 5 min. Next added bis(triphenylphosphine) palladium(II) chloride (10.51 mg, 0.015 mmol) and the vial was sealed. The mixture was irradiated (microwave) at 140° C. for 12 h. The reaction mixture was filtered and the residue was washed with DMSO. The DMSO solution of crude product was purified using reverse-phase HPLC. The TFA salt of the product obtained was neutralized with saturated NaHCO$_3$, washed with water, and dried under high vacuum to give 12 mg (16%) of product. LCMS: (M+H)$^+$=406.2 $^1$H NMR (400 MHz, DMSO-d$_6$) δ ppm 1.45-1.60 (m, J=6.4 Hz, 6H), 2.13 (s, 3H), 2.23 (s, 3H), 4.39 (d, J=4.6 Hz, 2H), 5.27 (quin, J=6.7 Hz, 1H), 5.90 (s, 1H), 7.91 (s, 1H), 8.22-8.31 (m, 1H), 8.33 (m, 2H), 8.77 (t, J=4.7 Hz, 1H).

Example 72

6-(2-Amino-5-pyrimidinyl)-N-[(4,6-dimethyl-2-oxo-1,2-dihydro-3-pyridinyl)methyl]-1-(1-methylethyl)-1H-pyrazolo[3,4-b]pyridine-4-carboxamide

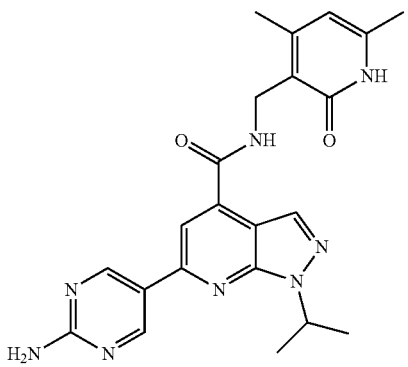 [SMILES: Cc1cc(C)c(CNC(=O)c2cc(-c3cnc(N)nc3)nc3c2cnn3C(C)C)c(=O)[nH]1]

To a 5-mL microwave vial was added DMSO (2 mL) and it was degassed with nitrogen for 5 min. Next added 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (70 mg, 0.187 mmol), 5-(4,4,5,5-tetramethyl-1,3,2-dioxaborolan-2-yl)-2-pyrimidinamine (49.7 mg, 0.225 mmol), sodium carbonate (59.5 mg, 0.562 mmol) and bis(triphenylphosphine)palladium(II) chloride (9.20 mg, 0.013 mmol). The mixture was degassed for additional 5 min, sealed, and irradiated (microwave) at 135° C. for 15 h. The mixture was filtered and the residue was washed with DMSO. The DMSO solution of the crude product was purified using reverse-phase HPLC. The TFA salt of the product was neutralized with saturated NaHCO$_3$ solution, filtered, washed with water, and dried under high vacuum to give 14 mg (17%) of product. LCMS E-S (M+H)=433.2 $^1$H NMR (400 MHz, DMSO-d$_6$) δ ppm 1.52 (d, J=6.4 Hz, 6H), 2.13 (s, 3H), 2.22 (s, 3H), 4.40 (d, J=4.6 Hz, 2H) 5.22-5.41 (m, 1H), 5.90 (s, 1H), 7.18 (m, 2H), 8.08 (s, 1H), 8.34 (s, 1H), 8.86 (m, 1H), 9.11 (s, 2H), 11.58 (br. s., 1H).

Example 73

N-[(4,6-Dimethyl-2-oxo-1,2-dihydro-3-pyridinyl)methyl]-1-(1-methylethyl)-6-(3-pyridinyl)-1H-pyrazolo[3,4-b]pyridine-4-carboxamide

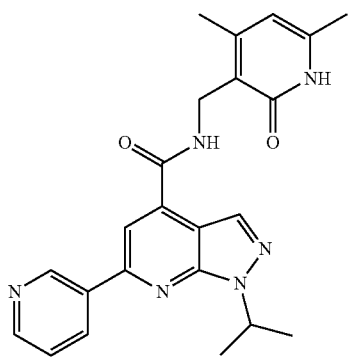 [SMILES: Cc1cc(C)c(CNC(=O)c2cc(-c3cccnc3)nc3c2cnn3C(C)C)c(=O)[nH]1]

To a 5-mL microwave vial were added 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (70 mg, 0.187 mmol), 3-pyridinylboronic acid (29.9 mg, 0.243 mmol), DMSO (1.5 mL) and sodium carbonate (0.281 mL, 0.562 mmol), and the mixture was degassed with nitrogen for 10 min. Next was added bis(triphenylphosphine)palladium (II) chloride (10.51 mg, 0.015 mmol) and the vial was sealed. The reaction mixture was irradiated (microwave) at 140° C. overnight. The reaction mixture was filtered and the residue was washed with DMSO. The crude product in DMSO was purified using reverse-phase HPLC. The TFA salt of the product was neutralized using saturated NaHCO$_3$, filtered, washed with water and dried under high vacuum to give 33 mg (42%) of product. LCMS E-S (M+H)=417.2 $^1$H NMR (400 MHz, DMSO-d$_6$) δ ppm 1.56 (d, J=6.4 Hz, 6H), 2.13 (s, 3H), 2.23 (s, 3H), 4.42 (d, J=4.29 Hz, 2H), 5.26-5.43 (m, 1H), 5.91 (s, 1H), 7.62 (dd, J=7.3, 5.0 Hz, 1H), 8.26 (s, 1H), 8.43 (s, 1H), 8.64 (d, J=7.8 Hz, 1H), 8.70-8.79 (m, 1H), 8.96 (br. s., 1H), 9.46 (br. s., 1H), 11.59 (br. s., 1H).

Example 74

N-[(4,6-Dimethyl-2-oxo-1,2-dihydro-3-pyridinyl)methyl]-6-(1H-indazol-5-yl)-1-(1-methylethyl)-1H-pyrazolo[3,4-b]pyridine-4-carboxamide

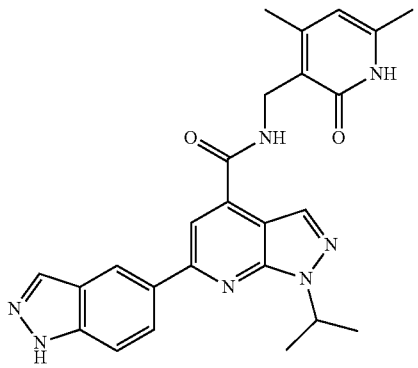 [SMILES: Cc1cc(C)c(CNC(=O)c2cc(-c3ccc4[nH]ncc4c3)nc3c2cnn3C(C)C)c(=O)[nH]1]

To a 5-mL microwave vial were added 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (70 mg, 0.187 mmol), 5-(4,4,5,5-tetramethyl-1,3,2-dioxaborolan-2-yl)-1H-indazole (59.4 mg, 0.243 mmol), DMSO (1.5 mL) and sodium carbonate (0.281 mL, 0.562 mmol), and the mixture was degassed with nitrogen for 10 min. Next was added bis(triphenylphosphine)palladium(II) chloride (10.51 mg, 0.015 mmol). The contents were sealed and irradiated (microwave) at 140° C. overnight. The mixture was filtered and the residue was washed with DMSO. The crude product in DMSO was purified using reverse-phase HPLC. The TFA salt of the product was neutralized using saturated NaHCO$_3$, filtered, washed with water and dried under high vacuum to give 41 mg (48%) of product. LCMS E-S (M+H)=456.0 $^1$H NMR (400 MHz, DMSO-d$_6$) δ ppm 1.56 (d, J=6.8 Hz, 6H), 2.14 (s, 3H), 2.23 (s, 3H), 4.38-4.53 (m, 2H), 5.27-5.49 (m, 1H), 5.91 (s, 1H), 7.59-7.75 (m, 1H), 8.24 (s, 2H), 8.37 (s, 2H), 8.69 (s, 1H), 8.95-9.09 (m, 1H), 11.49-11.67 (m, 1H), 13.21-13.35 (m, 1H).

Example 75

N-[(4,6-Dimethyl-2-oxo-1,2-dihydro-3-pyridinyl)methyl]-6-(1H-indazol-6-yl)-1-(1-methylethyl)-1H-pyrazolo[3,4-b]pyridine-4-carboxamide

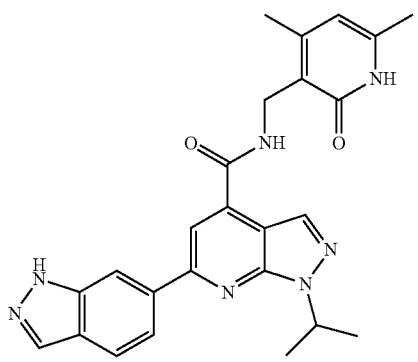 [SMILES: Cc1cc(C)c(CNC(=O)c2cc(-c3ccc4cn[nH]c4c3)nc3c2cnn3C(C)C)c(=O)[nH]1]

The title compound was prepared in the same manner as described in example 74 from 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (70 mg, 0.187 mmol), 6-(4,4,5,5-tetramethyl-1,3,2-dioxaborolan-2-yl)-1H-indazole (59.4 mg, 0.243 mmol), DMSO (1.5 mL), sodium carbonate (0.281 mL, 0.562 mmol), and bis(triphenylphosphine)palladium(II) chloride (10.51 mg, 0.015 mmol). The final product was collected as 55 mg (65%). LCMS E-S (M+H)=456.0 $^1$H NMR (400 MHz, DMSO-d$_6$) δ ppm 1.49-1.65 (m, J=6.4 Hz, 6H), 2.14 (s, 3H), 2.23 (s, 3H), 4.43 (d, J=4.6 Hz, 2H), 5.36 (quin, J=6.7 Hz, 1H), 5.87-5.97 (m, 1H), 7.52-7.72 (m, 2H) 7.92 (d, J=8.6 Hz, 1H), 8.08 (d, J=8.6 Hz, 1H), 8.16 (s, 1H), 8.26 (s, 1H), 8.37-8.49 (m, 2H), 8.96-9.14 (m, 1H), 11.59 (br. s., 1H).

Example 76

6-(1H-1,2,3-Benzotriazol-5-yl)-N-[(4,6-dimethyl-2-oxo-1,2-dihydro-3-pyridinyl)methyl]-1-(1-methylethyl)-1H-pyrazolo[3,4-b]pyridine-4-carboxamide

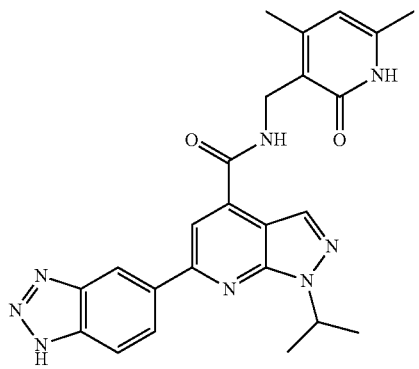 [SMILES: Cc1cc(C)c(CNC(=O)c2cc(-c3ccc4[nH]nnc4c3)nc3c2cnn3C(C)C)c(=O)[nH]1]

The title compound was prepared in the same manner as described in example 74 using 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (70 mg, 0.187 mmol), 1H-1,2,3-benzotriazol-5-ylboronic acid (39.7 mg, 0.243 mmol), DMSO (2 mL), sodium carbonate (0.281 mL, 0.562 mmol) and bis(triphenylphosphine)palladium(II) chloride (10.51 mg, 0.015 mmol). The final product was collected as 22 mg (26%). LCMS E-S (M+H)=457.1 $^1$H NMR (400 MHz, DMSO-d$_6$) δ ppm 1.57 (d, 6 J=6.4 Hz, H), 2.14 (s, 3H), 2.24 (s, 3H), 4.43 (d, J=4.3 Hz, 2H), 5.31-5.46 (m, 1H), 5.91 (s, 1H), 8.07 (br. s., 1H), 8.34 (s, 1H), 8.41 (m, 2H), 8.85 (br. s., 1H), 9.02 (br. s., 1H), 11.59 (br. s., 1H).

Example 77

N-[(4,6-dimethyl-2-oxo-1,2-dihydro-3-pyridinyl)methyl]-3-methyl-1-(1-methylethyl)-6-(2-oxo-2,3-dihydro-1H-benzimidazol-5-yl)-1H-pyrazolo[3,4-b]pyridine-4-carboxamide

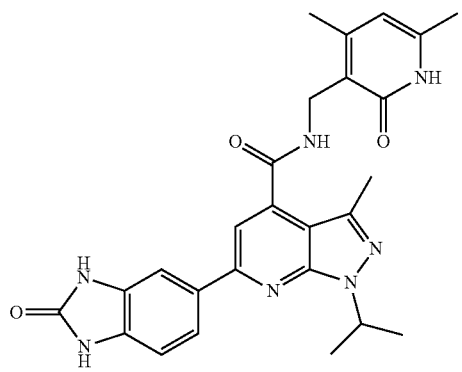 [SMILES: Cc1cc(C)c(CNC(=O)c2cc(-c3ccc4[nH]c(=O)[nH]c4c3)nc3c2c(C)nn3C(C)C)c(=O)[nH]1]

The title compound was prepared in the same manner as described in example 74 using 6-chloro-N-[(4,6-dimethyl-2- oxo-1,2-dihydro-3-pyridinyl)methyl]-1-(1-methylethyl)-1H-pyrazolo[3,4-b]pyridine-4-carboxamide (70 mg, 0.187 mmol), 5-(4,4,5,5-tetramethyl-1,3,2-dioxaborolan-2-yl)-1,3-dihydro-2H-benzimidazol-2-one (61.0 mg, 0.235 mmol), DMSO (1.5 mL) sodium carbonate (0.281 mL, 0.562 mmol), and bis(triphenylphosphine)palladium(II) chloride (10.13 mg, 0.014 mmol). The final product was collected as 19 mg (21%). LCMS E-S (M+H)=486.3 $^1$H NMR (400 MHz, DMSO-d$_6$) δ ppm 1.50 (d, J=6.8 Hz, 6H), 2.12 (s, 3H), 2.24 (s, 3H), 2.43 (s, 3H), 4.39 (d, J=4.6 Hz, 2H), 5.15-5.35 (m, 1H), 5.89 (s, 1H), 7.05 (d, J=8.1 Hz, 1H), 7.61 (s, 1H), 7.77-7.93 (m, 2H), 8.70-8.85 (m, 1H), 10.79 (br. s., 1H), 10.87 (br. s., 1H), 11.54 (br. s., 1H).

Example 78

N-[(4,6-Dimethyl-2-oxo-1,2-dihydro-3-pyridinyl)methyl]-1-(1-methylethyl)-6-(2-oxo-2,3-dihydro-1H-indol-6-yl)-1H-pyrazolo[3,4-b]pyridine-4-carboxamide

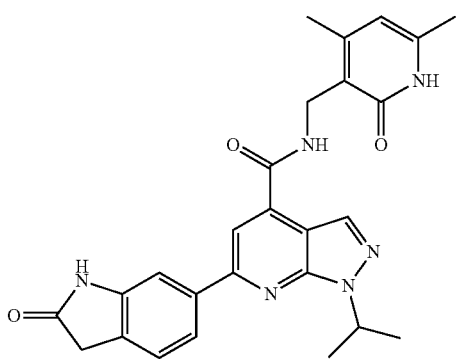 [SMILES: Cc1cc(C)c(CNC(=O)c2cc(-c3ccc4c(c3)NC(=O)C4)nc3c2cnn3C(C)C)c(=O)[nH]1]

The title compound was prepared in the same manner as described in example 74 using 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (70 mg, 0.187 mmol), 6-(4,4,5,5-tetramethyl-1,3,2-dioxaborolan-2-yl)-1,3-dihydro-2H-indol-2-one (63.1 mg, 0.243 mmol), DMSO (1.5 mL), sodium carbonate (0.281 mL, 0.562 mmol), and bis(triphenylphosphine)palladium(II) chloride (10.51 mg, 0.015 mmol). The final product was collected as 10 mg (11%). LCMS E-S (M+H)=471.1 $^1$H NMR (400 MHz, DMSO-d$_6$) δ ppm 1.55 (d, J=6.8 Hz, 6H), 2.13 (s, 3H), 2.22 (s, 3H), 3.58 (s, 2H), 4.41 (d, J=4.8 Hz, 2H), 5.31 (quin, J=6.6 Hz, 1H), 5.91 (s, 1H), 7.38 (d, J=7.6 Hz, 1H), 7.73 (d, J=1.0 Hz, 1H), 7.87 (dd, J=7.8, 1.5 Hz, 1H), 8.12 (s, 1H), 8.37 (s, 1H), 9.00 (t, J=4.8 Hz, 1H), 10.55 (s, 1H), 11.58 (s, 1H).

Example 79

N-[(4,6-Dimethyl-2-oxo-1,2-dihydro-3-pyridinyl)methyl]-1-(1-methylethyl)-6-(2-oxo-2,3-dihydro-1H-indol-5-yl)-1H-pyrazolo[3,4-b]pyridine-4-carboxamide

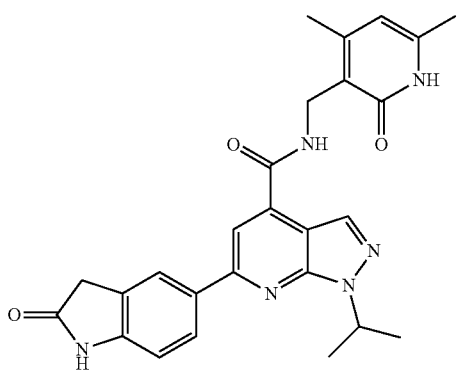 [SMILES: Cc1cc(C)c(CNC(=O)c2cc(-c3ccc4c(c3)CC(=O)N4)nc3c2cnn3C(C)C)c(=O)[nH]1]

The title compound was prepared in the same manner as described in example 74 using 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (70 mg, 0.187 mmol), 5-(4,4,5,5-tetramethyl-1,3,2-dioxaborolan-2-yl)-1,3-dihydro-2H-indol-2-one (63.1 mg, 0.243 mmol), DMSO (1.5 mL), sodium carbonate (0.281 mL, 0.562 mmol), and bis(triphenylphosphine)palladium(II) chloride (10.51 mg, 0.015 mmol). The final product was collected as 30 mg (34%). LCMS E-S (M+H)=471.3 $^1$H NMR (400 MHz, DMSO-d$_6$) δ ppm 1.54 (d, J=6.4 Hz, 6H), 2.13 (s, 3H), 2.22 (s, 3H), 3.40 (br. s., 2H), 4.41 (d, J=4.6 Hz, 2H), 5.25-5.41 (m, 1H), 5.91 (s, 1H), 6.97 (d, J=8.1 Hz, 1H), 8.08-8.21 (m, 3H), 8.34 (s, 1H), 8.96 (br. s., 1H), 10.64 (s, 1H), 11.58 (br. s., 1H).

Example 80

N-[(4,6-Dimethyl-2-oxo-1,2-dihydro-3-pyridinyl)methyl]-1-(1-methylethyl)-6-(2-oxo-2,3-dihydro-1H-benzimidazol-5-yl)-1H-pyrazolo[3,4-b]pyridine-4-carboxamide

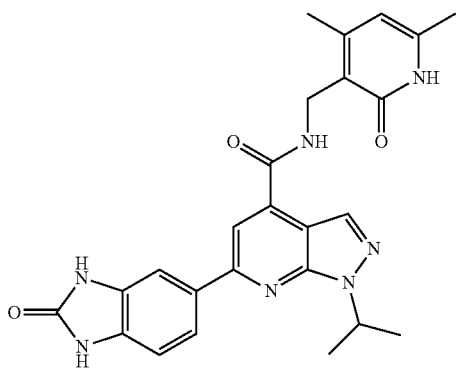 [SMILES: Cc1cc(C)c(CNC(=O)c2cc(-c3ccc4[nH]c(=O)[nH]c4c3)nc3c2cnn3C(C)C)c(=O)[nH]1]

The title compound was prepared in the same manner as described in example 74 using 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (70 mg, 0.187 mmol), 5-(4,4,5,5-tetramethyl-1,3,2-dioxaborolan-2-yl)-1,3-dihydro-2H-benzimidazol-2-one (63.3 mg, 0.243 mmol), DMSO (2 mL), sodium carbonate (0.281 mL, 0.562 mmol), and bis(triphenylphosphine)palladium(II) chloride (10.51 mg, 0.015 mmol). The final product was collected as 35 mg (40%). LCMS E-S (M+H)=472.4 $^1$H NMR (400 MHz, DMSO-$d_6$) δ ppm 1.55 (d, J=6.4 Hz, 6H), 2.13 (s, 3H), 2.22 (s, 3H), 4.41 (d, J=4.8 Hz, 2H), 5.30 (quin, J=6.6 Hz, 1H), 5.91 (s, 1H), 7.07 (d, J=8.3 Hz, 1H), 7.86 (s, 1H), 7.92 (dd, J=8.3, 1.8 Hz, 1H), 8.10 (s, 1H), 8.30-8.41 (m, 1H), 8.98 (t, J=4.8 Hz, 1H), 10.82 (s, 1H), 10.89 (s, 1H). 11.58 (s, 1H).

Example 81

N-[(4,6-Dimethyl-2-oxo-1,2-dihydro-3-pyridinyl)methyl]-1-(1-methylethyl)-6-[6-(4-methyl-1-piperazinyl)-3-pyridinyl]-1H-pyrazolo[3,4-b]pyridine-4-carboxamide

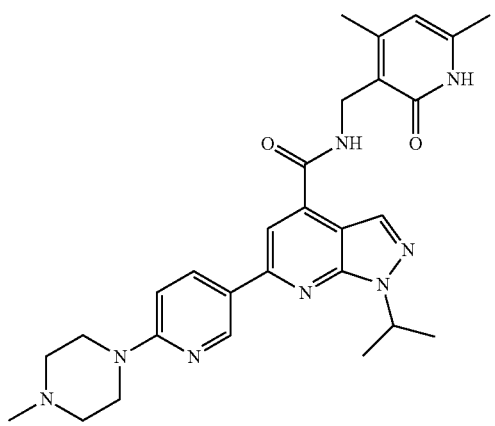

The title compound was prepared in the same manner as described in example 74 using 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (70 mg, 0.187 mmol), 1-methyl-4-[5-(4,4,5,5-tetramethyl-1,3,2-dioxaborolan-2-yl)-2-pyridinyl]piperazine (73.8 mg, 0.243 mmol), DMSO (2 mL), sodium carbonate (0.281 mL, 0.562 mmol), and bis(triphenylphosphine)palladium(II) chloride (10.51 mg, 0.015 mmol). The final product was collected as 12 mg (13%). LCMS E-S (M+H)=515.1 $^1$H NMR (400 MHz, DMSO-$d_6$) δ ppm 1.53 (d, J=6.4 Hz, 6H), 2.13 (s, 3H), 2.23 (m, 6H), 2.37-2.46 (m, 4H), 3.56-3.69 (m, 4H), 4.40 (d, J=4.6 Hz, 2H), 5.30 (quin, J=6.7 Hz, 1H), 5.91 (s, 1H), 6.99 (d, J=9.1 Hz, 1H), 8.10 (s, 1H), 8.32 (s, 1H), 8.38 (dd, J=9.1, 2.5 Hz, 1H), 8.91 (br. s., 1H), 9.03 (d, J=2.3 Hz, 1H).

Example 82

N-[(4,6-Dimethyl-2-oxo-1,2-dihydro-3-pyridinyl)methyl]-1-(1-methylethyl)-6-[6-(4-methyl-1-piperazinyl)-3-pyridinyl]-1H-pyrazolo[3,4-b]pyridine-4-carboxamide

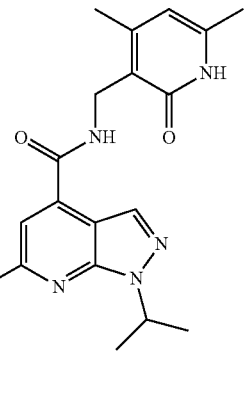

The title compound was prepared in the same manner as described in example 74 using 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (70 mg, 0.187 mmol), 1-methyl-4-[4-(4,4,5,5-tetramethyl-1,3,2-dioxaborolan-2-yl)phenyl]piperazine (73.6 mg, 0.243 mmol), 1,2-Dimethoxyethane (DME) (3 mL), water (1 mL) sodium carbonate (0.281 mL, 0.562 mmol), and bis(triphenylphosphine)palladium(II) chloride (12.23 mg, 0.015 mmol), wherein the reaction time was 30 min. The crude product was purified by column chromatography (eluent: gradient of 0 to 15% (9:1 MeOH/NH$_4$OH)/DCM). The product was dried under high vacuum and collected as 58 mg (59%). LCMS E-S (M+H)=514.3 $^1$H NMR (400 MHz, DMSO-$d_6$) δ ppm 1.51-1.58 (m, 6H), 2.13 (s, 3H), 2.23 (s, 6H), 2.24 (s, 3H), 2.47 (m, 4H), 3.24-3.30 (m, 4H), 4.41 (d, J=5.05 Hz, 2H), 5.30 (quin, J=6.63 Hz, 1H), 5.90 (s, 1H), 7.07 (d, J=9.09 Hz, 2H), 8.06 (s, 1H), 8.15 (d, J=8.84 Hz, 2H), 8.30 (s, 1H), 8.92 (t, J=4.80 Hz, 1H), 11.55 (s, 1H).

Example 83

N-[(4,6-Dimethyl-2-oxo-1,2-dihydro-3-pyridinyl)methyl]-3-methyl-1-(1-methylethyl)-6-[6-(4-morpholinyl)-3-pyridinyl]-1H-pyrazolo[3,4-b]pyridine-4-carboxamide

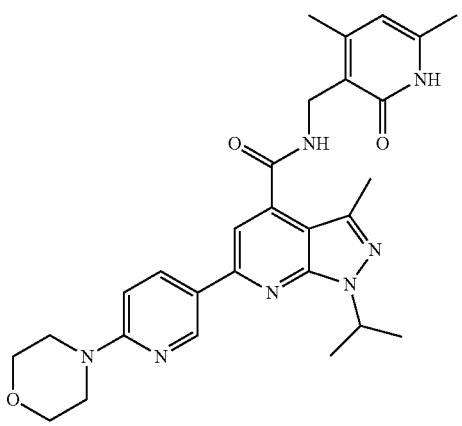 [SMILES: Cc1cc(C)c(CNC(=O)c2cc(-c3ccc(N4CCOCC4)nc3)nc3c2c(C)nn3C(C)C)c(=O)[nH]1]

The title compound was prepared in the same manner as described in example 74 using 6-chloro-N-[(4,6-dimethyl-2-oxo-1,2-dihydro-3-pyridinyl)methyl]-3-methyl-1-(1-methylethyl)-1H-pyrazolo[3,4-b]pyridine-4-carboxamide (70 mg, 0.180 mmol), [6-(4-morpholinyl)-3-pyridinyl]boronic acid (48.8 mg, 0.235 mmol), DMSO (2.0 mL), sodium carbonate (0.271 mL, 0.541 mmol), and bis(triphenylphosphine) palladium(II) chloride (10.13 mg, 0.014 mmol), wherein the reaction time was 8 h. The mixture was filtered and the residue was washed with DMSO. The crude product in DMSO was purified by reverse-phase HPLC (mobile phase: 25-60% CAN in $H_2O$, 0.1% TFA). The TFA product salt obtained was neutralized with saturated $NaHCO_3$, filtered, washed with water, and dried under high vacuum to give the product as 24 mg (25%). LCMS E-S (M+H)=516.2 $^1$H NMR (400 MHz, DMSO-$d_6$) δ ppm 1.50 (d, J=6.57 Hz, 6H), 2.12 (s, 3H), 2.25 (s, 3H), 2.42 (s, 3H), 3.54-3.63 (m, 4H), 3.73 (m, 4H), 4.39 (d, J=4.80 Hz, 2H), 5.14-5.29 (m, 1H), 5.89 (s, 1H), 6.97 (d, J=8.84 Hz, 1H), 7.63 (s, 1H), 8.37 (dd, J=9.09, 2.53 Hz, 1H), 8.68 (t, J=4.93 Hz, 1H), 8.98 (d, J=2.27 Hz, 1H), 11.51 (s, 1H).

Example 84

N-[(4,6-Dimethyl-2-oxo-1,2-dihydro-3-pyridinyl)methyl]-1-(1-methylethyl)-6-(4-pyridinylamino)-1H-pyrazolo[3,4-b]pyridine-4-carboxamide

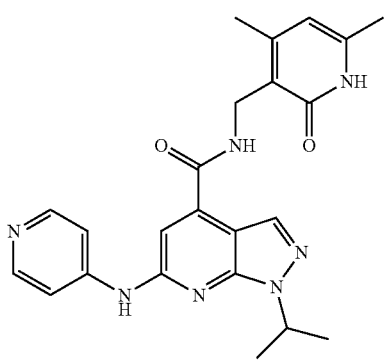 [SMILES: Cc1cc(C)c(CNC(=O)c2cc(Nc3ccncc3)nc3c2cnn3C(C)C)c(=O)[nH]1]

The title compound was prepared in the same manner as described in example 74 using 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (50 mg, 0.134 mmol), 4-pyridinamine (12.59 mg, 0.134 mmol), cesium carbonate (131 mg, 0.401 mmol), 1,4-dioxane (2 mL), palladium (II) acetate (1.501 mg, 6.69 µmol) and BINAP (8.33 mg, 0.013 mmol), wherein the reaction time was 2 h. The final product was collected as 29 mg (50%). LCMS E-S (M+H) =432.3 $^1$H NMR (400 MHz, DMSO-$d_6$) δ ppm 1.45-1.59 (d, J=6.8 Hz, 6H), 2.14 (s, 3H), 2.23 (s, 3H), 4.36 (d, J=5.0 Hz, 2H), 5.16 (m, 1H), 5.91 (s, 1H), 7.09 (s, 1H), 7.99 (d, J=6.1 Hz, 2H), 8.12 (s, 1H) 8.49 (d, J=6.6 Hz, 2H), 8.74 (t, J=5.1 Hz, 1H), 10.58 (s, 1H), 11.58 (s, 1H).

Example 85

N-[(4,6-Dimethyl-2-oxo-1,2-dihydro-3-pyridinyl)methyl]-1-(1-methylethyl)-6-[(2-oxo-2,3-dihydro-1H-benzimidazol-5-yl)amino]-1H-pyrazolo[3,4-b]pyridine-4-carboxamide

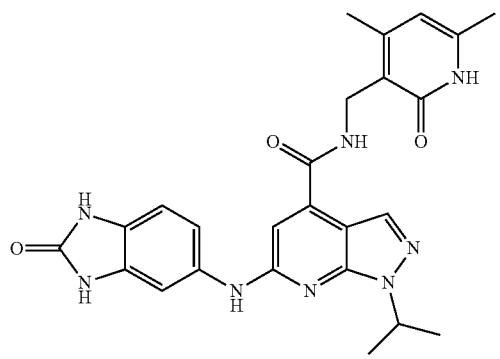 [SMILES: Cc1cc(C)c(CNC(=O)c2cc(Nc3ccc4[nH]c(=O)[nH]c4c3)nc3c2cnn3C(C)C)c(=O)[nH]1]

The title compound was prepared in the same manner as described in example 74 using 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (70 mg, 0.187 mmol), 5-amino-1,3-dihydro-2H-benzimidazol-2-one (33.5 mg, 0.225 mmol), cesium carbonate (92 mg, 0.281 mmol), N,N-dimethylacetamide (DMA) (2 mL), palladium(II) acetate (2.52 mg, 0.011 mmol) and Xantphos (10.83 mg, 0.019 mmol) wherein the reaction temperature was 150° C. and reaction time was 8 h. The final product was collected as 25 mg (27%). LCMS E-S (M+H)=487.2 $^1$H NMR (400 MHz, DMSO-$d_6$) δ ppm 1.50-1.61 (m, 6H), 2.13 (s, 3H), 2.23 (s, 3H), 4.38 (d, J=5.0 Hz, 2H), 5.20 (quin, J=6.6 Hz, 1H), 5.90 (s, 1H), 6.79-6.91 (m, 2H), 8.04 (d, J=8.3 Hz, 1H), 8.26-8.33 (m, 2H), 8.84 (t, J=5.0 Hz, 1H), 11.50 (s, 1H).

Example 86

6-{[4-(Aminocarbonyl)phenyl]amino}-N-[(4,6-dimethyl-2-oxo-1,2-dihydro-3-pyridinyl)methyl]-1-(1-methylethyl)-1H-pyrazolo[3,4-b]pyridine-4-carboxamide

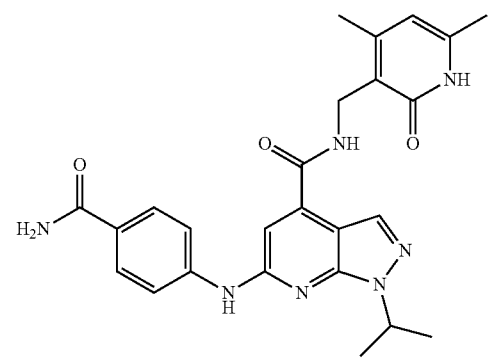 [SMILES: Cc1cc(C)c(CNC(=O)c2cc(Nc3ccc(C(N)=O)cc3)nc3c2cnn3C(C)C)c(=O)[nH]1]

The title compound was prepared in the same manner as described in example 74 using 6-chloro-N-[(4,6-dimethyl-2- oxo-1,2-dihydro-3-pyridinyl)methyl]-3-methyl-1-(1-methylethyl)-1H-pyrazolo[3,4-b]pyridine-4-carboxamide (70 mg, 0.180 mmol), 4-aminobenzamide (29.5 mg, 0.217 mmol), cesium carbonate (88 mg, 0.271 mmol), N,N-dimethylacetamide (DMA) (1.5 mL), palladium(II) acetate (2.431 mg, 10.83 μmol) and Xantphos (10.44 mg, 0.018 mmol) wherein the reaction temperature was 150° C. and reaction time was 1 h. The final product was collected as 12 mg (14%). LCMS E-S (M+H)=488.2 $^1$H NMR (400 MHz, DMSO-d$_6$) δ ppm 1.48 (d, J=6.4 Hz, 6H), 2.13 (s, 3H), 2.23 (s, 3H), 2.32 (s, 3H), 4.35 (d, J=4.8 Hz, 2H), 4.99 (quin, J=6.8 Hz, 1H), 5.89 (s, 1H), 6.65 (s, 1H), 7.15 (br. s., 1H), 7.75-7.82 (m, 1H), 7.84-7.96 (m, 4H), 8.56 (t, J=4.9 Hz, 1H), 9.77 (s, 1H).

Example 87

1-(1,1-Dimethylethyl)-N-[(4,6-dimethyl-2-oxo-1,2-dihydro-3-pyridinyl)methyl]-3-methyl-6-[6-(4-methyl-1-piperazinyl)-3-pyridinyl]-1H-pyrazolo[3,4-b]pyridine-4-carboxamide

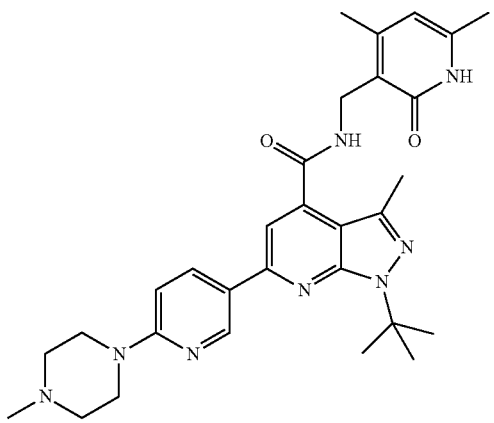

The title compound was prepared in the same manner as described in example 74 using 6-chloro-1-(1,1-dimethylethyl)-N-[(4,6-dimethyl-2-oxo-1,2-dihydro-3-pyridinyl)methyl]-3-methyl-1H-pyrazolo[3,4-b]pyridine-4-carboxamide (70 mg, 0.174 mmol), 1-methyl-4-[5-(4,4,5,5-tetramethyl-1,3,2-dioxaborolan-2-yl)-2-pyridinyl]piperazine (68.7 mg, 0.226 mmol), DME (3 mL), water (1.00 mL), sodium carbonate (0.261 mL, 0.523 mmol) and PdCl$_2$(dppf)-CH$_2$Cl$_2$ adduct (11.38 mg, 0.014 mmol), wherein the reaction time was 40 min. The crude product was purified by column chromatography (eluent: gradient of 0 to 15% (9:1 MeOH/NH$_4$OH)/DCM). The final product was collected as a solid, 41 mg (43%). LCMS E-S (M+H)=543.2 $^1$H NMR (400 MHz, DMSO-d$_6$) δ ppm 1.78 (s, 9H), 2.12 (s, 3H), 2.24 (m, 7H), 2.38 (s, 3H), 2.39-2.49 (m, 4H), 3.34 (s, 3H), 4.38 (m, 2H), 5.88 (s, 1H), 6.98 (d, J=9.09 Hz, 1H), 7.59 (s, 1H), 8.93-8.97 (m, 1H), 11.49-11.57 (m, 1H), 11.53 (s, 1H), 11.53 (s, 1H).

Example 88

1-(1,1-Dimethylethyl)-N-[(4,6-dimethyl-2-oxo-1,2-dihydro-3-pyridinyl)methyl]-3-methyl-6-(2-oxo-2,3-dihydro-1H-benzimidazol-5-yl)-1H-pyrazolo[3,4-b]pyridine-4-carboxamide

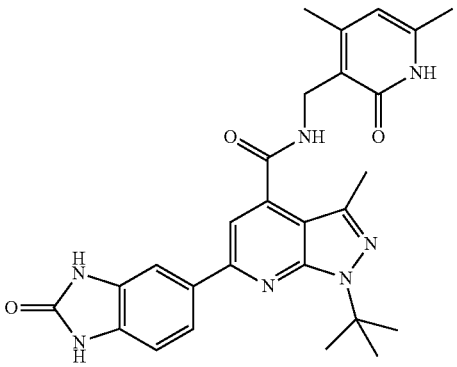 [SMILES: Cc1cc(C)c(CNC(=O)c2cc(-c3ccc4[nH]c(=O)[nH]c4c3)nc3c2c(C)nn3C(C)(C)C)c(=O)[nH]1]

The title compound was prepared in the same manner as described in example 74 using 6-chloro-1-(1,1-dimethylethyl)-N-[(4,6-dimethyl-2-oxo-1,2-dihydro-3-pyridinyl)methyl]-3-methyl-1H-pyrazolo[3,4-b]pyridine-4-carboxamide (70 mg, 0.174 mmol), 5-(4,4,5,5-tetramethyl-1,3,2-dioxaborolan-2-yl)-1,3-dihydro-2H-benzimidazol-2-one (58.9 mg, 0.226 mmol), DME (3 mL), water (1.00 mL), sodium carbonate (0.261 mL, 0.523 mmol) and PdCl$_2$(dppf)-CH$_2$Cl$_2$ adduct (11.38 mg, 0.014 mmol) wherein the reaction time was 40 min. The crude product was purified by column chromatography (eluent: gradient of 0 to 15% (9:1 MeOH/NH$_4$OH)/DCM). The final product was collected as a solid, 24 mg (27%). LCMS E-S (M+H)=500.2 $^1$H NMR (400 MHz, DMSO-d$_6$) δ ppm 1.77 (m, 9H), 2.12 (s, 3H), 2.24 (s, 3H), 2.40 (s, 3H), 4.38 (d, J=4.55 Hz, 2H), 5.89 (s, 1H), 7.06 (d, J=8.08 Hz, 1H), 7.59 (s, 1H), 7.72-7.86 (m, 2H), 8.73 (br. s., 2H), 10.74-10.92 (m, 1H), 11.53 (br. s., 1H).

Example 89

1-(1,1-Dimethylethyl)-N-[(4,6-dimethyl-2-oxo-1,2-dihydro-3-pyridinyl)methyl]-3-methyl-6-[6-(4-morpholinyl)-3-pyridinyl]-1H-pyrazolo[3,4-b]pyridine-4-carboxamide

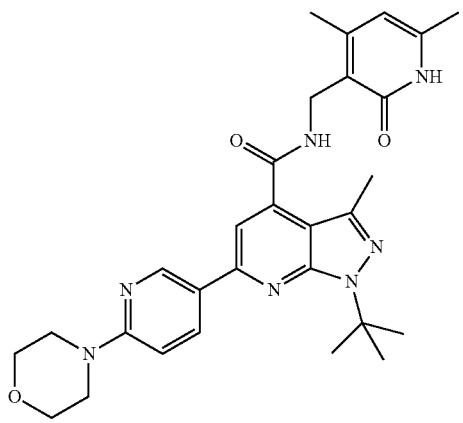 [SMILES: Cc1cc(C)c(CNC(=O)c2cc(-c3ccc(N4CCOCC4)nc3)nc3c2c(C)nn3C(C)(C)C)c(=O)[nH]1]

The title compound was prepared in the same manner as described in example 74 using 6-chloro-1-(1,1-dimethylethyl)-N-[(4,6-dimethyl-2-oxo-1,2-dihydro-3-pyridinyl)methyl]-3-methyl-1H-pyrazolo[3,4-b]pyridine-4-carboxamide (70 mg, 0.174 mmol), [6-(4-morpholinyl)-3-pyridinyl]boronic acid (47.1 mg, 0.226 mmol), DME (3 mL), water (1.00 mL), sodium carbonate (0.261 mL, 0.523 mmol) and PdCl$_2$(dppf)-CH$_2$Cl$_2$ adduct (11.38 mg, 0.014 mmol) wherein the reaction time was 40 min. The crude product was purified by column chromatography (eluent: gradient of 0 to 15% (9:1 MeOH/NH$_4$OH)/DCM). The final product was collected as a solid, 61 mg (65%). LCMS E-S (M+H)=530.0 $^1$H NMR (400 MHz, DMSO-d$_6$) δ ppm 1.78 (s, 9H), 2.12 (s, 3H), 2.24 (s, 3H), 2.38 (s, 3H), 3.52-3.64 (m, 4H), 3.68-3.80 (m, 4H), 4.38 (d, J=5.05 Hz, 2H), 5.88 (s, 1H), 6.99 (d, J=9.09 Hz, 1H), 7.61 (s, 1H), 8.34 (dd, J=8.84, 2.53 Hz, 1H), 8.68 (t, J=5.05 Hz, 1H), 8.97 (d, J=2.27 Hz, 1H), 11.53 (s, 1H).

Example 90

6-(2,1,3-Benzoxadiazol-5-yl)-N-[(4,6-dimethyl-2-oxo-1,2-dihydro-3-pyridinyl)methyl]-3-methyl-1-(1-methylethyl)-1H-pyrazolo[3,4-b]pyridine-4-carboxamide

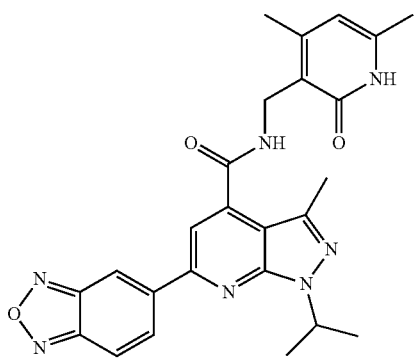 [SMILES: Cc1cc(C)c(CNC(=O)c2cc(-c3ccc4nonc4c3)nc3c2c(C)nn3C(C)C)c(=O)[nH]1]

The title compound was prepared in the same manner as described in example 74 using 6-chloro-N-[(4,6-dimethyl-2-oxo-1,2-dihydro-3-pyridinyl)methyl]-3-methyl-1-(1-methylethyl)-1H-pyrazolo[3,4-b]pyridine-4-carboxamide (70 mg, 0.180 mmol), 5-(4,4,5,5-tetramethyl-1,3,2-dioxaborolan-2-yl)-2,1,3-benzoxadiazole (57.7 mg, 0.235 mmol), DMSO (2 mL), sodium carbonate (0.271 mL, 0.541 mmol), and bis(triphenylphosphine)palladium(II) chloride (12.67 mg, 0.018 mmol) wherein the reaction time was 8 h. The final product was collected as 17 mg (20%). LCMS LCMS E-S (M+H)=472.4 $^1$H NMR (400 MHz, DMSO-d$_6$) δ ppm 1.53 (d, J=6.8 Hz, 6H), 2.12 (s, 3H), 2.27 (s, 3H) 4.42 (d, J=4.8 Hz, 2H) 5.32 (quin, J=6.6 Hz, 1H), 5.90 (s, 1H), 8.00 (s, 1H), 8.23 (d, J=9.4 Hz, 1H), 8.54-8.64 (m, 1H), 8.79 (t, J=4.7 Hz, 1H), 8.91 (s, 1H), 11.54 (br. s., 1H).

Example 91

6-(2-Amino-6-quinazolinyl)-N-[(4,6-dimethyl-2-oxo-1,2-dihydro-3-pyridinyl)methyl]-3-methyl-1-(1-methylethyl)-1H-pyrazolo[3,4-b]pyridine-4-carboxamide

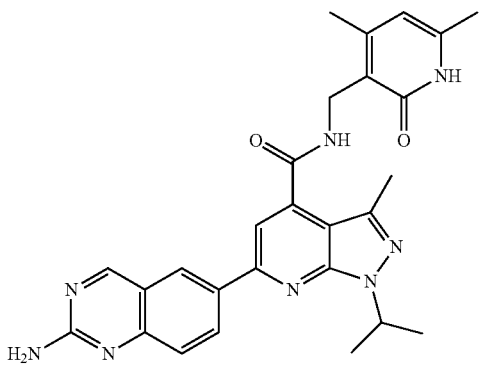 [SMILES: Cc1cc(C)c(CNC(=O)c2cc(-c3ccc4nc(N)ncc4c3)nc3c2c(C)nn3C(C)C)c(=O)[nH]1]

The title compound was prepared in the same manner as described in example 74 using 6-chloro-N-[(4,6-dimethyl-2-oxo-1,2-dihydro-3-pyridinyl)methyl]-3-methyl-1-(1-methylethyl)-1H-pyrazolo[3,4-b]pyridine-4-carboxamide (70 mg, 0.180 mmol), 5-(4,4,5,5-tetramethyl-1,3,2-dioxaborolan-2-yl)-2,1,3-benzoxadiazole (57.7 mg, 0.235 mmol), DMSO (2 mL), sodium carbonate (0.271 mL, 0.541 mmol), and bis(triphenylphosphine)palladium(II) chloride (12.67 mg, 0.018 mmol), wherein the reaction time was 8 h. The final product was collected as 28 mg (31%). LCMS E-S (M+H)=497.3 $^1$H NMR (400 MHz, DMSO-d$_6$) δ ppm 1.52 (d, J=6.8 Hz, 6H), 2.12 (s, 3H), 2.26 (s, 3H), 4.41 (d, J=5.0 Hz, 2H) 5.30 (quin, J=6.6 Hz, 1H), 5.89 (s, 1H), 7.16 (br. s., 2H), 7.56 (d, J=9.1 Hz, 1H), 7.78 (s, 1H) 8.60 (dd, J=8.8, 2.0 Hz, 1H), 8.69 (d, J=1.8 Hz, 1H), 8.76 (t, J=4.9 Hz, 1H), 9.28 (s, 1H), 11.53 (s, 1H).

Example 92

N-[(4,6-Dimethyl-2-oxo-1,2-dihydro-3-pyridinyl)methyl]-3-methyl-6-{4-[(methylamino)sulfonyl]phenyl}-1-(1-methylethyl)-1H-pyrazolo[3,4-b]pyridine-4-carboxamide

Example 93

6-[4-(Acetylamino)phenyl]-N-[(4,6-dimethyl-2-oxo-1,2-dihydro-3-pyridinyl)methyl]-3-methyl-1-(1-methylethyl)-1H-pyrazolo[3,4-b]pyridine-4-carboxamide

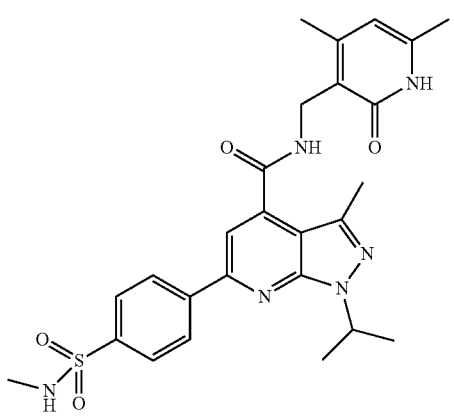

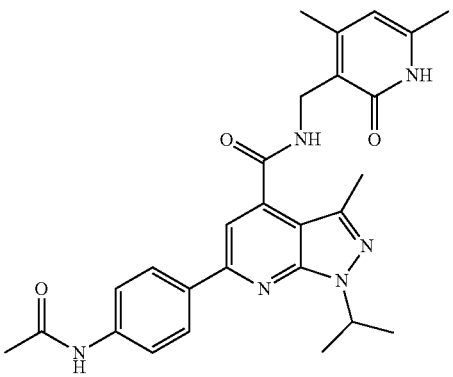 [SMILES: CC(=O)Nc1ccc(-c2cc(C(=O)NCc3c(C)cc(C)[nH]c3=O)c3c(C)nn(C(C)C)c3n2)cc1]

6-Chloro-N-[(4,6-dimethyl-2-oxo-1,2-dihydro-3-pyridinyl)methyl]-3-methyl-1-(1-methylethyl)-1H-pyrazolo[3,4-b]pyridine-4-carboxamide (80 mg, 0.21 mmol), {4-[(methylamino)sulfonyl]phenyl}boronic acid (66.5 mg, 0.31 mmol) and bis(triphenylphosphine)palladium(II) chloride (8.4 mg, 0.01 mmol) were suspended in DME/water (4 mL, 3:1) and stirred for 10 min under nitrogen at room temperature. Sodium bicarbonate (52 mg, 0.62 mmol) was added and the heterogenous mixture was irradiated (microwave) at 150° C. for 30 min. After cooling to room temperature, water was added to the black mixture, and the contents were vacuum filtered. The crude product was dissolved in DCM/MeOH (1:1) and preabsorbed onto silica gel. The product was purified by silica gel chromatography (eluent: DCM/MeOH/NH$_4$OH, gradient of 0 to 90:10:1). The light beige solid that was collected was suspended in EtOH, sonicated, and filtered. The solid was then air-dried for 15 min, and then in vacuum oven overnight. The final product was collected as 77 mg (70%). LCMS E-S (M+H)=523.2 $^1$H NMR (400 MHz, DMSO-d$_6$) δ ppm 11.54 (br. s., 1H) 8.78 (t, J=5.05 Hz, 1H) 8.43 (m, J=8.59 Hz, 2H) 7.93 (m, J=8.59 Hz, 2H) 7.78 (s, 1H) 7.58 (br. s., 1H) 5.89 (s, 1H) 5.29 (quin, J=6.63 Hz, 1H) 4.40 (d, J=4.80 Hz, 2H) 2.46 (d, J=1.26 Hz, 6H) 2.25 (s, 3H) 2.12 (s, 3H) 1.52 (s, 3H) 1.51 (s, 3H).

The title compound was prepared in the same manner as described in example 93 using 6-chloro-N-[(4,6-dimethyl-2-oxo-1,2-dihydro-3-pyridinyl)methyl]-3-methyl-1-(1-methylethyl)-1H-pyrazolo[3,4-b]pyridine-4-carboxamide (80 mg, 0.21 mmol), [4-(acetylamino)phenyl]boronic acid (55.4 mg, 0.31 mmol), bis(triphenylphosphine)palladium(II) chloride (8.4 mg, 0.01 mmol), DME/water (4 mL, 3:1) and sodium bicarbonate (52 mg, 0.62 mmol). The crude product was dissolved in DCM/MeOH (1:1) and preabsorbed onto silica gel. The product was purified by silica gel chromatography (eluent: DCM/MeOH/NH$_4$OH. gradient of 0 to 80:20:2). The collected solid was suspended in EtOH/EtOAc (1:1), sonicated, and filtered. After further washing with hexanes, the solid was then air-dried for 15 min, and then in vacuum oven overnight. The final product was collected as 70 mg (69%). LCMS E-S (M+H)=487.3 $^1$H NMR (400 MHz, DMSO-d$_6$) δ ppm 11.53 (br. s., 1H) 10.16 (s, 1H) 8.73 (t, J=5.05 Hz, 1H) 8.17 (m, J=8.84 Hz, 2H) 7.74 (m, J=8.84 Hz, 2H) 7.64 (s, 1H) 5.89 (s, 1H) 5.25 (quin, J=6.69 Hz, 1H) 4.39 (d, J=4.80 Hz, 2H) 2.43 (s, 3H) 2.25 (s, 3H) 2.12 (s, 3H) 2.09 (s, 3H) 1.51 (s, 3H) 1.49 (s, 3H).

Example 94

6-[4-(Aminocarbonyl)phenyl]-N-[(4,6-dimethyl-2-oxo-1,2-dihydro-3-pyridinyl)methyl]-1-(1-methylethyl)-1H-pyrazolo[3,4-b]pyridine-4-carboxamide

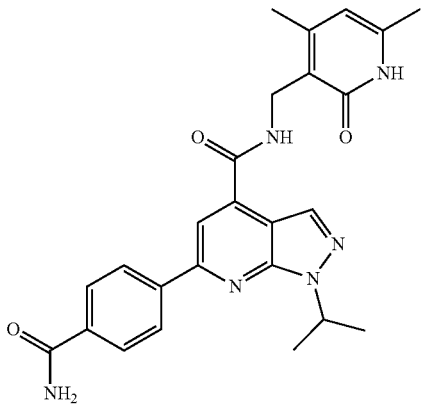 [SMILES: Cc1cc(C)c(CNC(=O)c2cc(-c3ccc(C(N)=O)cc3)nc3c2cnn3C(C)C)c(=O)[nH]1]

The title compound was prepared in the same manner as described in example 93 using 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (80 mg, 0.21 mmol), [4-(aminocarbonyl)phenyl]boronic acid (52.9 mg, 0.31 mmol), bis(triphenylphosphine)palladium(II) chloride (8.7 mg, 0.01 mmol), DME/water (4 mL, 3:1) and sodium bicarbonate (54 mg, 0.62 mmol). The crude product was dissolved in DCM/MeOH (1:1) and preabsorbed onto silica gel. The product was purified by silica gel chromatography (eluent: DCM/MeOH/NH$_4$OH (gradient 0 to 90:10:1). The collected solid was suspended in EtOH, sonicated, and filtered. After further washing with EtOH/DCM, the filtered solid was then air-dried for 15 min, and then in vacuum oven overnight. The final product was collected as 70 mg (69%). LCMS E-S (M+H)=459.3 $^1$H NMR (400 MHz, DMSO-d$_6$) δ ppm 11.58 (s, 1H) 9.00 (t, J=4.93 Hz, 1H) 8.41 (s, 1H) 8.36 (s, 1H) 8.34 (s, 1H) 8.24 (s, 1H) 8.13 (s, 1H) 8.06 (s, 1H) 8.04 (s, 1H) 7.51 (s, 1H) 5.91 (s, 1H) 5.37 (quin, J=6.69 Hz, 1H) 4.42 (d, J=4.80 Hz, 2H) 2.23 (s, 3H) 2.13 (s, 3H) 1.56 (s, 3H) 1.55 (s, 3H).

Example 95

N-[(4,6-Dimethyl-2-oxo-1,2-dihydro-3-pyridinyl)methyl]-1-(1-methylethyl)-6-{[2-(2-pyridinylamino)ethyl]amino}-1H-pyrazolo[3,4-b]pyridine-4-carboxamide

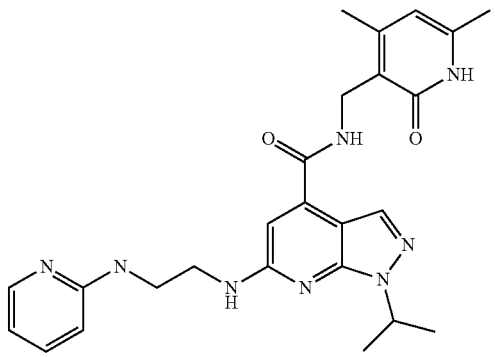 [SMILES: Cc1cc(C)c(CNC(=O)c2cc(NCCNc3ccccn3)nc3c2cnn3C(C)C)c(=O)[nH]1]

6-Chloro-N-[(4,6-dimethyl-2-oxo-1,2-dihydro-3-pyridinyl)methyl]-1-(1-methylethyl)-1H-pyrazolo[3,4-b]pyridine-4-carboxamide (80 mg, 0.21 mmol) and (2-aminoethyl)-2-pyridinylamine (88 mg, 0.64 mmol) were suspended in 2 mL of NMP and irradiated (microwave) as follows: 180° C. for 30 min, 200° C. for 30 min, 220° C. for 30 min, 230° C. for 30 min and then 240° C. for 1 h. After cooling to room temperature, some of the solvent was removed in vacuo and the residue was purified by silica gel chromatography (eluent: DCM/MeOH/NH$_4$OH, gradient 0 to 90:10:1). The collected solid was partitioned between water and EtOAc/toluene (1:1) and then extracted twice with DCM/isopropanol. The combined organic layers were washed with water, dried over MgSO$_4$, filtered, and concentrated in vacuo to afford a dark brown oil. After drying under vacuum overnight, the residue was again purified by silica gel chromatography (eluent: DCM/MeOH/NH$_4$OH (gradient 0 to 90:10:1). The collected solid was suspended in EtOH, sonicated, and filtered. The solid was further washed with EtOH/DCM, filtered, and dried in vacuum-oven for 2 days. The final product was collected as 47 mg (45%). LCMS E-S (M+H)=475.0 $^1$H NMR (400 MHz, DMSO-d$_6$) δ ppm 11.56 (br. s., 1H) 8.47 (t, J=5.05 Hz, 1H) 7.97 (dd, J=4.93, 1.14 Hz, 1H) 7.85 (s, 1H) 7.32-7.39 (m, 2H) 6.65 (s, 1H) 6.61 (t, J=5.43 Hz, 1H) 6.46-6.51 (m, 2H) 5.89 (s, 1H) 4.97 (quin, J=6.69 Hz, 1H) 4.32 (d, J=5.05 Hz, 2H) 3.49 (dt, J=15.28, 5.62 Hz, 4H) 2.21 (s, 3H) 2.13 (s, 3H) 1.44 (s, 3H) 1.43 (s, 3H).

Example 96

N-[(4,6-Dimethyl-2-oxo-1,2-dihydro-3-pyridinyl)methyl]-1-(1-methylethyl)-6-(7-oxo-1,5,6,7-tetrahydro-1,8-naphthyridin-3-yl)-1H-pyrazolo[3,4-b]pyridine-4-carboxamide

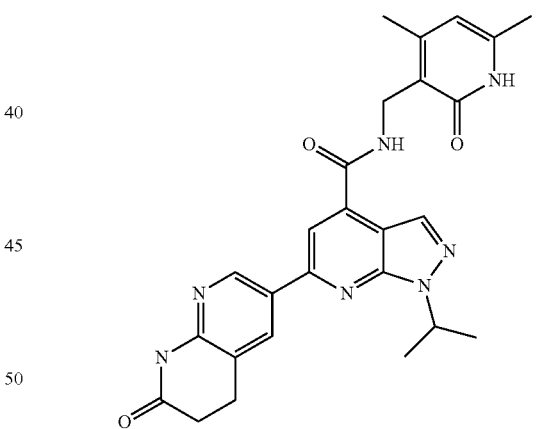

6-Bromo-3,4-dihydro-1,8-naphthyridin-2(1H)-one (200 mg, 0.881 mmol) (J. Med. Chem. 2003; 46; 9; 1627-1635), bis(pinacolato)diboron (268 mg, 1.057 mmol), Pd(dppf) (35.7 mg, 0.044 mmol) and potassium acetate (259 mg, 2.64 mmol) were suspended in 1,4-Dioxane (8 mL), and stirred with heating at 100° C. for 1 h. After cooling to room temperature, 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (329 mg, 0.881 mmol), bis(triphenylphosphine)palladium(II) chloride (71.9 mg, 0.088 mmol) and sodium bicarbonate (222 mg, 2.64 mmol) were added, followed by DME (5 mL) and water (3 mL). The reaction mixture was irradiated (microwave) at 120° C. for 2 h. The reaction mixture was cooled cooled to room temperature and filtered through Na$_2$SO$_4$. The contents were purified directly by silica gel chromatography (eluent: 5% MeOH/CH$_2$Cl$_2$) to furnish the desired product as a grey solid after evaporation and precipitation from warm EtOAc/MeOH (1:9). The product was collected as 55 mg (13%). LCMS E-S (M+H)=486.3 $^1$H NMR (400 MHz, DMSO-d$_6$) δ ppm 11.57 (br. s., 1H), 10.74 (s, 1H), 8.99 (d, J=2.27 Hz, 1H), 8.93 (t, J=4.93 Hz, 1H), 8.44 (d, J=1.77 Hz, 1H), 8.37 (s, 1H), 8.16 (s, 1H), 5.91 (s, 1H), 5.29-5.40 (m, 1H), 4.42 (d, J=5.05 Hz, 2H), 3.04 (t, J=7.58 Hz, 2H), 2.53-2.62 (m, 2H), 2.23 (s, 3H), 2.13 (s, 3H), 1.54 (d, 6H).

Example 97

N-[(4,6-Dimethyl-2-oxo-1,2-dihydro-3-pyridinyl)methyl]-6-{6-[(methylamino)sulfonyl]-3-pyridinyl}-1-(1-methylethyl)-1H-pyrazolo[3,4-b]pyridine-4-carboxamide

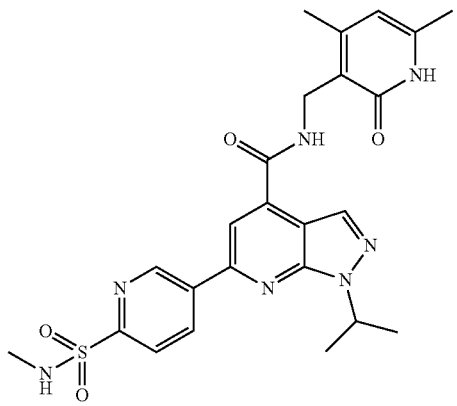

5-Bromo-N-methyl-2-pyridinesulfonamide (225 mg, 0.896 mmol), Bis(pinacolato)diboron (296 mg, 1.165 mmol), Pd(dppf) (35.7 mg, 0.044 mmol) and potassium acetate (264 mg, 2.69 mmol) were suspended in 1,4-Dioxane (8 mL), and stirred with heating at 100° C. for 1 h. After cooling to room temperature, 6-chloro-N-[(4,6-dimethyl-2-oxo-1,2-dihydro-3-pyridinyl)methyl]-1-(1-methylethyl)-1H-pyrazolo[3,4-b]pyridine-4-carboxamide (368 mg, 0.986 mmol), bis(triphenylphosphine)palladium(II) chloride (73.2 mg, 0.090 mmol) and sodium bicarbonate (226 mg, 2.69 mmol) were added, followed by DME (5 mL) and water (3 mL). The reaction mixture was irradiated (microwave) at 120° C. for 2 h. The reaction mixture was cooled cooled to room temperature and filtered through Na$_2$SO$_4$. The contents were purified directly by silica gel chromatography (eluent: 15% MeOH/CH$_2$Cl$_2$) to furnish the desired product as a grey solid after evaporation and precipitation from warm EtOAc/MeOH (1:9). The product was again purified by silica gel chromatography (eluent: 5% MeOH/CH$_2$Cl$_2$) to afford the final product as a white solid, 83 mg (18%). LCMS E-S (M+H)=510.0 $^1$H NMR (400 MHz, DMSO-d$_6$) δ ppm 11.59 (br. s., 1H), 9.56 (d, J=1.52 Hz, 1H), 8.86 (dd, J=8.34, 2.27 Hz, 1H), 8.46 (s, 1H), 8.34 (s, 1H), 8.12 (d, J=8.34 Hz, 1H), 7.85 (br. s., 1H), 5.91 (s, 1H), 5.27-5.46 (m, 1H), 4.43 (d, J=4.80 Hz, 2H), 2.60 (s, 3H), 2.23 (s, 3H), 2.13 (s, 3H), 1.56 (d, 6H).

Intermediate 17

5-Bromo-N-methyl-2-pyridinesulfonamide

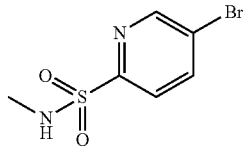

5-Bromo-2-pyridinesulfonyl chloride (500 mg, 1.949 mmol) was added to a 0° C. solution of pyridine (0.315 ml, 3.90 mmol), methylamine (0.975 ml, 1.949 mmol, 2M in THF) and CH$_2$Cl$_2$ (2 mL). The reaction mixture was stirred at room temperature for 1 hr, then quenched with brine. The contents were extracted with DCM, dried, filtered, and concentrated in vacuo. The crude product was purified by silica gel chromatography (eluent: 50%, EtOAC/CH$_2$Cl$_2$). The product was collected as a clear oil, 225 mg (75%). LCMS E-S (M+H)=251.1. $^1$H NMR (400 MHz, Chloroform-d) δ ppm 8.77 (s, 1H), 8.07 (dd, J=8.34, 2.27 Hz, 1H), 7.92 (d, J=8.34 Hz, 1H), 5.45 (d, J=5.05 Hz, 1H), 2.76 (d, 3H).

Intermediate 18

1-{[4-(Methyloxy)phenyl]methyl}-1H-pyrazol-5-amine

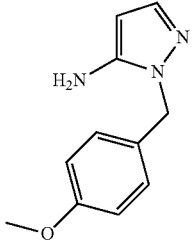

Hydrazine hydrate (12.82 g, 400 mmol) was added dropwise to a cooled (<20° C.) solution of 2-propenenitrile (21.76 g, 410 mmol) and ethanol (200 mL). After 16 h stirring the reaction mixture was cooled in an ice water bath and 4-(methyloxy)benzaldehyde (53.8 g, 395 mmol) was added dropwise. The mixture was stirred at room temperature for 16 h. The reaction mixture was concentrated to dryness. The residue was dissolved in n-butanol (200 mL), sodium hydroxide was added (1 g, 25.00 mmol), and the mixture heated at 120° C. for 6 h. The reaction mixture was concentrated to 50% volume under reduced pressure, poured onto 300 mL of water, and then extracted with Et$_2$O (2×200 mL). The combined ether phases were extracted with 1N HCl (3×100 mL). The combined HCl extracts were combined and cooled in an ice/water bath. Added next was 6N NaOH until basic (pH>12). The contents were extracted with Et$_2$O (4×100 mL), washed with water, dried over MgSO$_4$, filtered, and concentrated under reduced pressure. The residue was purified via silica gel chromatography (eluent: 0-50% EtOAc:Hex). The final product was collected as 8.94 g (11%). $^1$H NMR (400 MHz, CHLOROFORM-d) δ ppm 3.79 (s, 3H), 5.14 (s, 2H), 5.55 (d, J=1.77 Hz, 1H), 6.81-6.94 (m, 2H), 7.12 (d, J=8.84 Hz, 2H), 7.31 (d, J=2.02 Hz, 1H).

Intermediate 19

1-Cyclobutyl-3-methyl-1H-pyrazol-5-amine

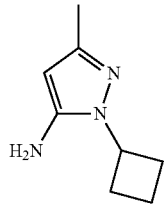

(2Z)-3-Amino-2-butenenitrile (1.339 g, 16.31 mmol) and cyclobutylhydrazine HCl (2 g, 16.31 mmol) were added to ethanol (20 mL) and heated at 75° C. for 16 h. After cooling to room temperature, the solvent was removed under reduced pressure. The crude residue was suspended in saturated NaHCO$_3$ (30 mL) and EtOAc (50 mL), and stirred for 10 min. The phases were separated and the aq. phase extracted with EtOAc (3×50 mL). The combined EtOAc extracts were washed with brine, dried over MgSO$_4$, filtered, and concentrated in vacuo. The crude residue was purified via silica gel chromatography (eluent: 0 to 5% EtOAc:DCM, then gradient to 100% EtOAc). The final product was collected as 0.4 g (16%). LCMS E-S (M+H)=:152.0. $^1$H NMR (400 MHz, CHLOROFORM-d) δ ppm 1.67-2.00 (m, 2H) 2.21 (s, 3H) 2.32-2.43 (m, 2H) 2.69 (ddd, J=10.55, 9.41, 2.53 Hz, 2H) 3.26-3.55 (br s, 2H) 4.48-4.59 (m, 1H) 5.36 (s, 1H)

Intermediate 20

1-Cyclopentyl-3-methyl-1H-pyrazol-5-amine

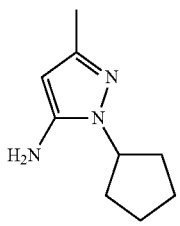

The title compound was prepared in the same manner as described for intermediate 19 using cyclopentylhydrazine hydrochloride (2 g, 14.64 mmol), (2Z)-3-amino-2-butenenitrile (1.202 g, 14.64 mmol) and ethanol (20 mL). The final product was collected as 0.57 g (24%). LCMS E-S (M+H)=166.0. $^1$H NMR (400 MHz, CHLOROFORM-d) δ ppm 1.60-1.69 (m, 2H), 1.86-1.95 (m, 2H), 1.99-2.09 (m, 4H), 2.19 (s, 3H), 3.46 (br. s., 2H), 4.38 (quin, J=7.89 Hz, 1H), 5.36 (s, 1H).

Intermediate 21

1-(Phenylmethyl)-1H-pyrazol-5-amine

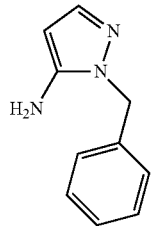 [SMILES: Nc1ccnn1Cc1ccccc1]

A solution of hydrazine hydrate (14.55 mL, 300 mmol) and ethanol (75 mL) was cooled in an ice water bath and then 2-propenenitrile (15.3 g, 288 mmol) was added dropwise. After stirring at room temperature for 2 h, benzaldehyde (31.8 g, 300 mmol) was added dropwise and the reaction mixture was allowed to stir at room temperature for 2 d. The solvent was removed under reduced pressure. The crude oil was cooled in an ice/water bath followed by dropwise addition of a n-BuONa solution (Na 6.9 g, (300 mmol) in n-Butanol (300 mL)). The reaction mixture was heated at reflux for 1 h, and then cooled to room temperature. The contents were poured onto 300 mL of water and then extracted with Et$_2$O (2×200 mL). The ether phase was extracted with 1N HCl (3×100 mL). The combined HCl extracts were combined and cooled in a ice/water bath, followed by addition of 6N NaOH until basic (pH>12). The mixture was extracted with Et$_2$O (4×100 mL), washed with water, dried over MgSO$_4$, filtered, and concentrated under reduced pressure. The crude residue was purified via silica gel chromatography (eluent: 0 to 50% EtOAc:Hex). The final product was collected as 6.96 g (14%). LCMS E-S (M+H)=174.0. $^1$H NMR (400 MHz, CHLOROFORM-d) δ ppm 3.39 (br. s., 2H), 5.23 (s, 2H), 5.59 (d, J=1.77 Hz, 1H), 7.17 (d, J=6.82 Hz, 2H), 7.28-7.37 (m, 4H)

Intermediate 22

1,1-Dimethylethyl 2-(tetrahydro-2H-pyran-4-yl)hydrazinecarboxylate

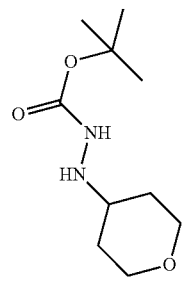

Tetrahydro-4H-pyran-4-one (9.69 g, 97 mmol) was added to a solution of 1,1-dimethylethyl hydrazinecarboxylate (14.07 g, 106 mmol) in methanol (100 mL) and stirred at room temperature for 3 h. The solvent was removed in vacuo, and the crude residue was suspended in acetic acid (140 mL). Next added sodium cyanoborohydride (6.69 g, 106 mmol) in portions over 3 minutes. The contents were stirred at room temperature for 60 h. The solvent was removed in vacuo, and the crude residue was suspended in DCM (100 mL). The reaction mixture was adjusted to pH 7 with 6N NaOH. The layers were separated, and the aq. layer extracted with DCM. The combined organic layers were washed with saturated NaHCO$_3$, and brine. The organic layer was dried over MgSO$_4$, filtered, and concentrated in vacuo to afford the product as a solid, 18.4 g (88%). $^1$H NMR (400 MHz, DMSO-d$_6$) δ ppm 1.22 (m, 2H), 1.39 (s, 9H), 1.43-1.48 (m, 1H), 1.59-1.69 (m, 2H), 2.82-2.98 (m, 1H), 3.20-3.32 (m, 2H), 3.80 (d, J=11.62 Hz, 2H), 4.36 (br. s., 1H), 8.07-8.34 (m, 1H).

Intermediate 23

Tetrahydro-2H-pyran-4-ylhydrazine

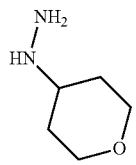

1,1-Dimethylethyl 2-(tetrahydro-2H-pyran-4-yl)hydrazinecarboxylate was added to 1,4-Dioxane (10 mL) followed by hydrochloric acid (4M in 1,4-Dioxane, 10 mL, 329 mmol). The reaction mixture was stirred at room temperature for 60 h. The reaction mixture was filtered to afford the product as a solid, 1.02 g. (72%). $^1$H NMR (400 MHz, CHLOROFORM-d) δ ppm 1.45 (qd, J=11.79, 4.29 Hz, 2H), 1.81-2.01 (m, 2H), 3.00-3.19 (m, 1H), 3.20-3.35 (m, 2H), 3.78-3.97 (m, 2H), 6.5-9.5 (br m, 3H).

Intermediate 24

3-Methyl-1-(tetrahydro-2H-pyran-4-yl)-1H-pyrazol-5-amine

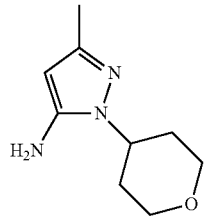

(2Z)-3-Amino-2-butenenitrile (0.538 g, 6.55 mmol), tetrahydro-2H-pyran-4-ylhydrazine (1 g, 6.55 mmol) and triethylamine (0.913 mL, 6.55 mmol) were added to ethanol (300 mL), and the reaction mixture was stirred at 75° C. for 16 hours. The solvent was removed in vacuo, and the crude material suspended in EtOAc. The organic phase was washed with water and then brine. The organic layer was then dried over MgSO$_4$, filtered, and concentrated in vacuo. Half of the crude material was purified by reverse HPLC (mobile phase: 0-30% ACN/H$_2$O, 0.1% TFA) to afford 380 mg of the desired product. The other half of the crude material was purified via silica gel chromatography (eluent: 0% to 100% EtOAc:Hex then 0% to 20% MeOH:DCM). An additional 300 mg of the desired product was obtained (overall yield: 57%). LCMS E-S (M+H)=182.0. $^1$H NMR (400 MHz, CHLOROFORM-d) δ ppm 1.78 (dd, 2H), 1.94 (qd, J=12.13, 4.55 Hz, 2H), 2.19 (s, 3H), 3.30-3.46 (m, 2H), 3.99 (dd, J=11.49, 4.17 Hz, 2H), 4.49 (m, J=11.65, 11.65, 4.11, 3.92 Hz, 1H), 5.53 (s, 1H).

Intermediate 25

6-Methyl-1-(phenylmethyl)-1H-pyrazolo[3,4-b]pyridin-4-ol

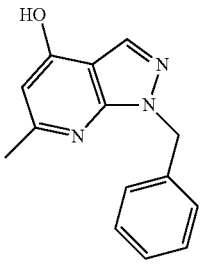 [SMILES: Cc1cc(O)c2cnn(Cc3ccccc3)c2n1]

A mixture of 1-(phenylmethyl)-1H-pyrazol-4-amine (6.25 g, 36.1 mmol), ethyl 3-oxobutanoate (4.70 g, 36.1 mmol), acetic acid (0.2 mL, 3.49 mmol) and benzene (50 mL) were refluxed for 16 h (Dean-Stark trap used). The solvent was removed under reduced pressure and the crude residue purified via silica gel chromatography (eluent; 0 to 60% EtOAc: Hex). The collected product (7.35 g, 25.8 mmol) was then dissolved in 10 mL of Dowtherm A and this solution added dropwise to 10 mL of refluxing Dowtherm A. After refluxing for an additional 20 minutes, the reaction mixture was cooled to room temperature, and 20 mL of petroleum ether were added. After stirring at room temperature for 16 hr, the solid product was filtered and dried on hi-vacuum. The final product was collected as 6.23 g (72%). LCMS E-S (M+H)=240.0. $^1$H NMR (400 MHz, MeOD) ppm 4.89 (s, 3H), 5.59 (s, 2H), 6.17 (br. s., 1H), 7.17 (d, J=6.82 Hz, 2H), 7.25-7.37 (m, 3H), 8.05 (s, 1H).

Intermediate 26

4-Bromo-6-methyl-1-(phenylmethyl)-1H-pyrazolo[3,4-b]pyridine

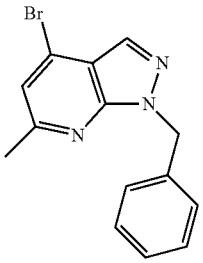 [SMILES: Cc1cc(Br)c2cnn(Cc3ccccc3)c2n1]

Phosphorus oxybromide (5.31 g, 18.54 mmol) was added to a suspension of 6-methyl-1-(phenylmethyl)-1H-pyrazolo [3,4-b]pyridin-4-ol (3.08 g, 12.87 mmol) and toluene (25 mL). The contents were heated to reflux for 1 h, wherein 10 mL DMF were added during this process. The solvent was removed under reduced pressure. The crude residue was suspended in 30 mL water containing ice. The contents were adjusted to pH=10 by addition of sat. NaHCO$_3$. The solid product was filtered and dried under hi-vacuum. The final product was collected as 3.55 g (91%). LCMS E-S (M+H)=302.1/304.0. $^1$H NMR (400 MHz, DMSO-d$_6$) δ ppm 2.61 (s, 3H), 5.65 (s, 2H), 7.16-7.35 (m, 5H), 7.48 (s, 1H), 8.12 s, 1H).

Intermediate 27

6-Methyl-1-(phenylmethyl)-1H-pyrazolo[3,4-b]pyridine-4-carbonitrile

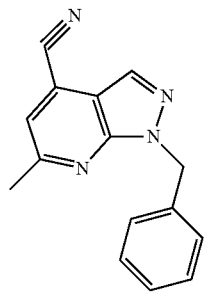 [SMILES: Cc1cc(C#N)c2cnn(Cc3ccccc3)c2n1]

A mixture of 4-bromo-6-methyl-1-(phenylmethyl)-1H-pyrazolo[3,4-b]pyridine (3.45 g, 11.42 mmol), dicyanozinc (1.542 g, 13.13 mmol), tris(dibenzylideneacetone)dipalladium(0) (0.523 g, 0.571 mmol), SPhos (0.562 g, 1.370 mmol), DMF (49 mL), and water (0.5 mL) was degassed with nitrogen for 10 minutes. The reaction mixture was heated at 120° C. for 2 hours, and then cooled to room temperature. The contents were concentrated to 50% volume and then 50 mL of 1N NaOH and 50 mL of EtOAc were added. The solids were filtered off. The phases were separated and the aqueous phase extracted with EtOAc (3×50 mL). The combined EtOAc extracts were washed with water (3×50 mL), brine (50 mL), dried over MgSO$_4$, filtered, and concentrated in vacuo. The crude product containing SPhos reagent (~30-40%) was collected as 3.69 g and used without further purification. LCMS E-S (M+H)=249.1. $^1$H NMR (400 MHz, CHLOROFORM-d) δ ppm 2.77 (s, 3H), 5.73 (s, 2H), 7.08-7.44 (m, 6H), 8.16 (s, 1H)

Intermediate 28

6-Methyl-1-(phenylmethyl)-1H-pyrazolo[3,4-b]pyridine-4-carboxylic acid

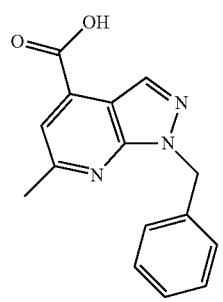 [SMILES: Cc1cc(C(=O)O)c2cnn(Cc3ccccc3)c2n1]

6-Methyl-1-(phenylmethyl)-1H-pyrazolo[3,4-b]pyridine-4-carbonitrile (1 g), sodium hydroxide (0.805 g, 20.14 mmol), ethanol (25 mL) and water (10 mL) were heated at reflux for 2 hours. After cooling to room temperature, the solvent was removed under reduced pressure. The crude product was suspended in water (50 mL) and acidified by dropwise addition of 6N HCl. The solid product was filtered off and dissolved in 100 ml of EtOAc. The solution dried over MgSO$_4$, filtered, and concentrated in vacuo. The final product was obtained as 0.730 g. LCMS E-S (M+H)=267.9. $^1$H NMR (400 MHz, DMSO-d$_6$) δ ppm 2.71 (s, 3H), 5.70 (s, 2H), 7.15-7.37 (m, 5H), 7.63 (s, 1H), 8.33 (s, 1H), 13.86 (s, 1H).

Intermediate 29 ethyl 4-cyclopropyl-2,4-dioxobutanoate

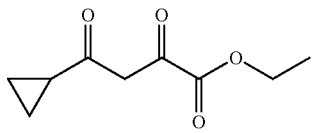

Sodium metal (2.411 g, 105 mmol) was dissolved in ethanol (50 mL). The solution was heated to reflux followed by addition of a mixture of 1-cyclopropylethanone (8.4 g, 100 mmol) and diethyl oxalate (14.59 g, 100 mmol) dropwise over 30 minutes. The reaction mixture was heated at reflux for an additional 2 h, and then allowed to cool to room temperature over a 2 d period. The contents were diluted with water (200 mL) and acidified by dropwise addition of 6N HCl. The contents were extracted with EtOAc (3×75 mL), washed with water, brine, dried over MgSO$_4$, filtered, and concentrated in vacuo. The final product was collected as 14.3 g (74%). LCMS E-S (M+H)=184.8 $^1$H NMR (400 MHz, CHLOROFORM-d) δ ppm 1.03 (d, J=7.83 Hz, 2H) 1.13-1.19 (m, 2H) 1.31 (t, J=7.07 Hz, 3H) 1.81-1.90 (m, 1H) 4.29 (q, J=7.16 Hz, 2H) 6.43 (s, 1H).

Intermediate 30

Ethyl 6-cyclopropyl-1-{[4-(methyloxy)phenyl]methyl}-1H-pyrazolo[3,4-b]pyridine-4-carboxylate

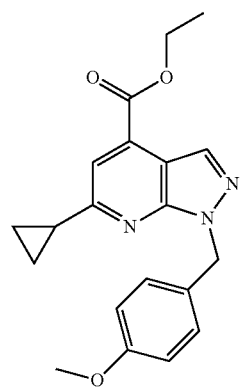 [SMILES: CCOC(=O)c1cc(C2CC2)nc2c1cnn2Cc1ccc(OC)cc1]

A mixture of 1-{[4-(methyloxy)phenyl]methyl}-1H-pyrazol-5-amine (3 g, 14.76 mmol), ethyl 4-cyclopropyl-2,4-dioxobutanoate (2.72 g, 14.76 mmol) and benzene (50 mL) were heated at 63° C. for 16 h. The solvent was removed under reduced pressure. The crude residue was purified via silica gel chromatography (eluent: 0 to 25% EtOAc:Hex) to afford 2.56 g of the desired cyclized product and 1.71 g of the uncyclized adduct. The uncyclized adduct was dissolved in 25 mL of AcOH and heated to reflux for 16 hours. The solvent was removed under reduced pressure and the residue purified via silica gel chromatography (eluent: 0 to 25% EtOAc:Hex) to afford an additional 1.15 g of the desired cyclized product (combined yield=71%). LCMS E-S (M+H)=352.3. $^1$H NMR (400 MHz, DMSO-$d_6$) δ ppm 1.07-1.13 (m, 4H) 1.38 (t, J=7.07 Hz, 3H) 2.39 (s, 1H) 3.67 (s, 3H) 4.41 (q, J=7.07 Hz, 2H) 5.51 (s, 2H) 6.84 (d, J=8.84 Hz, 2H) 7.21 (d, J=8.59 Hz, 2H) 7.64 (s, 1H) 8.23 (s, 1H).

Intermediate 31

Ethyl 6-cyclopropyl-1H-pyrazolo[3,4-b]pyridine-4-carboxylate

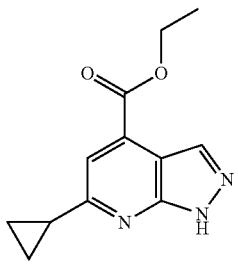 [SMILES: CCOC(=O)c1cc(C2CC2)nc2[nH]ncc12]

To a 20 mL microwave vial were combined ethyl 6-cyclopropyl-1-{[4-(methyloxy)phenyl]methyl}-1H-pyrazolo[3,4-b]pyridine-4-carboxylate (2.05 g, 5.83 mmol), trifluoroacetic acid (6.74 ml, 88 mmol) and anisole (1.912 ml, 17.50 mmol). The reaction vessel was sealed and irradiated (microwave) at 100° C. for 5 minutes. After cooling to room temperature, the reaction mixture was concentrated in vacuo. The residue was diluted with water (20 mL) and then saturated NaHCO$_3$ until basic. The contents were extracted with DCM (4×20 mL). The combined organic layers were washed with water, brine, dried over MgSO$_4$, filtered and concentrated in vacuo. The crude product was purified via silica gel chromatography (eluent: 0 to 20% EtOAc:Hex). The final product was obtained as 1.06 g (79%). LCMS E-S (M+H)=232.2. $^1$H NMR (400 MHz, DMSO-$d_6$) δ ppm 0.95-1.21 (m, 4H) 1.41 (t, J=7.07 Hz, 3H) 2.33-2.46 (m, 1H) 4.44 (q, J=7.07 Hz, 2H) 7.67 (s, 1H) 8.26 (d, J=1.26 Hz, 1H) 13.75 (s, 1H).

Intermediate 32

Ethyl 1-amino-6-cyclopropyl-1H-pyrazolo[3,4-b]pyridine-4-carboxylate

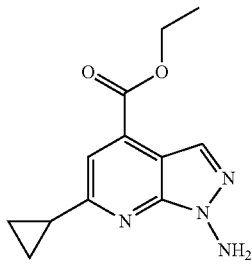 [SMILES: CCOC(=O)c1cc(C2CC2)nc2c1cnn2N]

Ethyl 6-cyclopropyl-1H-pyrazolo[3,4-b]pyridine-4-carboxylate (200 mg, 0.865 mmol) was dissolved in N-Methyl-2-pyrrolidone (NMP) (8 mL), followed by addition of potassium tert-butoxide (116 mg, 1.038 mmol). After 20 minutes stirring, 0-{[4-(methyloxy)phenyl]carbonyl}hydroxylamine 1-[(aminooxy)carbonyl]-4-(methyloxy)benzene (289 mg, 1.730 mmol) was added and the mixture stirred at room temperature for 16 h. The contents were diluted with EtOAc, and then washed with brine, and saturated NaHCO$_3$. The organic phase was dried over MgSO$_4$, filtered, and concentrated in vacuo. The crude product was purified via silica gel chromatography (eluent: 0 to 50% EtOAc). The final product as collected as 106 mg (50%). LCMS E-S (M+H)=274.4. $^1$H NMR (400 MHz, DMSO-$d_6$) δ ppm 1.00-1.14 (m, 4H), 1.41 (t, J=7.07 Hz, 3H), 2.34-2.47 (m, 1H), 4.44 (q, J=7.07 Hz, 2H), 6.39 (s, 2H), 7.64 (s, 1H), 8.09 (s, 1H).

Intermediate 33

Ethyl 6-cyclopropyl-3-methyl-1-(1-methylethyl)-1H-pyrazolo[3,4-b]pyridine-4-carboxylate

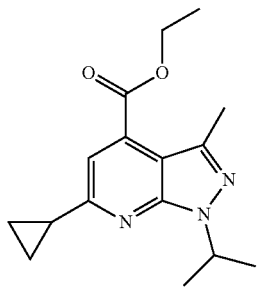 [SMILES: CCOC(=O)c1cc(C2CC2)nc2c1c(C)nn2C(C)C]

A solution of ethyl 4-cyclopropyl-2,4-dioxobutanoate (700 mg, 3.76 mmol), 3-methyl-1-(1-methylethyl)-1H-pyrazol-5-amine (523 mg, 3.76 mmol) and benzene (20 mL) were heated at 65° C. for 6 hr, and then allowed to cool to room temperature for 2 d. The solvent was removed under reduced pressure and the residue purified via silica gel chromatography (eluent: 0 to 25% EtOAc:Hex). The final product was collected as 0.77 g (71%). LCMS E-S (M+H)=288.0. $^1$H NMR (400 MHz, CHLOROFORM-d) δ ppm 1.04-1.11 (m, 2H), 1.13-1.20 (m, 4H), 1.47 (t, J=7.20 Hz, 6H), 1.55 (d, J=6.82 Hz, 12H), 2.16-2.25 (m, 2H), 2.68 (s, 6H), 4.49 (q, J=7.07 Hz, 4H), 5.20 (spt, J=6.78 Hz, 2H), 7.41 (s, 1H).

Intermediate 34

Ethyl 1-cyclobutyl-6-cyclopropyl-3-methyl-1H-pyrazolo[3,4-b]pyridine-4-carboxylate

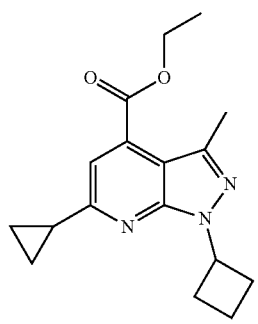 [SMILES: CCOC(=O)c1cc(C2CC2)nc2c1c(C)nn2C1CCC1]

The title compound was prepared in the same manner as described for intermediate 33 using 1-cyclobutyl-3-methyl-1H-pyrazol-5-amine (400 mg, 2.65 mmol), ethyl 4-cyclopropyl-2,4-dioxobutanoate (487 mg, 2.65 mmol) and benzene (50 mL), wherein the reaction time was 4 h. The final product was collected as 0.556 g (70%). LCMS E-S (M+H)=300.6 $^1$H NMR (400 MHz, CHLOROFORM-d) δ ppm 1.02-1.22 (m, 4H) 1.47 (t, J=7.07 Hz, 3H) 1.80-2.01 (m, 2H) 2.15-2.28 (m, 1H) 2.38-2.51 (m, 2H) 2.70 (s, 3H) 2.82 (td, J=9.85, 2.53 Hz, 2H) 4.49 (q, J=7.07 Hz, 2H) 5.32-5.57 (m, 1H) 7.41 (s, 1H).

Intermediate 35 ethyl 1-cyclopentyl-6-cyclopropyl-3-methyl-1H-pyrazolo[3,4-b]pyridine-4-carboxylate

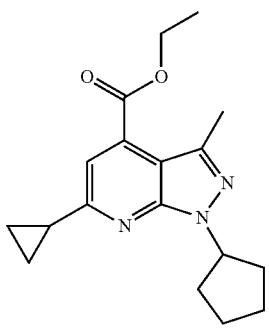 [SMILES: CCOC(=O)c1cc(C2CC2)nc2c1c(C)nn2C1CCCC1]

The title compound was prepared in the same manner as described for intermediate 33 using 1-cyclopentyl-3-methyl-1H-pyrazol-5-amine (570 mg, 3.45 mmol), ethyl 4-cyclopropyl-2,4-dioxobutanoate (635 mg, 3.45 mmol), and benzene (50 mL) wherein the reaction time was 4 h. The crude product was purified via silica gel chromatography (eluent: 0 to 10% EtOAc:Hex). The final product was collected as 0.740 g (68%). LCMS E-S (M+H)=314.3 $^1$H NMR (400 MHz, CHLOROFORM-d) δ ppm 1.04-1.21 (m, 4H) 1.47 (t, J=7.20 Hz, 3H) 1.73 (br. s., 2H) 2.00 (d, J=2.78 Hz, 2H) 2.08-2.16 (m, 4H) 2.21 (s, 1H) 2.67 (s, 3H) 4.49 (q, J=7.16 Hz, 2H) 5.32 (t, J=7.83 Hz, 1H) 7.40 (s, 1H).

Intermediate 36 ethyl 6-cyclopropyl-1-(1,1-dimethylethyl)-3-methyl-1H-pyrazolo[3,4-b]pyridine-4-carboxylate

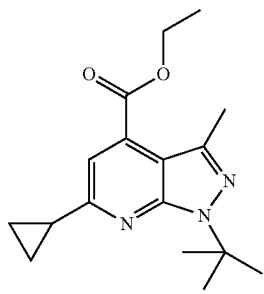 [SMILES: CCOC(=O)c1cc(C2CC2)nc2c1c(C)nn2C(C)(C)C]

The title compound was prepared in the same manner as described for intermediate 33 using ethyl 4-cyclopropyl-2,4-dioxobutanoate (481 mg, 2.61 mmol), 1-(1,1-dimethylethyl)-3-methyl-1H-pyrazol-5-amine (400 mg, 2.61 mmol), and toluene (20 mL), wherein the reaction time was 3 h. The crude product was purified via silica gel chromatography (eluent: 0 to 10% EtOAc:Hex). The final product was collected as 0.24 g (30%). LCMS E-S (M+H)=302.5. $^1$H NMR (400 MHz, CHLOROFORM-d) δ ppm 1.02-1.23 (m, 4H) 1.47 (t, J=7.20 Hz, 3H) 1.79 (s, 9H) 2.19 (s, 1H) 2.66 (s, 3H) 4.49 (q, J=7.07 Hz, 2H) 7.44 (s, 1H).

Intermediate 37

Ethyl 6-cyclopropyl-1-(1-cyclopropylethyl)-3-methyl-1H-pyrazolo[3,4-b]pyridine-4-carboxylate

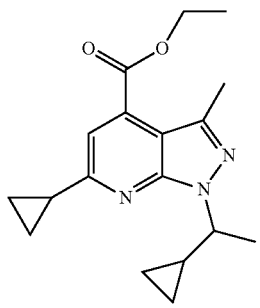 [SMILES: CCOC(=O)c1cc(C2CC2)nc2c1c(C)nn2C(C)C1CC1]

1-(1-Cyclopropylethyl)-3-methyl-1H-pyrazol-5-amine (500 mg, 3.03 mmol) and ethyl 4-cyclopropyl-2,4-dioxobutanoate (557 mg, 3.03 mmol) were suspended in Toluene (10 mL) and heated at 70° C. for 16 h. The solvent was removed in vacuo and the crude residue was purified via silica gel chromatography (eluent: gradient of 0 to 10% EtOAc:Hex). The final product was collected as a solid, 0.722 g (76%). LCMS E-S (M+H)=314.3 $^1$H NMR (400 MHz, DMSO-$d_6$) ppm 0.17-0.32 (m, 2H), 0.39 (m, J=9.69, 4.82, 4.82, 4.67 Hz, 1H), 0.51-0.62 (m, 1H), 0.94-1.11 (m, 4H), 1.28-1.41 (m, 4H), 1.58 (d, J=6.82 Hz, 3H), 2.30-2.38 (m, 1H), 2.56 (s, 3H), 4.19 (dq, J=9.44, 6.87 Hz, 1H), 4.43 (q, J=7.07 Hz, 2H), 7.48 (s, 1H)

Intermediate 38

Ethyl 1-cyclohexyl-6-cyclopropyl-3-methyl-1H-pyrazolo[3,4-b]pyridine-4-carboxylate

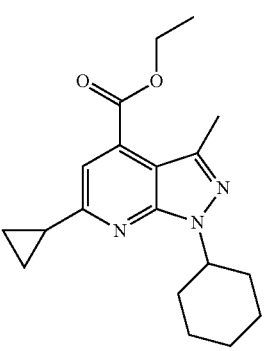 [SMILES: CCOC(=O)c1cc(C2CC2)nc2c1c(C)nn2C1CCCCC1]

The title compound was prepared in the same manner as described for intermediate 37 using 1-(1-cyclohexyl)-3-methyl-1H-pyrazol-5-amine (500 mg, 2.79 mmol) and ethyl 4-cyclopropyl-2,4-dioxobutanoate (514 mg, 2.79 mmol). The final product was collected as a solid, 0.827 g (91%). LCMS E-S (M+H)=328.3 $^1$H NMR (400 MHz, DMSO-$d_6$) δ ppm 1.01-1.10 (m, 3H), 1.20-1.30 (m, 1H), 1.37 (t, J=7.07 Hz, 3H), 1.41-1.52 (m, 2H), 1.70 (d, 1H), 1.79-1.98 (m, 6H), 2.30-2.38 (m, 1H), 2.54 (s, 3H), 4.42 (q, J=7.07 Hz, 2H), 4.60-4.74 (m, 1H), 7.44 (s, 1H).

Intermediate 39

Ethyl 6-cyclopropyl-3-methyl-1-(1-methyl-4-piperidinyl)-1H-pyrazolo[3,4-b]pyridine-4-carboxylate

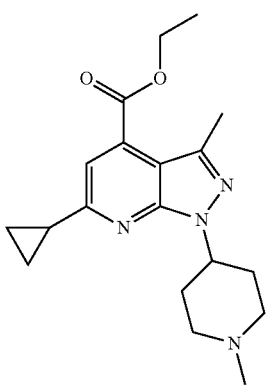 [SMILES: CCOC(=O)c1cc(C2CC2)nc2c1c(C)nn2C1CCN(C)CC1]

3-Methyl-1-(1-methyl-4-piperidinyl)-1H-pyrazol-5-amine (500 mg, 2.57 mmol) and ethyl 4-cyclopropyl-2,4-dioxobutanoate (474 mg, 2.57 mmol) were suspended in Toluene (10 mL) and heated at 70° C. for 5 h. The solvent was removed in vacuo and the crude residue was purified via silica gel chromatography (eluent: gradient of 0 to 10% MeOH:DCM). The final product was collected as a solid, 0.722 g (76%). LCMS E-S (M+H)=343.1 ¹H NMR (400 MHz, DMSO-d₆) δ ppm 1.03-1.11 (m, 4H), 1.38 (t, J=7.07 Hz, 3H), 1.83 (d, J=6.06 Hz, 2H), 2.12-2.22 (m, 4H), 2.27 (s, 3H), 2.35 (m, J=7.83, 7.83, 5.05, 4.80 Hz, 1H), 2.54 (s, 3H), 2.94 (d, J=6.57 Hz, 2H), 4.42 (q, J=7.16 Hz, 2H), 4.57-4.73 (m, 1H), 7.46 (s, 1H).

Intermediate 40

Ethyl 6-cyclopropyl-3-methyl-1-(tetrahydro-2H-pyran-4-yl)-1H-pyrazolo[3,4-b]pyridine-4-carboxylate

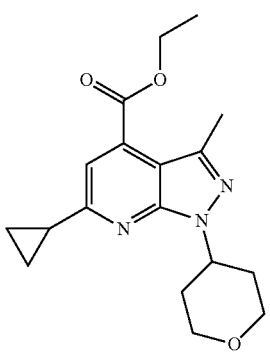 [SMILES: CCOC(=O)c1cc(C2CC2)nc2c1c(C)nn2C1CCOCC1]

A mixture of 3-methyl-1-(tetrahydro-2H-pyran-4-yl)-1H-pyrazol-5-amine (380 mg, 2.097 mmol), ethyl (3Z)-4-cyclopropyl-4-hydroxy-2-oxo-3-butenoate (386 mg, 2.097 mmol) and acetic acid (50 mL) were heated at 117° C. for 2 hours. The solvent was removed in vacuo, and the crude residue was purified via silica gel chromatography (eluent: 0 to 25% EtOAc:Hex). The desired product was collected as a solid, 300 mg (43%). LCMS E-S (M+H)=330.3 ¹H NMR (400 MHz, DMSO-d₆) δ ppm 1.00-1.12 (m, 4H), 1.37 (t, J=7.20 Hz, 3H), 1.82 (dd, J=12.51, 2.40 Hz, 2H), 2.16 (qd, J=12.21, 4.55 Hz, 2H), 2.29-2.42 (m, 1H), 2.54 (s, 3H), 3.47-3.60 (m, 2H), 3.99 (dd, J=11.37, 3.79 Hz, 2H), 4.42 (q, J=7.24 Hz, 2H), 4.92 (tt, J=11.59, 4.20 Hz, 1H), 7.46 (s, 1H).

Intermediate 41

Ethyl 6-cyclopropyl-1-[2-({[(1,1-dimethylethyl)oxy]carbonyl}amino)ethyl]-1H-pyrazolo[3,4-b]pyridine-4-carboxylate

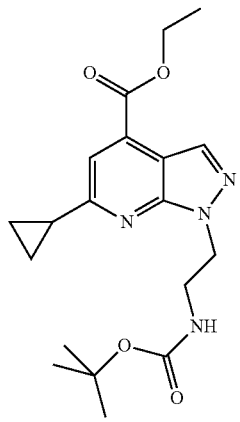 [SMILES: CCOC(=O)c1cc(C2CC2)nc2c1cnn2CCNC(=O)OC(C)(C)C]

Ethyl 6-cyclopropyl-1H-pyrazolo[3,4-b]pyridine-4-carboxylate (125 mg, 0.541 mmol) was dissolved in DMF (10 mL), followed by addition of potassium tert-butoxide (79 mg, 0.703 mmol). After stirring for 15 minutes, 1,1-dimethylethyl (2-bromoethyl)carbamate (121 mg, 0.541 mmol) was added and the mixture was stirred at room temperature for 16 h. The reaction mixture was concentrated to dryness. The crude residue was diluted with water (50 mL) and acidified with acetic acid. The contents were extracted with DCM (4×50 mL). The combined organic layers were washed with water, brine, dried over MgSO₄, filtered, and concentrated in vacuo. The crude residue was purified via silica gel chromatography (eluent: 0 to 50% EtOAc:Hex). The final product was obtained as 0.114 g (56%). LCMS E-S (M+H)=375.1. ¹H NMR (400 MHz, DMSO-d₆) δ ppm 1.04-1.14 (m, 4H), 1.15-1.20 (m, 2H), 1.27 (s, 7H), 1.41 (t, J=7.07 Hz, 3H), 2.36-2.45 (m, 1H), 3.31-3.41 (m, 3H), 4.36-4.50 (m, 5H), 6.84 (t, J=5.81 Hz, 1H), 7.65 (s, 1H), 8.24 (s, 3H).

Intermediate 42

Ethyl 6-cyclopropyl-3-methyl-1-(4-pyridinyl)-1H-pyrazolo[3,4-b]pyridine-4-carboxylate

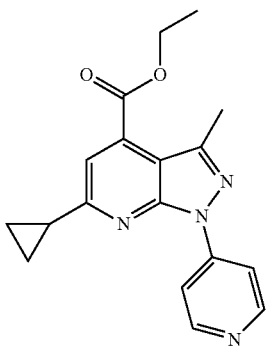 [SMILES: CCOC(=O)c1cc(C2CC2)nc2c1c(C)nn2-c1ccncc1]

The title compound was prepared in the same manner as described for intermediate 30 using 3-methyl-1-(4-pyridinyl)-1H-pyrazol-5-amine (310 mg, 1.780 mmol), ethyl 4-cyclopropyl-2,4-dioxobutanoate (328 mg, 1.780 mmol), benzene (50 mL), and acetic acid (25 mL). The final product was collected as 3.71 (71% overall). LCMS E-S (M+H)=323.5 $^1$H NMR (400 MHz, DMSO-$d_6$) δ ppm 1.15-1.22 (m, 4H), 1.41 (t, J=7.07 Hz, 3H), 2.64-2.69 (m, 4H), 4.47 (q, J=7.07 Hz, 2H), 7.74 (s, 1H), 8.27-8.36 (m, 2H), 8.66-8.71 (m, 2H).

Intermediate 43

6-Cyclopropyl-1-ethyl-1H-pyrazolo[3,4-b]pyridine-4-carboxylic acid

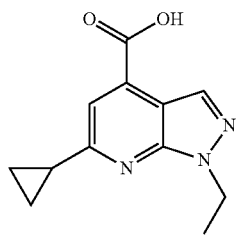 [SMILES: CCn1ncc2c(C(=O)O)cc(C3CC3)nc21]

To a solution of ethyl 6-cyclopropyl-1H-pyrazolo[3,4-b]pyridine-4-carboxylate (200 mg, 0.865 mmol) in DMF (10 mL) was carefully added sodium hydride (29.1 mg, 1.211 mmol). After 15 minutes stirring, iodoethane (0.077 mL, 0.951 mmol) was added and the mixture stirred at room temperature for 2 hr. Sodium hydroxide (1 mL, 1.000 mmol) was added and the mixture allowed to stir at room temperature for 1 h. The contents were concentrated in vacuo. The crude residue was diluted with water (50 mL) and acidified with acetic acid. The contents were then extracted with DCM (4×50 mL). The combined organic layers were washed with water, brine, dried over MgSO4, filtered and concentrated in vacuo. The crude product was purified by silica gel chromatography (eluent: hexanes to 100% EtOAc, then DCM to 20% MeOH:DCM). The final product was collected as 90 mg (45%). LCMS E-S (M+H)=232.1 $^1$H NMR (400 MHz, DMSO-$d_6$) δ ppm 1.06-1.17 (m, 4H) 1.41 (t, J=7.33 Hz, 3H) 2.35-2.45 (m, 1H) 4.34-4.57 (m, 2H) 7.62 (s, 1H) 8.24 (s, 1H) 13.83 (br. s., 1H). Regiochemical assignment supported by 2D HNMR.

Intermediate 44

6-Cyclopropyl-1-propyl-1H-pyrazolo[3,4-b]pyridine-4-carboxylic acid

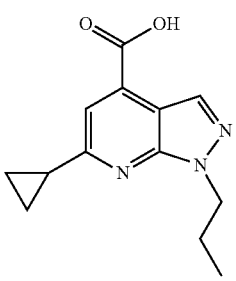 [SMILES: CCCn1ncc2c(C(=O)O)cc(C3CC3)nc21]

The title compound was prepared as in the same manner as described for intermediate 43 using ethyl 6-cyclopropyl-1H-pyrazolo[3,4-b]pyridine-4-carboxylate (200 mg, 0.865 mmol), sodium hydride (29.1 mg, 1.211 mmol), DMF (10 mL), 1-iodopropane (162 mg, 0.951 mmol), and NaOH (1 mL). The crude product was purified by silica gel chromatography (eluent: 0 to 10% MeOH:DCM) to afford the final product as a solid, 90 mg (42%). Regiochemical assignment supported by 2D HNMR. LCMS E-S (M+H)=246.0 $^1$H NMR (400 MHz, DMSO-$d_6$) δ ppm 13.83 (br s, 1H), 8.24 (s, 1H), 7.62 (s, 1H), 4.26 (t, 2H, J=7.2 Hz), 2.37-2.40 (m, 2H), 1.83-1.89 (m, 2H), 1.07-1.11 (m, 4H), 0.77 (t, 3H, J=7.2 Hz).

Intermediate 45

1-Amino-6-cyclopropyl-1H-pyrazolo[3,4-b]pyridine-4-carboxylic acid

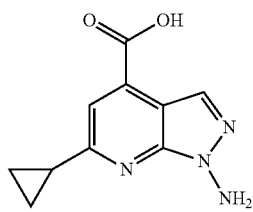 [SMILES: Nn1ncc2c(C(=O)O)cc(C3CC3)nc21]

To a solution of ethyl 1-amino-6-cyclopropyl-1H-pyrazolo[3,4-b]pyridine-4-carboxylate (100 mg, 0.406 mmol) in ethanol (10 mL) was added sodium hydroxide (1 ml, 0.406 mmol), and the mixture stirred at room temperature for 2 h. The solvent was removed in vacuo, and the residue diluted with EtOAc (30 mL) and water (20 mL). The reaction mixture was acidified to pH 3 with citric acid. The phases were separated and the aq. phase extracted with EtOAc (4×20 mL). The combined organic layers were washed with water, dried over $MgSO_4$, filtered, and concentrated in vacuo. The final product was collected as 0.075 g (84%). LCMS E-S (M+H)=219.5. $^1$H NMR (400 MHz, DMSO-$d_6$) δ ppm 1.00-1.13 (m, 4H), 2.27-2.45 (m, 1H), 6.36 (s, 2H), 7.60 (s, 1H), 8.06 (s, 1H), 13.81 (br. s., 1H).

Intermediate 46

6-Cyclopropyl-3-methyl-1-(1-methylethyl)-1H-pyrazolo[3,4-b]pyridine-4-carboxylic acid

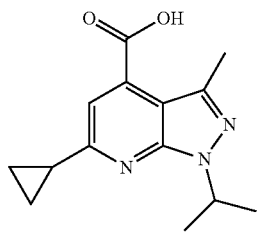 [SMILES: Cc1nn(C(C)C)c2nc(C3CC3)cc(C(=O)O)c12]

To a solution of ethyl 6-cyclopropyl-3-methyl-1-(1-methylethyl)-1H-pyrazolo[3,4-b]pyridine-4-carboxylate (200 mg, 0.696 mmol) in ethanol (5 mL) was added sodium hydroxide (2.088 mL, 2.088 mmol), and the mixture stirred at room temperature for 30 min. The reaction mixture was concentrated in vacuo. The residue was diluted with water (30 mL) and then acidified with acetic acid. The contents were extracted with DCM (3×30 mL). The combined organic layers were washed with water, brine, dried over MgSO$_4$, filtered, and concentrated in vacuo. The final product was obtained as 0.17 g (94%). LCMS E-S (M+H)=260.0. $^1$H NMR (400 MHz, DMSO-d$_6$) δ ppm 0.97-1.12 (m, 4H) 1.44 (d, J=6.57 Hz, 6H) 2.27-2.38 (m, 1H) 2.55 (s, 3H) 5.07 (quin, J=6.69 Hz, 1H) 7.43 (s, 1H) 13.30-14.08 (m, 1H).

Intermediate 47

6-Cyclopropyl-1-[2-({[(1,1-dimethylethyl)oxy]carbonyl}amino)ethyl]-1H-pyrazolo[3,4-b]pyridine-4-carboxylic acid

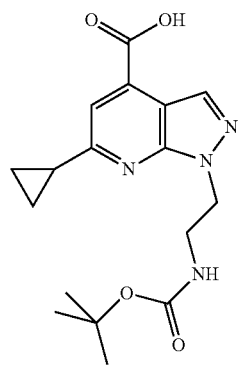 [SMILES: CC(C)(C)OC(=O)NCCn1ncc2c(C(=O)O)cc(C3CC3)nc21]

The title compound was prepared in the same manner as described for intermediate 46 using ethyl 6-cyclopropyl-1-[2-({[(1,1-dimethylethyl)oxy]carbonyl}amino)ethyl]-1H-pyrazolo[3,4-b]pyridine-4-carboxylate (110 mg, 0.294 mmol), sodium hydroxide (1 mL, 0.294 mmol), and ethanol (10 mL) wherein the stir time was 16 h. The final product was collected as 0.060 g (59%). LCMS E-S (M+H)=347.1 $^1$H NMR (400 MHz, DMSO-d$_6$) δ ppm 1.06-1.13 (m, 4H) 1.27 (s, 9H) 2.33-2.43 (m, 1H) 3.37 (q, J=5.81 Hz, 2H) 4.44 (t, J=5.94 Hz, 2H) 6.84 (t, J=5.81 Hz, 1H) 7.62 (s, 5H) 8.24 (s, 1H).

Intermediate 48

1-Cyclobutyl-6-cyclopropyl-3-methyl-1H-pyrazolo[3,4-b]pyridine-4-carboxylic acid

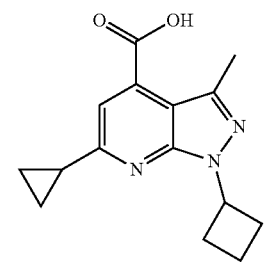 [SMILES: Cc1nn(C2CCC2)c2nc(C3CC3)cc(C(=O)O)c12]

The title compound was prepared in the same manner as described for intermediate 46 using ethyl 1-cyclobutyl-6-cyclopropyl-3-methyl-1H-pyrazolo[3,4-b]pyridine-4-carboxylate (550 mg, 1.837 mmol), sodium hydroxide (3 ml, 3.00 mmol), and ethanol (30 mL) wherein the stir time was 1 h. The final product was collected as 0.490 g (98%). LCMS E-S (M+H)=272.5 $^1$H NMR (400 MHz, DMSO-d$_6$) δ ppm 1.03-1.10 (m, 4H), 1.80-1.91 (m, 2H), 2.26-2.43 (m, 3H), 2.58 (s, 3H), 2.59-2.71 (m, 2H), 5.35 (dq, J=8.59, 8.42 Hz, 1H), 7.44 (s, 1H), 13.73 (br. s., 1H).

Intermediate 49

1-Cyclopentyl-6-cyclopropyl-3-methyl-1H-pyrazolo[3,4-b]pyridine-4-carboxylic acid

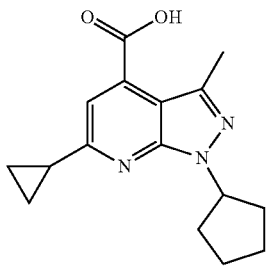 [SMILES: Cc1nn(C2CCCC2)c2nc(C3CC3)cc(C(=O)O)c12]

The title compound was prepared in the same manner as described for intermediate 46 using ethyl 1-cyclopentyl-6-cyclopropyl-3-methyl-1H-pyrazolo[3,4-b]pyridine-4-carboxylate (740 mg, 2.361 mmol), sodium hydroxide (4 ml, 4.00 mmol), and ethanol (30 mL), wherein the stir time was 1 h. The final product was collected as 0.530 g (79%). LCMS E-S (M+H)=286.3 $^1$H NMR (400 MHz, DMSO-d$_6$) δ ppm 0.96-1.12 (m, 4H) 1.52-1.74 (m, 2H) 1.82-2.13 (m, 6H) 2.26-2.37 (m, 1H) 2.55 (s, 3H) 5.17-5.30 (m, 1H) 7.43 (s, 1H) 13.70 (br. s., 1H).

Intermediate 50

6-Cyclopropyl-1-(1,1-dimethylethyl)-3-methyl-1H-pyrazolo[3,4-b]pyridine-4-carboxylic acid

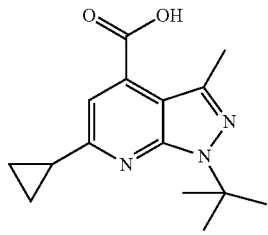 [SMILES: Cc1nn(C(C)(C)C)c2nc(C3CC3)cc(C(=O)O)c12]

The title compound was prepared in the same manner as described for intermediate 46 using ethyl 6-cyclopropyl-1-(1,1-dimethylethyl)-3-methyl-1H-pyrazolo[3,4-b]pyridine-4-carboxylate (240 mg, 0.796 mmol), sodium hydroxide (4 mL, 4.00 mmol), and ethanol (30 mL), wherein the stir time was 1 h. The final product was collected as 0.210 g (96%). LCMS E-S (M+H)=274.4. $^1$H NMR (400 MHz, DMSO-$d_6$) δ ppm 1.05 (m, 4H) 1.70 (s, 9H) 2.33 (m, 1H) 2.51 (s, 3H) 7.46 (s, 1H) 13.70 (br. s., 1H).

Intermediate 51

6-Cyclopropyl-3-methyl-1-(4-pyridinyl)-1H-pyrazolo[3,4-b]pyridine-4-carboxylic acid

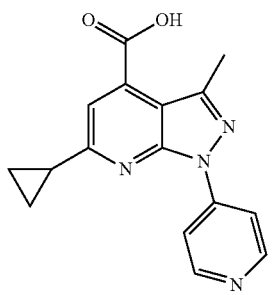 [SMILES: Cc1nn(-c2ccncc2)c2nc(C3CC3)cc(C(=O)O)c12]

The title compound was prepared in the same manner as described for intermediate 46 using ethyl 6-cyclopropyl-1-(4-pyridinyl)-3-methyl-1H-pyrazolo[3,4-b]pyridine-4-carboxylate (240 mg, 0.796 mmol), sodium hydroxide (4 mL, 4.00 mmol), and ethanol (30 mL), wherein the stir time was 1 h. The final product was collected as 0.210 g (89%). LCMS E-S (M+H)=295.3.

Intermediate 52

6-Cyclopropyl-1-(1-cyclopropylethyl)-3-methyl-1H-pyrazolo[3,4-b]pyridine-4-carboxylic acid

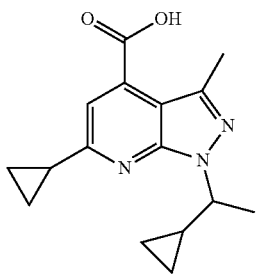 [SMILES: Cc1nn(C(C)C2CC2)c2nc(C3CC3)cc(C(=O)O)c12]

To an EtOH (10 mL) solution of ethyl 6-cyclopropyl-1-(1-cyclopropylethyl)-3-methyl-1H-pyrazolo[3,4-b]pyridine-4-carboxylate (720 mg, 2.297 mmol) was added sodium hydroxide (6.89 mL, 6.89 mmol) and the mixture heated at 70° C. for 1 hour. The solvent was removed in vacuo and the residue was dissolved in 20 mL of water. The contents were acidified with acetic acid, and extracted with EtOAc (4×30 mL). The combined organic extracts were washed with water, brine, dried over MgSO$_4$, filtered, and concentrated in vacuo. The final product was collected as a solid, 0.560 g (85%). LCMS E-S (M+H)=286.3 $^1$H NMR (400 MHz, DMSO-$d_6$) δ ppm 0.15-0.33 (m, 2H), 0.38 (dq, J=9.57, 4.89 Hz, 1H), 0.50-0.65 (m, 1H), 0.90-1.10 (m, 4H), 1.27-1.42 (m, 1H), 1.57 (d, J=6.82 Hz, 3H), 2.23-2.36 (m, 1H), 2.57 (s, 3H), 4.18 (dq, J=9.32, 6.83 Hz, 1H), 7.44 (s, 1H), 12.79 (br. s., 1H).

Intermediate 53

1-cyclohexyl-6-cyclopropyl-3-methyl-1H-pyrazolo[3,4-b]pyridine-4-carboxylic acid

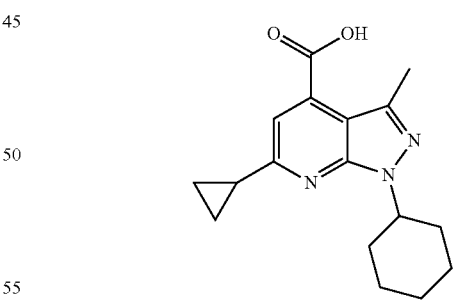

The title compound was prepared in the same manner as described for intermediate 52 using ethyl 6-cyclopropyl-1-(1-cyclohexyl)-3-methyl-1H-pyrazolo[3,4-b]pyridine-4-carboxylate (820 mg, 2.5 mmol) and sodium hydroxide (7.51 mL, 7.51 mmol). The final product was collected as a solid, 0.660 g (88%). LCMS E-S (M+H)=300.4 $^1$H NMR (400 MHz, DMSO-$d_6$) δ ppm 1.01-1.11 (m, 4H), 1.16-1.31 (m, 1H), 1.36-1.55 (m, 2H), 1.70 (d, J=12.38 Hz, 1H), 1.80-1.98 (m, 6H), 2.32 (m, J=7.80, 7.80, 5.05, 4.86 Hz, 1H), 2.55 (s, 3H), 4.60-4.73 (m, 1H), 7.40 (s, 1H), 13.71 (br. s., 1H).

Intermediate 54

6-Cyclopropyl-3-methyl-1-(1-methyl-4-piperidinyl)-1H-pyrazolo[3,4-b]pyridine-4-carboxylic acid

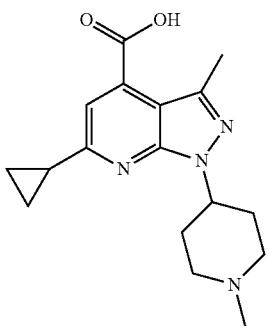 [SMILES: Cc1nn(C2CCN(C)CC2)c2nc(C3CC3)cc(C(=O)O)c12]

To an EtOH solution (10 mL) of ethyl 6-cyclopropyl-3-methyl-1-(1-methyl-4-piperidinyl)-1H-pyrazolo[3,4-b]pyridine-4-carboxylate (620 mg, 1.811 mmol) was added sodium hydroxide (5.43 mL, 5.43 mmol) and the mixture heated at 70° C. for 1 hour. The solvent was removed in vacuo and the residue was dissolved in 20 mL of water. The contents were acidified with acetic acid, and extracted with EtOAc (4×30 mL). The combined organic extracts were washed with water, brine, dried over MgSO$_4$, filtered, and concentrated in vacuo to afford a minor amount of product. The aqueous phase was concentrated in vacuo and the crude residue purified by reverse phase HPLC purification (eluent: 0% ACN/H$_2$O, 0.1% TFA to 45% ACN/H$_2$O, 0.1% TFA). The isolated solid product was concentrated from toluene to afford the final product as 510 mg (90%). LCMS E-S (M+H)=315.2. $^1$H NMR (400 MHz, DMSO-d$_6$) δ ppm 1.08 (d, J=6.57 Hz, 4H), 2.10 (d, J=13.14 Hz, 2H), 2.30-2.42 (m, 3H), 2.55 (s, 3H), 2.77-2.92 (m, 3H), 3.30 (br. s., 2H), 3.57 (d, J=12.13 Hz, 2H), 4.98 (m, J=11.78, 11.78, 3.85, 3.66 Hz, 1H), 7.46 (s, 1H), 9.87 (br. s., 1H).

Intermediate 55

6-Cyclopropyl-3-methyl-1-(tetrahydro-2H-pyran-4-yl)-1H-pyrazolo[3,4-b]pyridine-4-carboxylic acid

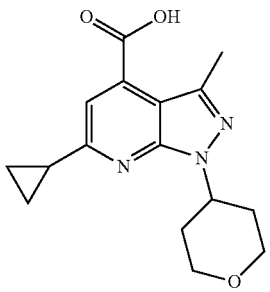 [SMILES: Cc1nn(C2CCOCC2)c2nc(C3CC3)cc(C(=O)O)c12]

To an EtOH solution (30 mL) of ethyl 6-cyclopropyl-3-methyl-1-(tetrahydro-2H-pyran-4-yl)-1H-pyrazolo[3,4-b]pyridine-4-carboxylate (300 mg, 0.911 mmol) was added sodium hydroxide (1.82 mL, 1.82 mmol) and the mixture stirred at room temperature for 16 h. The solvent was removed in vacuo and the residue was dissolved in 20 mL of water. The contents were acidified with acetic acid, and extracted with EtOAc (4×30 mL). The combined organic extracts were washed with water, brine, dried over MgSO$_4$, filtered, and concentrated in vacuo to afford the final product as 265 mg (97%). LCMS E-S (M+H)=302.4 $^1$H NMR (400 MHz, DMSO-d$_6$) δ ppm 1.02-1.09 (m, 4H), 1.81 (dd, J=12.38, 2.27 Hz, 2H), 2.15 (qd, J=12.25, 4.42 Hz, 2H), 2.28-2.37 (m, 1H), 2.54 (s, 3H), 3.46-3.60 (m, 2H), 3.89-4.02 (m, 2H), 4.91 (m, J=11.56, 11.56, 4.17, 4.04 Hz, 1H), 7.42 (s, 1H), 13.73 (br. s., 1H).

Intermediate 56

(4,6-dimethyl-2-oxo-1,2-dihydro-3-pyridinyl)methyl 6-cyclopropyl-1-[2-({[(1,1-dimethylethyl)oxy]carbonyl}amino)ethyl]-1H-pyrazolo[3,4-b]pyridine-4-carboxylate

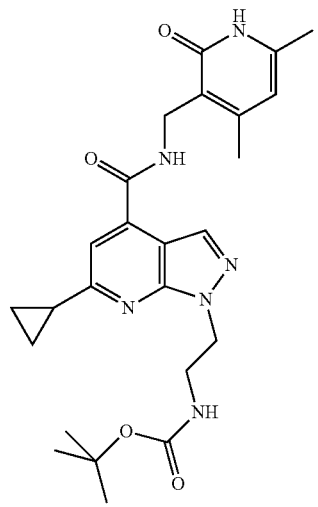 [SMILES: Cc1cc(C)c(CNC(=O)c2cc(C3CC3)nc3c2cnn3CCNC(=O)OC(C)(C)C)c(=O)[nH]1]

To a solution of DMSO (10 mL) were sequentially added 6-cyclopropyl-1-[2-({[(1,1-dimethylethyl)oxy]carbonyl}amino)ethyl]-1H-pyrazolo[3,4-b]pyridine-4-carboxylic acid (270 mg, 0.779 mmol), 3-(aminomethyl)-4,6-dimethyl-2(1H)-pyridinone (178 mg, 1.169 mmol), and 1-hydroxy-7-azabenzotriazole (212 mg, 1.559 mmol), and the mixture stirred at room temperature for 10 min. Next was added EDC (299 mg, 1.559 mmol) and N-methylmorpholine (0.343 mL, 3.12 mmol), and reaction mixture was stirred at room temperature for 16 h. The contents were diluted with water (25 mL) and stirred for 10 min. The solid product was filtered off, dried, and collected as 0.290 g (98%). LCMS E-S (M+H)=381.2. $^1$H NMR (400 MHz, DMSO-d$_6$) δ ppm 1.00-1.15 (m, 4H), 1.30 (s, 9H), 2.13 (s, 3H), 2.18-2.32 (m, 4H), 4.36 (d, J=4.80 Hz, 2H), 4.42 (t, J=5.81 Hz, 2H), 5.90 (s, 1H), 6.85 (t, J=5.56 Hz, 1H), 7.44 (s, 1H), 8.22 (s, 2H), 8.73 (t, J=4.67 Hz, 1H), 11.57 (br. s., 1H).

Example 98

1-(2-Aminoethyl)-6-cyclopropyl-N-[(4,6-dimethyl-2-oxo-1,2-dihydro-3-pyridinyl)methyl]-1H-pyrazolo[3,4-b]pyridine-4-carboxamide

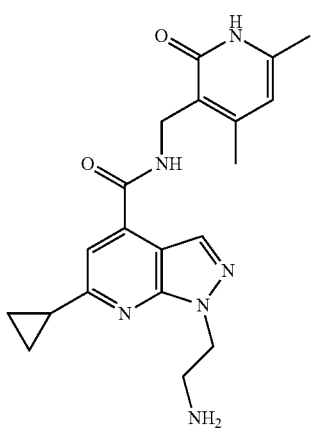 [SMILES: Cc1cc(C)c(CNC(=O)c2cc(C3CC3)nc3c2cnn3CCN)c(=O)[nH]1]

To a solution of 1,1-dimethylethyl {2-[6-cyclopropyl-4-({[(4,6-dimethyl-2-oxo-1,2-dihydro-3-pyridinyl)methyl]amino}carbonyl)-1H-pyrazolo[3,4-b]pyridin-1-yl]ethyl}carbamate (260 mg, 0.541 mmol) in DCM (15 mL) was added trifluoroacetic acid (3 ml, 38.9 mmol) and the mixture stirred at room temperature for 2 h. The contents were concentrated in vacuo and the crude residue purified by reverse phase HPLC. (mobile phase: 10 to 70% ACN in H$_2$O, 0.1% NH$_4$OH). The final product was collected as 0.170 g (89%). LCMS E-S (M+H)=353.3 $^1$H NMR (400 MHz, DMSO-d$_6$) δ ppm 1.07 (d, J=6.32 Hz, 4H), 2.13 (s, 3H), 2.21 (s, 4H), 3.00 (t, J=6.19 Hz, 2H), 4.29-4.47 (m, 4H), 5.90 (s, 1H) 7.43 (s, 1H), 8.22 (s, 1H), 8.75 (t, 1H).

Example 99

6-Cyclopropyl-N-[(4,6-dimethyl-2-oxo-1,2-dihydro-3-pyridinyl)methyl]-1-{2-[(methylsulfonyl)amino]ethyl}-1H-pyrazolo[3,4-b]pyridine-4-carboxamide

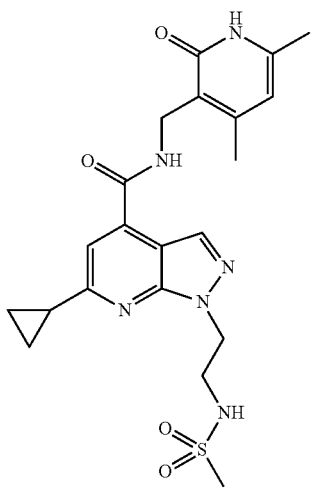 [SMILES: Cc1cc(C)c(CNC(=O)c2cc(C3CC3)nc3c2cnn3CCNS(C)(=O)=O)c(=O)[nH]1]

To a solution of 1-(2-aminoethyl)-6-cyclopropyl-N-[(4,6-dimethyl-2-oxo-1,2-dihydro-3-pyridinyl)methyl]-1H-pyrazolo[3,4-b]pyridine-4-carboxamide (120 mg, 0.315 mmol) in pyridine (2 mL) was added methanesulfonyl chloride (0.025 mL, 0.315 mmol) and the reaction mixture stirred at room temperature for 16 hours. The reaction mixture was concentrated in vacuo, diluted with water, and extracted with EtOAc. The combined organic extracts were washed with brine, dried over MgSO$_4$, filtered, and concentrated in vacuo. The crude product was purified by reverse phase HPLC to afford a solid (25 mg). This solid was suspended in MeOH (1 mL) and treated with 4N HCl (1 mL). The solvent was removed under reduced pressure to afford the final product as a solid which was collected as 15 mg (9%). LCMS E-S (M+H)=459.2. $^1$H NMR (400 MHz, DMSO-d$_6$) δ ppm 1.02-1.15 (m, 4H), 2.13 (s, 3H), 2.22 (s, 3H), 2.23-2.31 (m, 1H), 2.82 (s, 3H), 3.45 (q, 2H), 4.36 (d, J=5.05 Hz, 2H), 4.49 (t, J=6.44 Hz, 2H), 5.90 (s, 1H), 7.19 (s, 1H), 7.47 (s, 1H), 8.25 (s, 1H), 8.76 (t, J=4.93 Hz, 1H), 11.56 (s, 1H).

Example 100

N-[(4,6-Dimethyl-2-oxo-1,2-dihydro-3-pyridinyl)methyl]-6-methyl-1-(phenylmethyl)-1H-pyrazolo[3,4-b]pyridine-4-carboxamide

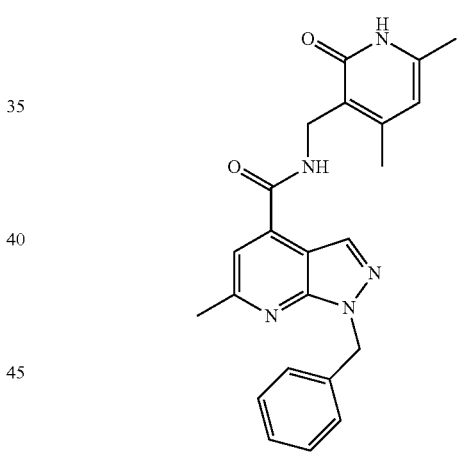

The title compound was prepared in the same manner as described for intermediate 56 using 6-methyl-1-(phenylmethyl)-1H-pyrazolo[3,4-b]pyridine-4-carboxylic acid (200 mg, 0.748 mmol), 3-(aminomethyl)-4,6-dimethyl-2(1H)-pyridinone (142 mg, 0.935 mmol), 1-hydroxy-7-azabenzotriazole (204 mg, 1.497 mmol), DMSO (10 mL), EDC (287 mg, 1.497 mmol), and N-methylmorpholine (0.329 mL, 2.99 mmol). The final product was collected as 0.25 g (83%). LCMS E-S (M+H)=402.2. $^1$H NMR (400 MHz, DMSO-d$_6$) δ ppm 0.93-1.12 (m, 4H), 1.42 (d, J=6.82 Hz, 6H), 2.12 (s, 3H), 2.22 (s, 4H), 2.36 (s, 3H), 4.34 (d, J=4.80 Hz, 2H), 4.90-5.11 (m, 1H), 5.87 (s, 1H), 6.99 (s, 1H), 8.58 (s, 1H), 11.51 (s, 1H.

Example 101

6-Cyclopropyl-N-[(4,6-dimethyl-2-oxo-1,2-dihydro-3-pyridinyl)methyl]-1-ethyl-1H-pyrazolo[3,4-b]pyridine-4-carboxamide

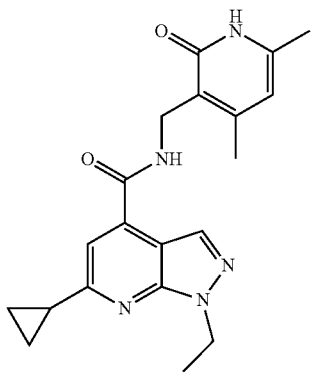 [SMILES: CCn1ncc2c(C(=O)NCc3c(C)cc(C)[nH]c3=O)cc(C3CC3)nc21]

The title compound was prepared in the same manner as described for intermediate 56 using 6-cyclopropyl-1-ethyl-1H-pyrazolo[3,4-b]pyridine-4-carboxylic acid (91 mg, 0.394 mmol), 3-(aminomethyl)-4,6-dimethyl-2(1H)-pyridinone (75 mg, 0.493 mmol), 1-hydroxy-7-azabenzotriazole (107 mg, 0.788 mmol), DMSO (10 mL), EDC (151 mg, 0.788 mmol), and N-methylmorpholine (0.173 mL, 1.577 mmol). The final product was collected as 0.090 g (63%). LCMS E-S (M+H)=366.3 $^1$H NMR (400 MHz, DMSO-$d_6$) δ ppm 1.07 (d, J=6.32 Hz, 4H), 1.39 (t, J=7.20 Hz, 3H), 2.13 (s, 3H), 2.19-2.32 (m, 4H), 4.36 (d, J=4.80 Hz, 2H), 4.42 (q, J=7.07 Hz, 2H), 5.90 (s, 1H), 7.43 (s, 1H), 8.21 (s, 1H), 8.75 (t, J=4.67 Hz, 1H), 11.57 (br. s., 1H).

Example 102

6-Cyclopropyl-N-[(4,6-dimethyl-2-oxo-1,2-dihydro-3-pyridinyl)methyl]-1-propyl-1H-pyrazolo[3,4-b]pyridine-4-carboxamide

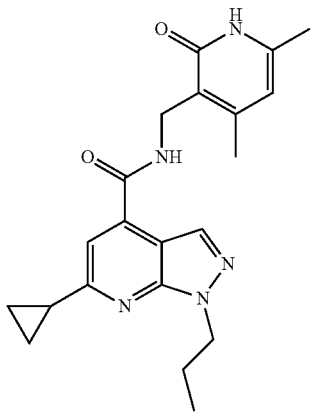 [SMILES: CCCn1ncc2c(C(=O)NCc3c(C)cc(C)[nH]c3=O)cc(C3CC3)nc21]

The title compound was prepared in the same manner as described for intermediate 56 using 6-cyclopropyl-1-propyl-1H-pyrazolo[3,4-b]pyridine-4-carboxylic acid (90 mg, 0.368 mmol), 3-(aminomethyl)-4,6-dimethyl-2(1H)-pyridinone (70 mg, 0.460 mmol), 1-hydroxy-7-azabenzotriazole (100 mg, 0.736 mmol), DMSO (10 mL), EDC (141 mg, 0.736 mmol), and N-methylmorpholine (0.162 mL, 1.472 mmol). The final product was collected as 0.118 g (84%). LCMS E-S (M+H)=380.3. $^1$H NMR (400 MHz, DMSO-$d_6$) δ ppm 0.78 (t, 3H), 0.99-1.16 (m, 4H), 1.85 (d, J=7.33 Hz, 2H), 2.13 (s, 3H), 2.22 (s, 4H), 4.25-4.43 (m, 4H), 5.90 (s, 1H), 7.43 (s, 1H), 8.21 (s, 1H), 8.75 (s, 1H), 11.57 (s, 1H).

Example 103

6-Cyclopropyl-N-[(4,6-dimethyl-2-oxo-1,2-dihydro-3-pyridinyl)methyl]-3-methyl-1-(1-methylethyl)-1H-pyrazolo[3,4-b]pyridine-4-carboxamide

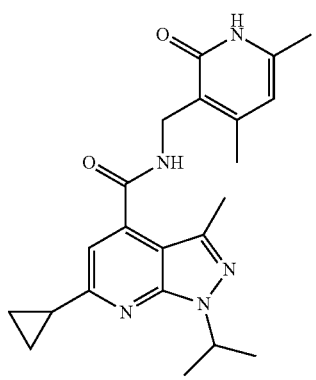 [SMILES: Cc1cc(C)c(CNC(=O)c2cc(C3CC3)nc3c2c(C)nn3C(C)C)c(=O)[nH]1]

The title compound was prepared in the same manner as described for intermediate 56 using 6-cyclopropyl-1-(2-methylpropyl)-1H-pyrazolo[3,4-b]pyridine-4-carboxylic acid (80 mg, 0.309 mmol), 3-(aminomethyl)-4,6-dimethyl-2(1H)-pyridinone (70.4 mg, 0.463 mmol), 1-hydroxy-7-azabenzotriazole (84 mg, 0.617 mmol), DMSO (10 mL), EDC (118 mg, 0.617 mmol), and N-methylmorpholine (0.136 mL, 1.234 mmol). The final product was collected as 0.123 g (100%). LCMS E-S (M+H)=394.2 $^1$H NMR (400 MHz, DMSO-$d_6$) δ ppm 0.93-1.12 (m, 4H), 1.42 (d, J=6.82 Hz, 6H), 2.12 (s, 3H), 2.22 (s, 4H), 2.36 (s, 3H), 4.34 (d, J=4.80 Hz, 2H), 4.90-5.11 (m, 1H), 5.87 (s, 1H), 6.99 (s, 1H), 8.58 (s, 1H), 11.51 (s, 1H).

Example 104

1-Amino-6-cyclopropyl-N-[(4,6-dimethyl-2-oxo-1,2-dihydro-3-pyridinyl)methyl]-1H-pyrazolo[3,4-b]pyridine-4-carboxamide

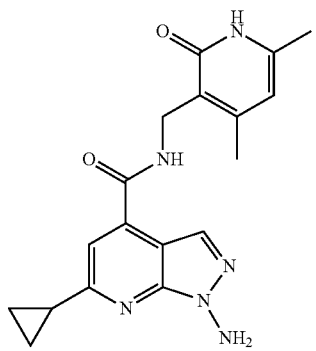 [SMILES: Cc1cc(C)c(CNC(=O)c2cc(C3CC3)nc3c2cnn3N)c(=O)[nH]1]

The title compound was prepared in the same manner as described for intermediate 56 using 1-amino-6-cyclopropyl-1H-pyrazolo[3,4-b]pyridine-4-carboxylic acid (73 mg, 0.335 mmol), 3-(aminomethyl)-4,6-dimethyl-2(1H)-pyridinone (76 mg, 0.502 mmol), 1-hydroxy-7-azabenzotriazole (91 mg, 0.669 mmol), DMSO (10 mL), EDC (128 mg, 0.669 mmol), and N-methylmorpholine (0.147 mL, 1.338 mmol). The aq. phase was extracted with EtOAc (5×30 mL). The combined EtOAc extracts were dried over MgSO$_4$, filtered, and concentrated in vacuo. The final product was collected as 0.068 g (58%). LCMS E-S (M+H)=353.3. $^1$H NMR (400 MHz, DMSO-d$_6$) δ ppm 0.99-1.14 (m, 4H), 2.13 (s, 3H), 2.22 (s, 4H), 4.35 (d, J=4.80 Hz, 2H), 5.90 (s, 1H), 6.31 (s, 2H), 7.41 (s, 1H), 8.04 (s, 1H), 8.74 (s, 1H), 11.58 (br. s., 1H).

Example 105

1-Cyclobutyl-6-cyclopropyl-N-[(4,6-dimethyl-2-oxo-1,2-dihydro-3-pyridinyl)methyl]-3-methyl-1H-pyrazolo[3,4-b]pyridine-4-carboxamide

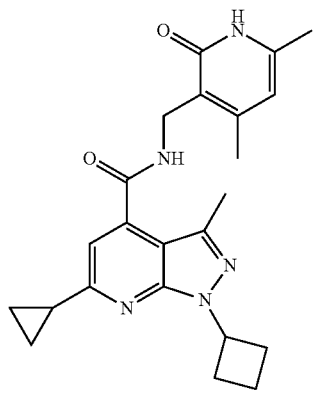 [SMILES: Cc1cc(C)c(CNC(=O)c2cc(C3CC3)nc3c2c(C)nn3C2CCC2)c(=O)[nH]1]

The title compound was prepared in the same manner as described for intermediate 56 using 1-cyclobutyl-6-cyclopropyl-3-methyl-1H-pyrazolo[3,4-b]pyridine-4-carboxylic acid (164 mg, 0.604 mmol), 3-(aminomethyl)-4,6-dimethyl-2 (1H)-pyridinone (129 mg, 0.846 mmol), 1-hydroxy-7-azabenzotriazole (165 mg, 1.209 mmol), EDC (232 mg, 1.209 mmol), N-methylmorpholine (0.266 mL, 2.418 mmol), and DMSO (10 mL). The final product was collected as 0.240 g (98%). LCMS E-S (M+H)=406.3. $^1$H NMR (400 MHz, DMSO-d$_6$) δ ppm 1.03 (d, J=6.06 Hz, 4H), 1.85 (dd, J=9.35, 5.05 Hz, 3H), 2.12 (s, 4H), 2.16-2.28 (m, 6H), 2.30-2.44 (m, 7H), 2.63 (d, J=19.96 Hz, 3H), 4.34 (d, J=4.29 Hz, 2H), 5.31 (t, J=8.34 Hz, 1H), 5.87 (s, 1H), 7.01 (s, 1H), 8.59 (br. s., 1H), 11.52 (br. s., 1H).

Example 106

1-Cyclopentyl-6-cyclopropyl-N-[(4,6-dimethyl-2-oxo-1,2-dihydro-3-pyridinyl)methyl]-3-methyl-1H-pyrazolo[3,4-b]pyridine-4-carboxamide

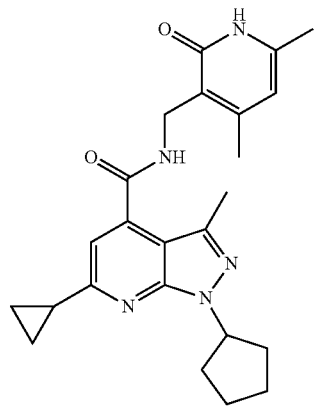 [SMILES: Cc1cc(C)c(CNC(=O)c2cc(C3CC3)nc3c2c(C)nn3C2CCCC2)c(=O)[nH]1]

The title compound was prepared in the same manner as described for intermediate 56 using 1-cyclopentyl-6-cyclopropyl-3-methyl-1H-pyrazolo[3,4-b]pyridine-4-carboxylic acid (160 mg, 0.561 mmol), 3-(aminomethyl)-4,6-dimethyl-2(1H)-pyridinone (119 mg, 0.785 mmol), 1-hydroxy-7-azabenzotriazole (153 mg, 1.121 mmol), EDC (215 mg, 1.121 mmol), N-methylmorpholine (0.247 mL, 2.243 mmol) and DMSO (10 mL). The final product was collected as 0.205 g (87%). LCMS E-S (M+H)=420.0. $^1$H NMR (400 MHz, DMSO-d$_6$) δ ppm 1.03 (d, J=6.06 Hz, 4H), 1.85 (dd, J=9.35, 5.05 Hz, 3H), 2.12 (s, 4H), 2.16-2.28 (m, 6H), 2.30-2.44 (m, 7H), 2.63 (d, J=19.96 Hz, 3H), 4.34 (d, J=4.29 Hz, 2H), 5.31 (t, J=8.34 Hz, 1H), 5.87 (s, 1H), 7.01 (s, 1H), 8.59 (br. s., 1H), 11.52 (br. s., 1H).

Example 107

6-Cyclopropyl-1-(1,1-dimethylethyl)-N-[(4,6-dimethyl-2-oxo-1,2-dihydro-3-pyridinyl)methyl]-3-methyl-1H-pyrazolo[3,4-b]pyridine-4-carboxamide

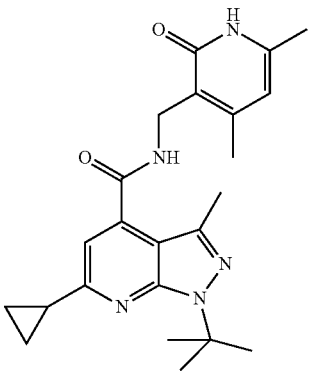 [SMILES: Cc1cc(C)c(CNC(=O)c2cc(C3CC3)nc3c2c(C)nn3C(C)(C)C)c(=O)[nH]1]

The title compound was prepared in the same manner as described for intermediate 56 using 6-cyclopropyl-1-(1,1-dimethylethyl)-3-methyl-1H-pyrazolo[3,4-b]pyridine-4-carboxylic acid (210 mg, 0.768 mmol), 3-(aminomethyl)-4,6-dimethyl-2(1H)-pyridinone (158 mg, 1.037 mmol), 1-hydroxy-7-azabenzotriazole (209 mg, 1.537 mmol), EDC (295 mg, 1.537 mmol), N-methylmorpholine (0.338 mL, 3.07 mmol), and DMSO (10 mL). The final product was collected as 0.280 g (89%). LCMS E-S (M+H)=408.2. $^1$H NMR (400 MHz, DMSO-$d_6$) δ ppm 1.02 (dddd, 4H), 1.69 (m, 9H), 2.12 (s, 3H), 2.22 (m, 4H), 2.33 (s, 3H), 4.34 (d, J=4.80 Hz, 2H), 5.87 (s, 1H), 7.04 (s, 1H), 8.55 (m, 1H), 11.51 (s, 1H).

Example 108

6-Cyclopropyl-N-[(4,6-dimethyl-2-oxo-1,2-dihydro-3-pyridinyl)methyl]-1-(4-pyridinyl)-1H-pyrazolo[3,4-b]pyridine-4-carboxamide

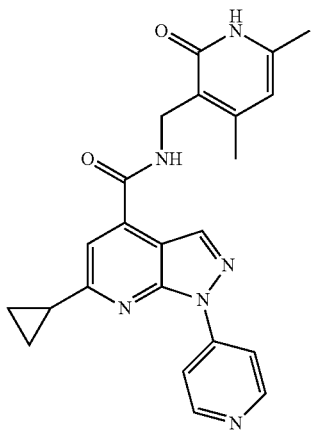 [SMILES: Cc1cc(C)c(CNC(=O)c2cc(C3CC3)nc3c2cnn3-c2ccncc2)c(=O)[nH]1]

The title compound was prepared in the same manner as described for intermediate 56 using 6-cyclopropyl-3-methyl-1-(4-pyridinyl)-1H-pyrazolo[3,4-b]pyridine-4-carboxylic acid (89 mg, 0.302 mmol), 3-(aminomethyl)-4,6-dimethyl-2(1H)-pyridinone (69.0 mg, 0.454 mmol), 1-hydroxy-7-azabenzotriazole (82 mg, 0.605 mmol), DMSO (20 mL), EDC (116 mg, 0.605 mmol), and N-methylmorpholine (0.133 mL, 1.210 mmol). The final product was collected as 0.110 g (80%). LCMS E-S (M+H)=429.1 $^1$H NMR (400 MHz, DMSO-$d_6$) δ ppm 1.15 (br. s., 4H), 2.13 (br. s., 3H), 2.25 (br. s., 4H), 3.34 (br. s., 3H), 4.37 (br. s., 2H), 5.89 (br. s., 1H), 7.30 (br. s., 1H), 8.33 (br. s., 2H), 8.67 (br. s., 3H), 11.54 (br. s., 1H).

Example 109

6-Cyclopropyl-1-(1-cyclopropylethyl)-N-[(4,6-dimethyl-2-oxo-1,2-dihydro-3-pyridinyl)methyl]-3-methyl-1H-pyrazolo[3,4-b]pyridine-4-carboxamide

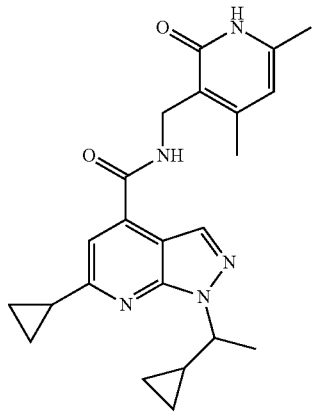 [SMILES: Cc1cc(C)c(CNC(=O)c2cc(C3CC3)nc3c2cnn3C(C)C2CC2)c(=O)[nH]1]

6-Cyclopropyl-1-(1-cyclopropylethyl)-3-methyl-1H-pyrazolo[3,4-b]pyridine-4-carboxylic acid (186 mg, 0.652 mmol), 3-(aminomethyl)-4,6-dimethyl-2(1H)-pyridinone (160 mg, 0.847 mmol), 1-hydroxy-7-azabenzotriazole (177 mg, 1.304 mmol), EDC (250 mg, 1.304 mmol) and N-methylmorpholine (0.287 mL, 2.61 mmol) were dissolved in DMSO (10 mL) and stirred at room temperature for 3 days. The reaction mixture was diluted with water (25 mL), stirred, and filtered. The product was dried and collected as a solid, 0.200 g (73%). LCMS E-S (M+H)=420.0. $^1$H NMR (400 MHz, DMSO-$d_6$) δ ppm 0.14-0.30 (m, 2H), 0.32-0.43 (m, 1H), 0.48-0.64 (m, 1H), 0.89-1.11 (m, 4H), 1.22-1.43 (m, 1H), 1.55 (d, J=6.82 Hz, 3H), 2.11 (s, 3H), 2.18-2.28 (m, 4H), 2.37 (s, 3H), 4.05-4.21 (m, 1H), 4.34 (d, J=4.80 Hz, 2H), 5.87 (s, 1H), 6.99 (s, 1H), 8.59 (t, J=4.67 Hz, 1H), 11.51 (br. s., 1H).

Example 110

1-Cyclohexyl-6-cyclopropyl-N-[(4,6-dimethyl-2-oxo-1,2-dihydro-3-pyridinyl)methyl]-3-methyl-1H-pyrazolo[3,4-b]pyridine-4-carboxamide

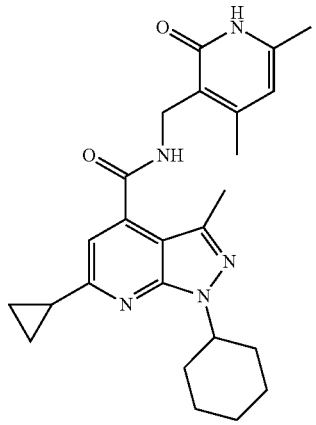 [SMILES: Cc1cc(C)c(CNC(=O)c2cc(C3CC3)nc3c2c(C)nn3C2CCCCC2)c(=O)[nH]1]

The title compound was prepared in the same manner as described in example 109 using 6-cyclopropyl-1-(1-cyclohexyl)-3-methyl-1H-pyrazolo[3,4-b]pyridine-4-carboxylic acid (150 mg, 0.501 mmol), and 3-(aminomethyl)-4,6-dimethyl-2(1H)-pyridinone (123 mg, 0.651 mmol). The product was collected as a solid, 0.190 g (87%). LCMS E-S (M+H)=434.2. ¹H NMR (400 MHz, DMSO-d₆) δ ppm 0.95-1.07 (m, 4H), 1.15-1.31 (m, 1H), 1.36-1.52 (m, 2H), 1.68 (br. s., 1H), 1.77-1.99 (m, 6H), 2.11 (s, 3H), 2.18-2.29 (m, 4H), 2.35 (s, 3H), 4.33 (d, J=4.80 Hz, 2H), 4.53-4.73 (m, 1H), 5.87 (s, 1H), 6.96 (s, 1H), 8.58 (t, J=4.93 Hz, 1H), 11.51 (s, 1H).

Example 111

6-Cyclopropyl-N-[(4,6-dimethyl-2-oxo-1,2-dihydro-3-pyridinyl)methyl]-3-methyl-1-(1-methyl-4-piperidinyl)-1H-pyrazolo[3,4-b]pyridine-4-carboxamide

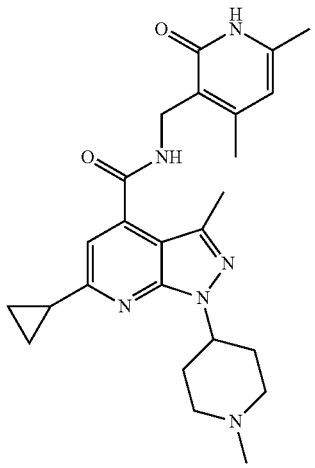 [SMILES: Cc1cc(C)c(CNC(=O)c2cc(C3CC3)nc3c2c(C)nn3C2CCN(C)CC2)c(=O)[nH]1]

6-Cyclopropyl-3-methyl-1-(1-methyl-4-piperidinyl)-1H-pyrazolo[3,4-b]pyridine-4-carboxylic acid (150 mg, 0.477 mmol), 3-(aminomethyl)-4,6-dimethyl-2(1H)-pyridinone (117 mg, 0.620 mmol), 1-hydroxy-7-azabenzotriazole (130 mg, 0.954 mmol), EDC (183 mg, 0.954 mmol) and N-methylmorpholine (0.210 mL, 1.909 mmol) were suspended in DMSO (10 mL) and stirred at room temperature for 16 h. Next was added 25 mL of water, stirred for 10 minutes, and then extracted with EtOAc (5×). The organic layers were concentrated in vacuo to afford 20 mg product. The aqueous phase was concentrated in vacuo and the crude residue purified by reverse phase HPLC (mobile phase: 10-60% ACN in H₂O, 0.1% NH₄OH) to afford additional product. The final product was collected as a solid, 0.100 g (47%). LCMS E-S (M+H)=449.0. ¹H NMR (400 MHz, DMSO-d₆) δ ppm 0.97-1.05 (m, 4H), 1.79 (d, J=9.60 Hz, 2H), 2.11 (s, 3H), 2.15 (d, J=8.34 Hz, 3H), 2.21 (s, 3H), 2.23-2.27 (m, 3H), 2.35 (s, 3H), 2.91 (d, J=8.08 Hz, 2H), 4.33 (d, J=4.80 Hz, 2H), 4.49-4.72 (m, 1H), 5.86 (s, 1H), 6.97 (s, 1H), 6.92-7.07 (m, 1H), 8.58 (t, J=4.93 Hz, 1H), 11.50 (s, 1H).

Example 112

6-Cyclopropyl-N-[(4,6-dimethyl-2-oxo-1,2-dihydro-3-pyridinyl)methyl]-3-methyl-1-(tetrahydro-2H-pyran-4-yl)-1H-pyrazolo[3,4-b]pyridine-4-carboxamide

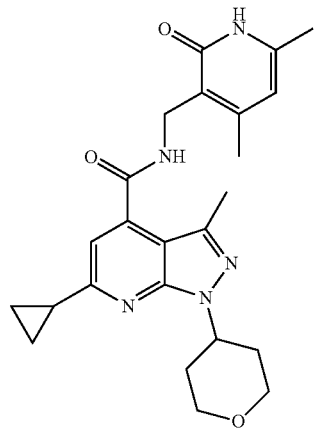 [SMILES: Cc1cc(C)c(CNC(=O)c2cc(C3CC3)nc3c2c(C)nn3C2CCOCC2)c(=O)[nH]1]

The title compound was prepared in the same manner as described in example 109 using 6-cyclopropyl-3-methyl-1-(tetrahydro-2H-pyran-4-yl)-1H-pyrazolo[3,4-b]pyridine-4-carboxylic acid (150 mg, 0.498 mmol), and 3-(aminomethyl)-4,6-dimethyl-2(1H)-pyridinone (98 mg, 0.647 mmol). The product was collected as a solid, 0.170 g (78%). LCMS E-S (M+H)=436.1. ¹H NMR (400 MHz, DMSO-d₆) δ ppm 0.95-1.14 (m, 4H), 1.79 (dd, J=12.63, 2.27 Hz, 2H), 2.05-2.18 (m, 5H), 2.19-2.27 (m, 4H), 2.36 (s, 3H), 3.53 (t, J=11.12 Hz, 2H), 3.98 (dd, J=11.49, 3.41 Hz, 2H), 4.33 (d, J=4.80 Hz, 2H), 4.87 (m, J=11.53, 11.53, 4.11, 3.92 Hz, 1H), 5.87 (s, 1H), 6.99 (s, 1H), 8.59 (t, J=4.93 Hz, 1H), 11.51 (s, 1H).

Intermediate 57

Ethyl 1-(1-methylethyl)-6-propyl-1H-pyrazolo[3,4-b]pyridine-4-carboxylate

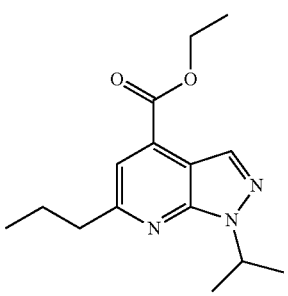 [SMILES: CCCc1cc(C(=O)OCC)c2cnn(C(C)C)c2n1]

To a solution of ethyl 2,4-dioxoheptanoate (446 mg, 2.397 mmol) in benzene (5 mL) was added 1-(1-methylethyl)-1H-pyrazol-5-amine (300 mg, 2.397 mmol), and the mixture was stirred at 62° C. for 18 h. The reaction mixture was concentrated in vacuo and the residue purified by column chromatography (Silica gel, gradient of 0 to 100% EtOAc/hexanes) to give 370 mg (56%) of product. LCMS E-S (M+H)=276.1. ¹H NMR (400 MHz, CHLOROFORM-d) δ ppm 0.99-1.12

(m, 3H), 1.46-1.54 (m, 3H), 1.58-1.70 (m, 6H), 1.82-1.96 (m, 2H), 2.91-3.02 (m, 2H), 4.51 (q, J=7.2 Hz, 2H), 5.28-5.44 (m, 1H), 7.58-7.68 (s, 1H), 8.27-8.40 (s, 1H).

Intermediate 58

1-(1-Methylethyl)-6-propyl-1H-pyrazolo[3,4-b]pyridine-4-carboxylic acid

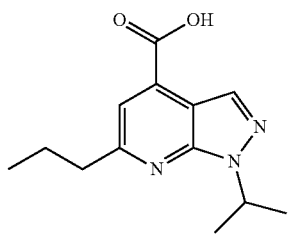 [SMILES: CCCc1cc(C(=O)O)c2cnn(C(C)C)c2n1]

To a solution of ethyl 1-(1-methylethyl)-6-propyl-1H-pyrazolo[3,4-b]pyridine-4-carboxylate (180 mg, 0.654 mmol) in ethanol (5 mL) and THF (1 mL) was added sodium hydroxide (1.090 mL, 3.27 mmol), and the mixture was stirred at 40° C. for 1 h. The volatiles were removed under reduced pressure. The aqueous phase was acidified to pH 3 with aq. 1N HCl. The solid precipitate formed was collected by filtration and dried under high vacuum to give 144 mg (89%) of product, which was used for next reaction without further purification. LCMS E-S (M+H)=248.1 $^1$H NMR (400 MHz, DMSO-$d_6$) δ ppm 0.82-1.12 (m, 3H), 1.50 (d, J=6.6 Hz, 6H), 1.78 (m, 2H), 2.80-3.11 (m, 2H), 5.09-5.38 (m, 1H), 7.47-7.72 (s, 1H), 8.18-8.46 (s, 1H), 13.82 (s, 1H).

Intermediate 60

Ethyl 4-[4-(methyloxy)phenyl]-2,4-dioxobutanoate

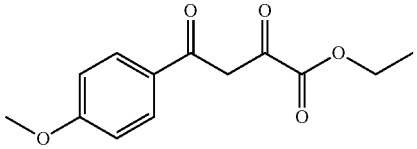 [SMILES: CCOC(=O)C(=O)CC(=O)c1ccc(OC)cc1]

The title compound was prepared in the same manner as intermediate 29 using sodium metal (0.168 g, 7.32 mmol), 1-[4-(methyloxy)phenyl]ethanone (1 g, 6.66 mmol), and diethyl ethanedioate (0.903 mL, 6.66 mmol). The crude product was purified using column chromatography (0 to 100% EtOAc/hexanes) to give 0.95 g of product (57%). LCMS E-S (M+H)=250.9. $^1$H NMR (400 MHz, CHLOROFORM-d) δ ppm 1.43 (m, 3H), 3.91 (s, 3H), 4.41 (q, J=6.65 Hz, 2H), 6.94-7.12 (m, 3H), 8.01 (d, J=8.59 Hz, 2H).

Intermediate 61

Ethyl 1-(1-methylethyl)-6-[4-(methyloxy)phenyl]-1H-pyrazolo[3,4-b]pyridine-4-carboxylate

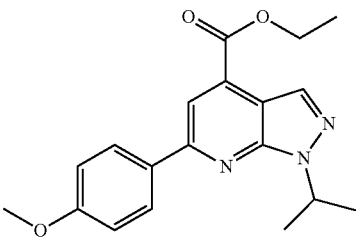 [SMILES: CCOC(=O)c1cc(-c2ccc(OC)cc2)nc2c1cnn2C(C)C]

To a solution of ethyl 4-[4-(methyloxy)phenyl]-2,4-dioxobutanoate (600 mg, 2.397 mmol) in benzene (5 mL) was added 1-(1-methylethyl)-1H-pyrazol-5-amine (300 mg, 2.397 mmol), and the reaction mixture was stirred at 62° C. overnight. The mixture was concentrated in vacuo and the residue was dissolved into acetic acid (3 mL). The solution was stirred at reflux for 1 h and concentrated in vacuo. The residue was purified using column chromatography (Silica gel, 0 to 100% EtOAc/hexanes) to give 530 mg (65%) of product. LCMS E-S (M+H)=340.1 $^1$H NMR (400 MHz, CHLOROFORM-d) δ ppm 1.47-1.57 (m, 3H), 1.61-1.71 (m, 6H), 3.88-3.96 (s, 3H), 4.55 (q, J=7.2 Hz, 2H), 5.46 (m, 1H), 7.03-7.12 (m, 2H), 8.13-8.25 (m, 3H), 8.36-8.43 (m, 1H).

Intermediate 62

1-(1-Methylethyl)-6-[4-(methyloxy)phenyl]-1H-pyrazolo[3,4-b]pyridine-4-carboxylic acid

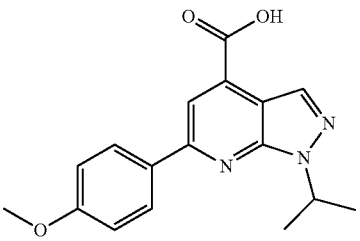 [SMILES: COc1ccc(-c2cc(C(=O)O)c3cnn(C(C)C)c3n2)cc1]

The title compound was prepared in the same manner as described for intermediate 58 using ethyl 1-(1-methylethyl)-6-[4-(methyloxy)phenyl]-1H-pyrazolo[3,4-b]pyridine-4-carboxylate (200 mg, 0.589 mmol), Ethanol (4 mL) and THF (1 mL), and sodium hydroxide (0.982 mL, 2.95 mmol). The final product was collected as 181 mg (98%). LCMS E-S (M+H)=312.3. $^1$H NMR (400 MHz, DMSO-$d_6$) δ ppm 1.51-1.63 (m, 6H), 3.85 (s, 3H), 5.35 (m, 1H), 7.11 (d, J=9.1 Hz, 2H), 8.15 (s, 1H), 8.18-8.25 (m, 2H), 8.33 (s, 1H), 13.95 (br. s., 1H).

Example 113

N-[(4,6-Dimethyl-2-oxo-1,2-dihydro-3-pyridinyl)methyl]-1-(1-methylethyl)-6-[4-(methyloxy)phenyl]-1H-pyrazolo[3,4-b]pyridine-4-carboxamide

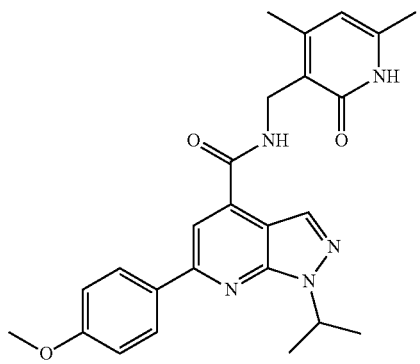

The title compound was prepared in the same manner as described in example 109 using 1-(1-methylethyl)-6-[4-(methyloxy)phenyl]-1H-pyrazolo[3,4-b]pyridine-4-carboxylic acid (70 mg, 0.225 mmol), DMSO (3 mL), 3-(aminomethyl)-4,6-dimethyl-2(1H)-pyridinone (63.6 mg, 0.337 mmol) HCl salt, N-methylmorpholine (0.099 mL, 0.899 mmol), 1-hydroxy-7-azabenzotriazole (61.2 mg, 0.450 mmol), and EDC (86 mg, 0.450 mmol). The final product was collected as 89 mg (89%). LCMS E-S (M+H)=446.5. $^1$H NMR (400 MHz, DMSO-$d_6$) δ ppm 1.54 (d, J=6.8 Hz, 6H), 2.13 (s, 3H), 2.23 (s, 3H), 3.85 (s, 3H), 4.41 (d, J=4.8 Hz, 2H), 5.20-5.48 (m, 1H), 5.91 (s, 1H), 7.11 (d, J=8.8 Hz, 2H), 8.11 (s, 1H), 8.24 (d, J=8.8 Hz, 2H), 8.34 (s, 1H), 8.95 (m, 1H), 11.58 (s, 1H).

Intermediate 63

Ethyl 2,4-dioxo-4-(4-pyridinyl)butanoate

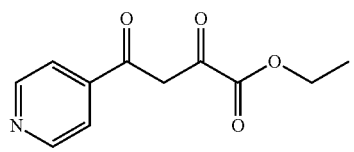 [SMILES: CCOC(=O)C(=O)CC(=O)c1ccncc1]

The title compound was prepared in the same manner as intermediate 29 using sodium metal (0.466 g, 20.26 mmol), 1-(4-pyridinyl)ethanone (1 g, 6.66 mmol), and diethyl ethanedioate (2.388 mL, 17.62 mmol). The crude product was purified using column chromatography (0 to 100% EtOAc/hexanes) to give 0.95 g of product (24%). LCMS E-S (M+H)=222.0 $^1$H NMR (400 MHz, CHLOROFORM-d) δ ppm 1.37-1.55 (m, 3H), 4.43 (q, J=7.07 Hz, 2H), 7.06-7.16 (m, 1H), 7.72-7.92 (m, 2H), 8.82-8.94 (m, 2H).

Intermediate 64

Ethyl 1-(1-methylethyl)-6-(4-pyridinyl)-1H-pyrazolo[3,4-b]pyridine-4-carboxylate

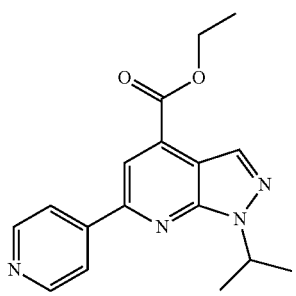 [SMILES: CCOC(=O)c1cc(-c2ccncc2)nc2c1cnn2C(C)C]

To a suspension of ethyl 2,4-dioxo-4-(4-pyridinyl)butanoate (442 mg, 1.997 mmol) in benzene (5 mL) was added 1-(1-methylethyl)-1H-pyrazol-5-amine (250 mg, 1.997 mmol), and the reaction mixture was stirred at 62° C. overnight. The reaction mixture was concentrated in vacuo and the residue was purified using column chromatography (Silica gel, 0 to 100% EtOAc/hexanes) to give 270 mg (43%) of product. LCMS E-S (M+H)=311.3 $^1$H NMR (400 MHz, CHLOROFORM-d) δ ppm 1.54 (t, J=7.2 Hz, 3H), 1.68 (d, J=6.6 Hz, 6H), 4.58 (q, J=7.1 Hz, 2H), 5.41-5.60 (m, 1H), 8.04-8.19 (m, 2H), 8.29 (s, 1H), 8.44-8.55 (m, 2H), 8.76-8.91 (m, 1H).

Intermediate 65

1-(1-Methylethyl)-6-(4-pyridinyl)-1H-pyrazolo[3,4-b]pyridine-4-carboxylic acid

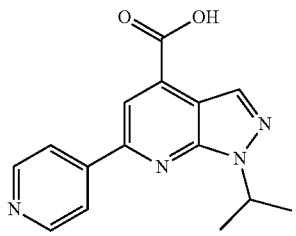 [SMILES: CC(C)n1ncc2c(C(=O)O)cc(-c3ccncc3)nc21]

The title compound was prepared in the same manner as described for intermediate 58 using ethyl 1-(1-methylethyl)-6-(4-pyridinyl)-1H-pyrazolo[3,4-b]pyridine-4-carboxylate (100 mg, 0.322 mmol), ethanol (4 mL), THF (0.8 mL), and sodium hydroxide (0.537 mL, 1.611 mmol). The final product was collected as 88 mg (97%). LCMS E-S (M+H)=283.2. $^1$H NMR (400 MHz, DMSO-$d_6$) δ ppm 1.58 (d, J=6.4 Hz, 6H), 5.40 (m, 1H), 8.25 (d, J=5.6 Hz, 2H), 8.32 (s, 1H), 8.44 (s, 1H), 8.79 (d, J=5.6 Hz, 2H), 14.12 (br. s., 1H).

Example 114

N-[(4,6-Dimethyl-2-oxo-1,2-dihydro-3-pyridinyl)methyl]-1-(1-methylethyl)-6-(4-pyridinyl)-1H-pyrazolo[3,4-b]pyridine-4-carboxamide

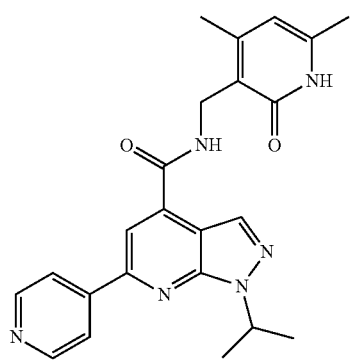 [SMILES: Cc1cc(C)c(CNC(=O)c2cc(-c3ccncc3)nc3c2cnn3C(C)C)c(=O)[nH]1]

The title compound was prepared in the same manner as described in example 109 using 1-(1-methylethyl)-6-(4-pyridinyl)-1H-pyrazolo[3,4-b]pyridine-4-carboxylic acid (60 mg, 0.213 mmol), DMSO (2 mL), 3-(aminomethyl)-4,6-dimethyl-2(1H)-pyridinone (60.1 mg, 0.319 mmol) HCl salt, N-methylmorpholine (0.093 mL, 0.850 mmol), 1-hydroxy-7-azabenzotriazole (57.9 mg, 0.425 mmol), and EDC (81 mg, 0.425 mmol). The final product was collected as 66 mg (74%). LCMS E-S (M+H)=446.5. $^1$H NMR (400 MHz, DMSO-$d_6$) δ ppm 1.56 (d, J=6.0 Hz, 6H), 2.13 (br. s., 3H), 2.23 (br. s., 3H), 4.43 (m, 2H), 5.37 (m, 1H), 5.91 (br. s., 1H), 8.15-8.34 (m, 3H), 8.44 (s, 1H), 8.78 (br. s., 2H), 9.00 (br. s., 1H), 11.58 (br. s., 1H).

Intermediate 66

Ethyl 4-(4-chlorophenyl)-2,4-dioxobutanoate

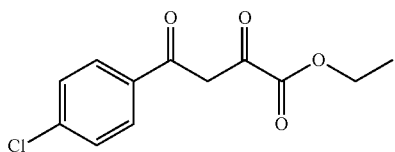 [SMILES: CCOC(=O)C(=O)CC(=O)c1ccc(Cl)cc1]

Sodium metal (0.143 g, 6.21 mmol) was dissolved into ethanol (3 mL) and the resulting solution was cooled with an ice bath. A mixture of 1-(4-chlorophenyl)ethanone (0.756 mL, 5.65 mmol) and diethyl ethanedioate (0.766 mL, 5.65 mmol) were added dropwise, and the reaction mixture was stirred for 16 h. The reaction mixture was quenched with ice water (5 mL) and acidified to ~pH 3 with 1N HCl. The precipitate was collected by filtration and dried under high vacuum to give 1.39 g (97%) of product. LCMS E-S (M+H)=255.1. $^1$H NMR (400 MHz, DMSO-$d_6$) δ ppm 1.29 (m, 3H), 4.27 (d, J=6.57 Hz, 2H), 7.60 (d, J=7.58 Hz, 2H), 8.02 (d, J=6.57 Hz, 2H).

Intermediate 67

Ethyl 6-(4-chlorophenyl)-1-(1-methylethyl)-1H-pyrazolo[3,4-b]pyridine-4-carboxylate

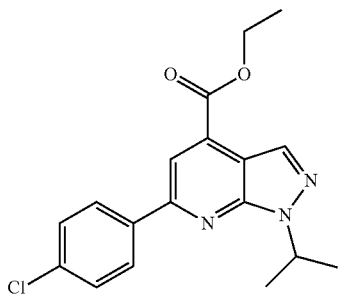 [SMILES: CCOC(=O)c1cc(-c2ccc(Cl)cc2)nc2c1cnn2C(C)C]

The title compound was prepared in the same manner as described for intermediate 61 using ethyl 4-(4-chlorophenyl)-2,4-dioxobutanoate (610 mg, 2.397 mmol), benzene (5 mL), 1-(1-methylethyl)-1H-pyrazol-5-amine (300 mg, 2.397 mmol), and acetic acid (4 mL). The crude product was purified by column chromatography (Silica gel, eluent: 0 to 100% EtOAc/hexanes) to give 621 mg (75%) of product. LCMS E-S (M+H)=344.1. $^1$H NMR (400 MHz, CHLOROFORM-d) δ ppm 1.48-1.57 (m, 3H), 1.64-1.74 (m, 6H), 4.56 (q, J=7.1 Hz, 2H), 5.46 (m, 1H), 7.49-7.55 (m, 2H), 8.15-8.18 (m, 2H), 8.21 (s, 1H), 8.42 (s, 1H).

Intermediate 68

6-(4-Chlorophenyl)-1-(1-methylethyl)-1H-pyrazolo[3,4-b]pyridine-4-carboxylic acid

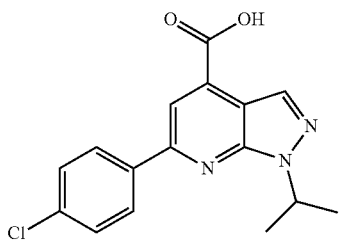 [SMILES: CC(C)n1ncc2c(C(=O)O)cc(-c3ccc(Cl)cc3)nc21]

The title compound was prepared in the same manner as described for intermediate 58 using ethyl 6-(4-chlorophenyl)-1-(1-methylethyl)-1H-pyrazolo[3,4-b]pyridine-4-carboxylate (400 mg, 1.163 mmol), Ethanol (6 mL), THF (1 mL), and added sodium hydroxide (1.939 mL, 5.82 mmol) wherein the reaction time was 2 h. The final product was collected as 330 mg (90%). LCMS E-S (M+H)=315.8. $^1$H NMR (400 MHz, DMSO-$d_6$) δ ppm 1.56 (d, J=6.8 Hz, 6H), 5.26-5.47 (m, 1H), 7.62 (d, J=8.6 Hz, 2H), 8.20 (s, 1H), 8.28 (d, J=8.6 Hz, 2H), 8.38 (s, 1H), 14.03 (s, 1H).

Example 115

6-(4-Chlorophenyl)-N-[(4,6-dimethyl-2-oxo-1,2-dihydro-3-pyridinyl)methyl]-1-(1-methylethyl)-1H-pyrazolo[3,4-b]pyridine-4-carboxamide

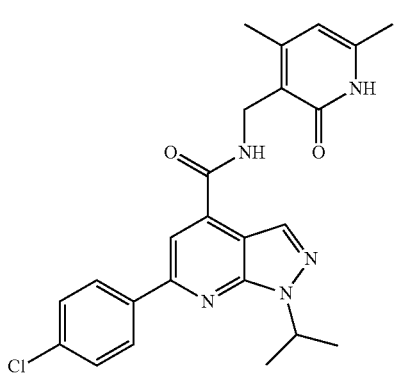 [SMILES: Cc1cc(C)c(CNC(=O)c2cc(-c3ccc(Cl)cc3)nc3c2cnn3C(C)C)c(=O)[nH]1]

The title compound was prepared in the same manner as described in example 109 using 6-(4-chlorophenyl)-1-(1-methylethyl)-1H-pyrazolo[3,4-b]pyridine-4-carboxylic acid (70 mg, 0.222 mmol), DMSO (2 mL), 3-(aminomethyl)-4,6-dimethyl-2(1H)-pyridinone HCl salt (62.7 mg, 0.333 mmol), N-methylmorpholine (0.097 mL, 0.887 mmol), 1-hydroxy-7-azabenzotriazole (60.3 mg, 0.443 mmol) and EDC (85 mg, 0.443 mmol). The final product was collected as 77 mg (78%). LCMS E-S (M+H)=450.3. $^1$H NMR (400 MHz, DMSO-$d_6$) δ ppm 1.55 (d, J=6.6 Hz, 6H), 2.13 (s, 3H), 2.22 (s, 3H), 4.41 (d, J=4.6 Hz, 2H), 5.34 (quin, J=6.7 Hz, 1H), 5.91 (s, 1H), 7.64 (d, J=8.6 Hz, 2H), 8.19 (s, 1H), 8.31 (d, J=8.6 Hz, 2H), 8.39 (s, 1H), 8.97 (t, J=4.7 Hz, 1H), 11.58 (s, 1H).

Intermediate 69

Ethyl 2,4-dioxo-4-(2-thienyl)butanoate

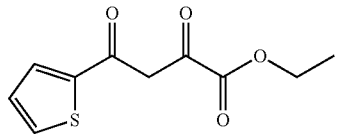

The title compound was prepared in the same manner as for intermediate 66 using sodium metal (0.180 g, 7.85 mmol), 1-(3-thienyl)ethanone (0.9 g, 7.13 mmol) and diethyl ethanedioate (0.967 mL, 7.13 mmol). The product was collected as 1.41 g (87%). LCMS E-S (M+H)=226.9. $^1$H NMR (400 MHz, DMSO-$d_6$) δ ppm 1.30 (m, 3H), 4.29 (q, J=6.82 Hz, 2H), 6.96 (br. s., 1H), 7.60-7.81 (m, 2H), 8.74 (br. s., 1H).

Intermediate 70

Ethyl 1-(1-methylethyl)-6-(3-thienyl)-1H-pyrazolo[3,4-b]pyridine-4-carboxylate

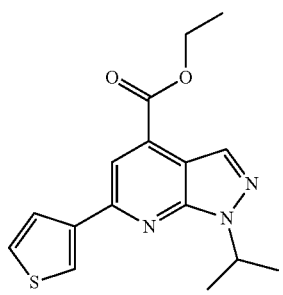 [SMILES: CCOC(=O)c1cc(-c2ccsc2)nc2c1cnn2C(C)C]

The title compound was prepared in the same manner as described for intermediate 61 using ethyl 2,4-dioxo-4-(3-thienyl)butanoate (542 mg, 2.397 mmol), benzene (5 mL), 1-(1-methylethyl)-1H-pyrazol-5-amine (300 mg, 2.397 mmol), and acetic acid (5 ml). The crude product was purified using column chromatography (silica gel, eluent: 0 to 100% EtOAc/hexanes) to afford the product as 590 mg (78%). LCMS E-S (M+H)=315.8. $^1$H NMR (400 MHz, CHLOROFORM-d) δ ppm 1.53 (t, J=6.8 Hz, 3H), 1.66 (d, J=6.8 Hz, 6H), 4.56 (q, J=7.1 Hz, 2H), 5.43 (spt, J=6.7 Hz, 1H), 7.47 (dd, J=5.1, 3.0 Hz, 1H), 7.84-7.95 (m, 1H), 8.08-8.18 (m, 2H), 8.32-8.43 (m, 1H).

Intermediate 71

1-(1-Methylethyl)-6-(3-thienyl)-1H-pyrazolo[3,4-b]pyridine-4-carboxylic acid

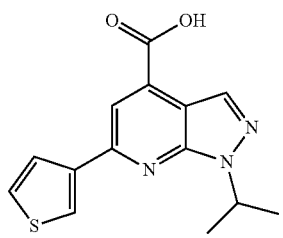 [SMILES: CC(C)n1ncc2c(C(=O)O)cc(-c3ccsc3)nc21]

The title compound was prepared in the same manner as described for intermediate 58 using ethyl 1-(1-methylethyl)-6-(3-thienyl)-1H-pyrazolo[3,4-b]pyridine-4-carboxylate (400 mg, 1.268 mmol), Ethanol (5 mL) THF (1 mL), and sodium hydroxide (2.114 mL, 6.34 mmol). The final product was collected as 370 mg (100%). LCMS E-S (M+H)=287.9. $^1$H NMR (400 MHz, DMSO-$d_6$) δ ppm 1.55 (d, J=6.8 Hz, 6H), 5.34 (quin, J=6.6 Hz, 1H), 7.72 (dd, J=5.0, 3.0 Hz, 1H), 7.93 (dd, J=5.0, 1.3 Hz, 1H), 8.15 (s, 1H), 8.34 (s, 1H), 8.49 (dd, J=3.0, 1.3 Hz, 1H), 13.97 (s, 1H).

Example 116

N-[(4,6-Dimethyl-2-oxo-1,2-dihydro-3-pyridinyl)methyl]-1-(1-methylethyl)-6-(3-thienyl)-1H-pyrazolo[3,4-b]pyridine-4-carboxamide

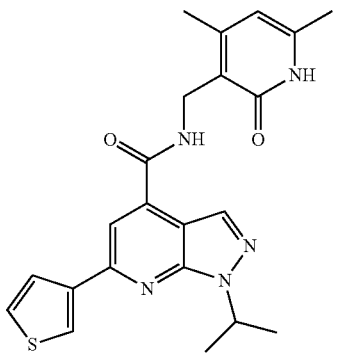 [SMILES: Cc1cc(C)c(CNC(=O)c2cc(-c3ccsc3)nc3c2cnn3C(C)C)c(=O)[nH]1]

The title compound was prepared in the same manner as described in example 109 using 1-(1-methylethyl)-6-(3-thienyl)-1H-pyrazolo[3,4-b]pyridine-4-carboxylic acid (70 mg, 0.244 mmol), DMSO (2 mL), 3-(aminomethyl)-4,6-dimethyl-2(1H)-pyridinone (68.9 mg, 0.365 mmol) HCl salt, N-methylmorpholine (0.107 mL, 0.974 mmol), 1-hydroxy-7-azabenzotriazole (33.2 mg, 0.244 mmol) and EDC (93 mg, 0.487 mmol). The final product was collected as 75 mg (73%). LCMS E-S (M+H)=422.2. $^1$H NMR (400 MHz, DMSO-$d_6$) δ ppm 1.53 (d, J=6.8 Hz, 6H), 2.13 (s, 3H), 2.23 (s, 3H), 4.41 (d, J=4.8 Hz, 2H), 5.30 (quin, J=6.6 Hz, 1H), 5.91 (s, 1H), 7.71 (dd, J=5.0, 3.0 Hz, 1H), 7.92 (d, J=5.0 Hz, 1H), 8.09 (s, 1H), 8.34 (s, 1H), 8.37 (d, J=1.8 Hz, 1H), 8.79-8.95 (m, 1H), 11.58 (s, 1H).

Intermediate 72

Ethyl 3-methyl-1-(1-methylethyl)-6-(4-pyridinyl)-1H-pyrazolo[3,4-b]pyridine-4-carboxylate

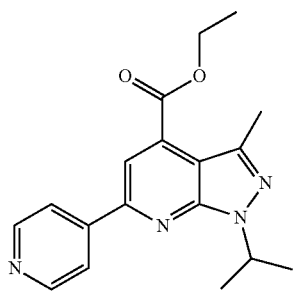 [SMILES: CCOC(=O)c1cc(-c2ccncc2)nc2c1c(C)nn2C(C)C]

The title compound was prepared in the same manner as described for intermediate 64 using ethyl 2,4-dioxo-4-(4-pyridinyl)butanoate (766 mg, 2.87 mmol), benzene (6 mL), and 3-methyl-1-(1-methylethyl)-1H-pyrazol-5-amine (400 mg, 2.87 mmol). The crude product was purified using column chromatography (Silica gel, eluent: 0 to 30% MeOH/DCM) to give 95 mg (10%) of product. LCMS E-S (M+H)=325.3. $^1$H NMR (400 MHz, CHLOROFORM-d) δ ppm 1.48-1.56 (m, 3H), 1.61-1.73 (m, 6H), 2.77 (s, 3H), 4.56 (q, J=7.2 Hz, 2H), 5.37-5.50 (m, 1H), 8.02-8.16 (m, 3H), 8.76-8.83 (m, 2H).

Intermediate 73

3-Methyl-1-(1-methylethyl)-6-(4-pyridinyl)-1H-pyrazolo[3,4-b]pyridine-4-carboxylic acid

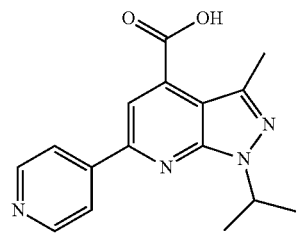 [SMILES: Cc1nn(C(C)C)c2nc(-c3ccncc3)cc(C(=O)O)c12]

The title compound was prepared in the same manner as described for intermediate 58 using ethyl 3-methyl-1-(1-methylethyl)-6-(4-pyridinyl)-1H-pyrazolo[3,4-b]pyridine-4-carboxylate (36 mg, 0.111 mmol), Ethanol (2 ml) and sodium hydroxide (0.185 mL, 0.555 mmol). The final product was collected as 26 mg 79%). LCMS E-S (M+H)=297.2. $^1$H NMR (400 MHz, DMSO-$d_6$) δ ppm 1.54 (d, J=6.4 Hz, 6H), 2.65 (s, 3H), 5.35 (m, 1H), 8.17 (s, 1H) 8.24 (m, 2H), 8.78 (m, 2H).

Example 117

N-[(4,6-Dimethyl-2-oxo-1,2-dihydro-3-pyridinyl)methyl]-3-methyl-1-(1-methylethyl)-6-(4-pyridinyl)-1H-pyrazolo[3,4-b]pyridine-4-carboxamide

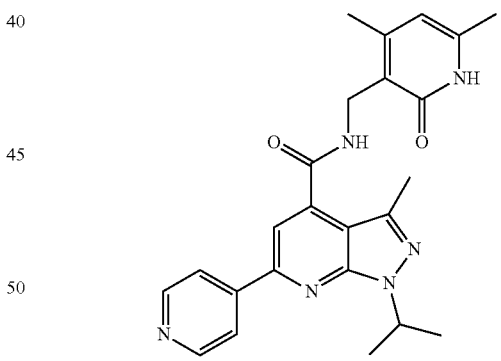

The title compound was prepared in the same manner as described in example 109 using 3-methyl-1-(1-methylethyl)-6-(4-pyridinyl)-1H-pyrazolo[3,4-b]pyridine-4-carboxylic acid (20 mg, 0.067 mmol), DMSO (1 mL), 3-(aminomethyl)-4,6-dimethyl-2(1H)-pyridinone (19.10 mg, 0.101 mmol), N-methylmorpholine (0.030 mL, 0.270 mmol), 1-hydroxy-7-azabenzotriazole (18.37 mg, 0.135 mmol) and EDC (25.9 mg, 0.135 mmol). The final product was collected as 29 mg (100%). LCMS E-S (M+H)=431.2. $^1$H NMR (400 MHz, DMSO-$d_6$) δ ppm 1.52 (d, J=6.57 Hz, 6H), 2.12 (s, 3H), 2.25 (s, 3H), 2.46 (s, 3H), 4.40 (d, J=5.0 Hz, 2H), 5.29 (quin, J=6.7 Hz, 1H), 5.89 (s, 1H), 7.83 (s, 1H), 8.19 (d, J=6.1 Hz, 2H), 8.64-8.89 (m, 3H), 11.55 (br. s., 1H).

Intermediate 74

Ethyl 1,6-bis(1,1-dimethylethyl)-3-methyl-1H-pyrazolo[3,4-b]pyridine-4-carboxylate

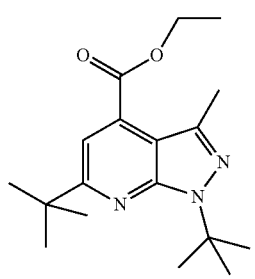 [SMILES: CCOC(=O)c1cc(C(C)(C)C)nc2c1c(C)nn2C(C)(C)C]

The title compound was prepared in the same manner as described for intermediate 61 using ethyl 5,5-dimethyl-2,4-dioxohexanoate (392 mg, 1.958 mmol), benzene (10 mL), 1-(1,1-dimethylethyl)-3-methyl-1H-pyrazol-5-amine (300 mg, 1.958 mmol), and acetic acid (2 mL). The crude product was purified by column chromatography (Silica gel, eluent: 0 to 100% EtOAc/hexanes) to give 530 mg (85%) of product. LCMS E-S (M+H)=318.3. $^1$H NMR (400 MHz, CHLOROFORM-d) δ ppm 1.43-1.52 (m, 12H), 1.84 (s, 9H), 2.67 (s, 3H), 4.50 (q, J=7.07 Hz, 2H), 7.59 (s, 1H).

Intermediate 75

1,6-Bis(1,1-dimethylethyl)-3-methyl-1H-pyrazolo[3,4-b]pyridine-4-carboxylic acid

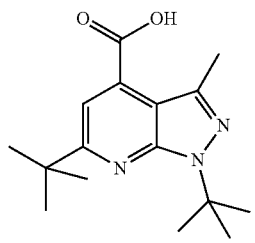 [SMILES: Cc1nn(C(C)(C)C)c2nc(C(C)(C)C)cc(C(=O)O)c12]

To an EtOH solution (8 mL) of ethyl 1,6-bis(1,1-dimethylethyl)-3-methyl-1H-pyrazolo[3,4-b]pyridine-4-carboxylate (528 mg, 1.663 mmol) was added sodium hydroxide (2.77 mL, 8.32 mmol), and the mixture was stirred for at room temperature for 2 h. The volatiles were removed under reduced pressure and the aqueous phase was acidified using 1H HCl to ~pH 3. The precipitate was filtered, washed with water, and dried under high vacuum to give the product as 445 mg (92%). LCMS E-S (M+H)=289.4. $^1$H NMR (400 MHz, DMSO-d$_6$) δ ppm 1.49 (s, 9H), 1.76 (s, 9H), 2.51 (s, 3H), 7.51 (s, 1H).

Example 118

1,6-Bis(1,1-dimethylethyl)-N-[(4,6-dimethyl-2-oxo-1,2-dihydro-3-pyridinyl)methyl]-3-methyl-1H-pyrazolo[3,4-b]pyridine-4-carboxamide

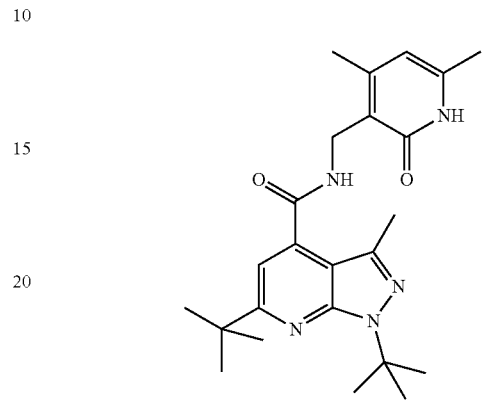

The title compound was prepared in the same manner as described in example 109 using 1,6-bis(1,1-dimethylethyl)-3-methyl-1H-pyrazolo[3,4-b]pyridine-4-carboxylic acid (70 mg, 0.242 mmol), DMSO (2 mL), 3-(aminomethyl)-4,6-dimethyl-2(1H)-pyridinone (68.5 mg, 0.363 mmol), N-methylmorpholine (0.106 mL, 0.968 mmol), 1-hydroxy-7-azabenzotriazole (65.9 mg, 0.484 mmol) and EDC (93 mg, 0.484 mmol). The final product was collected as 91 mg (87%). LCMS E-S (M+H)=424.0. $^1$H NMR (400 MHz, DMSO-d$_6$) δ ppm $^1$H NMR (400 MHz, DMSO-d$_6$) δ ppm 1.38 (s, 9H), 1.74 (s, 9H), 2.12 (s, 3H), 2.23 (s, 3H), 2.35 (s, 3H), 4.35 (d, J=4.80 Hz, 2H), 5.88 (s, 1H), 7.15 (s, 1H), 8.61 (t, J=4.93 Hz, 1H), 11.52 (s, 1H).

Intermediate 76

Ethyl 4-[4-(methylthio)phenyl]-2,4-dioxobutanoate

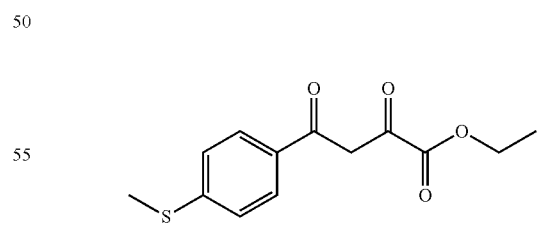

The title compound was prepared in the same manner as for intermediate 66 using sodium metal (0.160 g, 6.95 mmol), 1-[4-(methylthio)phenyl]ethanone (1.05 g, 6.32 mmol) and diethyl ethanedioate (0.856 mL, 6.32 mmol). The product was collected as 1.58 g (59%). LCMS E-S (M+H)=266.9. $^1$H NMR (400 MHz, CHLOROFORM-d) δ ppm 1.29-1.50 (m, 3H), 2.41-2.62 (m, 3H), 4.23-4.49 (m, 2H), 7.15-7.38 (m, 2H), 7.89 (dd, J=8.72, 2.15 Hz, 2H).

Intermediate 77

Ethyl 1-(1-methylethyl)-6-[4-(methylthio)phenyl]-1H-pyrazolo[3,4-b]pyridine-4-carboxylate

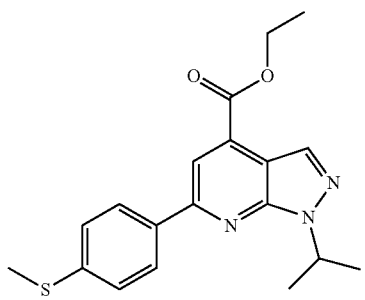 [SMILES: CCOC(=O)c1cc(-c2ccc(SC)cc2)nc2c1cnn2C(C)C]

The title compound was prepared in the same manner as described for intermediate 61 using ethyl 4-[4-(methylthio)phenyl]-2,4-dioxobutanoate (851 mg, 3.20 mmol), benzene (6 mL), 1-(1-methylethyl)-1H-pyrazol-5-amine (400 mg, 3.20 mmol), and acetic acid (3 mL). The crude product was purified by column chromatography (Silica gel, eluent; 0 to 100% EtOAc/hexanes) to give 870 mg (63%) of product. LCMS E-S (M+H)=433.2. $^1$H NMR (400 MHz, CHLOROFORM-d) δ ppm 1.47-1.57 (m, 3H), 1.66 (d, J=6.8 Hz, 6H), 2.58 (s, 3H), 4.56 (q, J=7.2 Hz, 2H), 5.38-5.55 (m, 1H), 7.36-7.46 (m, 2H), 8.12-8.19 (m, 2H), 8.22 (s, 1H), 8.40 (s, 1H).

Intermediate 78

Ethyl 1-(1-methylethyl)-6-[4-(methylsulfonyl)phenyl]-1H-pyrazolo[3,4-b]pyridine-4-carboxylate

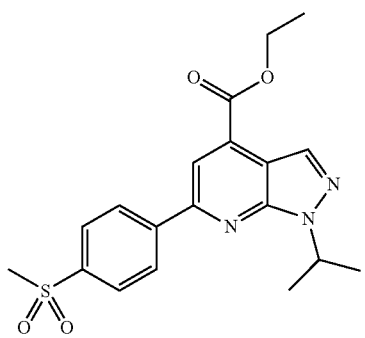 [SMILES: CCOC(=O)c1cc(-c2ccc(S(C)(=O)=O)cc2)nc2c1cnn2C(C)C]

Oxone (1712 mg, 2.79 mmol) was added to a solution of ethyl 1-(1-methylethyl)-6-[4-(methylthio)phenyl]-1H-pyrazolo[3,4-b]pyridine-4-carboxylate (330 mg, 0.928 mmol) in acetone (6 mL) and water (2 mL), and the reaction mixture was stirred for 6 h. The reaction mixture was quenched with water (10 mL) and then neutralized with NaHCO$_3$ solution. The mixture was extracted with EtOAc (3×) and the combined extracts dried over Na$_2$SO$_4$, filtered and concentrated in vacuo. The residue was purified using column chromatography (Silica gel, 0 to 100% EtOAc/hexanes) to give 295 mg (82%) of product. LCMS E-S (M+H)=388.1. $^1$H NMR (400 MHz, CHLOROFORM-d) δ ppm 1.54 (t, J=7.2 Hz, 3H), 1.67-1.69 (d, J=6.8 Hz, 6H), 3.14 (s, 3H), 4.58 (q, J=7.2 Hz, 2H), 5.48 (spt, J=6.7 Hz, 1H), 8.06-8.18 (m, 2H), 8.29 (s, 1H), 8.39-8.44 (m, 2H), 8.47 (s, 1H).

Intermediate 79

1-(1-Methylethyl)-6-[4-(methylsulfonyl)phenyl]-1H-pyrazolo[3,4-b]pyridine-4-carboxylic acid

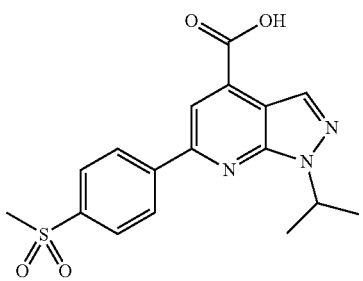 [SMILES: CC(C)n1ncc2c(C(=O)O)cc(-c3ccc(S(C)(=O)=O)cc3)nc21]

The title compound was prepared in the same manner as described for intermediate 58 using ethyl 1-(1-methylethyl)-6-[4-(methylsulfonyl)phenyl]-1H-pyrazolo[3,4-b]pyridine-4-carboxylate (260 mg, 0.671 mmol), Ethanol (4 mL), THF (1 mL) and sodium hydroxide (2N, 1.118 mL, 3.36 mmol). The final product was collected as 231 mg (96%). LCMS E-S (M+H)=360.1. $^1$H NMR (400 MHz, DMSO-d$_6$) δ ppm 1.58 (d, J=6.8 Hz, 6H), 3.30 (s, 3H), 5.34-5.49 (m, 1H), 8.11 (d, J=8.6 Hz, 2H), 8.30 (s, 1H), 8.44 (s, 1H), 8.51 (d, J=8.6 Hz, 2H).

Example 119

N-[(4,6-Dimethyl-2-oxo-1,2-dihydro-3-pyridinyl)methyl]-1-(1-methylethyl)-6-[4-(methylsulfonyl)phenyl]-1H-pyrazolo[3,4-b]pyridine-4-carboxamide

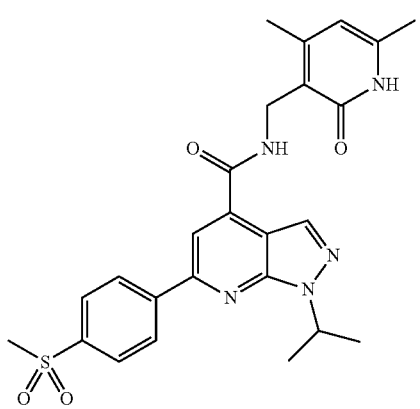

The title compound was prepared in the same manner as described in example 109 using 1-(1-methylethyl)-6-[4-(methylsulfonyl)phenyl]-1H-pyrazolo[3,4-b]pyridine-4-carboxylic acid (90 mg, 0.250 mmol), DMSO (2 mL), 3-(aminomethyl)-4,6-dimethyl-2(1H)-pyridinone (70.9 mg, 0.376 mmol), N-methylmorpholine (0.110 mL, 1.002 mmol), 1-hydroxy-7-azabenzotriazole (68.2 mg, 0.501 mmol) and EDC (96 mg, 0.501 mmol). The final product was collected as 106 mg (85%). LCMS E-S (M+H)=494.2. $^1$H NMR (400 MHz, DMSO-$d_6$) δ ppm 1.56 (d, J=5.6 Hz, 6H), 2.13 (br. s., 3H), 2.23 (br. s., 3H), 4.42 (m, 2H), 5.36 (br. s., 1H), 5.91 (br. s., 1H), 8.11 (d, J=7.3 Hz, 2H), 8.27 (br. s., 1H), 8.39-8.64 (m, 3H), 9.01 (br. s., 1H), 11.58 (br. s., 1H).

Intermediate 80

Ethyl 4-(4-bromophenyl)-2,4-dioxobutanoate

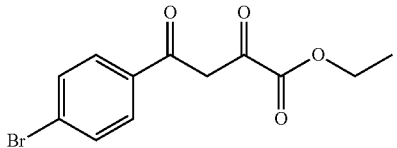

The title compound was prepared in the same manner as for intermediate 66 using sodium metal (0.404 g, 17.58 mmol), 1-(4-bromophenyl)ethanone (3.5 g, 17.58 mmol), and diethyl ethanedioate (2.384 mL, 17.58 mmol). The product was collected as 5.1 g (97%). LCMS E-S (M+H)=299.1. $^1$H NMR (400 MHz, DMSO-$d_6$) δ ppm 1.22-1.37 (m, 3H), 4.25 (d, J=6.57 Hz, 2H), 7.72 (m, 2H), 7.92 (m, 2H).

Intermediate 81

Ethyl 6-(4-bromophenyl)-1-(1-methylethyl)-1H-pyrazolo[3,4-b]pyridine-4-carboxylate

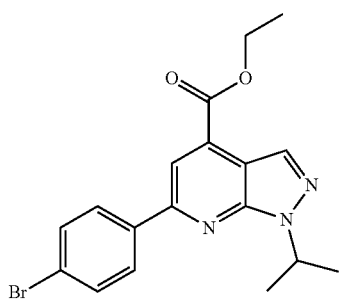

The title compound was prepared in the same manner as described for intermediate 61 using ethyl 4-(4-bromophenyl)-2,4-dioxobutanoate (956 mg, 3.20 mmol), benzene (10 mL), 1-(1-methylethyl)-1H-pyrazol-5-amine (400 mg, 3.20 mmol), and acetic acid (4 mL). The crude product was purified using column chromatography (Silica gel, eluent: 0 to 100% EtOAc/hexanes) to give 1.1 g (89%) of product. LCMS E-S (M+H)=388.1. $^1$H NMR (400 MHz, CHLOROFORM-d) δ ppm 1.49-1.57 (t, J=67.2 Hz, 3H), 1.63-1.74 (d, J=6.8 Hz 6H), 4.56 (q, J=7.2 Hz, 2H), 5.46 (spt, J=6.7 Hz, 1H), 7.65-7.71 (m, 2H), 8.04-8.15 (m, 2H), 8.21 (s, 1H), 8.42 (s, 1H).

Intermediate 82

1-(1-Methylethyl)-6-[4-(1H-pyrazol-4-yl)phenyl]-1H-pyrazolo[3,4-b]pyridine-4-carboxylic acid

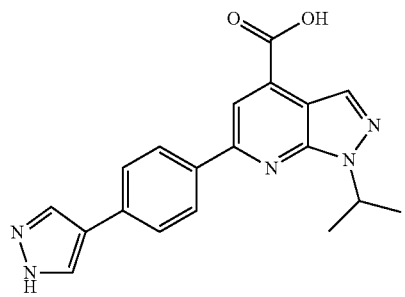 [SMILES: CC(C)n1ncc2c(C(=O)O)cc(-c3ccc(-c4cn[nH]c4)cc3)nc21]

To a 5-mL microwave vial were added ethyl 6-(4-bromophenyl)-1-(1-methylethyl)-1H-pyrazolo[3,4-b]pyridine-4-carboxylate (80 mg, 0.206 mmol), 4-(4,4,5,5-tetramethyl-1,3,2-dioxaborolan-2-yl)-1H-pyrazole (56.0 mg, 0.288 mmol), 1,4-dioxane (2 mL) and sodium carbonate (0.206 mL, 0.412 mmol), and the mixture was degassed with nitrogen for 10 min. Next added PdP(Ph$_3$)$_4$ (19.05 mg, 0.016 mmol) and the vial was sealed. The reaction mixture was irradiated (microwave) at 120° C. overnight. The reaction mixture was filtered and concentrated in vacuo. The residue was purified using reverse-phase HPLC to give 25 mg (35%) of product. LCMS E-S (M+H)=348.1. $^1$H NMR (400 MHz, DMSO-$d_6$) δ ppm 1.58 (d, J=6.8 Hz, 6H), 5.38 (quin, J=6.6 Hz, 1H), 7.81 (d, J=8.3 Hz, 2H), 8.14-8.30 (m, 4H), 8.36 (s, 1H).

Example 120

N-[(4,6-Dimethyl-2-oxo-1,2-dihydro-3-pyridinyl)methyl]-1-(1-methylethyl)-6-[4-(1H-pyrazol-4-yl)phenyl]-1H-pyrazolo[3,4-b]pyridine-4-carboxamide

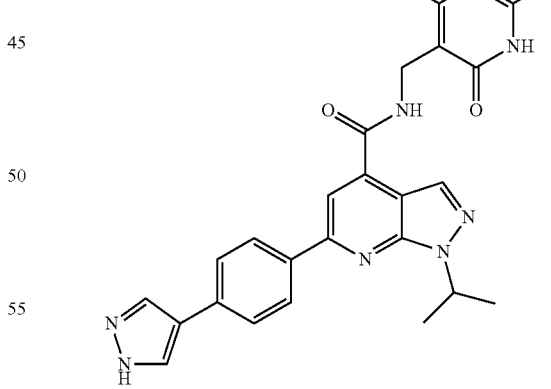

The title compound was prepared in the same manner as described in example 109 using 1-(1-methylethyl)-6-[4-(1H-pyrazol-4-yl)phenyl]-1H-pyrazolo[3,4-b]pyridine-4-carboxylic acid (20 mg, 0.058 mmol), DMSO (1 mL), 3-(aminomethyl)-4,6-dimethyl-2(1H)-pyridinone (16.29 mg, 0.086 mmol), N-methylmorpholine (0.025 mL, 0.230 mmol), 1-hydroxy-7-azabenzotriazole (15.67 mg, 0.115 mmol) and EDC (22.07 mg, 0.115 mmol). The final product was collected as 12 mg (43%). LCMS E-S (M+H)=482.0. ¹H NMR (400 MHz, DMSO-d₆) δ ppm 1.56 (d, J=6.4 Hz, 6H), 2.14 (s, 3H), 2.24 (s, 3H), 4.42 (d, J=4.8 Hz, 2H) 5.27-5.47 (m, 1H), 5.91 (s, 1H), 7.79 (d, J=8.3 Hz, 2H), 8.04 (br. s., 1H), 8.15-8.21 (m, 1H), 8.27 (d, J=8.3 Hz, 2H), 8.35-8.42 (m, 1H), 8.99 (t, J=4.8 Hz, 1H), 11.58 (br. s., 3H).

Intermediate 83

Ethyl 1-(1,1-dimethylethyl)-3-methyl-6-[4-(methyloxy)phenyl]-1H-pyrazolo[3,4-b]pyridine-4-carboxylate

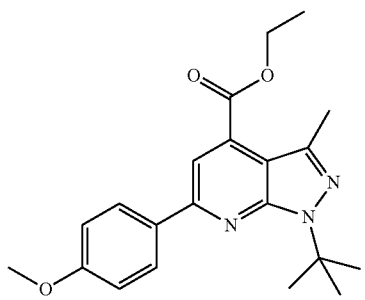 [SMILES: CCOC(=O)c1cc(-c2ccc(OC)cc2)nc2c1c(C)nn2C(C)(C)C]

The title compound was prepared in the same manner as described for intermediate 61 using ethyl 4-[4-(methyloxy)phenyl]-2,4-dioxobutanoate (327 mg, 1.305 mmol), benzene (8 mL), 1-(1,1-dimethylethyl)-3-methyl-1H-pyrazol-5-amine (200 mg, 1.305 mmol), and acetic acid (2 mL). The crude product was purified using column chromatography (Silica gel, eluent: 0 to 100% EtOAc/hexanes) to give 0.41 g (85%) of product. LCMS E-S (M+H)=368.1. ¹H NMR (400 MHz, DMSO-d₆) δ ppm 1.81 (s, 9H), 2.55 (s, 3H), 7.11 (d, J=8.84 Hz, 2H), 7.89 (s, 1H), 8.16 (d, J=8.84 Hz, 2H).

Intermediate 84

1-(1,1-Dimethylethyl)-3-methyl-6-[4-(methyloxy)phenyl]-1H-pyrazolo[3,4-b]pyridine-4-carboxylic acid

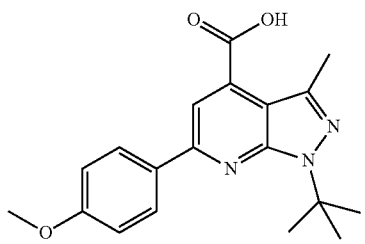 [SMILES: COc1ccc(-c2cc(C(=O)O)c3c(C)nn(C(C)(C)C)c3n2)cc1]

The title compound was prepared in the same manner as described for intermediate 75 using ethyl 1-(1,1-dimethylethyl)-3-methyl-6-[4-(methyloxy)phenyl]-1H-pyrazolo[3,4-b]pyridine-4-carboxylate (400 mg, 1.089 mmol), 3N sodium hydroxide (1.814 mL, 5.44 mmol), and EtOH (6 mL). The product was collected as 347 mg (94%). LCMS E-S (M+H)=340.2. ¹H NMR (400 MHz, DMSO-d₆) δ ppm 1.81 (s, 9H), 2.55 (s, 3H), 7.11 (d, J=8.84 Hz, 2H), 7.89 (s, 1H), 8.16 (d, J=8.84 Hz, 2H).

Example 121

1-(1,1-Dimethylethyl)-N-[(4,6-dimethyl-2-oxo-1,2-dihydro-3-pyridinyl)methyl]-3-methyl-6-[4-(methyloxy)phenyl]-1H-pyrazolo[3,4-b]pyridine-4-carboxamide

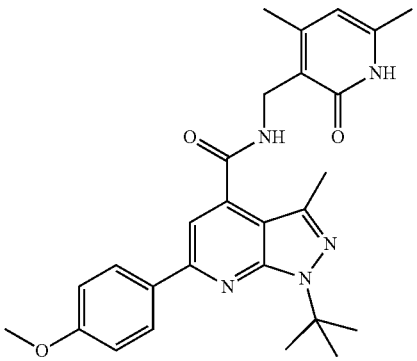

To a solution of 1-(1,1-dimethylethyl)-3-methyl-6-[4-(methyloxy)phenyl]-1H-pyrazolo[3,4-b]pyridine-4-carboxylic acid (70 mg, 0.206 mmol) in DMSO (1 mL) were added 3-(aminomethyl)-4,6-dimethyl-2(1H)-pyridinone (19.10 mg, 0.101 mmol), N-methylmorpholine (0.030 mL, 0.270 mmol), 1-hydroxy-7-azabenzotriazole (18.37 mg, 0.135 mmol) and EDC (25.9 mg, 0.135 mmol), and the mixture was stirred overnight at room temperature. The reaction mixture was quenched with water (10 mL), stirred for 10 min., and filtered. The contents were dried under high vacuum and collected as 71 mg (71%). LCMS E-S (M+H)=474.1. ¹H NMR (400 MHz, DMSO-d₆) δ ppm 1.79 (s, 9H), 2.12 (s, 3H), 2.25 (s, 3H), 2.39 (s, 3H), 3.33 (s, 1H), 4.38 (d, J=4.80 Hz, 2H), 5.88 (s, 1H), 7.10 (d, J=8.84 Hz, 2H), 7.61 (s, 1H), 8.16 (d, J=8.84 Hz, 2H), 8.70 (s, 1H), 11.53 (s, 1H).

Intermediate 85

Ethyl 1-(1,1-dimethylethyl)-3-methyl-6-{[(trifluoromethyl)sulfonyl]oxy}-1H-pyrazolo[3,4-b]pyridine-4-carboxylate

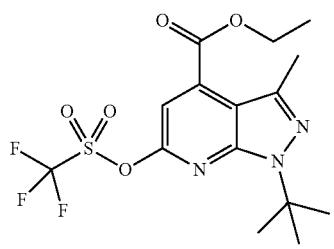 [SMILES: CCOC(=O)c1cc(OS(=O)(=O)C(F)(F)F)nc2c1c(C)nn2C(C)(C)C]

Trifluoromethanesulfonic anhydride (0.457 mL, 2.70 mmol) was added dropwise to a solution of ethyl 1-(1,1-dimethylethyl)-3-methyl-6-oxo-6,7-dihydro-1H-pyrazolo[3,4-b]pyridine-4-carboxylate (500 mg, 1.803 mmol) in pyridine (10 mL), and the reaction mixture was stirred at room temperature for 16 h. The contents were diluted with EtOAc and washed with saturated NaHCO₃, and then brine. The organic layer was dried over MgSO₄, filtered, and concentrated in vacuo. The crude residue was purified via silica gel chromatography (0% to 100% DCM:Hex) to afford the final product as a solid, 670 mg (91%). LCMS E-S (M+H)=410.0. $^1$H NMR (400 MHz, DMSO-d$_6$) δ ppm 1.38 (t, J=7.07 Hz, 3H), 1.71 (s, 9H), 2.58 (s, 3H), 4.46 (q, J=7.07 Hz, 2H), 7.63 (s, 1H).

Intermediate 86

Ethyl 1-(1,1-dimethylethyl)-3-methyl-6-(3-pyridinyl)-1H-pyrazolo[3,4-b]pyridine-4-carboxylate

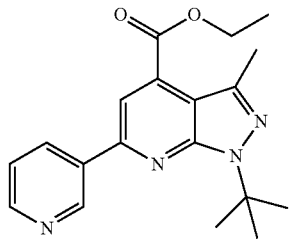 [SMILES: CCOC(=O)c1cc(-c2cccnc2)nc2c1c(C)nn2C(C)(C)C]

Ethyl 1-(1,1-dimethylethyl)-3-methyl-6-{[(trifluoromethyl)sulfonyl]oxy}-1H-pyrazolo[3,4-b]pyridine-4-carboxylate (100 mg, 0.244 mmol), 3-pyridinylboronic acid (39.0 mg, 0.318 mmol), aq. saturated NaHCO$_3$ (1 mL) and 1,4-dioxane (3 mL) were degassed with nitrogen (10 min) followed by addition of PdCl$_2$(dppf)-CH$_2$Cl$_2$ adduct (9.97 mg, 0.012 mmol). The sealed mixture was irradiated (microwave) at 120° C. for 40 min. The reaction mixture was diluted with EtOAc and filtered. The filtrate was concentrated in vacuo and the crude residue was purified by silica gel chromatography (0 to 100% EtOAc/hexanes). The final product was collected as a solid, 72 mg (87%). LCMS E-S (M+H)=339.3. $^1$H NMR (400 MHz, DMSO-d$_6$) δ ppm 1.46-1.57 (m, 3H), 1.90 (s, 9H), 2.72 (s, 3H), 4.45-4.64 (m, 2H), 7.47 (dd, J=8.08, 4.80 Hz, 1H), 8.03 (s, 1H), 8.46 (dt, J=8.08, 2.02 Hz, 1H), 8.72 (dd, J=4.80, 1.52 Hz, 1H), 9.43 (d, J=1.52 Hz, 1H).

Intermediate 87

1-(1,1-Dimethylethyl)-3-methyl-6-(3-pyridinyl)-1H-pyrazolo[3,4-b]pyridine-4-carboxylic acid

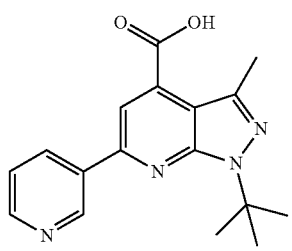 [SMILES: Cc1nn(C(C)(C)C)c2nc(-c3cccnc3)cc(C(=O)O)c12]

Ethyl 1-(1,1-dimethylethyl)-3-methyl-6-(3-pyridinyl)-1H-pyrazolo[3,4-b]pyridine-4-carboxylate (68 mg, 0.201 mmol) was suspended in ethanol (2 mL) followed by addition of sodium hydroxide (0.335 mL, 1.005 mmol). The mixture was stirred at room temperature for 2.5 h. The mixture was concentrated and the residue was diluted with water (1 mL) and acidified to pH 3 using 1N HCl. The precipitate was collected by filtration and further dried under high vacuum to give the product as an HCl salt, 60 mg (86%). LCMS E-S (M+H)=311.5. $^1$H NMR (400 MHz, DMSO-d$_6$) δ ppm 1.82 (s, 9H), 2.60 (s, 3H), 7.60 (dd, J=7.96, 4.67 Hz, 1H), 8.08 (s, 1H), 8.57 (dt, J=8.34, 1.89 Hz, 1H), 8.70 (dd, J=4.80, 1.52 Hz, 1H), 9.39 (d, J=1.52 Hz, 1H), 14.03 (br. s., 1H).

Example 122

1-(1,1-Dimethylethyl)-N-[(4,6-dimethyl-2-oxo-1,2-dihydro-3-pyridinyl)methyl]-3-methyl-6-(3-pyridinyl)-1H-pyrazolo[3,4-b]pyridine-4-carboxamide

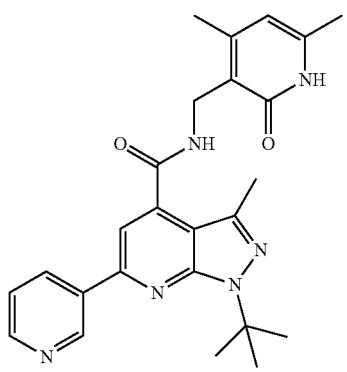 [SMILES: Cc1cc(C)c(CNC(=O)c2cc(-c3cccnc3)nc3c2c(C)nn3C(C)(C)C)c(=O)[nH]1]

The title compound was prepared in the same manner as described in example 121 using 1-(1,1-dimethylethyl)-3-methyl-6-[3-pyridinyl]-1H-pyrazolo[3,4-b]pyridine-4-carboxylic acid (58 mg, 0.167 mmol), 3-(aminomethyl)-4,6-dimethyl-2(1H)-pyridinone (47 mg, 0.251 mmol), N-methylmorpholine (0.092 mL, 0.836 mmol), 1-hydroxy-7-azabenzotriazole (46 mg, 0.334 mmol), EDC (64 mg, 0.334 mmol), and DMSO (1 mL). The product was collected as 73 mg (96%). LCMS E-S (M+H)=445.1. $^1$H NMR (400 MHz, DMSO-d$_6$) δ ppm 1.81 (s, 9H), 2.12 (s, 3H), 2.25 (s, 3H), 2.42 (s, 3H), 4.39 (d, J=5.05 Hz, 2H), 5.89 (s, 1H), 7.59 (dd, J=8.08, 4.80 Hz, 1H), 7.78 (s, 1H), 8.55 (dt, J=8.15, 1.86 Hz, 1H), 8.68 (dd, J=4.80, 1.52 Hz, 1H), 8.74 (t, J=5.05 Hz, 1H) 9.38 (d, J=1.77 Hz, 1H), 11.54 (s, 1H).

Example 123

3-Bromo-N-[(4,6-dimethyl-2-oxo-1,2-dihydro-3-pyridinyl)methyl]-1-(1-methylethyl)-6-phenyl-1H-pyrazolo[3,4-b]pyridine-4-carboxamide

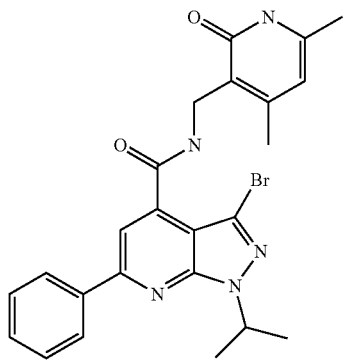 [SMILES: Cc1cc(C)c(CNC(=O)c2cc(-c3ccccc3)nc3c2c(Br)nn3C(C)C)c(=O)[nH]1]

3-Bromo-1-(1-methylethyl)-6-phenyl-1H-pyrazolo[3,4-b]pyridine-4-carboxylic acid (93 mg, 0.258 mmol), 3-(aminomethyl)-4,6-dimethyl-2(1H)-pyridinone hydrochloride (64 mg, 0.336 mmol), HOBT (60 mg, 0.387 mmol) and EDC (74 mg, 0.387 mmol) were suspended in DMSO (14 mL) and stirred at room temperature for 10 minutes, after which time DIEA (0.9 ml, 5.16 mmol) was added. After stirring for 2 h, 4-methylmorpholine (1 ml, 9.04 mmol) was added. The reaction mixture was stirred first at room temperature for 21 h, and then at 80° C. (aluminum heating block) for 31 h. The reaction mixture was cooled to room temperature and then added dropwise to a cold, slightly basic solution (pH ~8-10) of water (100 mL) and 1N Na$_2$CO$_3$ (8 mL). After stirring for 20 min., the contents were extracted with EtOAc (2×100 mL). The combined organic layers are washed with brine, dried over Na$_2$SO$_4$, filtered, and concentrated to a residue. The crude residue was dissolved in 10% MeOH/DCM and purified by silica gel chromatography (eluent: 10-95% gradient EtOAc/Hexanes and then 10% (5% NH$_4$OH/MeOH)/DCM and EtOAc, 10-90% gradient). The product was collected as an off-white solid. (35 mg, 27%). LCMS E-S (M+H)=494.1/496.0. $^1$H NMR (400 MHz, CHLOROFORM-d) δ 11.58 (br. s., 1H), 8.11 (dd, J=1.89, 7.71 Hz, 2H), 7.68 (br. s., 1H), 7.60 (br. s., 1H), 7.44-7.53 (m, 3H), 5.92 (s, 1H), 5.42 (quin, J=6.69 Hz, 1H), 4.63 (br. s., 1H), 2.41 (br. s., 3H), 2.11 (br. s., 3H), 1.62 (d, J=6.57 Hz, 6H).

Intermediate 88

3-Bromo-1-(1-methylethyl)-6-phenyl-1H-pyrazolo[3,4-b]pyridine-4-carboxylic acid

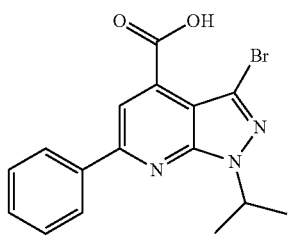 [SMILES: CC(C)n1nc(Br)c2c(C(=O)O)cc(-c3ccccc3)nc21]

Ethyl 3-bromo-1-(1-methylethyl)-6-phenyl-1H-pyrazolo[3,4-b]pyridine-4-carboxylate (112 mg, 0.288 mmol) was suspended in THF (0.5 mL) and ethanol (1.5 mL), followed by addition of 3N NaOH (150 µl, 0.433 mmol). The reaction mixture was stirred at 55° C. for 3 hours, and then allowed to cool to room temperature. The reaction mixture was diluted with water (1.5 mL), cooled in an ice bath, and acidified with 1N HCl in a dropwise manner. The mixture was extracted with EtOAc. The organic layer was separated and concentrated in vacuo to afford a solid that dried on the high vacuum 3 hours. The product was collected as a pale yellow solid (93.6 mg, 90%). LCMS E-S (M+H)=360.0/362.2. $^1$H NMR (400 MHz, MeOD) 68.22 (dd, J=1.52, 8.08 Hz, 2H), 8.05 (s, 1H), 7.48-7.59 (m, 3H), 5.47 (quin, J=6.76 Hz, 1H), 1.63 (d, J=6.82 Hz, 6H)

Intermediate 89

Ethyl 3-bromo-1-(1-methylethyl)-6-phenyl-1H-pyrazolo[3,4-b]pyridine-4-carboxylate

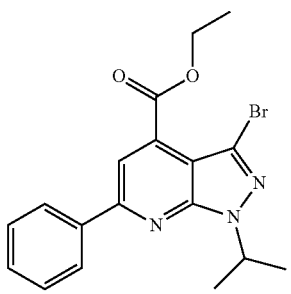 [SMILES: CCOC(=O)c1cc(-c2ccccc2)nc2c1c(Br)nn2C(C)C]

Ethyl 1-(1-methylethyl)-6-phenyl-1H-pyrazolo[3,4-b]pyridine-4-carboxylate (120 mg, 0.388 mmol), was suspended in acetic acid (2 mL) followed by addition of bromine (26 µl, 0.504 mmol). The reaction mixture was stirred with heating at 80° C. After 1 h, a second portion of bromine was added (26 µl, 0.504 mmol) and the reaction mixture heated at 80° C. for an additional 2 h. After cooling to room temperature, the solution was added to a saturated aqueous solution of sodium bicarbonate (6 mL) and extracted with dichloromethane (2×10 mL) The combined organic layers were concentrated in vacuo. The crude product was purified by silica gel chromatography (eluent: EtOAc/Hexanes, 0-50% gradient). The product was collected as a white powder (112 mg, 74%). LCMS E-S (M+H)=388.0/390.2. $^1$H NMR (400 MHz, CHLOROFORM-d) δ 8.18 (dd, J=1.52, 8.08 Hz, 2H), 8.00 (s, 1H), 7.48-7.58 (m, 3H), 5.47 (quin, J=6.76 Hz, 1H), 4.58 (q, J=7.16 Hz, 2H), 1.65 (d, J=6.82 Hz, 6H), 1.52 (t, J=7.20 Hz, 3H).

Intermediate 90

Ethyl 1-(1-methylethyl)-6-phenyl-1H-pyrazolo[3,4-b]pyridine-4-carboxylate

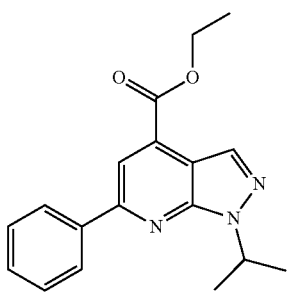 [SMILES: CCOC(=O)c1cc(-c2ccccc2)nc2c1cnn2C(C)C]

The title compound was prepared in the same manner as described for intermediate 61 using ethyl 2,4-dioxo-4-phenylbutanoate (5 g, 22.7 mmol), 1-(1-methylethyl)-1H-pyrazol-5-amine (2.84 g, 22.7 mmol), benzene (70 mL), and acetic Acid (44 mL) The crude product was purified by silica gel chromatography (eluent: 0 to 100% EtOAc/hexanes) to give 6.72 g (95%) as a pale yellow solid. LCMS E-S (M+H)=310.5. $^1$H NMR (400 MHz, DMSO-d$_6$) δ 8.39 (s, 1H), 8.17-8.28 (m, 3H), 7.49-7.64 (m, 3H), 5.38 (quin, J=6.69 Hz, 1H), 4.49 (q, J=7.07 Hz, 2H), 1.57 (d, J=6.57 Hz, 6H), 1.44 (t, 3H).

Example 124

N-[(4,6-Dimethyl-2-oxo-1,2-dihydro-3-pyridinyl)methyl]-1-(1-methylethyl)-6-(2-nitrophenyl)-1H-pyrazolo[3,4-b]pyridine-4-carboxamide

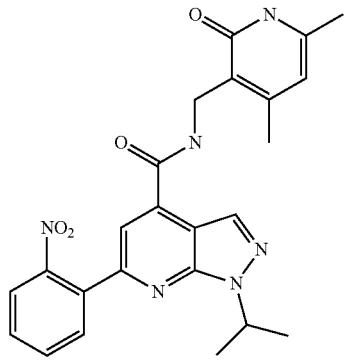 [SMILES: Cc1cc(C)c(CNC(=O)c2cc(-c3ccccc3[N+](=O)[O-])nc3c2cnn3C(C)C)c(=O)[nH]1]

1-(1-Methylethyl)-3-nitro-6-phenyl-1H-pyrazolo[3,4-b]pyridine-4-carboxylic acid (24 mg, 0.074 mmol), 3-(aminomethyl)-4,6-dimethyl-2(1H)-pyridinone hydrochloride (18 mg, 0.096 mmol), HOAT (17 mg, 0.110 mmol) and EDC (21 mg, 0.110 mmol) were suspended in DMSO (800 µL) and the reaction mixture stirred at room temperature. Next added 4-methylmorpholine (41 µl, 0.368 mmol), and the reaction was stirred at room temperature for 16 h. The reaction mixture was added dropwise to cold, slightly basic solution of water (3 mL) and 1N Na$_2$CO$_3$ (0.5 mL). After stirring for 20 min., the precipitated solids were collected via vacuum filtration and washed with water. The solid was dried on the high vacuum (72 h). The product, was collected as an off-white powder (28 mg, 82%). LCMS E-S (M+H)=461.1. $^1$H NMR (400 MHz, DMSO-d$_6$) δ 9.01 (br. s., 1H), 8.42 (s, 1H), 8.02 (ddd, J=1.14, 4.99, 7.77 Hz, 2H), 7.99 (s, 1H), 7.86 (td, J=1.26, 7.58 Hz, 1H), 7.72-7.77 (m, 1H), 5.90 (s, 1H), 5.04 (quin, J=6.69 Hz, 1H), 4.41 (d, J=4.55 Hz, 1H), 3.34 (s, 2H), 2.22 (s, 3H), 2.12 (s, 3H), 1.49 (d, J=6.57 Hz, 6H).

Intermediate 91

1-(1-Methylethyl)-6-(2-nitrophenyl)-1H-pyrazolo[3,4-b]pyridine-4-carboxylic acid

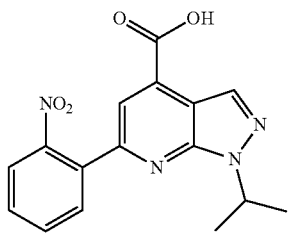 [SMILES: CC(C)n1ncc2c(C(=O)O)cc(-c3ccccc3[N+](=O)[O-])nc21]

Ethyl 1-(1-methylethyl)-3-nitro-6-phenyl-1H-pyrazolo[3,4-b]pyridine-4-carboxylate was suspended in THF (0.5 ml) and ethanol (1 mL), followed by addition of 3N NaOH aq (50 µL). The reaction mixture was heated at 55° C. for 1 h, and then allowed to cool to room temperature. The volatiles were removed in vacuo and the residue was dissolved in water (1.5 mL). The reaction mixture was cooled in an ice bath and acidified by dropwise addition of 1N HCl. After stirring for 20 minutes, the precipitated solids were collected by vacuum filtration dried under high vacuum overnight for 16 h. The product was collected as a white solid (24.5 mg, 76%). LCMS E-S (M+H)=327.2. $^1$H NMR (400 MHz, DMSO-d$_6$) δ 14.14 (br. s., 1H), 8.43 (s, 1H), 8.04 (dd, J=1.14, 7.96 Hz, 1H), 7.98-8.02 (m, J=1.26 Hz, 2H), 7.86 (td, J=1.26, 7.58 Hz, 1H), 7.72-7.80 (m, 1H), 5.09 (qd, J=6.57, 6.74 Hz, 1H), 1.51 (d, J=6.57 Hz, 6H).

Intermediate 92

Ethyl 1-(1-methylethyl)-6-(2-nitrophenyl)-1H-pyrazolo[3,4-b]pyridine-4-carboxylate

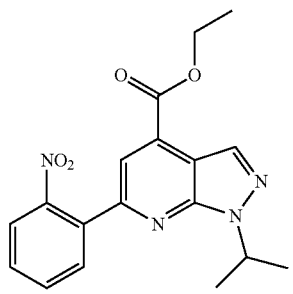 [SMILES: CCOC(=O)c1cc(-c2ccccc2[N+](=O)[O-])nc2c1cnn2C(C)C]

Ethyl 1-(1-methylethyl)-6-phenyl-1H-pyrazolo[3,4-b]pyridine-4-carboxylate (120 mg, 0.388 mmol) was dissolved in concentrated nitric acid (1.7 mL) followed by addition of concentrated sulfuric acid (0.200 mL), and the reaction mixture was stirred at room temperature. After 40 min., the reaction mixture was cooled in an ice bath and with stirring was diluted with water (3 mL) and then slowly with saturated Na$_2$CO$_3$ (1 mL). The reaction mixture was extracted with EtOAc (2×6 mL). The combined organic layers were concentrated in vacuo and the crude product purified by silica gel chromatography (eluent: EtOAc/Hexanes, 0-70% gradient). The product, was collected as a white solid (35 mg, 26%). LCMS E-S (M+H)=355.2. $^1$H NMR (400 MHz, CHLOROFORM-d) 8.46 (s, 1H), 7.99 (s, 1H), 7.94 (dd, J=1.14, 7.96 Hz, 1H), 7.76-7.81 (m, 1H), 7.73 (td, J=1.26, 7.58 Hz, 1H), 7.59-7.66 (m, 1H), 5.25 (ddd, J=6.57, 6.69, 13.52 Hz, 1H), 4.51-4.59 (m, 2H), 1.61 (d, J=6.82 Hz, 6H), 1.52 (t, J=7.07 Hz, 3H).

Example 125

N-[(4,6-Dimethyl-2-oxo-1,2-dihydro-3-pyridinyl)methyl]-1-(1-methylethyl)-6-propyl-1H-pyrazolo[3,4-b]pyridine-4-carboxamide

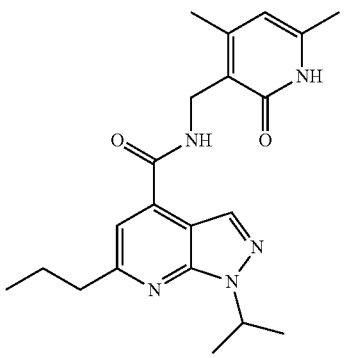 [SMILES: CCCc1cc(C(=O)NCc2c(C)cc(C)[nH]c2=O)c2cnn(C(C)C)c2n1]

The title compound was prepared in the same manner as described in example 109 using 1-(1-methylethyl)-6-propyl- 1H-pyrazolo[3,4-b]pyridine-4-carboxylic acid (70 mg, 0.283 mmol), DMSO (3 mL), 3-(aminomethyl)-4,6-dimethyl-2 (1H)-pyridinone (80 mg, 0.425 mmol), N-methylmorpholine (0.124 mL, 1.132 mmol), 1-hydroxy-7-azabenzotriazole (77 mg, 0.566 mmol), and EDC (109 mg, 0.566 mmol). The collected solid was washed with water and methanol and dried under high vacuum to give 73 mg (68%) of product. LCMS E-S (M+H)=382.3 $^1$H NMR (400 MHz, DMSO-$d_6$) δ ppm 0.82-1.10 (m, 3H), 1.48 (d, J=6.8 Hz, 6H), 1.77 (m, 2H), 2.13 (s, 3H), 2.21 (s, 3H), 2.85 (t, J=7.6 Hz, 2H), 4.36 (d, J=4.8 Hz, 2H), 5.20 (m, 1H), 5.90 (s, 1H), 7.38-7.58 (m, 1H), 8.26 (s, 1H), 8.73 (t, J=4.7 Hz, 1H), 11.57 (br. s., 1H).

Intermediate 93

3-(Aminomethyl)-6-ethyl-4-methyl-2(1H)-pyridinone

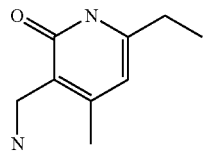

Step 1

2,4-Hexanedione (2.283 g, 20 mmol) and cyanacetamide (1.682 g, 20.00 mmol) were added to ethanol (20 mL). The contents were initially heterogenous, but gradually dissolved upon reaching ca. 70° C. Next added piperidine (1.976 mL, 20.00 mmol) and stirred with warming to reflux. After 30 min, the heterogenous contents were removed from heating and allowed to stir with cooling to room temperature. The contents were filtered in vacuo to afford a light yellowish colored solid and yellow filtrate. The collected solid filter cake was copiously washed with water which removed the yellow color. The final product was collected as fine white crystalline solid (1.66 g after drying). LCMS E-S (M+H)=163.2. $^1$H NMR (400 MHz, CHLOROFORM-d) δ ppm 1.34 (t, J=7.58 Hz, 3H) 2.47 (s, 3H) 2.71 (q, J=7.58 Hz, 2H), 6.12 (s, 1H).

Step 2

To a stirred solution of 6-ethyl-4-methyl-2-oxo-1,2-dihydro-3-pyridinecarbonitrile (1.462 g, 9.01 mmol) in Methanol (50 mL), cooled to 0° C. were added di-tertbutoxycarbonyl anhydride (4.19 mL, 18.03 mmol) and nickel(II) chloride-.hexahydrate (0.214 g, 0.901 mmol). Sodium borohydride (2.387 g, 63.1 mmol) was added portionwise over 30 min, then the mixture was allowed to warm to room temperature and stirred overnight. Additional sodium borohydride (2.387 g, 63.1 mmol) was added and the reaction stirred overnight again. Diethylenetriamine (0.979 mL, 9.01 mmol) was added, and the reaction mixture was stirred for 30 min. at room temperature. The solvent was evaporated, and the residue was dissolved in ethyl acetate (20 mL) and extracted with sodium bicarbonate (2×10 mL). The organics were dried over sodium sulfate, and concentrated. The residue was dissolved in chloroform (25 mL) and TFA (3.47 mL, 45.1 mmol) was added. The reaction was heated to 50° C. for 3 h, then cooled to room temperature and concentrated. The reaction mixture was concentrated in vacuo and the crude product was purified by reverse phase HPLC (eluent; 0-30% gradient ACN in H2O, 0.1% TFA) to afford the title compound (TFA salt, 1.37 g, 54.1% yield) as a white solid. LC-MS (ES) m/z=167 [M+H]+. $^1$H NMR (400 MHz, DMSO-d) δ ppm 1.12 (t, J=7.58 Hz, 3H), 2.20 (s, 3H), 2.44 (q, J=7.58 Hz, 2H), 3.78-3.83 (m, 2H), 6.01 (s, 1H), 7.75-7.9 (br s, 3H), 11.86 (s, 1H).

Intermediate 94

3-(Aminomethyl)-5-fluoro-4,6-dimethyl-2(1H)-pyridinone

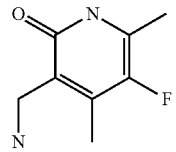

Step 1

2,4-Pentanedione (12 g, 120 mmol) was suspended in deuterated MeCN (39 mL), to which was added Selectfluor (44.7 g, 120 mmol) in one portion. The resulting paste was then heated in an oil bath to 50° C. After 5 min, an exotherm was observed, and the mixture was removed from the oil bath. The mixture was then heated at 50° C. for 1 h. The mixture was then aged at room temperature for 16 h, and then distilled under vacuum. The desired product distilled at 40-60° C. at 10-15 torr and was collected as a light yellowish liquid (1.8 mL, 1.95 g). A less pure fraction (ca. 80%) distilled at 25-35° C. at 15-20 torr, and was collected as a light yellowish liquid (3.33 g). $^1$H NMR (400 MHz, ACETONITRILE-$d_3$) δ ppm 2.24 (s, 3H), 2.26 (s, 3H), 5.46 (d, J=48.0 Hz, 1H).

Step 2

A mixture of 3-fluoro-2,4-pentanedione (247 mg, 2.10 mmol), cyanoacetamide (176 mg, 2.1 mmol, 1 equiv) and piperidine (0.21 mL, 2.1 mmol, 1 equiv) in 3 mL of EtOH was heated at 85° C. for 16 h, resulting in a clear but dark brown solution. The mixture was concentrated in vacuo. The residue was taken up in 2 mL of 1N HCl to give a suspension, which was filtered. The tan solids collected were dried under vacuum to give the desired product as 80 mg. $^1$H NMR (400 MHz, CHLOROFORM-d) δ ppm 2.33 (s, 3H), 2.42 (s, 3H).

Step 3

5-Fluoro-4,6-dimethyl-2-oxo-1,2-dihydro-3-pyridinecarbonitrile (1.0 g, 6.02 mmol) was suspended in 50 mL of HOAc at room temperature to give a dark brownish solution. NaOAc (1.0 g, 12.3 mmol, 2 equiv), PtO$_2$ (20 mg) and 5% Pd/C (1.3 g) were charged into a 500 mL Parr bottle, followed by wetting with some acetic acid under nitrogen. The substrate solution was then added, and rinsed with another 50 mL of acetic acid. The mixture was hydrogenated under a pressure of 40 psi. There was initial drop of hydrogen pressure and the vessel was refilled. The mixture was hydroganted for 6 h. The mixture was filtered through Celite, and concentrated in vacuo to give a solid residue, which was suspended in 6 mL of conc. HCl to give a paste. The paste was filtered, and the cake was washed with 1 mL of conc HCl (in duplicate). The filtrate was concentrated in vacuo. The solid residue dissolved in 0.4 mL of conc. HCl and 6 mL of EtOH as a suspension, which was stored in the freezer for 2 h, followed by filtration. The cake was washed with 2 mL of cold EtOH (in duplicate). The solids were dried under vacuum at room temperature for 18 h to give the title compound as a cream-colored solid (1.03 g). LC-MS (ES) m/z=171 [M+H]$^+$ and a dominant peak at 154. $^1$H NMR (400 MHz, DMSO-d$_6$) δ ppm, 2.20 (d, J=3.0 Hz, 3H), 2.22 (d, J=2.0 Hz, 3H), 3.83 (q, J=5.2 Hz, 2H), 7.99 (br. s., 3H), 11.99 (br. s., 1H).

Assay Protocol

Part A. Compound Preparation
1. Prepare 10 mM stock of compounds from solid in 100% DMSO.
2. In a 384-well Greiner plate (Cat #781280), plate compounds in columns 1 and 13.
3. Set up a Multiprobe instrument to do an 11 point serial dilution (1:3 dilution, columns 6 and 18 are DMSO controls).
4. Stamp 100 nL of compound from the dilution plate into reaction plates (Corning, 384-well, Cat#3706) using the Hummingbird.

Part B. Reagent Preparation
1. Prepare 2× assay buffer mix with final concentrations of 50 mM Tris pH 8, 5 mM MgCl$_2$, 4 mM DTT, 0.00185% Tween-20, and 7 µg/ml Hela nucleosomes (GRITS36431).
2. Prepare 2×EZH2 (GRITS37108) enzyme mix in assay buffer with a final enzyme concentration of 10 nM.
3. Prepare 2× mix of hot and cold SAM in ddH$_2$O with final concentrations of 0.24 µM cold SAM (Sigma) and 0.02 µCi/µL $^3$H-SAM (Perkin Elmer).
4. Prepare 500 µM SAH quench solution in ddH$_2$0 with 5-10 drops of concentrated HCl to dissolve.
5. Prepare 6 mg/ml RNA binding SPA beads (Perkin Elmer) suspended in 0.2 M Citric Acid, pH 2.2

| Reagent | Stock | 2x [Final] | [Final] |
|---|---|---|---|
| Mix 1. Assay Buffer Mix | | | |
| Tris pH 8 | 1000 mM | 100 mM | 50 mM |
| MgCl$_2$ | 1000 mM | 10 mM | 5 mM |
| DTT | 1000 mM | 8 mM | 4 mM |
| Tween-20 | 1% | 0.0037% | 0.00185% |
| Hela nucleosomes In ddH$_2$0 | 492 µg/ml | 14 µg/ml | 7 µg/ml |
| Mix 2. Enzyme Mix | | | |
| EZH2 GRITS37108 In Mix 1. Buffer | 1351 nM | 20 nM | 10 nM |
| Mix 3. SAM Substrate Mix, 500 nM total SAM | | | |
| Cold SAM | 100 µM | 0.48 µM | 0.24 µM |
| $^3$H-SAM 78 Ci/mmol | 0.5 µCi/µL5 | 0.04 µCi/µL | 0.02 µCi/µL |
| DMSO In ddH$_2$0 | 100% | 2% | 1% |

*Assay is run at apparent substrate K$_m$ for SAM and nucleosomes.

Part C. Assay Reaction in 384-Well Corning 3706 Plates
In Reaction Plates Stamped with 100 nL Compound,
1. Dispense 5 µL no enzyme control (assay buffer mix) to column 18 of plates.
2. Dispense 5 µL of enzyme mix to the remaining wells in the plate. Centrifuge plate to mix and incubate at room temperature for 30 minutes.
3. Dispense 5 µL of substrate mix to all wells to initiate the reactions. Centrifuge plate to mix and incubate at room temperature for 2 hours.
4. Quench the reactions with 10 µL of 500 µM SAH solution (250 µM final).
5. Dispense 10 µL of 6 mg/ml RNA binding SPA beads prepared in 0.2 M citric acid, pH 2.2 using the Evolution instrument. Continuously shake the beads while adding to plates to prevent beads from settling.
6. Seal the plates with Perkin Elmer top seals and allow the beads to equilibrate in the plate for at least 30 minutes at room temperature.
7. Centrifuge the plates >2000 RPM (657 rcf) for one minute. Read plates in Microbeta after at least 5 hours incubation. Plates can be read immediately, but signal increases over time.

Reagent addition can be done manually or with automated liquid handler.

*The final DMSO concentration in this assay is 1%.

*The positive control is in column 6; negative control is in column 18.

*Final starting concentration of compounds is 100 µM.

Part D. Data Analysis

Results were analyzed using a 2-parameter IC$_{50}$ fit in GraFit data analysis program (Erithacus Software Ltd, P. O. Bos 274, Horley, Surrey UK; www.erithacus.com).

Compounds of the several Examples above gave the following IC$_{50}$ data: Ex 1, 475; Ex 2, 806; Ex 4, 116; Ex 5, 705; Ex 6, 695; Ex 7, 1296; Ex 8, 167; Ex 9, 1309; Ex 10, 569; Ex 11, 18; Ex 12, 55; Ex 13, 55; Ex 14, 735; Ex 15, 179; Ex 16, 105; Ex 17, 2591; Ex 18, 40; Ex 19, 3372; Ex 20, 4647; Ex 21, 1040; Ex 22, 1362; Ex 23, 1428; Ex 24, 873; Ex 25, 685; Ex 26, 673; Ex 27, 24; Ex 28, 348; Ex 29, 234; Ex 30, 154; Ex 31, 232; Ex 32, 856; Ex 33, 70; Ex 35, 673; Ex 36, 924; Ex 37, 1095; Ex 38, 392; Ex 41, 86; Ex 42, 56; Ex 43, 204; Ex 44, 74; Ex 45, 248; Ex 46, 128; Ex 47, 88; Ex 48, 198; Ex 49, 115; Ex 50, 81; Ex 51, 161; Ex 53, 436; Ex 54, 514; Ex 55, 260; Ex 56, 2111; Ex 57, 784; Ex 58, 78; Ex 59, 155; Ex 60, 198; Ex 61, 112; Ex 62, 581; Ex 63, 96; Ex 64, 79; Ex 65, 55; Ex 66, 81; Ex 67, 58; Ex 68, 76; Ex 69, 25; Ex 70, 1893; Ex 71, 402; Ex 72, 171; Ex 73, 533; Ex 74, 151; Ex 75, 131; Ex 76, 82; Ex 77, 52; Ex 78, 43; Ex 79, 140; Ex 80, 71; Ex 81, 30; Ex 82, 108; Ex 83, 43; Ex 84, 99; Ex 85, 31; Ex 86, 142; Ex 87, 18; Ex 88, 52; Ex 89, 67; Ex 90, 173; Ex 92, 76; Ex 93, 83; Ex 94, 103; Ex 95, 489; Ex 96, 57; Ex 97, 55; Ex 99, 25044; Ex 100, 5747; Ex 103, 373; Ex 105, 315; Ex 106, 119; Ex 107, 75; Ex 109, 207; Ex 110, 231; Ex 111, 367; Ex 112, 693; Ex 113, 248; Ex 114, 199; Ex 117, 190; Ex 118, 273; Ex 119, 333; Ex 120, 270; Ex 121, 407; Ex 122, 153; Ex 123, 218; Ex 124, 1052; Ex 125, 2164.

The values in this table are single-point-in-time values and repeating the assay run(s) my result in a somewhat different number for any given test run and compound.

Compounds of this invention are not expected to have an unacceptable untoward effect when used in accordance with the teachings herein above and when used in accordance with appropriate and usual scientific and medical practice The foregoing examples are provided to illustrate the invention and are not intended to limit it in any way. What is reserved to the inventors can be found by reference to the claims.

What is claimed is:

1. A compound of formula (I):

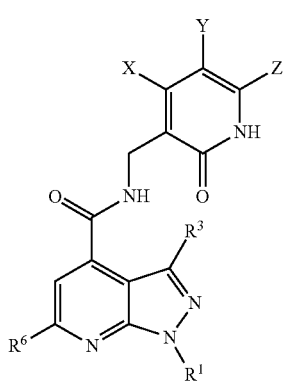

wherein
- X and Z are selected independently from the group consisting of hydrogen, $(C_1-C_8)$alkyl, $(C_2-C_8)$alkenyl, $(C_2-C_8)$alkynyl, unsubstituted or substituted $(C_3-C_8)$cycloalkyl, unsubstituted or substituted $(C_3-C_8)$cycloalkyl-$(C_1-C_8)$alkyl or -$(C_2-C_8)$alkenyl, unsubstituted or substituted $(C_5-C_8)$cycloalkenyl, unsubstituted or substituted $(C_5-C_8)$cycloalkenyl-$(C_1-C_8)$alkyl or -$(C_2-C_8)$alkenyl, $(C_6-C_{10})$bicycloalkyl, unsubstituted or substituted heterocycloalkyl, unsubstituted or substituted heterocycloalkyl-$(C_1-C_8)$alkyl or -$(C_2-C_8)$alkenyl, unsubstituted or substituted aryl, unsubstituted or substituted aryl-$(C_1-C_8)$alkyl or -$(C_2-C_8)$alkenyl, unsubstituted or substituted heteroaryl, unsubstituted or substituted heteroaryl-$(C_1-C_8)$alkyl or -$(C_2-C_8)$alkenyl, halo, cyano, $-COR^a$, $-CO_2R^a$, $-CONR^aR^b$, $-CONR^aNR^aR^b$, $-SR^a$, $-SOR^a$, $-SO_2R^a$, $-SO_2NR^aR^b$, nitro, $-NR^aR^b$, $-NR^aC(O)R^b$, $-NR^aC(O)NR^aR^b$, $-NR^aC(O)OR^a$, $-NR^aSO_2R^b$, $-NR^aSO_2NR^aR^b$, $-NR^aNR^aR^b$, $-NR^aNR^aC(O)R^b$, $-NR^aNR^aC(O)NR^aR^b$, $-NR^aNR^aC(O)OR^a$, $-OR^a$, $-OC(O)R^a$, and $-OC(O)NR^aR^b$;
- Y is H or halo;
- $R^1$ is $(C_1-C_8)$alkyl, $(C_2-C_8)$alkenyl, $(C_2-C_8)$alkynyl, unsubstituted or substituted $(C_3-C_8)$cycloalkyl, unsubstituted or substituted $(C_3-C_8)$cycloalkyl-$(C_1-C_8)$alkyl or -$(C_2-C_8)$alkenyl, unsubstituted or substituted $(C_5-C_8)$cycloalkenyl, unsubstituted or substituted $(C_5-C_8)$cycloalkenyl-$(C_1-C_8)$alkyl or -$(C_2-C_8)$alkenyl, unsubstituted or substituted $(C_6-C_{10})$bicycloalkyl, unsubstituted or substituted heterocycloalkyl, unsubstituted or substituted heterocycloalkyl-$(C_1-C_8)$alkyl or -$(C_2-C_8)$alkenyl, unsubstituted or substituted aryl, unsubstituted or substituted aryl-$(C_1-C_8)$alkyl or -$(C_2-C_8)$alkenyl, unsubstituted or substituted heteroaryl, unsubstituted or substituted heteroaryl-$(C_1-C_8)$alkyl or -$(C_2-C_8)$alkenyl, $-COR^a$, $-CO_2R^a$, $-CONR^aR^b$, or $-CONR^aNR^aR^b$;
- $R^3$ is hydrogen, $(C_1-C_8)$alkyl, cyano, trifluoromethyl, $-NR^aR^b$, or halo;
- $R^6$ is selected from the group consisting of hydrogen, halo, $(C_1-C_8)$alkyl, $(C_2-C_8)$alkenyl, $(C_2-C_8)$alkynyl, unsubstituted or substituted $(C_3-C_8)$cycloalkyl, unsubstituted or substituted $(C_3-C_8)$cycloalkyl-$(C_1-C_8)$alkyl, unsubstituted or substituted $(C_5-C_8)$cycloalkenyl, unsubstituted or substituted $(C_5-C_8)$cycloalkenyl-$(C_1-C_8)$alkyl, $(C_6-C_{10})$bicycloalkyl, unsubstituted or substituted heterocycloalkyl, unsubstituted or substituted heterocycloalkyl-$(C_1-C_8)$alkyl, unsubstituted or substituted aryl, unsubstituted or substituted aryl-$(C_1-C_8)$alkyl, unsubstituted or substituted heteroaryl, unsubstituted or substituted heteroaryl-$(C_1-C_8)$alkyl, cyano, $-COR^a$, $-CO_2R^a$, $-CONR^aR^b$, $-CONR^aNR^aR^b$, $-SR^a$, $-SOR^a$, $-SO_2R^a$, $-SO_2NR^aR^b$, nitro, $-NR^aR^b$, $-NR^aC(O)R^b$, $-NR^aC(O)NR^aR^b$, $-NR^aC(O)OR^a$, $-NR^aSO_2R^b$, $-NR^aSO_2NR^aR^b$, $-NR^aNR^aR^b$, $-NR^aNR^aC(O)R^b$, $-NR^aNR^aC(O)NR^aR^b$, $-NR^aNR^aC(O)OR^a$, $-OR^a$, $-OC(O)R^a$, and $-OC(O)NR^aR^b$;

wherein any $(C_1-C_8)$alkyl, $(C_2-C_8)$alkenyl, $(C_2-C_8)$alkynyl, cycloalkyl, cycloalkenyl, bicycloalkyl, heterocycloalkyl, aryl, or heteroaryl group is optionally substituted by 1, 2, or 3 groups independently selected from the group consisting of halo, $(C_1-C_6)$alkyl, $(C_3-C_8)$cycloalkyl, $(C_5-C_8)$cycloalkenyl, $(C_1-C_6)$haloalkyl, cyano, $-COR^a$, $-CO_2R^a$, $-CONR^aR^b$, $-SR^a$, $-SOR^a$, $-SO_2R^a$, $-SO_2NR^aR^b$, nitro, $-NR^aR^b$, $-NR^aC(O)R^b$, $-NR^aC(O)NR^aR^b$, $-NR^aC(O)OR^a$, $-NR^aSO_2R^b$, $-NR^aSO_2NR^aR^b$, $-OR^a$, $-OC(O)R^a$, $-OC(O)NR^aR^b$, heterocycloalkyl, aryl, heteroaryl, aryl$(C_1-C_4)$alkyl, and heteroaryl$(C_1-C_4)$alkyl;

wherein any aryl or heteroaryl moiety of said aryl, heteroaryl, aryl$(C_1-C_4)$alkyl, or heteroaryl$(C_1-C_4)$alkyl is optionally substituted by 1, 2, or 3 groups independently selected from the group consisting of halo, $(C_1-C_6)$alkyl, $(C_3-C_8)$cycloalkyl, $(C_5-C_8)$cycloalkenyl, $(C_1-C_6)$haloalkyl, cyano, $-COR^a$, $-CO_2R^a$, $-CONR^aR^b$, $-SR^a$, $-SOR^a$, $-SO_2R^a$, $-SO_2NR^aR^b$, nitro, $-NR^aR^b$, $-NR^aC(O)R^b$, $-OR^a$, $-OC(O)R^a$, and $-OC(O)NR^aR^b$; and $R^a$ and $R^b$ are each independently hydrogen, $(C_1-C_8)$alkyl, $(C_2-C_8)$alkenyl, $(C_2-C_8)$alkynyl, $(C_3-C_8)$cycloalkyl, $(C_5-C_8)$cycloalkenyl, $(C_6-C_{10})$bicycloalkyl, heterocycloalkyl, aryl, or heteroaryl, wherein said $(C_1-C_8)$alkyl, $(C_2-C_8)$alkenyl, $(C_2-C_8)$alkynyl, cycloalkyl, cycloalkenyl, bicycloalkyl, heterocycloalkyl, aryl, or heteroaryl group is optionally substituted by 1, 2, or 3 groups independently selected from halo, hydroxyl, $(C_1-C_4)$alkoxy, amino, $(C_1-C_4)$alkylamino, $((C_1-C_4)$alkyl)$((C_1-C_4)$alkyl)amino, $-CO_2H$, $-CO_2(C_1-C_4)$alkyl, $-CONH_2$, $-CONH(C_1-C_4)$alkyl, $-CON((C_1-C_4)$alkyl)$((C_1-C_4)$alkyl), $-SO_2(C_1-C_4)$alkyl, $-SO_2NH_2$, $-SO_2NH(C_1-C_4)$alkyl, and $-SO_2N((C_1-C_4)$alkyl)$((C_1-C_4)$alkyl);

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2, or 3 groups independently selected from $(C_1-C_4)$alkyl, $(C_1-C_4)$haloalkyl, amino, $(C_1-C_4)$alkylamino, $((C_1-C_4)$alkyl)$((C_1-C_4)$alkyl)amino, hydroxyl, oxo, $(C_1-C_4)$alkoxy, and $(C_1-C_4)$alkoxy$(C_1-C_4)$alkyl, wherein said ring is optionally fused to a $(C_3-C_8)$cycloalkyl, heterocycloalkyl, aryl, or heteroaryl ring;

or $R^a$ and $R^b$ taken together with the nitrogen to which they are attached represent a 6- to 10-membered bridged bicyclic ring system optionally fused to a $(C_3-C_8)$cycloalkyl, heterocycloalkyl, aryl, or heteroaryl ring;

or a pharmaceutically acceptable salt thereof.

2. The compound or pharmaceutically acceptable salt according to claim 1 wherein:

X and Z are selected from the group consisting of $(C_1-C_8)$alkyl, $(C_3-C_8)$cycloalkyl, heterocycloalkyl, aryl, heteroaryl, —$NR^aR^b$, and —$OR^a$;

Y is H or F;

$R^1$ is selected from the group consisting of $(C_1-C_8)$alkyl, $(C_3-C_8)$cycloalkyl, heterocycloalkyl, aryl, and heteroaryl;

$R^3$ is selected from the group consisting of hydrogen, $(C_1-C_8)$alkyl, cyano, trifluoromethyl, —$NR^aR^b$, and halo;

$R^6$ is selected from the group consisting of hydrogen, halo, cyano, trifluoromethyl, amino, $(C_1-C_8)$alkyl, $(C_3-C_8)$cycloalkyl, aryl, heteroaryl, acylamino, $(C_2-C_8)$alkynyl, aryl$(C_2-C_8)$alkynyl, heteroaryl$(C_2-C_8)$alkynyl, —$SO_2R^a$, —$SO_2NR^aR^b$, and —$NR^aSO_2R^b$;

wherein any $(C_1-C_8)$alkyl, $(C_3-C_8)$cycloalkyl, $(C_2-C_8)$alkynyl, aryl$(C_2-C_8)$alkynyl, or heteroaryl$(C_2-C_8)$alkynyl group is optionally substituted by 1, 2, or 3 groups independently selected from halo, $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$, heterocycloalkyl, aryl, heteroaryl, aryl$(C_1-C_4)$alkyl, and heteroaryl$(C_1-C_4)$alkyl; and $R^a$ and $R^b$ are each independently hydrogen, $(C_1-C_8)$alkyl, $(C_2-C_8)$alkenyl, $(C_2-C_8)$alkynyl, $(C_3-C_8)$cycloalkyl, $(C_5-C_8)$cycloalkenyl, $(C_6-C_{10})$bicycloalkyl, heterocycloalkyl, aryl, or heteroaryl, wherein said $(C_1-C_8)$alkyl, $(C_2-C_8)$alkenyl, $(C_2-C_8)$alkynyl, cycloalkyl, cycloalkenyl, bicycloalkyl, heterocycloalkyl, aryl, or heteroaryl group is optionally substituted by 1, 2, or 3 groups independently selected from halo, hydroxyl, $(C_1-C_4)$alkoxy, amino, $(C_1-C_4)$alkylamino, $((C_1-C_4)$alkyl$)((C_1-C_4)$alkyl$)$amino, —$CO_2H$, —$CO_2(C_1-C_4)$alkyl, —$CONH_2$, —$CONH(C_1-C_4)$alkyl, —$CON((C_1-C_4)$alkyl$)((C_1-C_4)$alkyl$)$, —$SO_2(C_1-C_4)$alkyl, —$SO_2NH_2$, —$SO_2NH(C_1-C_4)$alkyl, and —$SO_2N((C_1-C_4)$alkyl$)((C_1-C_4)$alkyl$)$;

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2, or 3 groups independently selected from $(C_1-C_4)$alkyl, $(C_1-C_4)$haloalkyl, amino, $(C_1-C_4)$alkylamino, $((C_1-C_4)$alkyl$)((C_1-C_4)$alkyl$)$amino, hydroxyl, oxo, $(C_1-C_4)$alkoxy, and $(C_1-C_4)$alkoxy$(C_1-C_4)$alkyl, wherein said ring is optionally fused to a $(C_3-C_8)$cycloalkyl, heterocycloalkyl, aryl, or heteroaryl ring;

or $R^a$ and $R^b$ taken together with the nitrogen to which they are attached represent a 6- to 10-membered bridged bicyclic ring system optionally fused to a $(C_3-C_8)$cycloalkyl, heterocycloalkyl, aryl, or heteroaryl ring;

wherein any aryl or heteroaryl group is selected independently from the group consisting of furan, thiophene, pyrrole, oxazole, thiazole, imidazole, pyrazole, oxadiazole, thiadiazole, triazole, tetrazole, benzofuran, benzothiophene, benzoxazole, benzothiazole, phenyl, pyridine, pyridazine, pyrimidine, pyrazine, triazine, tetrazine, quinoline, cinnoline, quinazoline, quinoxaline, and naphthyridine, or another aryl or heteroaryl group as follows:

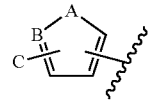
(1)

wherein in (1),
A is O, NH, or S; B is CH or N, and C is hydrogen or $C_1-C_8$ alkyl; or

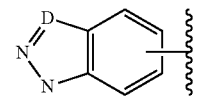
(2)

wherein in (2),
D is N or C optionally substituted by hydrogen or $C_1-C_8$ alkyl; or

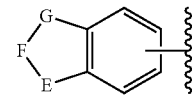
(3)

wherein in (3),
E is NH or $CH_2$; F is O or CO; and G is NH or $CH_2$; or

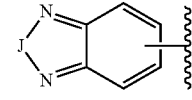
(4)

wherein in (4),
J is O, S, or CO; or

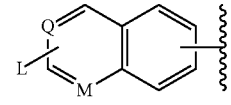
(5)

wherein in (5),
Q is CH or N;
M is CH or N; and
L/(5) is hydrogen, halo, amino, cyano, $(C_1-C_8)$alkyl, $(C_3-C_8)$cycloalkyl, —$COR^a$, —$CO_2R^a$, —$CONR^aR^b$, —$CONR^aNR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, or —$OR^a$;

wherein any $(C_1-C_8)$alkyl or $(C_3-C_8)$cycloalkyl group is optionally substituted by 1, 2, or 3 groups independently selected from $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, and —$OC(O)NR^aR^b$; or

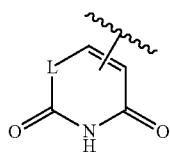

(6)

wherein in 6,
L/(6) is NH or CH₂; or

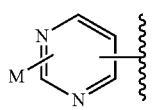

(7)

wherein in 7,
M/(7) is hydrogen, halo, amino, cyano, (C₁-C₈)alkyl, (C₃-C₈)cycloalkyl, heterocycloalkyl, —COR$^a$, —CO₂R$^a$, —CONR$^a$R$^b$, —CONR$^a$NR$^a$R$^b$, —SO₂R$^a$, —SO₂NR$^a$R$^b$, —NR$^a$R$^b$, —NR$^a$C(O)R$^b$, NR$^a$SO₂R$^b$, —NR$^a$SO₂NR$^a$R$^b$, —NR$^a$NR$^a$R$^b$, —NR$^a$NR$^a$C(O)R$^b$, —NR$^a$NR$^a$C(O)NR$^a$R$^b$, or —OR$^a$;
wherein any (C₁-C₈)alkyl, (C₃-C₈)cycloalkyl, or heterocycloalkyl group is optionally substituted by 1, 2, or 3 groups independently selected from (C₁-C₆)alkyl, (C₃-C₈)cycloalkyl, (C₅-C₈)cycloalkenyl, (C₁-C₆)haloalkyl, cyano, —COR$^a$, —CO₂R$^a$, —CONR$^a$R$^b$, —SR$^a$, —SOR$^a$, —SO₂R$^a$, —SO₂NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO₂R$^b$, —NR$^a$SO₂NR$^a$R$^b$, —OR$^a$, —OC(O)R$^a$, and —OC(O)NR$^a$R$^b$; or

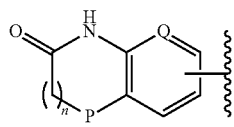

(8)

wherein in (8),
P is CH₂, NH, O, or S; Q/(8) is CH or N; and n is 0-2; or

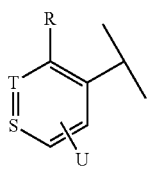

(9)

wherein in (9),
S/(9) and T(9) are each CH, or S/(9) is CH and T(9) is N, or S/(9) is N and T/(9) is CH;
R is hydrogen, amino, methyl, trifluoromethyl, or halo;
U is hydrogen, halo, amino, cyano, nitro, trifluoromethyl, (C₁-C₈)alkyl, (C₃-C₈)cycloalkyl, —COR$^a$, —CO₂R$^a$, —CONR$^a$R$^b$, —SO₂R$^a$, —SO₂NR$^a$R$^b$, —NR$^a$R$^b$, NR$^a$C(O)R$^b$, NR$^a$SO₂R$^b$, —NR$^a$SO₂NR$^a$R$^b$, —NR$^a$NR$^a$R$^b$, —NR$^a$NR$^a$C(O)R$^b$, —OR$^a$, or 4-(1H-pyrazol-4-yl);

wherein any (C₁-C₈)alkyl or (C₃-C₈)cycloalkyl group is optionally substituted by 1, 2, or 3 groups independently selected from (C₁-C₆)alkyl, (C₃-C₈)cycloalkyl, (C₅-C₈)cycloalkenyl, (C₁-C₆)haloalkyl, cyano, —COR$^a$, —CO₂R$^a$, —CONR$^a$R$^b$, —SR$^a$, —SOR$^a$, —SO₂R$^a$, —SO₂NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO₂R$^b$, —NR$^a$SO₂NR$^a$R$^b$, —OR$^a$, —OC(O)R$^a$, and —OC(O)NR$^a$R$^b$.

3. The compound according to claim 1 wherein:
X and Z are selected independently from the group consisting of (C₁-C₈)alkyl, (C₃-C₈)cycloalkyl, heterocycloalkyl, aryl, heteroaryl, —NR$^a$R$^b$, and —OR$^a$;
Y is H;
R¹ is (C₁-C₈)alkyl, (C₃-C₈)cycloalkyl, or heterocycloalkyl;
R³ is hydrogen, (C₁-C₈)alkyl, or halo;
R⁶ is hydrogen, halo, cyano, trifluoromethyl, amino, (C₁-C₈)alkyl, (C₃-C₈)cycloalkyl, aryl, heteroaryl, acylamino, (C₂-C₈)alkynyl, aryl(C₂-C₈)alkynyl, heteroaryl(C₂-C₈)alkynyl, —SO₂R$^a$, —SO₂NR$^a$R$^b$, or —NR$^a$SO₂R$^b$;
wherein any (C₁-C₈)alkyl, (C₃-C₈)cycloalkyl, (C₂-C₈) alkynyl, aryl(C₂-C₈)alkynyl, or heteroaryl(C₂-C₈) alkynyl group is optionally substituted by 1, 2, or 3 groups independently selected from halo, (C₁-C₆) alkyl, (C₃-C₈)cycloalkyl, (C₅-C₈)cycloalkenyl, (C₁-C₆)haloalkyl, cyano, —COR$^a$, —CO₂R$^a$, —CONR$^a$R$^b$, —SR$^a$, —SOR$^a$, —SO₂R$^a$, —SO₂NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO₂R$^b$, —NR$^a$SO₂NR$^a$R$^b$, —OR$^a$, —OC(O)R$^a$, —OC(O)NR$^a$R$^b$, heterocycloalkyl, aryl, heteroaryl, aryl(C₁-C₄)alkyl, and heteroaryl(C₁-C₄)alkyl; and
R$^a$ and R$^b$ are each independently hydrogen, (C₁-C₈)alkyl, (C₂-C₈)alkenyl, (C₂-C₈)alkynyl, (C₃-C₈)cycloalkyl, (C₅-C₈)cycloalkenyl, (C₆-C₁₀)bicycloalkyl, heterocycloalkyl, aryl, or heteroaryl, wherein said (C₁-C₈)alkyl, (C₂-C₈)alkenyl, (C2-C8)alkynyl, cycloalkyl, cycloalkenyl, bicycloalkyl, heterocycloalkyl, aryl, or heteroaryl group is optionally substituted by 1, 2, or 3 groups independently selected from halo, hydroxyl, (C₁-C₄)alkoxy, amino, (C₁-C₄)alkylamino, ((C₁-C₄)alkyl)((C₁-C₄)alkyl)amino, —CO₂H, —CO₂(C₁-C₄)alkyl, —CONH₂, —CONH(C₁-C₄)alkyl, —CON((C₁-C₄)alkyl)((C₁-C₄)alkyl), —SO₂(C₁-C₄)alkyl, —SO₂NH₂, —SO₂NH(C₁-C₄)alkyl, and —SO₂N((C₁-C₄)alkyl)((C₁-C₄)alkyl);
or R$^a$ and R$^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2, or 3 groups independently selected from (C₁-C₄)alkyl, (C₁-C₄)haloalkyl, amino, (C₁-C₄)alkylamino, ((C₁-C₄)alkyl)((C₁-C₄)alkyl)amino, hydroxyl, oxo, (C₁-C₄) alkoxy, and (C₁-C₄)alkoxy(C₁-C₄)alkyl, wherein said ring is optionally fused to a (C₃-C₈)cycloalkyl, heterocycloalkyl, aryl, or heteroaryl ring;
or R$^a$ and R$^b$ taken together with the nitrogen to which they are attached represent a 6- to 10-membered bridged bicyclic ring system optionally fused to a (C₃-C₈)cycloalkyl, heterocycloalkyl, aryl, or heteroaryl ring;
wherein any aryl or heteroaryl is selected from the group consisting of furan, thiophene, pyrrole, oxazole, thiazole, imidazole, pyrazole, oxadiazole, thiadiazole, triazole, tetrazole, benzofuran, benzothiophene, benzoxazole, benzothiazole, phenyl, pyridine, pyridazine, pyrimidine, pyrazine, triazine, tetrazine, quinoline, cinnoline, quinazoline, quinoxaline, and naphthyridine, or another aryl or heteroaryl group as follows:

(1)

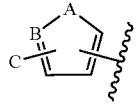

wherein in (1),
A is O, NH, or S; B is CH or N, and C is hydrogen or $C_1$-$C_8$ alkyl; or (2)

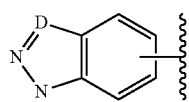

wherein in (2),
D is N or C optionally substituted by hydrogen or $C_1$-$C_8$ alkyl; or (3)

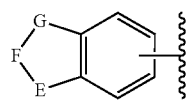

wherein in (3),
E is NH or $CH_2$; F is O or CO; and G is NH or $CH_2$; or (4)

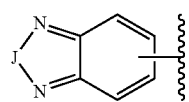

wherein in (4),
J is O, S, or CO; or (5)

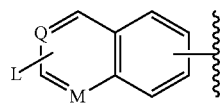

wherein in (5),
Q is CH or N;
M is CH or N; and
L/(5) is hydrogen, halo, amino, cyano, ($C_1$-$C_8$)alkyl, ($C_3$-$C_8$)cycloalkyl, —$COR^a$, —$CO_2R^a$, —$CONR^aR^b$, —$CONR^aNR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^b$, —$NR^aNR^aC(O)R^b$, —$Nr^aNR^aC(O)NR^aR^b$, or —$OR^a$;
wherein any ($C_1$-$C_8$)alkyl or ($C_3$-$C_8$)cycloalkyl group is optionally substituted by 1, 2, or 3 groups independently selected from ($C_1$-$C_6$)alkyl, ($C_3$-$C_8$)cycloalkyl, ($C_5$-$C_8$)cycloalkenyl, ($C_1$-$C_6$)haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, and —$OC(O)NR^aR^b$; or (6)

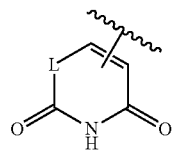

wherein in (6),
L/(6) is NH or $CH_2$; or (7)

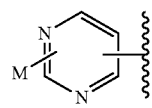

wherein in (7),
M/(7) is hydrogen, halo, amino, cyano, ($C_1$-$C_8$)alkyl, ($C_3$-$C_8$)cycloalkyl, heterocycloalkyl, —$COR^a$, —$CO_2R^a$, —$CONR^aR^b$, —$CONR^aNR^aR^b$, —$SO_2R^a$, —$SO_2NR^aR^b$, —$NR^aR^b$, —$NR^aC(O)R^b$, $NR^aSO_2R^b$, —$NR^aSO_2NR^aR^b$, —$NR^aNR^aR^b$, —$NR^aNR^aC(O)R^b$, —$NR^aNR^aC(O)NR^aR^b$, or —$OR^a$;
wherein any ($C_1$-$C_8$)alkyl, ($C_3$-$C_8$)cycloalkyl, or heterocycloalkyl group is optionally substituted by 1, 2, or 3 groups independently selected from ($C_1$-$C_6$)alkyl, ($C_3$-$C_8$)cycloalkyl, ($C_5$-$C_8$)cycloalkenyl, ($C_1$-$C_6$)haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, and —$OC(O)NR^aR^b$; or (8)

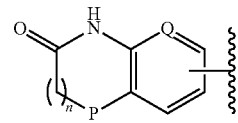

wherein in (8),
P is $CH_2$, NH, O, or S; Q/(8) is CH or N; and n is 0-2; or (9)

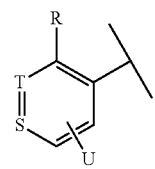

wherein in (9),
S/(9) and T(9) are each CH, or S/(9) is CH and T(9) is N, or S/(9) is N and T/(9) is CH;
R is hydrogen, amino, methyl, trifluoromethyl, or halo;

U is hydrogen, halo, amino, cyano, nitro, trifluoromethyl, ($C_1$-$C_8$)alkyl, ($C_3$-$C_8$)cycloalkyl, —$COR^a$, —$CO_2R^a$, —$CONR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, —$OR^a$, or 4-(1H-pyrazol-4-yl);

wherein any ($C_1$-$C_8$)alkyl or ($C_3$-$C_8$)cycloalkyl group is optionally substituted by 1, 2, or 3 groups independently selected from ($C_1$-$C_6$)alkyl, ($C_3$-$C_8$)cycloalkyl, ($C_5$-$C_8$)cycloalkenyl, ($C_1$-$C_6$)haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, $NR^aC(O)OR^a$, —$NR^aSO_2R^b$, —$NR^aSO_2NR^aR^b$, —$ORa$, —$OC(O)R^a$, and —$OC(O)NR^aR^b$;

or a pharmaceutically acceptable salt thereof.

4. The compound according to claim 1 wherein:

X is methyl, ethyl, n-propyl, isopropyl, cyclopropyl, cyclobutyl, cyclopentyl, cyclohexyl, phenyl, trifluoromethyl, tetrahydropyran, hydroxymethyl, methoxymethyl, or benzyl;

Y is H;

Z is methyl, ethyl, n-propyl, isopropyl, trifluoromethyl, or benzyl;

$R^1$ is isopropyl, tert-butyl, cyclobutyl, cyclopentyl, cyclohexyl, (1-methylethyl)cyclopropyl, 1,1-dioxo-tetrahydrothiophene-3-yl, 1-Me-piperidin-4-yl, tetrahydrofuran-3-yl, tetrahydropyran-4-yl, N,N-dimethyl-1-propanaminyl, benzyl, or 4-pyridyl;

$R^3$ is H, methyl, or Br; and $R^6$ is methyl, cyclopropyl, propyl, dimethylamino, ethylamino, (2-hydroxyethyl)amino, 2-propen-1-ylamino, 1-piperazinyl, 1-piperidinyl, 4-morpholinyl, 4-piperidinylamino, tetrahydro-2H-pyran-4-ylamino, phenylamino, (phenylmethyl)amino, (4-pyridinylmethyl)amino, [2-(2-pyridinylamino)ethyl]amino, 2-(dimethylamino)ethyl]amino, 4-pyridinylamino, 4-(aminocarbonyl)phenyl]amino, 3-hydroxy-3-methyl-1-butyn-1-yl, 4-pyridinylethynyl, phenylethynyl, 2-furanyl, 3-thienyl, 1H-pyrazol-4-yl, 1H-indazol-5-yl, 1H-indazol-6-yl, 3-methyl-1H-indazol-5-yl, 1H-1,2,3-benzotriazol-5-yl, 2-oxo-2,3-dihydro-1H-benzimidazol-5-yl, 2-oxo-2,3-dihydro-1H-indol-5-yl, 2-oxo-2,3-dihydro-1H-indol-6-yl, 2,1,3-benzoxadiazol-5-yl, 2-amino-6-quinazolinyl, 2,4-dioxo-1,2,3,4-tetrahydro-5-pyrimidinyl, 2-amino-5-pyrimidinyl, 7-oxo-1,5,6,7-tetrahydro-1,8-naphthyridin-3-yl, phenyl, 2-methylphenyl, 2-nitrophenyl, 2-phenylethyl, 3-aminophenyl, 4-aminophenyl, 4-chlorophenyl, 4-fluorophenyl, 4-(methyloxy)phenyl, 3-(acetylamino)phenyl, 4-(acetylamino)phenyl, 4-(aminocarbonyl)phenyl, 4-(1H-pyrazol-4-yl)phenyl, 4-(aminosulfonyl)phenyl, 4-(methylsulfonyl)phenyl, 4-[(dimethylamino)sulfonyl]phenyl, 4-[(methylamino)carbonyl]phenyl, 4-[(methylamino)sulfonyl]phenyl, 4-[(methylsulfonyl)amino]phenyl, 3-pyridinyl, 4-pyridinyl, 2-(4-morpholinyl)-4-pyridinyl, 2-amino-4-pyridinyl, 5-(methyloxy)-3-pyridinyl, 5-(methylsulfonyl)-3-pyridinyl, 5-[(cyclopropylsulfonyl)amino]-6-(methyloxy)-3-pyridinyl, 5-[(phenylsulfonyl)amino]-3-pyridinyl, 6-(4-methyl-1-piperazinyl)-3-pyridinyl, 6-(4-morpholinyl)-3-pyridinyl, 6-(acetylamino)-3-pyridinyl, 6-(dimethylamino)-3-pyridinyl, 6-(methyloxy)-3-pyridinyl, 6-[(methylamino)carbonyl]-3-pyridinyl, 6-[(methylamino)sulfonyl]-3-pyridinyl, 6-methyl-3-pyridinyl, or 4-pyridinyloxy;

or a pharmaceutically acceptable salt thereof.

5. The compound according to claim 1 which is:

6-chloro-N-[(4,6-dimethyl-2-oxo-1,2-dihydro-3-pyridinyl)methyl]-1-(1-methylethyl)-1H-pyrazolo[3,4-b]pyridine-4-carboxamide;

6-chloro-N-[(4,6-dimethyl-2-oxo-1,2-dihydro-3-pyridinyl)methyl]-3-methyl-1-(1-methylethyl)-1H-pyrazolo[3,4-b]pyridine-4-carboxamide;

6-chloro-1-(1,1-dimethylethyl)-N-[(4,6-dimethyl-2-oxo-1,2-dihydro-3-pyridinyl)methyl]-3-methyl-1H-pyrazolo[3,4-b]pyridine-4-carboxamide;

N-[(4,6-dimethyl-2-oxo-1,2-dihydro-3-pyridinyl)methyl]-1-(1-methylethyl)-6-(4-pyridinyloxy)-1H-pyrazolo[3,4-b]pyridine-4-carboxamide;

N-[(4,6-dimethyl-2-oxo-1,2-dihydro-3-pyridinyl)methyl]-1-(1-methylethyl)-6-(2-propen-1-ylamino)-1H-pyrazolo[3,4-b]pyridine-4-carboxamide;

6-amino-N-[(4,6-dimethyl-2-oxo-1,2-dihydro-3-pyridinyl)methyl]-1-(1-methylethyl)-1H-pyrazolo[3,4-b]pyridine-4-carboxamide;

6-cyclopropyl-1-(1-methylethyl)-N-[(4-methyl-2-oxo-6-propyl-1,2-dihydro-3-pyridinyl)methyl]-1H-pyrazolo[3,4-b]pyridine-4-carboxamide;

6-cyclopropyl-1-(1-methylethyl)-N-{[6-methyl-4-(1-methylethyl)-2-oxo-1,2-dihydro-3-pyridinyl]methyl}-1H-pyrazolo[3,4-b]pyridine-4-carboxamide;

1-(1-methylethyl)-N-[(4-methyl-2-oxo-6-propyl-1,2-dihydro-3-pyridinyl)methyl]-6-(4-pyridinyl)-1H-pyrazolo[3,4-b]pyridine-4-carboxamide;

N-[(6-ethyl-4-methyl-2-oxo-1,2-dihydro-3-pyridinyl)methyl]-1-(1-methylethyl)-6-(4-pyridinyl)-1H-pyrazolo[3,4-b]pyridine-4-carboxamide;

1-(1-methylethyl)-N-[(6-methyl-2-oxo-4-propyl-1,2-dihydro-3-pyridinyl)methyl]-6-(4-pyridinyl)-1H-pyrazolo[3,4-b]pyridine-4-carboxamide;

1-(1-methylethyl)-N-{[6-methyl-4-(1-methylethyl)-2-oxo-1,2-dihydro-3-pyridinyl]methyl}-6-(4-pyridinyl)-1H-pyrazolo[3,4-b]pyridine-4-carboxamide;

6-cyclopropyl-1-(1-methylethyl)-N-[(6-methyl-2-oxo-4-propyl-1,2-dihydro-3-pyridinyl)methyl]-1H-pyrazolo[3,4-b]pyridine-4-carboxamide;

1-(1-methylethyl)-N-[(6-methyl-2-oxo-4-phenyl-1,2-dihydro-3-pyridinyl)methyl]-6-(4-pyridinyl)-1H-pyrazolo[3,4-b]pyridine-4-carboxamide;

N-[(4-cyclohexyl-6-methyl-2-oxo-1,2-dihydro-3-pyridinyl)methyl]-1-(1-methylethyl)-6-(4-pyridinyl)-1H-pyrazolo[3,4-b]pyridine-4-carboxamide;

N-[(4-cyclohexyl-6-methyl-2-oxo-1,2-dihydro-3-pyridinyl)methyl]-6-cyclopropyl-1-(1-methylethyl)-1H-pyrazolo[3,4-b]pyridine-4-carboxamide;

6-cyclopropyl-1-(1-methylethyl)-N-[(6-methyl-2-oxo-4-phenyl-1,2-dihydro-3-pyridinyl)methyl]-1H-pyrazolo[3,4-b]pyridine-4-carboxamide;

N-[(4-cyclopropyl-6-methyl-2-oxo-1,2-dihydro-3-pyridinyl)methyl]-1-(1-methylethyl)-6-(4-pyridinyl)-1H-pyrazolo[3,4-b]pyridine-4-carboxamide;

6-cyclopropyl-N-[(6-cyclopropyl-4-methyl-2-oxo-1,2-dihydro-3-pyridinyl)methyl]-1-(1-methylethyl)-1H-pyrazolo[3,4-b]pyridine-4-carboxamide;

N-[(5-fluoro-4,6-dimethyl-2-oxo-1,2-dihydro-3-pyridinyl)methyl]-1-(1-methylethyl)-6-(4-pyridinyl)-1H-pyrazolo[3,4-b]pyridine-4-carboxamide;

N-[(4,6-dimethyl-2-oxo-1,2-dihydro-3-pyridinyl)methyl]-6-(ethylamino)-1-(1-methylethyl)-1H-pyrazolo[3,4-b]pyridine-4-carboxamide;

N-[(4,6-dimethyl-2-oxo-1,2-dihydro-3-pyridinyl)methyl]-1-(1-methylethyl)-1H-pyrazolo[3,4-b]pyridine-4-carboxamide;

6-cyclopropyl-1-(1-methylethyl)-N-{[6-methyl-2-oxo-4-(trifluoromethyl)-1,2-dihydro-3-pyridinyl]methyl}-1H-pyrazolo[3,4-b]pyridine-4-carboxamide;

6-(dimethylamino)-N-[(4,6-dimethyl-2-oxo-1,2-dihydro-3-pyridinyl)methyl]-1-(1-methylethyl)-1H-pyrazolo[3,4-b]pyridine-4-carboxamide;

N-[(4,6-dimethyl-2-oxo-1,2-dihydro-3-pyridinyl)methyl]-1-(1-methylethyl)-6-(1-piperidinyl)-1H-pyrazolo[3,4-b]pyridine-4-carboxamide;

N-[(4,6-dimethyl-2-oxo-1,2-dihydro-3-pyridinyl)methyl]-1-(1-methylethyl)-6-(4-morpholinyl)-1H-pyrazolo[3,4-b]pyridine-4-carboxamide;

N-[(4,6-dimethyl-2-oxo-1,2-dihydro-3-pyridinyl)methyl]-3-methyl-1-(1-methylethyl)-6-[6-(4-methyl-1-piperazinyl)-3-pyridinyl]-1H-pyrazolo[3,4-b]pyridine-4-carboxamide;

N-[(4,6-dimethyl-2-oxo-1,2-dihydro-3-pyridinyl)methyl]-1-(1-methylethyl)-6-(1-piperazinyl)-1H-pyrazolo[3,4-b]pyridine-4-carboxamide;

N-[(4,6-dimethyl-2-oxo-1,2-dihydro-3-pyridinyl)methyl]-6-(3-hydroxy-3-methyl-1-butyn-1-yl)-1-(1-methylethyl)-1H-pyrazolo[3,4-b]pyridine-4-carboxamide;

N-[(4,6-dimethyl-2-oxo-1,2-dihydro-3-pyridinyl)methyl]-1-(1-methylethyl)-6-(3-methyl-1H-indazol-5-yl)-1H-pyrazolo[3,4-b]pyridine-4-carboxamide;

N-[(4,6-dimethyl-2-oxo-1,2-dihydro-3-pyridinyl)methyl]-1-(1-methylethyl)-6-(phenylethynyl)-1H-pyrazolo[3,4-b]pyridine-4-carboxamide;

N-[(4,6-dimethyl-2-oxo-1,2-dihydro-3-pyridinyl)methyl]-1-(1-methylethyl)-6-(2-phenylethyl)-1H-pyrazolo[3,4-b]pyridine-4-carboxamide;

N-[(4,6-dimethyl-2-oxo-1,2-dihydro-3-pyridinyl)methyl]-1-(1-methylethyl)-6-(4-pyridinylethynyl)-1H-pyrazolo[3,4-b]pyridine-4-carboxamide;

N-[(4,6-dimethyl-2-oxo-1,2-dihydro-3-pyridinyl)methyl]-1-(1-methylethyl)-6-(phenylamino)-1H-pyrazolo[3,4-b]pyridine-4-carboxamide;

N-[(4,6-dimethyl-2-oxo-1,2-dihydro-3-pyridinyl)methyl]-1-(1-methylethyl)-6-[(phenylmethyl)amino]-1H-pyrazolo[3,4-b]pyridine-4-carboxamide;

N-[(4,6-dimethyl-2-oxo-1,2-dihydro-3-pyridinyl)methyl]-6-methyl-1-(1-methylethyl)-1H-pyrazolo[3,4-b]pyridine-4-carboxamide;

N-[(4,6-dimethyl-2-oxo-1,2-dihydro-3-pyridinyl)methyl]-1,6-bis(1-methylethyl)-1H-pyrazolo[3,4-b]pyridine-4-carboxamide;

N-[(4,6-dimethyl-2-oxo-1,2-dihydro-3-pyridinyl)methyl]-1-(1-methylethyl)-6-phenyl-1H-pyrazolo[3,4-b]pyridine-4-carboxamide;

N-[(4,6-dimethyl-2-oxo-1,2-dihydro-3-pyridinyl)methyl]-6-(4-fluorophenyl)-1-(1-methylethyl)-1H-pyrazolo[3,4-b]pyridine-4-carboxamide;

6-{4-[(dimethylamino)sulfonyl]phenyl}-N-[(4,6-dimethyl-2-oxo-1,2-dihydro-3-pyridinyl)methyl]-1-(1-methylethyl)-1H-pyrazolo[3,4-b]pyridine-4-carboxamide;

6-[6-(dimethylamino)-3-pyridinyl]-N-[(4,6-dimethyl-2-oxo-1,2-dihydro-3-pyridinyl)methyl]-1-(1-methylethyl)-1H-pyrazolo[3,4-b]pyridine-4-carboxamide;

N-[(4,6-dimethyl-2-oxo-1,2-dihydro-3-pyridinyl)methyl]-6-{4-[(methylamino)sulfonyl]phenyl}-1-(1-methylethyl)-1H-pyrazolo[3,4-b]pyridine-4-carboxamide;

6-(4-aminophenyl)-N-[(4,6-dimethyl-2-oxo-1,2-dihydro-3-pyridinyl)methyl]-1-(1-methylethyl)-1H-pyrazolo[3,4-b]pyridine-4-carboxamide;

6-[4-(acetylamino)phenyl]-N-[(4,6-dimethyl-2-oxo-1,2-dihydro-3-pyridinyl)methyl]-1-(1-methylethyl)-1H-pyrazolo[3,4-b]pyridine-4-carboxamide;

6-(3-aminophenyl)-N-[(4,6-dimethyl-2-oxo-1,2-dihydro-3-pyridinyl)methyl]-1-(1-methylethyl)-1H-pyrazolo[3,4-b]pyridine-4-carboxamide;

N-[(4,6-dimethyl-2-oxo-1,2-dihydro-3-pyridinyl)methyl]-6-{4-[(methylamino)carbonyl]phenyl}-1-(1-methylethyl)-1H-pyrazolo[3,4-b]pyridine-4-carboxamide;

6-[3-(acetylamino)phenyl]-N-[(4,6-dimethyl-2-oxo-1,2-dihydro-3-pyridinyl)methyl]-1-(1-methylethyl)-1H-pyrazolo[3,4-b]pyridine-4-carboxamide;

N-[(4,6-dimethyl-2-oxo-1,2-dihydro-3-pyridinyl)methyl]-6-(2,4-dioxo-1,2,3,4-tetrahydro-5-pyrimidinyl)-1-(1-methylethyl)-1H-pyrazolo[3,4-b]pyridine-4-carboxamide;

6-(2-amino-4-pyridinyl)-N-[(4,6-dimethyl-2-oxo-1,2-dihydro-3-pyridinyl)methyl]-1-(1-methylethyl)-1H-pyrazolo[3,4-b]pyridine-4-carboxamide;

6-[4-(aminosulfonyl)phenyl]-N-[(4,6-dimethyl-2-oxo-1,2-dihydro-3-pyridinyl)methyl]-1-(1-methylethyl)-1H-pyrazolo[3,4-b]pyridine-4-carboxamide;

N-[(4,6-dimethyl-2-oxo-1,2-dihydro-3-pyridinyl)methyl]-1-(1-methylethyl)-6-{4-[(methylsulfonyl)amino]phenyl}-1H-pyrazolo[3,4-b]pyridine-4-carboxamide;

6-{4-[(dimethylamino)sulfonyl]phenyl}-N-[(4,6-dimethyl-2-oxo-1,2-dihydro-3-pyridinyl)methyl]-3-methyl-1-(1-methylethyl)-1H-pyrazolo[3,4-b]pyridine-4-carboxamide;

N-[(4,6-dimethyl-2-oxo-1,2-dihydro-3-pyridinyl)methyl]-1-(1-methylethyl)-6-(4-piperidinylamino)-1H-pyrazolo[3,4-b]pyridine-4-carboxamide;

N-[(4,6-dimethyl-2-oxo-1,2-dihydro-3-pyridinyl)methyl]-1-(1-methylethyl)-6-(tetrahydro-2H-pyran-4-ylamino)-1H-pyrazolo[3,4-b]pyridine-4-carboxamide;

N-[(4,6-dimethyl-2-oxo-1,2-dihydro-3-pyridinyl)methyl]-1-(1-methylethyl)-6-[(4-pyridinylmethyl)amino]-1H-pyrazolo[3,4-b]pyridine-4-carboxamide;

6-{[2-(dimethylamino)ethyl]amino}-N-[(4,6-dimethyl-2-oxo-1,2-dihydro-3-pyridinyl)methyl]-1-(1-methylethyl)-1H-pyrazolo[3,4-b]pyridine-4-carboxamide;

N-[(4,6-dimethyl-2-oxo-1,2-dihydro-3-pyridinyl)methyl]-6-[(2-hydroxyethyl)amino]-1-(1-methylethyl)-1H-pyrazolo[3,4-b]pyridine-4-carboxamide;

N-[(4,6-dimethyl-2-oxo-1,2-dihydro-3-pyridinyl)methyl]-1-(1-methylethyl)-6-[5-(methyloxy)-3-pyridinyl]-1H-pyrazolo[3,4-b]pyridine-4-carboxamide;

N-[(4,6-dimethyl-2-oxo-1,2-dihydro-3-pyridinyl)methyl]-1-(1-methylethyl)-6-[2-(methyloxy)-4-pyridinyl]-1H-pyrazolo[3,4-b]pyridine-4-carboxamide;

6-(6-amino-3-pyridinyl)-N-[(4,6-dimethyl-2-oxo-1,2-dihydro-3-pyridinyl)methyl]-1-(1-methylethyl)-1H-pyrazolo[3,4-b]pyridine-4-carboxamide;

N-[(4,6-dimethyl-2-oxo-1,2-dihydro-3-pyridinyl)methyl]-1-(1-methylethyl)-6-[5-(methylsulfonyl)-3-pyridinyl]-1H-pyrazolo[3,4-b]pyridine-4-carboxamide;

N-[(4,6-dimethyl-2-oxo-1,2-dihydro-3-pyridinyl)methyl]-6-(2-furanyl)-1-(1-methylethyl)-1H-pyrazolo[3,4-b]pyridine-4-carboxamide;

N-[(4,6-dimethyl-2-oxo-1,2-dihydro-3-pyridinyl)methyl]-6-{6-[(methylamino)carbonyl]-3-pyridinyl}-1-(1-methylethyl)-1H-pyrazolo[3,4-b]pyridine-4-carboxamide;

6-[5-[(cyclopropylsulfonyl)amino]-6-(methyloxy)-3-pyridinyl]-N-[(4,6-dimethyl-2-oxo-1,2-dihydro-3-pyridinyl)methyl]-1-(1-methylethyl)-1H-pyrazolo[3,4-b]pyridine-4-carboxamide;

N-[(4,6-dimethyl-2-oxo-1,2-dihydro-3-pyridinyl)methyl]-1-(1-methylethyl)-6-{5-[(phenylsulfonyl)amino]-3-pyridinyl}-1H-pyrazolo[3,4-b]pyridine-4-carboxamide;

N-[(4,6-dimethyl-2-oxo-1,2-dihydro-3-pyridinyl)methyl]-1-(1-methylethyl)-6-[2-(4-morpholinyl)-4-pyridinyl]-1H-pyrazolo[3,4-b]pyridine-4-carboxamide;

N-[(4,6-dimethyl-2-oxo-1,2-dihydro-3-pyridinyl)methyl]-1-(1-methylethyl)-6-[6-(4-morpholinyl)-3-pyridinyl]-1H-pyrazolo[3,4-b]pyridine-4-carboxamide;

N-[(4,6-dimethyl-2-oxo-1,2-dihydro-3-pyridinyl)methyl]-1-(1-methylethyl)-6-[6-(methyloxy)-3-pyridinyl]-1H-pyrazolo[3,4-b]pyridine-4-carboxamide;

6-[6-(acetylamino)-3-pyridinyl]-N-[(4,6-dimethyl-2-oxo-1,2-dihydro-3-pyridinyl)methyl]-1-(1-methylethyl)-1H-pyrazolo[3,4-b]pyridine-4-carboxamide;

N-[(4,6-dimethyl-2-oxo-1,2-dihydro-3-pyridinyl)methyl]-1-(1-methylethyl)-6-(2-methylphenyl)-1H-pyrazolo[3,4-b]pyridine-4-carboxamide;

N-[(4,6-dimethyl-2-oxo-1,2-dihydro-3-pyridinyl)methyl]-1-(1-methylethyl)-6-(1H-pyrazol-4-yl)-1H-pyrazolo[3,4-b]pyridine-4-carboxamide;

6-(2-amino-5-pyrimidinyl)-N-[(4,6-dimethyl-2-oxo-1,2-dihydro-3-pyridinyl)methyl]-1-(1-methylethyl)-1H-pyrazolo[3,4-b]pyridine-4-carboxamide;

N-[(4,6-dimethyl-2-oxo-1,2-dihydro-3-pyridinyl)methyl]-1-(1-methylethyl)-6-(3-pyridinyl)-1H-pyrazolo[3,4-b]pyridine-4-carboxamide;

N-[(4,6-dimethyl-2-oxo-1,2-dihydro-3-pyridinyl)methyl]-6-(1H-indazol-5-yl)-1-(1-methylethyl)-1H-pyrazolo[3,4-b]pyridine-4-carboxamide;

N-[(4,6-dimethyl-2-oxo-1,2-dihydro-3-pyridinyl)methyl]-6-(1H-indazol-6-yl)-1-(1-methylethyl)-1H-pyrazolo[3,4-b]pyridine-4-carboxamide;

6-(1H-1,2,3-benzotriazol-5-yl)-N-[(4,6-dimethyl-2-oxo-1,2-dihydro-3-pyridinyl)methyl]-1-(1-methylethyl)-1H-pyrazolo[3,4-b]pyridine-4-carboxamide;

N-[(4,6-dimethyl-2-oxo-1,2-dihydro-3-pyridinyl)methyl]-3-methyl-1-(1-methylethyl)-6-(2-oxo-2,3-dihydro-1H-benzimidazol-5-yl)-1H-pyrazolo[3,4-b]pyridine-4-carboxamide;

N-[(4,6-dimethyl-2-oxo-1,2-dihydro-3-pyridinyl)methyl]-1-(1-methylethyl)-6-(2-oxo-2,3-dihydro-1H-indol-6-yl)-1H-pyrazolo[3,4-b]pyridine-4-carboxamide;

N-[(4,6-dimethyl-2-oxo-1,2-dihydro-3-pyridinyl)methyl]-1-(1-methylethyl)-6-(2-oxo-2,3-dihydro-1H-indol-5-yl)-1H-pyrazolo[3,4-b]pyridine-4-carboxamide;

N-[(4,6-dimethyl-2-oxo-1,2-dihydro-3-pyridinyl)methyl]-1-(1-methylethyl)-6-(2-oxo-2,3-dihydro-1H-benzimidazol-5-yl)-1H-pyrazolo[3,4-b]pyridine-4-carboxamide;

N-[(4,6-dimethyl-2-oxo-1,2-dihydro-3-pyridinyl)methyl]-1-(1-methylethyl)-6-[6-(4-methyl-1-piperazinyl)-3-pyridinyl]-1H-pyrazolo[3,4-b]pyridine-4-carboxamide;

N-[(4,6-dimethyl-2-oxo-1,2-dihydro-3-pyridinyl)methyl]-1-(1-methylethyl)-6-[6-(4-methyl-1-piperazinyl)-3-pyridinyl]-1H-pyrazolo[3,4-b]pyridine-4-carboxamide;

N-[(4,6-dimethyl-2-oxo-1,2-dihydro-3-pyridinyl)methyl]-3-methyl-1-(1-methylethyl)-6-[6-(4-morpholinyl)-3-pyridinyl]-1H-pyrazolo[3,4-b]pyridine-4-carboxamide;

N-[(4,6-dimethyl-2-oxo-1,2-dihydro-3-pyridinyl)methyl]-1-(1-methylethyl)-6-(4-pyridinylamino)-1H-pyrazolo[3,4-b]pyridine-4-carboxamide;

N-[(4,6-dimethyl-2-oxo-1,2-dihydro-3-pyridinyl)methyl]-1-(1-methylethyl)-6-[(2-oxo-2,3-dihydro-1H-benzimidazol-5-yl)amino]-1H-pyrazolo[3,4-b]pyridine-4-carboxamide;

6-{[4-(aminocarbonyl)phenyl]amino}-N-[(4,6-dimethyl-2-oxo-1,2-dihydro-3-pyridinyl)methyl]-1-(1-methylethyl)-1H-pyrazolo[3,4-b]pyridine-4-carboxamide;

1-(1,1-dimethylethyl)-N-[(4,6-dimethyl-2-oxo-1,2-dihydro-3-pyridinyl)methyl]-3-methyl-6-[6-(4-methyl-1-piperazinyl)-3-pyridinyl]-1H-pyrazolo[3,4-b]pyridine-4-carboxamide;

1-(1,1-dimethylethyl)-N-[(4,6-dimethyl-2-oxo-1,2-dihydro-3-pyridinyl)methyl]-3-methyl-6-(2-oxo-2,3-dihydro-1H-benzimidazol-5-yl)-1H-pyrazolo[3,4-b]pyridine-4-carboxamide;

1-(1,1-dimethylethyl)-N-[(4,6-dimethyl-2-oxo-1,2-dihydro-3-pyridinyl)methyl]-3-methyl-6-[6-(4-morpholinyl)-3-pyridinyl]-1H-pyrazolo[3,4-b]pyridine-4-carboxamide;

6-(2,1,3-benzoxadiazol-5-yl)-N-[(4,6-dimethyl-2-oxo-1,2-dihydro-3-pyridinyl)methyl]-3-methyl-1-(1-methylethyl)-1H-pyrazolo[3,4-b]pyridine-4-carboxamide;

6-(2-amino-6-quinazolinyl)-N-[(4,6-dimethyl-2-oxo-1,2-dihydro-3-pyridinyl)methyl]-3-methyl-1-(1-methylethyl)-1H-pyrazolo[3,4-b]pyridine-4-carboxamide;

N-[(4,6-dimethyl-2-oxo-1,2-dihydro-3-pyridinyl)methyl]-3-methyl-6-{4-[(methylamino)sulfonyl]phenyl}-1-(1-methylethyl)-1H-pyrazolo[3,4-b]pyridine-4-carboxamide;

6-[4-(acetylamino)phenyl]-N-[(4,6-dimethyl-2-oxo-1,2-dihydro-3-pyridinyl)methyl]-3-methyl-1-(1-methylethyl)-1H-pyrazolo[3,4-b]pyridine-4-carboxamide;

6-[4-(aminocarbonyl)phenyl]-N-[(4,6-dimethyl-2-oxo-1,2-dihydro-3-pyridinyl)methyl]-1-(1-methylethyl)-1H-pyrazolo[3,4-b]pyridine-4-carboxamide;

N-[(4,6-dimethyl-2-oxo-1,2-dihydro-3-pyridinyl)methyl]-1-(1-methylethyl)-6-{[2-(2-pyridinylamino)ethyl]amino}-1H-pyrazolo[3,4-b]pyridine-4-carboxamide;

N-[(4,6-dimethyl-2-oxo-1,2-dihydro-3-pyridinyl)methyl]-1-(1-methylethyl)-6-(7-oxo-1,5,6,7-tetrahydro-1,8-naphthyridin-3-yl)-1H-pyrazolo[3,4-b]pyridine-4-carboxamide;

N-[(4,6-dimethyl-2-oxo-1,2-dihydro-3-pyridinyl)methyl]-6-{6-[(methylamino)sulfonyl]-3-pyridinyl}-1-(1-methylethyl)-1H-pyrazolo[3,4-b]pyridine-4-carboxamide;

1-(2-aminoethyl)-6-cyclopropyl-N-[(4,6-dimethyl-2-oxo-1,2-dihydro-3-pyridinyl)methyl]-1H-pyrazolo[3,4-b]pyridine-4-carboxamide;

6-cyclopropyl-N-[(4,6-dimethyl-2-oxo-1,2-dihydro-3-pyridinyl)methyl]-1-{2-[(methylsulfonyl)amino]ethyl}-1H-pyrazolo[3,4-b]pyridine-4-carboxamide;

N-[(4,6-dimethyl-2-oxo-1,2-dihydro-3-pyridinyl)methyl]-6-methyl-1-(phenylmethyl)-1H-pyrazolo[3,4-b]pyridine-4-carboxamide;

6-cyclopropyl-N-[(4,6-dimethyl-2-oxo-1,2-dihydro-3-pyridinyl)methyl]-1-ethyl-1H-pyrazolo[3,4-b]pyridine-4-carboxamide;

6-cyclopropyl-N-[(4,6-dimethyl-2-oxo-1,2-dihydro-3-pyridinyl)methyl]-1-propyl-1H-pyrazolo[3,4-b]pyridine-4-carboxamide;

6-cyclopropyl-N-[(4,6-dimethyl-2-oxo-1,2-dihydro-3-pyridinyl)methyl]-3-methyl-1-(1-methylethyl)-1H-pyrazolo[3,4-b]pyridine-4-carboxamide;

1-amino-6-cyclopropyl-N-[(4,6-dimethyl-2-oxo-1,2-dihydro-3-pyridinyl)methyl]-1H-pyrazolo[3,4-b]pyridine-4-carboxamide;
1-cyclobutyl-6-cyclopropyl-N-[(4,6-dimethyl-2-oxo-1,2-dihydro-3-pyridinyl)methyl]-3-methyl-1H-pyrazolo[3,4-b]pyridine-4-carboxamide;
1-cyclopentyl-6-cyclopropyl-N-[(4,6-dimethyl-2-oxo-1,2-dihydro-3-pyridinyl)methyl]-3-methyl-1H-pyrazolo[3,4-b]pyridine-4-carboxamide;
6-cyclopropyl-1-(1,1-dimethylethyl)-N-[(4,6-dimethyl-2-oxo-1,2-dihydro-3-pyridinyl)methyl]-3-methyl-1H-pyrazolo[3,4-b]pyridine-4-carboxamide;
6-cyclopropyl-N-[(4,6-dimethyl-2-oxo-1,2-dihydro-3-pyridinyl)methyl]-1-(4-pyridinyl)-1H-pyrazolo[3,4-b]pyridine-4-carboxamide;
6-cyclopropyl-1-(1-cyclopropylethyl)-N-[(4,6-dimethyl-2-oxo-1,2-dihydro-3-pyridinyl)methyl]-3-methyl-1H-pyrazolo[3,4-b]pyridine-4-carboxamide;
1-cyclohexyl-6-cyclopropyl-N-[(4,6-dimethyl-2-oxo-1,2-dihydro-3-pyridinyl)methyl]-3-methyl-1H-pyrazolo[3,4-b]pyridine-4-carboxamide;
6-cyclopropyl-N-[(4,6-dimethyl-2-oxo-1,2-dihydro-3-pyridinyl)methyl]-3-methyl-1-(1-methyl-4-piperidinyl)-1H-pyrazolo[3,4-b]pyridine-4-carboxamide;
6-cyclopropyl-N-[(4,6-dimethyl-2-oxo-1,2-dihydro-3-pyridinyl)methyl]-3-methyl-1-(tetrahydro-2H-pyran-4-yl)-1H-pyrazolo[3,4-b]pyridine-4-carboxamide;
N-[(4,6-dimethyl-2-oxo-1,2-dihydro-3-pyridinyl)methyl]-1-(1-methylethyl)-6-[4-(methyloxy)phenyl]-1H-pyrazolo[3,4-b]pyridine-4-carboxamide;
N-[(4,6-dimethyl-2-oxo-1,2-dihydro-3-pyridinyl)methyl]-1-(1-methylethyl)-6-(4-pyridinyl)-1H-pyrazolo[3,4-b]pyridine-4-carboxamide;
6-(4-chlorophenyl)-N-[(4,6-dimethyl-2-oxo-1,2-dihydro-3-pyridinyl)methyl]-1-(1-methylethyl)-1H-pyrazolo[3,4-b]pyridine-4-carboxamide;
N-[(4,6-dimethyl-2-oxo-1,2-dihydro-3-pyridinyl)methyl]-1-(1-methylethyl)-6-(3-thienyl)-1H-pyrazolo[3,4-b]pyridine-4-carboxamide;
N-[(4,6-dimethyl-2-oxo-1,2-dihydro-3-pyridinyl)methyl]-3-methyl-1-(1-methylethyl)-6-(4-pyridinyl)-1H-pyrazolo[3,4-b]pyridine-4-carboxamide;
1,6-bis(1,1-dimethylethyl)-N-[(4,6-dimethyl-2-oxo-1,2-dihydro-3-pyridinyl)methyl]-3-methyl-1H-pyrazolo[3,4-b]pyridine-4-carboxamide;
N-[(4,6-dimethyl-2-oxo-1,2-dihydro-3-pyridinyl)methyl]-1-(1-methylethyl)-6-[4-(methylsulfonyl)phenyl]-1H-pyrazolo[3,4-b]pyridine-4-carboxamide;
N-[(4,6-dimethyl-2-oxo-1,2-dihydro-3-pyridinyl)methyl]-1-(1-methylethyl)-6-[4-(1H-pyrazol-4-yl)phenyl]-1H-pyrazolo[3,4-b]pyridine-4-carboxamide;
1-(1,1-dimethylethyl)-N-[(4,6-dimethyl-2-oxo-1,2-dihydro-3-pyridinyl)methyl]-3-methyl-6-[4-(methyloxy)phenyl]-1H-pyrazolo[3,4-b]pyridine-4-carboxamide;
1-(1,1-dimethylethyl)-N-[(4,6-dimethyl-2-oxo-1,2-dihydro-3-pyridinyl)methyl]-3-methyl-6-(3-pyridinyl)-1H-pyrazolo[3,4-b]pyridine-4-carboxamide;
3-bromo-N-[(4,6-dimethyl-2-oxo-1,2-dihydro-3-pyridinyl)methyl]-1-(1-methylethyl)-6-phenyl-1H-pyrazolo[3,4-b]pyridine-4-carboxamide;
N-[(4,6-dimethyl-2-oxo-1,2-dihydro-3-pyridinyl)methyl]-1-(1-methylethyl)-6-(2-nitrophenyl)-1H-pyrazolo[3,4-b]pyridine-4-carboxamide; or
N-[(4,6-dimethyl-2-oxo-1,2-dihydro-3-pyridinyl)methyl]-1-(1-methylethyl)-6-propyl-1H-pyrazolo[3,4-b]pyridine-4-carboxamide;
or a pharmaceutically acceptable salt thereof.

6. A Pharmaceutical Composition Comprising the Compound or Pharmaceutically acceptable salt thereof according to claim 1 and a pharmaceutically acceptable excipient.

\* \* \* \* \*